US012774288B2

(12) United States Patent
Ouyang et al.

(10) Patent No.: US 12,774,288 B2
(45) Date of Patent: Oct. 27, 2026

(54) 4,5,6,7-TETRAHYDROTHIENO[2,3-C]PYRIDINE SUMO INHIBITORS AND USES THEREOF

(71) Applicant: CIT THERAPEUTICS, INC., Thousand Oaks, CA (US)

(72) Inventors: Xiaohu Ouyang, Rosemead, CA (US); Miles Douglas Kubota, Monrovia, CA (US); Andrew Stewart Tasker, Simi Valley, CA (US); Fang-Tsao Hong, Thousand Oaks, CA (US); Mary Walton, Camarillo, CA (US); Victor J. Cee, Thousand Oaks, CA (US)

(73) Assignee: CIT THERAPEUTICS, INC., La Jolla, CA (US)

( * ) Notice: Subject to any disclaimer, the term of this patent is extended or adjusted under 35 U.S.C. 154(b) by 931 days.

(21) Appl. No.: 17/793,191

(22) PCT Filed: Jan. 22, 2021

(86) PCT No.: PCT/US2021/014653
§ 371 (c)(1),
(2) Date: Jul. 15, 2022

(87) PCT Pub. No.: WO2021/150918
PCT Pub. Date: Jul. 29, 2021

(65) Prior Publication Data

US 2023/0303584 A1 Sep. 28, 2023

Related U.S. Application Data

(60) Provisional application No. 63/082,215, filed on Sep. 23, 2020, provisional application No. 62/964,160, filed on Jan. 22, 2020.

(51) Int. Cl.
*C07D 495/04* (2006.01)

(52) U.S. Cl.
CPC .................................. *C07D 495/04* (2013.01)

(58) Field of Classification Search
CPC .................................................... C07D 495/04
See application file for complete search history.

(56) References Cited

U.S. PATENT DOCUMENTS

2022/0177488 A1* 6/2022 Ouyang .............. C07D 471/04

FOREIGN PATENT DOCUMENTS

WO 2012/064897 A2 5/2012
WO 2020/191151 A1 9/2020

OTHER PUBLICATIONS

Berge et al., Pharmaceutical Salts, Journal of Pharmaceutical Science, 66, 1-19 (1977).
International Application No. PCT/US21/14653, International Preliminary Report on Patentability, mailed Aug. 4, 2022.
International Application No. PCT/US21/14653, International Search Report and Written Opinion, mailed Mar. 16, 2021.
Rao et al., Leveraging Compound Promiscuity to Identify Targetable Cysteines within the Kinome, Cell Chemical Biology, 26:1-12 (2019).

* cited by examiner

*Primary Examiner* — Valerie Rodriguez-Garcia
(74) *Attorney, Agent, or Firm* — MARSHALL, GERSTEIN & BORUN LLP

(57) ABSTRACT

The present invention relates to compounds and compositions capable of acting as inhibitors of small ubiquitin-like modifier (SUMO) family of proteins. The compounds and compositions may be used in the treatment of cancer. There are disclosed, inter alia, methods of inhibiting an E1 enzyme, and compounds useful for inhibiting an E1 enzyme.

23 Claims, No Drawings

Specification includes a Sequence Listing.

4,5,6,7-TETRAHYDROTHIENO[2,3-C]PYRIDINE SUMO INHIBITORS AND USES THEREOF

STATEMENT OF GOVERNMENT SUPPORT

This invention was made with government support under SBIR Grant 2R44CA189499, SBIR Grant 1R43CA217349-01A1 and SBIR Grant 1R43CA239820 each awarded by the National Institutes of Health from the National Cancer Institute. The government has certain rights in the invention.

INCORPORATION BY REFERENCE OF MATERIALS SUBMITTED ELECTRONICALLY

The application contains, as a separate part of the disclosure, a Sequence Listing in computer readable form: Filename: 54042_Seglisting.txt; Size: 1,681 Bytes; Created: Jan. 21, 2021, which is incorporated by reference in its entirety.

FIELD OF THE INVENTION

The present invention relates to compounds and compositions capable of acting as inhibitors of the small ubiquitin-like modifier (SUMO) family of proteins. The compounds and compositions may be used in the treatment of cancer.

Background of the Invention

Post-translational modifications of cellular proteins by the small ubiquitin-like modifier (SUMO) family of proteins are important epigenetic mechanisms for regulating various cellular functions. Aberrations in post-translational modification of cellular proteins by the small ubiquitin-like modifier (SUMO) family of proteins are associated with the pathogenesis of life-threatening diseases, such as cancer, neurodegenerative disorders, and viral infection. Indeed, the enzymes catalyzing SUMO-modification (e.g., E1 disclosed herein) are present in higher levels in cancer tissues versus normal tissues and in metastasized tumors versus normal cells, and play an important role in cancer proliferation and metastasis. Without wishing to be bound by any theory, it is believed that E1 is a target for the development of therapeutics (e.g., cancer therapeutics). Thus, there are disclosed herein methods of inhibiting an E1 enzyme, and compounds useful for inhibiting an E1 enzyme.

DESCRIPTION OF THE INVENTION

One embodiment relates to compounds of Formula XI (XI)

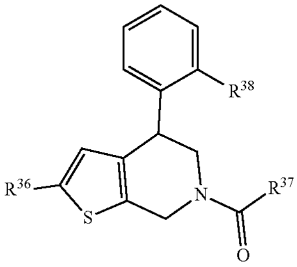

wherein $R^{36}$ is halo;

$R^{37}$ is $C_2$-$C_4$ alkenyl; and $R^{38}$ is selected from substituted or unsubstituted nitrogen containing 5-membered heteroaryl, substituted or unsubstituted nitrogen containing 5- or 6-membered partially unsaturated heterocyclyl and substituted or unsubstituted nitrogen containing 6-membered heteroaryl; provided $R^{38}$ is not 4-pyridyl; or an isomer or a pharmaceutically acceptable salt thereof.

In one embodiment, the substituted or unsubstituted nitrogen containing 5-membered heteroaryl is selected from pyrazolyl, isoxazolyl, isothiazolyl, pyrrolyl, thiazolyl, triazolyl and imidazolyl; the substituted or unsubstituted nitrogen containing 6-membered heteroaryl is pyridinyl, pyrimidinyl or pyrazinyl; the substituted or unsubstituted nitrogen containing 5-membered partially unsaturated heterocyclyl is pyrrolinyl, or imidazolidinyl; and substituted or unsubstituted nitrogen containing 6-membered partially unsaturated heterocyclyl is dihydropyridinyl; or an isomer or a pharmaceutically acceptable salt thereof.

In one embodiment, $R^{36}$ is chloro; or an isomer or a pharmaceutically acceptable salt thereof.

In one embodiment, $R^{37}$ is ethenyl; or an isomer or a pharmaceutically acceptable salt thereof.

In one embodiment, $R^{38}$ is selected from substituted 5-pyrazolyl, substituted 4-pyrazolyl, substituted 1-pyrazolyl, substituted or unsubstituted 4-isoxazolyl, substituted or unsubstituted 4-isothiazolyl, substituted or unsubstituted 3-pyrrolyl, substituted or unsubstituted 5-thiazolyl, substituted or unsubstituted 5-imidazolyl, substituted or unsubstituted 1-imidazolyl, substituted or unsubstituted [1,2,4]triazol-5-yl, substituted or unsubstituted 3-pyridyl, and substituted or unsubstituted 5-pyrimidinyl; or an isomer or a pharmaceutically acceptable salt thereof.

In one embodiment, $R^{38}$ is selected from 1-isopropyl-3-trifluoromethyl-pyrazol-4-yl, 1-ethyl-3-trifluoromethyl-pyrazol-4-yl, 1-butyl-3-trifluoromethyl-pyrazol-4-yl, 1-methoxymethyl-3-trifluoromethyl-pyrazol-4-yl, 1-propyl-3-trifluoromethyl-pyrazol-4-yl, 1,3-dimethyl-pyrazol-4-yl, 1,3,5-trimethyl-pyrazol-4-yl, 1-methyl-3-cyclopropyl-pyrazol-4-yl, 1-methyl-3-trifluoromethyl-pyrazol-4-yl, 1-benzyl-3-methyl-pyrazol-4-yl, 1-(3-pyridinylmethyl)-3-methyl-pyrazol-4-yl, 1-(2-pyridinylmethyl)-3-methyl-pyrazol-4-yl, 1-[2-pyridyl]-3-methyl-pyrazol-4-yl, 1-methyl-5-pyrazolyl, 1,3-dimethyl-5-pyrazolyl, 1-methyl-4-pyrazolyl, 1,5-dimethyl-4-pyrazolyl, 4-methyl-3-pyrazolyl, 1-methyl-[1,2,4]triazol-3-yl, 1-methyl-[1,2,4]triazol-5-yl, 4-isothiazolyl, 4-methyl-2-oxazolyl, isoxazole-4-yl,2,4-dimethylthiazol-5-yl, 3,5-dimethylisoxazol-4-yl, and 4-methyl-5-thiazolyl; or an isomer or a pharmaceutically acceptable salt thereof.

In one embodiment, $R^{38}$ is selected from 5-pyrimidinyl, 4-methyl-5-pyrimidinyl, 4-triflouromethyl-5-pyrimidinyl, 3-pyridinyl, 2-pyridinyl, 2-triflouromethyl-3-pyridinyl, 3-triflouromethyl-3-pyridinyl, 4-triflouromethyl-3-pyridinyl, 2-methyl-3-pyridinyl, 2,5-dimethyl-3-pyridinyl, 2,6-dimethyl-3-pyridinyl, 2,4-dimethyl-3-pyridinyl, 2-ethyl-3-pyridinyl, 5-methyl-3-pyridinyl, 2-ethoxy-3-pyridinyl, 2-ethoxy-5-methyl-3-pyridinyl, 2-methoxy-3-pyridinyl, 2-methoxy-6-methyl-3-pyridinyl, 2-cyclopropoxy-3-pyridinyl, 2-chloro-3-pyridinyl, 2-flouro-3-methyl-5-pyridinyl, 3-chloro-5-pyridinyl, 2-chloro-4-methyl-5-pyridinyl, 2-methoxy-5-pyridinyl, 3-methoxy-5-pyridinyl, 2-ethoxy-5-pyridinyl, 2,3-dimethyl-5-pyridinyl and 2-ethyl-6-pyridinyl; or an isomer or a pharmaceutically acceptable salt thereof.

In one embodiment, $R^{38}$ is selected from substituted or unsubstituted tetrahydroquinolinyl; substituted or unsubstituted 1-pyrrolin-3-yl, substituted or unsubstituted 1-imidazolidinyl, dihydropyridin-3-yl; or an isomer or a pharmaceutically acceptable salt thereof.

One embodiment relates to compounds wherein $R^{38}$ is substituted or unsubstituted 4-isoquinolinyl or substituted or unsubstituted 4-quinolinyl; or an isomer or a pharmaceutically acceptable salt thereof.

One embodiment relates to compounds of Formula XIA

[XIA]

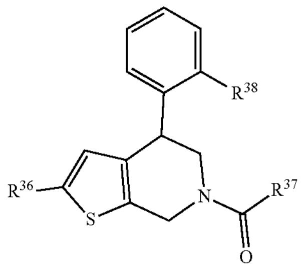

wherein $R^{36}$ is H, halo, $C_1$-$C_4$ alkyl, $C_2$-$C_4$ alkenyl or $C_3$-$C_6$ cycloalkyl;

$R^{37}$ is substituted or unsubstituted $C_2$-$C_4$ alkenyl or $C_2$-$C_4$ alkynyl; and $R^{38}$ is selected from substituted or unsubstituted nitrogen containing 5-membered heteroaryl, substituted or unsubstituted nitrogen containing 5- or 6-membered partially unsaturated heterocyclyl and substituted or unsubstituted nitrogen containing 6-10 membered heteroaryl; provided $R^{38}$ is not 4-pyridyl; or an isomer or stereoisomer of any of the foregoing, or a mixture thereof or a pharmaceutically acceptable salt thereof.

In one embodiment $R^{38}$ is selected from substituted or unsubstituted nitrogen containing 5-membered heteroaryl selected from pyrazolyl, isoxazolyl, isothiazolyl, pyrrolyl, thiazolyl, triazolyl and imidazolyl; substituted or unsubstituted nitrogen containing 6-membered heteroaryl selected from pyridinyl, pyrimidinyl and pyrazinyl; substituted or unsubstituted nitrogen containing 5-membered partially unsaturated heterocyclyl selected from pyrrolinyl, and imidazolidinyl; and substituted or unsubstituted dihydropyridinyl; or an isomer or a pharmaceutically acceptable salt thereof.

In one embodiment $R^{36}$ is selected from chloro, methyl, ethyl, isopropyl, allylyl, and cyclopropyl; or an isomer or a pharmaceutically acceptable salt thereof:

In one embodiment $R^{38}$ is selected from substituted 5-pyrazolyl, substituted 4-pyrazolyl, substituted 1-pyrazolyl, substituted or unsubstituted 4-isoxazolyl, substituted or unsubstituted 4-isothiazolyl, substituted or unsubstituted 3-pyrrolyl, substituted or unsubstituted 5-thiazolyl, substituted or unsubstituted 5-imidazolyl, substituted or unsubstituted 1-imidazolyl, substituted or unsubstituted [1,2,4]triazol-5-yl, substituted or unsubstituted 3-pyridyl, and substituted or unsubstituted 5-pyrimidinyl; or an isomer or a pharmaceutically acceptable salt thereof.

In one embodiment $R^{38}$ is selected from 3-trifluoromethyl-pyrazol-4-yl, 1-isopropyl-3-trifluoromethyl-pyrazol-4-yl, 1-ethyl-3-trifluoromethyl-pyrazol-4-yl, 1-methyl-3-difluoromethyl-pyrazol-4-yl, 1-butyl-3-trifluoromethyl-pyrazol-4-yl, 1-methoxymethyl-3-trifluoromethyl-pyrazol-4-yl, 1-propyl-3-trifluoromethyl-pyrazol-4-yl, 1,3-dimethyl-pyrazol-4-yl, 1,3,5-trimethyl-pyrazol-4-yl, 1-methyl-3-cyclopropyl-pyrazol-4-yl, 1-methyl-3-trifluoromethyl-pyrazol-4-yl, 1-ethyl-3-amino-pyrazol-4-yl, 1-ethyl-3-methoxy-pyrazol-4-yl, 1-hydroxyethyl-3-trifluoromethyl-pyrazol-4-yl, 1-[2-hydroxypropyl]-3-trifluoromethyl-pyrazol-4-yl, 1-[2-hydroxyisobutyl]-3-trifluoromethyl-pyrazol-4-yl, 1-methoxyethyl-3-trifluoromethyl-pyrazol-4-yl, 1-[N,N-dimethylaminoethyl]-3-trifluoromethyl-pyrazol-4-yl, 1-[N-methylaminocarbonylmethyl]-3-trifluoromethyl-pyrazol-4-yl, 1-[N-methylaminocarbonylethyl]-3-trifluoromethyl-pyrazol-4-yl, 1-[N,N-dimethylaminocarbonylmethyl]-3-trifluoromethyl-pyrazol-4-yl, 1-aminocarbonylmethyl-3-trifluoromethyl-pyrazol-4-yl, 1-methylcarbonylaminoethyl-3-trifluoromethyl-pyrazol-4-yl, 1-methylcarbonylaminobutyl-3-trifluoromethyl-pyrazol-4-yl, 1-aminocarbonylethyl-3-trifluoromethyl-pyrazol-4-yl, 1-aminocarbonylpropyl-3-trifluoromethyl-pyrazol-4-yl, 1-aminocarbonylisopropyl-3-trifluoromethyl-pyrazol-4-yl, 1-cyanopropyl-3-trifluoromethyl-pyrazol-4-yl, 1-[N,N-dimethylaminocarbonylethyl]-3-trifluoromethyl-pyrazol-4-yl, 1-carboxyethyl]-3-trifluoromethyl-pyrazol-4-yl, 1-carboxymethyl]-3-trifluoromethyl-pyrazol-4-yl, 1-methoxycarbonylmethyl]-3-trifluoromethyl-pyrazol-4-yl, 1-ethyl-3-carboxy-pyrazol-4-yl, 1-ethyl-5-carboxy-pyrazol-4-yl, 1-ethyl-3-methylaminocarbonyl-pyrazol-4-yl, 1-ethyl-3-[N,N-dimethylaminocarbonyl]-pyrazol-4-yl, 1-ethyl-5-methylaminocarbonyl-pyrazol-4-yl, 1-ethyl-5-[N,N-dimethylaminocarbonyl]-pyrazol-4-yl, 1-benzyl-3-methyl-pyrazol-4-yl, 1-(cyclopropylmethyl)-3-trifluoromethyl-pyrazol-4-yl, 1-cyclopropyl-3-trifluoromethyl-pyrazol-4-yl, 1-[1-methylazetidin-3-yl]-3-trifluoromethyl-pyrazol-4-yl, 1-[1-methylpyrrolidin-3-yl]-3-trifluoromethyl-pyrazol-4-yl, 1-[1-methylpiperidin-3-yl]-3-trifluoromethyl-pyrazol-4-yl, 1-[1-methylpiperidin-4-yl]-3-trifluoromethyl-pyrazol-4-yl, 1-(3-pyridinylmethyl)-3-methyl-pyrazol-4-yl, 1-(2-pyridinylmethyl)-3-methyl-pyrazol-4-yl, 1-[2-pyridyl]-3-methyl-pyrazol-4-yl, 1-methyl-5-pyrazolyl, 1-ethyl-5-trifluoromethylpyrazol-4-yl, 1,3-dimethyl-5-pyrazolyl, 1-methyl-3-cyclopropyl-pyrazol-5-yl, 1-methyl-4-pyrazolyl, 1-ethyl-3-methylpyrazol-4-yl, 1,5-dimethyl-4-pyrazolyl, 1,3,5-trimethyl-4-pyrazolyl, 1-methyl-3-pyrazolyl, 4-methyl-3-pyrazolyl, 1-methyl-[1,2,4]triazol-3-yl, 4-bromo-2-methyl-[1,2,4]triazol-5-yl, 4-bromo-2-ethyl-[1,2,4]triazol-5-yl, 1-methyl-[1,2,4]triazol-5-yl, 4-isothiazolyl, 4-methyl-2-oxazolyl, isoxazol-4-yl, 2,4-dimethylthiazol-5-yl, 3,5-dimethylisoxazol-4-yl, 2-methyl-5-thiazolyl and 4-methyl-5-thiazolyl; or an isomer or a pharmaceutically acceptable salt thereof.

In one embodiment $R^{31}$ is selected from 5-pyrimidinyl, 2-methyl-5-pyrimidinyl, 4-methyl-5-pyrimidinyl, 4,6-dimethoxy-5-pyrimidinyl, 4,6-dimethyl-5-pyrimidinyl, 4-triflouromethyl-5-pyrimidinyl, 4-pyrimidinyl, 2-methyl-4-pyrimidinyl, 4-methyl-6-pyrimidinyl, 2,4-dimethyl-6-pyrimidinyl, 3-pyridinyl, 2-pyridinyl, 4-methyl-2-pyridinyl, 2-triflouromethyl-3-pyridinyl, 4-triflouromethyl-3-pyridinyl, 2-methyl-3-pyridinyl, 2,5-dimethyl-3-pyridinyl, 2,6-dimethyl-3-pyridinyl, 2,4-dimethyl-3-pyridinyl, 2-ethyl-3-pyridinyl, 5-methyl-3-pyridinyl, 2-ethoxy-3-pyridinyl, 2-ethoxy-5-methyl-3-pyridinyl, 2-methoxy-3-pyridinyl, 2-methoxy-6-methyl-3-pyridinyl, 2-ethoxy-6-methyl-3-pyridinyl, 2-isopropoxy-3-pyridinyl, 2-(3-pentoxy)-3-pyridinyl, 2-methoxyethoxy-3-pyridinyl, 2-cyclopropoxy-3-pyridinyl, 2-cyclopentyloxy-3-pyridinyl, 2-cyclohexloxy-3-pyridinyl, 2-fluoro-3-pyridinyl, 2-chloro-3-pyridinyl, 2-phenyl-3-pyridinyl, 2-flouro-3-methyl-5-pyridinyl, 2-flouro-3-chloro-5-pyridinyl, 3-fluoro-5-pyridinyl, 3-chloro-5-pyridinyl, 2-chloro-4-methyl-5-pyridinyl, 2-methoxy-5-pyridinyl, 3-methoxy-5-pyridinyl, 2-ethoxy-5-pyridinyl, 3-ethoxy-5-pyridinyl, 3-triflouromethyl-5-pyridinyl, 3-ethyl-5-pyridinyl, 2,3-dimethyl-5-pyridinyl, 2-(2-hydroxymethylpyrrolidin-1-yl)-5-pyridinyl, 2-(morpholin-1-yl)-3-chloro-5-pyridinyl, 2-(dimethylaminoethoxy)-5-pyridinyl, 2-(2-dimethylaminomethylpyrrolidin-1-yl)-5-pyridinyl, 2-phenyl-5-pyridinyl, 2-methyl-6-pyridinyl, 2,4-dimethyl-6-pyridinyl and 2-ethyl-6-pyridinyl; or an isomer or a pharmaceutically acceptable salt thereof.

In one embodiment $R^{38}$ is selected from substituted or unsubstituted tetrahydroquinolinyl, substituted or unsubstituted 1-pyrrolin-3-yl, substituted or unsubstituted 1-imidazolidinyl, and substituted or unsubstituted dihydropyridin-3-yl; or an isomer or a pharmaceutically acceptable salt thereof.

In one embodiment $R^{38}$ is selected from 4-isoquinolinyl, 1-methoxy-4-isoquinolinyl, 1-chloro-4-isoquinolinyl, 6-methyl-4-isoquinolinyl, 1-oxo-2-methyl-4-isoquinolinyl, 3-quinolinyl, 4-quinolinyl, 5-pyrrolopyridinyl, [1,3,3a]-triazainden-5-yl, 1-ethyl-3-pyrrolopyridinyl, and 1-methyl-5-pyrrolopyridinyl; or an isomer or a pharmaceutically acceptable salt thereof.

In one embodiment $R^{37}$ is selected from ethenyl, fluoroethenyl, propynyl, dialkylaminopropenyl, alkylaminopropenyl, aminopropenyl and nitrogen-containing heterocyclylpropenyl; or an isomer or a pharmaceutically acceptable salt thereof.

One embodiment relates to compounds of Formula XI-B

[XI-B]

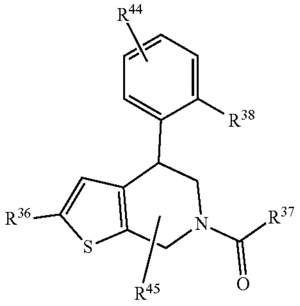

wherein $R^{36}$ is selected from H, halo, $C_1$-$C_4$ alkyl, $C_1$-$C_4$ haloalkyl, $C_2$-$C_4$ alkenyl, substituted or unsubstituted heteroaryl, and $C_3$-$C_6$ cycloalkyl;

$R^{37}$ is substituted or unsubstituted $C_2$-$C_4$ alkenyl or $C_2$-$C_4$ alkynyl;

$R^{38}$ is selected from substituted or unsubstituted nitrogen containing 5-membered heteroaryl, substituted or unsubstituted nitrogen containing 5- or 6-membered partially unsaturated heterocyclyl and substituted or unsubstituted nitrogen containing 6-10 membered heteroaryl;

$R^{44}$ is one or more substituents selected from H, halo, alkoxy and hydroxy; and $R^{45}$ is one or more substituents selected from H, D and alkyl;

provided $R^{38}$ is not 4-pyridyl; or an isomer or stereoisomer of any of the foregoing, or a mixture thereof or a pharmaceutically acceptable salt thereof.

In one embodiment $R^{36}$ is selected from H, halo, $C_1$-$C_4$ alkyl, $C_2$-$C_4$ alkenyl and $C_3$-$C_6$ cycloalkyl; $R^{37}$ is substituted or unsubstituted $C_2$-$C_4$ alkenyl or substituted or unsubstituted $C_2$-$C_4$ alkynyl; $R^{38}$ is selected from substituted or unsubstituted nitrogen containing 5-membered heteroaryl, substituted or unsubstituted nitrogen containing 5- or 6-membered partially unsaturated heterocyclyl and substituted or unsubstituted nitrogen containing 6-10 membered heteroaryl; $R^{44}$ is one or more substituents selected from H, alkoxy and hydroxy; and $R^{45}$ is H; or an isomer or stereoisomer of any of the foregoing, or a mixture thereof or a pharmaceutically acceptable salt thereof.

In one embodiment $R^{38}$ is selected from substituted or unsubstituted nitrogen containing 5-membered heteroaryl selected from pyrazolyl, isoxazolyl, isothiazolyl, pyrrolyl, thiazolyl, triazolyl and imidazolyl; substituted or unsubstituted nitrogen containing 6-membered heteroaryl selected from pyridinyl, pyrimidinyl and pyrazinyl; substituted or unsubstituted nitrogen containing 5-membered partially unsaturated heterocyclyl selected from pyrrolinyl, and imidazolidinyl; and substituted or unsubstituted dihydropyridinyl; or an isomer or a pharmaceutically acceptable salt thereof.

In one embodiment $R^{36}$ is selected from H, chloro, methyl, ethyl, isopropyl, ethenyl, allylyl, trifluoromethyl, furyl, pyridyl and cyclopropyl; and $R^{31}$ is selected from substituted 5-pyrazolyl, substituted 4-pyrazolyl, substituted 1-pyrazolyl, substituted or unsubstituted 4-isoxazolyl, substituted or unsubstituted 4-isothiazolyl, substituted or unsubstituted 3-pyrrolyl, substituted or unsubstituted 5-thiazolyl, substituted or unsubstituted 5-imidazolyl, substituted or unsubstituted 1-imidazolyl, substituted or unsubstituted [1,2,4]triazol-5-yl, substituted or unsubstituted 3-pyridyl, and substituted or unsubstituted 5-pyrimidinyl; or an isomer or a pharmaceutically acceptable salt thereof. 10271 In one embodiment $R^{36}$ is selected from H, chloro, methyl, ethyl, isopropyl, ethenyl, allylyl, trifluoromethyl, furyl, pyridyl and cyclopropyl; or an isomer or a pharmaceutically acceptable salt thereof.

In one embodiment $R^{38}$ is selected from substituted 5-pyrazolyl, substituted 4-pyrazolyl, substituted 1-pyrazolyl, substituted or unsubstituted 4-isoxazolyl, substituted or unsubstituted 4-isothiazolyl, substituted or unsubstituted 3-pyrrolyl, substituted or unsubstituted 5-thiazolyl, substituted or unsubstituted 5-imidazolyl, substituted or unsubstituted 1-imidazolyl, substituted or unsubstituted [1,2,4]triazol-5-yl, substituted or unsubstituted 3-pyridyl, and substituted or unsubstituted 5-pyrimidinyl; or an isomer or a pharmaceutically acceptable salt thereof.

In one embodiment $R^{36}$ is chloro, methyl, ethyl, isopropyl, allylyl or cyclopropyl; and R" is selected from substituted 5-pyrazolyl, substituted 4-pyrazolyl, substituted 1-pyrazolyl, substituted or unsubstituted 4-isoxazolyl, substituted or unsubstituted 4-isothiazolyl, substituted or unsubstituted 3-pyrrolyl, substituted or unsubstituted 5-thiazolyl, substituted or unsubstituted 5-imidazolyl, substituted or unsubstituted 1-imidazolyl, substituted or unsubstituted [1,2,4]triazol-5-yl, substituted or unsubstituted 3-pyridyl, and substituted or unsubstituted 5-pyrimidinyl; or an isomer or a pharmaceutically acceptable salt thereof.

In one embodiment $R^{38}$ is selected from 3-trifluoromethyl-pyrazol-4-yl, 1-isopropyl-3-trifluoromethyl-pyrazol-4-yl, 1-ethyl-pyrazol-4-yl, 1-ethyl-3-trifluoromethyl-pyrazol-4-yl, 1,3-diethyl-pyrazol-4-yl, 1-methyl-3-difluoromethyl-pyrazol-4-yl, 1-($d_3$-methyl)-3-difluoromethyl-pyrazol-4-yl, 1-butyl-3-trifluoromethyl-pyrazol-4-yl, 1-methoxymethyl-3-trifluoromethyl-pyrazol-4-yl, 1-propyl-3-trifluoromethyl-pyrazol-4-yl, 1,3-dimethyl-pyrazol-4-yl, 1,3,5-trimethyl-pyrazol-4-yl, 1-methyl-3-cyclopropyl-pyrazol-4-yl, 1-ethyl-3-cyclopropyl-pyrazol-4-yl, 1-methyl-3-trifluoromethyl-pyrazol-4-yl, 1-ethyl-3-amino-pyrazol-4-yl, 1-ethyl-3-methoxy-pyrazol-4-yl, l-hydroxyethyl-3-trifluoromethyl-pyrazol-4-yl, 1-[2-hydroxypropyl]-3-trifluoromethyl-pyrazol-4-yl, 1-[2-hydroxy-isobutyl]-3-trifluoromethyl-pyrazol-4-yl, 1-methoxyethyl-3-trifluoromethyl-pyrazol-4-yl, 1-[N,N-dimethylaminoethyl]-3-trifluoromethyl-pyrazol-4-yl, 1-[N-methylaminocarbonylmethyl]-3-trifluoromethyl-pyrazol-4-yl, 1-[N-methylaminocarbonylethyl]-3-trifluoromethyl-pyrazol-4-yl, 1-[N,N-dimethylaminicarbonylmethyl]-3-trifluoromethyl-pyrazol-4=yl, 1-aminocarbonylmethyl-3-trifluoromethyl-pyrazol-4-yl, 1-methylcarbonylaminoethyl-3-trifluoromethyl-pyrazol-4-yl, 1-methylcarbonylaminobutyl-3-trifluoromethyl-pyrazol-4-yl, 1-aminocarbonylethyl-3-trifluoromethyl-pyrazol-4-yl, 1-aminocarbonylpropyl-3-trifluoromethyl-pyrazol-4-yl, 1-aminocarbonylisopropyl-3-trifluoromethyl-pyrazol-4-yl, 1-cyanomethyl-3-trifluoromethyl-pyrazol-4-yl, 1-cyanoethyl-3-trifluoromethyl-pyrazol-4-yl, 1-cyanopropyl-3-trifluoromethyl-pyrazol-4-yl, 1-[N,N-dimethylaminocarbonylethyl]-3-trifluoromethyl-pyrazol-4-yl, 1-carboxyethyl-3-trifluoromethyl-pyrazol-4-yl, 1-carboxymethyl-3-trifluoromethyl-pyrazol-4-yl, 1-methoxycarbonylmethyl-3-trifluoromethyl-pyrazol-4-yl, 1-ethyl-3-carboxy-pyrazol-4-yl, 1-ethyl-5-carboxy-pyrazol-4-yl, 1-ethyl-3-methylaminocarbonyl-pyrazol-4-yl, 1-ethyl-3-[N,N-dimethylaminocarbonyl]-pyrazol-4-yl, 1-ethyl-5-methylaminocarbonyl-pyrazol-4-yl, 1-ethyl-5-[N,N-dimethylaminocarbonyl]-pyrazol-4-yl, 1-benzyl-3-methyl-pyrazol-4-yl, 1-(cyclopropylmethyl)-3-trifluoromethyl-pyrazol-4-yl, 1-cyclopropyl-3-trifluoromethyl-pyrazol-4-yl, 1-[1-methylazetidin-3-yl]-3-trifluoromethyl-pyrazol-4-yl, 1-[1-methylpyrrolidin-3-yl]-3-trifluoromethyl-pyrazol-4-yl, 1-[1-methylpiperidin-3-yl]-3-trifluoromethyl-pyrazol-4-yl, 1-[1-methylpiperidin-4-yl]-3-trifluoromethyl-pyrazol-4-yl, 1-(4-pyridinyl)-3-trifluoromethyl-pyrazol-4-yl, 1-(3-chloropyridin-4-yl)-3-trifluoromethyl-pyrazol-4-yl, 1-(3,5-difluoropyridin-4-yl)-3-trifluoromethyl-pyrazol-4-yl, 1-(3-pyridinylmethyl)-3-trifluoromethyl-pyrazol-4-yl, 1-(2-pyridinylmethyl)-3-trifluoromethyl-pyrazol-4-yl, 1-(5-oxadiazolylmethyl)-3-trifluoromethyl-pyrazol-4-yl, 1-(4-oxazolylmethyl)-3-trifluoromethyl-pyrazol-4-yl, 1-(3-pyridinylmethyl)-3-methyl-pyrazol-4-yl, 1-(2-pyridinylmethyl)-3-methyl-pyrazol-4-yl, 1-[2-pyridyl]-3-methyl-pyrazol-4-yl, 1-methyl-5-pyrazolyl, 1-ethyl-5-trifluoromethylpyrazol-4-yl, 1,3-dimethyl-5-pyrazolyl, 1-methyl-3-cyclopropyl-pyrazol-5-yl, 1-methyl-4-pyrazolyl, 1-ethyl-3-methylpyrazol-4-yl, 1,5-dimethyl-4-pyrazolyl, 1,3,5-trimethyl-4-pyrazolyl, 1-ethyl-3-trifluoromethyl-5 methyl-pyrazol-4-yl, 1-methyl-3-pyrazolyl, 4-methyl-3-pyrazolyl, 1-methyl-[1,2,4]triazol-3-yl, 4-bromo-2-methyl-[1,2,4]triazol-5-yl, 4-bromo-2-ethyl-[1,2,4]triazol-5-yl, 1-methyl-[1,2,4]triazol-5-yl, 4-isothiazolyl, 4-methyl-2-oxazolyl, isoxazol-4-yl, 2,4-dimethylthiazol-5-yl, 3,5-dimethylisoxazol-4-yl, 2-methyl-5-thiazolyl and 4-methyl-5-thiazolyl; or an isomer or a pharmaceutically acceptable salt thereof.

In one embodiment $R^{38}$ is selected from 3-trifluoromethyl-pyrazol-4-yl, 1-isopropyl-3-trifluoromethyl-pyrazol-4-yl, 1-ethyl-3-trifluoromethyl-pyrazol-4-yl, 1-methyl-3-difluoromethyl-pyrazol-4-yl, 1-butyl-3-trifluoromethyl-pyrazol-4-yl, 1-methoxymethyl-3-trifluoromethyl-pyrazol-4-yl, 1-propyl-3-trifluoromethyl-pyrazol-4-yl, 1,3-dimethyl-pyrazol-4-yl, 1,3,5-trimethyl-pyrazol-4-yl, 1-methyl-3-cyclopropyl-pyrazol-4-yl, 1-methyl-3-trifluoromethyl-pyrazol-4-yl, 1-ethyl-3-amino-pyrazol-4-yl, 1-ethyl-3-methoxy-pyrazol-4-yl, 1-hydroxyethyl-3-trifluoromethyl-pyrazol-4-yl, 1-[2-hydroxypropyl]-3-trifluoromethyl-pyrazol-4-yl, 1-[2-hydroxyisobutyl]-3-trifluoromethyl-pyrazol-4-yl, 1-methoxyethyl-3-trifluoromethyl-pyrazol-4-yl, 1-[N,N-dimethylaminoethyl]-3-trifluoromethyl-pyrazol-4-yl, 1-[N-methylaminocarbonylmethyl]-3-trifluoromethyl-pyrazol-4-yl, 1-[N-methylaminocarbonylethyl]-3-trifluoromethyl-pyrazol-4-yl, 1-[N,N-dimethylaminocarbonylmethyl]-3-trifluoromethyl-pyrazol-4-yl, 1-aminocarbonylmethyl-3-trifluoromethyl-pyrazol-4-yl, 1-methylcarbonylaminoethyl-3-trifluoromethyl-pyrazol-4-yl, 1-methylcarbonylaminobutyl-3-trifluoromethyl-pyrazol-4-yl, 1-aminocarbonylethyl-3-trifluoromethyl-pyrazol-4-yl, 1-aminocarbonylpropyl-3-trifluoromethyl-pyrazol-4-yl, 1-aminocarbonylisopropyl-3-trifluoromethyl-pyrazol-4-yl, 1-cyanopropyl-3-trifluoromethyl-pyrazol-4-yl, 1-[N,N-dimethylaminocarbonylethyl]-3-trifluoromethyl-pyrazol-4-yl, 1-carboxyethyl-3-trifluoromethyl-pyrazol-4-yl, 1-carboxymethyl-3-trifluoromethyl-pyrazol-4-yl, 1-methoxycarbonylmethyl-3-trifluoromethyl-pyrazol-4-yl, 1-ethyl-3-carboxy-pyrazol-4-yl, 1-ethyl-5-carboxy-pyrazol-4-yl, 1-ethyl-3-methylaminocarbonyl-pyrazol-4-yl, 1-ethyl-3-[N,N-dimethylaminocarbonyl]-pyrazol-4-yl, 1-ethyl-5-methylaminocarbonyl-pyrazol-4-yl, 1-ethyl-5-[N,N-dimethylaminocarbonyl]-pyrazol-4-yl, 1-benzyl-3-methyl-pyrazol-4-yl, 1-(cyclopropylmethyl)-3-trifluoromethyl-pyrazol-4-yl, 1-cyclopropyl-3-trifluoromethyl-pyrazol-4-yl, 1-[1-methylazetidin-3-yl]-3-trifluoromethyl-pyrazol-4-yl, 1-[1-methylpyrrolidin-3-yl]-3-trifluoromethyl-pyrazol-4-yl, 1-[1-methylpiperidin-3-yl]-3-trifluoromethyl-pyrazol-4-yl, 1-[1-methylpiperidin-4-yl]-3-trifluoromethyl-pyrazol-4-yl, 1-(3-pyridinylmethyl)-3-methyl-pyrazol-4-yl, 1-(2-pyridinylmethyl)-3-methyl-pyrazol-4-yl, 1-[2-pyridyl]-3-methyl-pyrazol-4-yl, 1-methyl-5-pyrazolyl, 1-ethyl-5-trifluoromethylpyrazol-4-yl, 1,3-dimethyl-5-pyrazolyl, 1-methyl-3-cyclopropyl-pyrazol-5-yl, 1-methyl-4-pyrazolyl, 1-ethyl-3-methylpyrazol-4-yl, 1,5-dimethyl-4-pyrazolyl, 1,3,5-trimethyl-4-pyrazolyl, 1-methyl-3-pyrazolyl, 4-methyl-3-pyrazolyl, 1-methyl-[1,2,4]triazol-3-yl, 4-bromo-2-methyl-[1,2,4]triazol-5-yl, 4-bromo-2-ethyl-[1,2,4]triazol-5-yl, 1-methyl-[1,2,4]triazol-5-yl, 4-isothiazolyl, 4-methyl-2-oxazolyl, isoxazol-4-yl, 2,4-dimethylthiazol-5-yl, 3,5-dimethylisoxazol-4-yl, 2-methyl-5-thiazolyl and 4-methyl-5-thiazolyl; or an isomer or a pharmaceutically acceptable salt thereof.

In one embodiment $R^{38}$ is selected from 5-pyrimidinyl, 2-methyl-5-pyrimidinyl, 4-methyl-5-pyrimidinyl, 4,6-dimethoxy-5-pyrimidinyl, 4,6-dimethyl-5-pyrimidinyl, 4-triflouromethyl-5-pyrimidinyl, 4-pyrimidinyl, 2-methyl-4-pyrimidinyl, 4-methyl-6-pyrimidinyl, 2,4-dimethyl-6-pyrimidinyl, 3-pyridinyl, 2-pyridinyl, 4-methyl-2-pyridinyl, 2-triflouromethyl-3-pyridinyl, 4-triflouromethyl-3-pyridinyl, 2-methyl-3-pyridinyl, 2,5-dimethyl-3-pyridinyl, 2,6-dimethyl-3-pyridinyl, 2,4-dimethyl-3-pyridinyl, 2-ethyl-3-pyridinyl, 5-methyl-3-pyridinyl, 2-ethoxy-3-pyridinyl, 2-ethoxy-5-methyl-3-pyridinyl, 2-methoxy-3-pyridinyl, 2-methoxy-6-methyl-3-pyridinyl, 2-ethoxy-6-methyl-3-pyridinyl, 2-isopropoxy-3-pyridinyl, 2-(3-pentoxy)-3-pyridinyl, 2-methoxyethoxy-3-pyridinyl, 2-cyclopropoxy-3-pyridinyl, 2-cyclopentyloxy-3-pyridinyl, 2-cyclohexloxy-3-pyridinyl, 2-fluoro-3-pyridinyl, 2-chloro-3-pyridinyl, 2-phenyl-3-pyridinyl, 2-flouro-3-methyl-5-pyridinyl, 2-flouro-3-chloro-5-pyridinyl, 3-fluoro-5-pyridinyl, 3-chloro-5-pyridinyl, 2-chloro-4-methyl-5-pyridinyl, 2-methoxy-5-pyridinyl, 3-methoxy-5-pyridinyl, 2-ethoxy-5-pyridinyl, 3-ethoxy-5-pyridinyl, 3-triflouromethyl-5-pyridinyl, 3-ethyl-5-pyridinyl, 2,3-dimethyl-5-pyridinyl, 2-(2-hydroxymethylpyrrolidin-1-yl)-5-pyridinyl, 2-(morpholin-1-yl)-3-chloro-5-pyridinyl, 2-(dimethylaminoethoxy)-5-pyridinyl, 2-(2-dimethylaminomethylpyrrolidin-1-yl)-5-pyridinyl, 2-phenyl-5-pyridinyl, 2-methyl-6-pyridinyl, 2,4-dimethyl-6-pyridinyl and 2-ethyl-6-pyridinyl; or an isomer or a pharmaceutically acceptable salt thereof.

In one embodiment $R^{38}$ is selected from substituted or unsubstituted tetrahydroquinolinyl; substituted or unsubstituted 1-pyrrolin-3-yl, substituted or unsubstituted 1-imidazolidinyl, and substituted or unsubstituted dihydropyridin-3-yl; or an isomer or a pharmaceutically acceptable salt thereof.

In one embodiment $R^{38}$ is selected from 1-methoxy-4-isoquinolinyl, 1-chloro-4-isoquinolinyl, 6-methyl-4-isoquinolinyl, 1-oxo-2-methyl-4-isoquinolinyl, 5-pyrrolopyridinyl, [1,3,3a]-triazainden-5-yl, 1-ethyl-3-pyrrolopyridinyl, 1-methyl-5-pyrrolopyridinyl, 3-quinolinyl, 4-isoquinolinyl and 4-quinolinyl; or an isomer or a pharmaceutically acceptable salt thereof.

In one embodiment $R^{37}$ is selected from ethenyl, fluoroethenyl, propenyl, fluoropropenyl, propynyl, dialkylaminopropenyl, alkylaminopropenyl, aminopropenyl and nitrogen-containing heterocyclyl-propenyl; or an isomer or a pharmaceutically acceptable salt thereof.

One embodiment relates to compounds of Formula XII (XII)

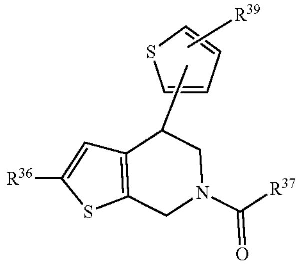

wherein $R^{36}$ is halo or $C_{1-6}$ alkyl;

$R^{37}$ is $C_2$-$C_4$ alkenyl; and $R^{39}$ is H, halo, $C_{1-6}$ alkyl, cyano, substituted or unsubstituted cycloalkyl, substituted or unsubstituted nitrogen containing 5- or 6-membered partially unsaturated heterocyclyl or substituted or unsubstituted 5-10-membered heteroaryl; or an isomer or a pharmaceutically acceptable salt thereof.

In one embodiment, $R^{36}$ is chloro; $R^{37}$ is ethenyl; and $R^{39}$ is selected from H, bromo, chloro, $C_{1-4}$ alkyl, substituted or unsubstituted pyrazolyl, substituted or unsubstituted isoxazolyl, substituted or unsubstituted pyridyl, and substituted or unsubstituted isoquinolinyl;

In one embodiment, $R^{39}$ is selected from H, bromo, chloro, methyl, cyano, isoquinoline-4-yl, 1,3-dimethylpyrazol-4-yl, 3,5-dimethylisoxazol-4-yl and 2-chloro-3-pyridyl; or an isomer or a pharmaceutically acceptable salt thereof.

One embodiment relates to compounds of Formula XIII

[XIII]

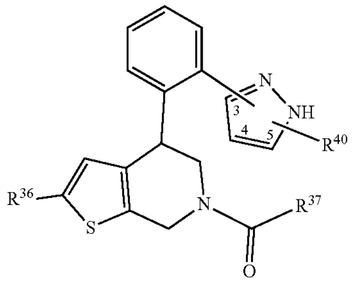

wherein $R^{36}$ is halo;

$R^{37}$ is $C_2$-$C_4$ alkenyl; and $R^{40}$ is one or more substituents selected from $C_{1-6}$ alkyl, $C_{1-6}$ haloalkyl, $C_{1-6}$ alkoxyalkyl, substituted or unsubstituted $C_{3-6}$ cycloalkyl, substituted or unsubstituted aryl-$C_{1-6}$ alkyl, substituted or unsubstituted 5 or 6 membered heteroaryl-$C_{1-6}$ alkyl, and substituted or unsubstituted 5 or 6 membered heteroaryl; or an isomer or stereoisomer of any of the foregoing, or a mixture thereof or a pharmaceutically acceptable salt thereof.

In one embodiment, $R^{36}$ is chloro or methyl; or an isomer or a pharmaceutically acceptable salt thereof.

In one embodiment, $R^{37}$ is ethenyl; or an isomer or a pharmaceutically acceptable salt thereof.

In one embodiment, $R^{40}$ is one or more substituents selected from isopropyl, trifluoromethyl, ethyl, butyl, methoxymethyl, propyl, methyl, cyclopropyl, benzyl, 3-pyridinylmethyl, 2-pyridinylmethyl, and 2-pyridyl; or an isomer or a pharmaceutically acceptable salt thereof.

In one embodiment, the pyrazole is attached to the phenyl ring at position 3, 4, or 5 of the pyrazole ring; or an isomer or a pharmaceutically acceptable salt thereof.

One embodiment relates to compounds of Formula XIIIA

[XIIIA]

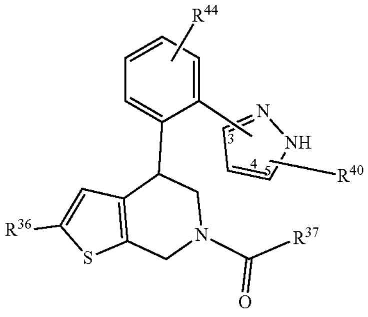

wherein $R^{36}$ is H, halo, $C_1$-$C_4$ alkyl, $C_2$-$C_4$ alkenyl or $C_3$-$C_6$ cycloalkyl; $R^{37}$ is substituted or unsubstituted $C_2$-$C_4$ alkenyl, or $C_2$-$C_4$ alkynyl; $R^{40}$ is one or more substituents selected from H, carboxy, amino, $C_{1-6}$ alkyl, $C_{1-6}$ haloalkyl, $C_{1-6}$ hydroxyalkyl, $C_{1-6}$ alkoxy, $C_{1-6}$ alkoxyalkyl, $C_{1-6}$ alkylamino, $C_{1-6}$ alkylamino-$C_{16}$ alkyl, $C_{1-6}$ alkylaminocarbonyl-$C_{1-6}$ alkyl, aminocarbonyl-$C_{1-6}$ alkyl, $C_{1-6}$ alkoxycarbonyl-$C_{1-6}$ alkyl, carboxy-$C_{1-6}$ alkyl, $C_{1-6}$ alkylaminocarbonyl, $C_{1-6}$ alkylcarbonylamino-$C_{1-6}$ alkyl, $C_{1-6}$ cyanoalkyl, $C_{3-6}$ cycloalkyl, $C_{3-6}$ cycloalkyl-$C_{1-6}$ alkyl, aryl-$C_{1-6}$ alkyl, 5 or 6 membered heteroaryl-$C_{1-6}$ alkyl, 5 or 6 membered heterocyclyl and 5 or 6 membered heteroaryl; and $R^{44}$ is one or more substituents selected from H, halo, alkoxy and hydroxy; or an isomer or stereoisomer of any of the foregoing, or a mixture thereof or a pharmaceutically acceptable salt thereof.

In one embodiment, $R^{40}$ is one or more substituents selected from H, isopropyl, trifluoromethyl, difluoromethyl, ethyl, butyl, methoxymethyl, propyl, methyl, 1-hydroxyethyl, 2-hydroxymethylethyl, 2-hydroxy-1,1-dimethylethyl, 2-hydroxypropyl, 2-hydroxy-2-methylpropyl, methoxy, methoxymethyl, carboxy, amino, dimethylamino, dimethylaminoethyl, dimethylaminocarbonylmethyl, dimethylaminocarbonylethyl, methylaminocarbonylethyl, methylaminocarbonylmethyl, aminocarbonylmethyl, aminocarbonylethyl, aminocarbonyl-1,1-dimethylmethyl, methylaminocarbonyl, dimethylaminocarbonyl, methylcarbonylaminoethyl, 1-methylcarbonylamino-2,2-dimethylethyl, methylcarbonylaminobutyl, carboxymethyl, carboxyethyl, methoxycarbonylmethyl, 2-cyano-2-methylethyl, cyclopropyl, cyclopropylmethyl, benzyl, 3-pyridinylmethyl, 2-pyridinylmethyl, 1-methylazetidin-3-yl, 1-methylpyrrolidin-3-yl, 1-methylpiperidin-4-yl, 1-methylpiperidin-3-yl and 2-pyridyl; or an isomer or a pharmaceutically acceptable salt thereof.

In one embodiment, the pyrazole is attached to the phenyl ring at position 3, 4, or 5 of the pyrazole ring; or an isomer or a pharmaceutically acceptable salt thereof.

In one embodiment, $R^{37}$ is selected from ethenyl, fluoroethenyl, propynyl, dialkylaminopropenyl, alkylaminopropenyl, aminopropenyl and nitrogen-containing heterocyclylpropenyl; or an isomer or stereoisomer of any of the foregoing, or a mixture thereof or a pharmaceutically acceptable salt thereof.

In one embodiment, $R^{37}$ is dimethylaminopropenyl, methylaminopropenyl, or aminopropenyl; or an isomer or stereoisomer of any of the foregoing, or a mixture thereof or a pharmaceutically acceptable salt thereof.

In one embodiment, $R^{36}$ is selected from H, chloro, methyl, ethyl, isopropyl, allylyl, and cyclopropyl; or an isomer or stereoisomer of any of the foregoing, or a mixture thereof or a pharmaceutically acceptable salt thereof.

In one embodiment, $R^{44}$ is one or more substituents selected from H, hydroxy, fluoro and methoxyl; or an isomer or a pharmaceutically acceptable salt thereof.

One embodiment relates to compounds of Formula XIV

XIV

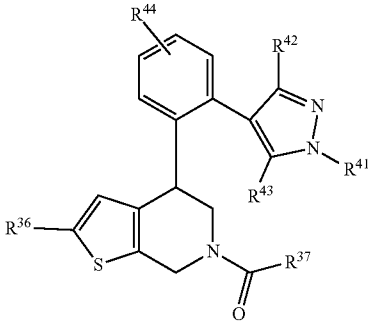

wherein $R^{36}$ is selected from H, halo, $C_1$-$C_4$ alkyl, $C_2$-$C_4$ alkenyl and $C_3$-$C_6$ cycloalkyl;

$R^{37}$ is substituted or unsubstituted $C_2$-$C_4$ alkenyl, or $C_2$-$C_4$ alkynyl; and $R^{41}$ is selected from H, $C_{1-6}$ alkyl, $C_{1-6}$ hydroxyalkyl, $C_{1-6}$ alkoxyalkyl, $C_{1-6}$ alkylamino-$C_{1-6}$ alkyl, $C_{1-6}$ alkylaminocarbonyl-$C_{16}$ alkyl, aminocarbonyl-$C_{1-6}$ alkyl, $C_{1-6}$ alkoxycarbonyl-$C_{1-6}$ alkyl, carboxy-$C_{16}$ alkyl, $C_{1-6}$ alkylcarbonylamino-$C_{1-6}$ alkyl, $C_{1-6}$ cyanoalkyl, $C_{3-6}$ cycloalkyl, $C_{3-6}$ cycloalkyl-$C_{1-6}$ alkyl, aryl-$C_{1-6}$ alkyl, substituted or unsubstituted 5 or 6 membered heteroaryl-$C_{1-6}$ alkyl, substituted or unsubstituted 5 or 6 membered heterocyclyl and substituted or unsubstituted 5 or 6 membered heteroaryl;

$R^{42}$ is selected from H, carboxy, amino, $C_{1-6}$ alkyl, $C_{1-3}$ haloalkyl, $C_{1-6}$ alkoxy, $C_{1-6}$ alkylamino, $C_{1-6}$ alkylaminocarbonyl, and $C_{3-6}$ cycloalkyl;

$R^{43}$ is selected from H, carboxy, $C_{1-4}$ alkyl, $C_{1-3}$ haloalkyl, and $C_{1-6}$ alkylaminocarbonyl; or an isomer or stereoisomer of any of the foregoing, and $R^{44}$ is one or more substituents selected from H, halo, alkoxy and hydroxy; or a mixture thereof or a pharmaceutically acceptable salt thereof.

In one embodiment, $R^{41}$ is selected from H, ethyl, isopropyl, butyl, propyl, methyl, 1-hydroxyethyl, 2-hydroxymethylethyl, 1-hydroxy-2,2-dimethylethyl, 2-hydroxypropyl, 2-hydroxy-2-methylpropyl, methoxymethyl, methoxyethyl, dimethylaminoethyl, carboxymethyl, carboxyethyl, methoxycarbonylmethyl, dimethylaminocarbonylmethyl, dimethylaminocarbonylethyl, methylaminocarbonylethyl, methylaminocarbonylmethyl, aminocarbonylmethyl, aminocarbonylethyl, aminocarbonyl-1,1-dimethylmethyl, methylcarbonylaminoethyl, 1-methylcarbonylamino-2,2-dimethylethyl, 2-cyano-2-methylethyl, cyclopropyl, cyclopropylmethyl, benzyl, 3-pyridinylmethyl, 2-pyridinylmethyl, 1-methylazetidin-3-yl, 1-methylpyrrolidin-3-yl, 1-methylpiperidin-4-yl, 1-methylpiperidin-3-yl and 2-pyridyl; or an isomer or a pharmaceutically acceptable salt thereof.

In one embodiment, $R^{37}$ is selected from ethenyl, fluoroethenyl, propynyl, dialkylaminopropenyl, alkylaminopropenyl, aminopropenyl and nitrogen-containing heterocyclylpropenyl; or an isomer or stereoisomer of any of the foregoing, or a mixture thereof or a pharmaceutically acceptable salt thereof.

In one embodiment, $R^{37}$ is dimethylaminopropenyl, methylaminopropenyl, or aminopropenyl; or an isomer or stereoisomer of any of the foregoing, or a mixture thereof or a pharmaceutically acceptable salt thereof.

In one embodiment, $R^{31}$ is selected from H, chloro, methyl, ethyl, isopropyl, allylyl, and cyclopropyl; or an isomer or stereoisomer of any of the foregoing, or a mixture thereof or a pharmaceutically acceptable salt thereof.

In one embodiment, $R^{42}$ is selected from H, trifluoromethyl, difluoromethyl, methyl, methoxy, amino, dimethylamino, carboxy. methylaminocarbonyl, dimethylaminocarbonyl, and cyclopropyl; or an isomer or a pharmaceutically acceptable salt thereof.

In one embodiment, $R^{43}$ is selected from H, trifluoromethyl, methyl, carboxy, and methylaminocarbonyl; or an isomer or a pharmaceutically acceptable salt thereof.

In one embodiment, $R^{44}$ is one or more substituents selected from H, hydroxy, fluoro and methoxyl; or an isomer or a pharmaceutically acceptable salt thereof.

One embodiment relates to compounds of Formula XV

XV

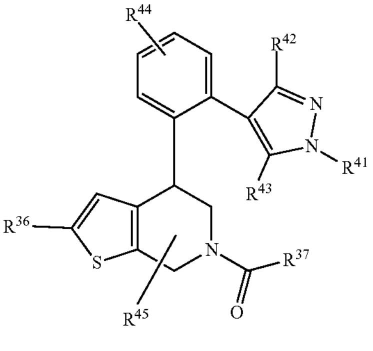

wherein $R^{36}$ is selected from H, halo, $C_1$-$C_4$ alkyl, $C_1$-$C_3$ haloalkyl, $C_2$-$C_4$ alkenyl, substituted or unsubstituted 5-6 membered heteroaryl and $C_3$-$C_6$ cycloalkyl;

$R^{37}$ is substituted or unsubstituted $C_2$-$C_4$ alkenyl, or $C_2$-$C_4$ alkynyl; and $R^{41}$ is selected from H, $C_{1-6}$ alkyl, $C_{1-6}$ hydroxyalkyl, $C_{1-6}$ alkoxy, $C_{1-6}$ alkoxyalkyl, Cia alkylamino-$C_1$-6 alkyl, $C_{1-6}$ alkylaminocarbonyl-$C_{1-6}$ alkyl, aminocarbonyl- $C_{1-6}$ alkyl, Cia alkoxycarbonyl-$C_{1-6}$ alkyl, carboxy-$C_{1-6}$ alkyl, $C_{1-6}$ alkylcarbonylamino-$C_{1-6}$ alkyl, $C_{1-6}$ cyanoalkyl, $C_{3-6}$ cycloalkyl, $C_{3-6}$ cycloalkyl-$C_{1-6}$ alkyl, aryl-$C_{16}$ alkyl, substituted or unsubstituted 5 or 6 membered heteroaryl-$C_{1-6}$ alkyl, substituted or unsubstituted 5 or 6 membered heterocyclyl and substituted or unsubstituted 5 or 6 membered heteroaryl;

$R^{42}$ is selected from H, carboxy, amino, $C_{1-6}$ alkyl, $C_{1-3}$ haloalkyl, $C_{1-6}$ alkoxy, $C_{1-6}$ alkylamino, $C_{1-6}$ alkylaminocarbonyl, and $C_{3-6}$ cycloalkyl;

$R^{43}$ is selected from H, carboxy, cyano, $C_{1-4}$ alkyl, $C_{1-3}$ haloalkyl, and $C_{1-6}$ alkylaminocarbonyl;

$R^{44}$ is H, halo, hydroxy or $C_{1-6}$ alkoxy; and $R^{45}$ is one or more substituents selected from H, D or $C_{1-4}$ alkyl; and or an isomer or stereoisomer of any of the foregoing, or a mixture thereof or a pharmaceutically acceptable salt thereof.

In one embodiment, $R^{41}$ is selected from H, ethyl, isopropyl, butyl, propyl, methyl, $D_3$-methyl, 1-hydroxyethyl, 2-hydroxymethylethyl, 1-hydroxy-2,2-dimethylethyl, 2-hydroxypropyl, 2-hydroxy-2-methylpropyl, methoxymethyl, methoxyethyl, dimethylaminoethyl, carboxymethyl, carboxyethyl, methoxycarbonylmethyl, dimethylaminocarbonylmethyl, dimethylaminocarbonylethyl, methylaminocarbonylethyl, methylaminocarbonylmethyl, aminocarbonylmethyl, aminocarbonylethyl, aminocarbonyl-1,1-dimethylmethyl, methylcarbonylaminoethyl, 1-methylcarbonylamino-2.2-dimethylethyl, 2-cyano-2-methylethyl, cyanomethyl, cyanoethyl, cyclopropyl, cyclopropylmethyl, benzyl, 3-pyridinylmethyl, 2-pyridinylmethyl, 4-oxazolylmethyl, oxadiazol-5-ylmethyl, 1-methylazetidin-3-yl, 1-methylpyrrolidin-3-yl, 1-methylpiperidin-4-yl, 1-methylpiperidin-3-yl, 3,5-difluoro-4-pyridyl, 3-chloro-4-pyridyl, 4-pyridyl and 2-pyridyl; or an isomer or a pharmaceutically acceptable salt thereof.

In one embodiment, $R^{36}$ is H, chloro, methyl, ethyl, isopropyl, propenyl, trifluoromethyl, 2-furyl, 2-pyridinyl, or cyclopropyl; or an isomer or stereoisomer of any of the foregoing, or a mixture thereof or a pharmaceutically acceptable salt thereof.

In one embodiment, $R^{37}$ is selected from ethenyl, fluoroethenyl, fluoropropenyl, propynyl, dialkylaminopropenyl, alkylaminopropenyl, aminopropenyl, substituted or unsubstituted 3-7 membered nitrogen-containing heterocyclylethenyl and substituted or unsubstituted 3-7 membered nitrogen-containing heterocyclyl-propenyl; or an isomer or stereoisomer of any of the foregoing, or a mixture thereof or a pharmaceutically acceptable salt thereof.

In one embodiment, $R^{37}$ is azetidin-1-ylpropenyl, 1-methylpyrrolidin-2-ylethenyl, dimethylaminopropenyl, methylaminopropenyl, piperidin-1-ylpropenyl, 4-hydroxy-piperidin-1-ylpropenyl, pyrrolidin-1-ylpropenyl, 3-hydroxypyrrolidin-1-ylpropenyl, morpholin-1-ylpropenyl, or aminopropenyl; or an isomer or stereoisomer of any of the foregoing, or a mixture thereof or a pharmaceutically acceptable salt thereof.

In one embodiment, $R^{42}$ is selected from H, trifluoromethyl, difluoromethyl, methyl, ethyl, methoxy, amino, dimethylamino, carboxy. methylaminocarbonyl, dimethylaminocarbonyl, and cyclopropyl; or an isomer or a pharmaceutically acceptable salt thereof.

In one embodiment, $R^{43}$ is selected from H, trifluoromethyl, methyl, ethyl, carboxy, cyano and methylaminocarbonyl; or an isomer or a pharmaceutically acceptable salt thereof.

In one embodiment, $R^{44}$ is one or more substituents selected from H, hydroxy, fluoro and methoxyl; or an isomer or a pharmaceutically acceptable salt thereof.

In one embodiment, $R^{45}$ is one or more substituents selected from H, D, and methyl; or an isomer or a pharmaceutically acceptable salt thereof.

In one embodiment, $R^{45}$ is H; or an isomer or a pharmaceutically acceptable salt thereof.

In an embodiment, a family of compounds consists of compounds provided in Table 1:

TABLE 1

| | |
|---|---|
| 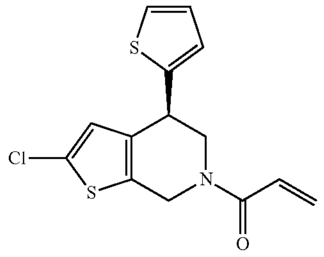 | 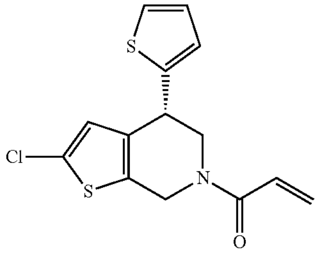 |
| 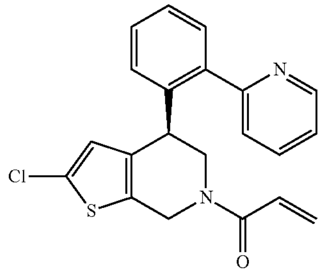 | 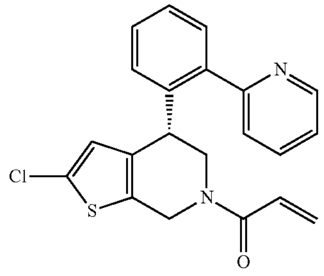 |

TABLE 1-continued
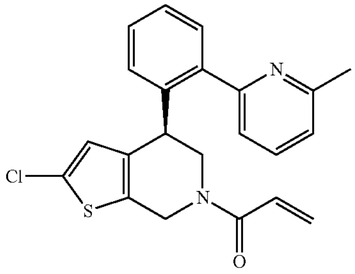
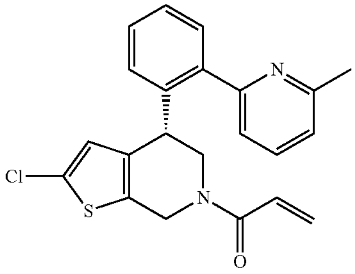
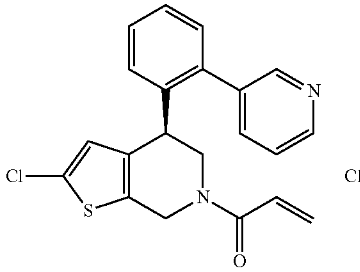
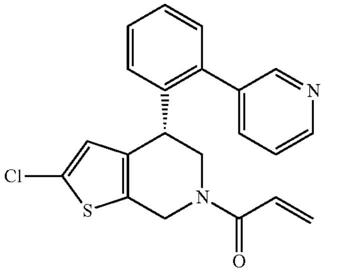
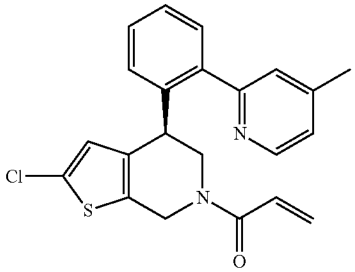
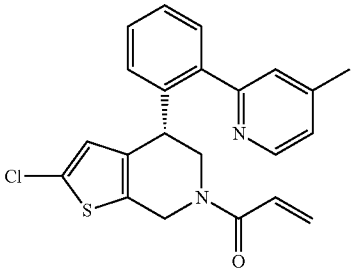
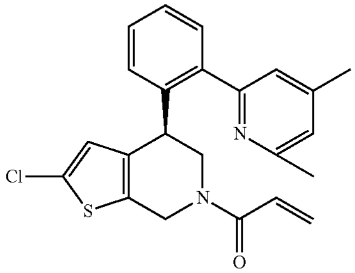
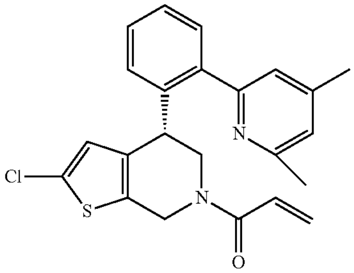
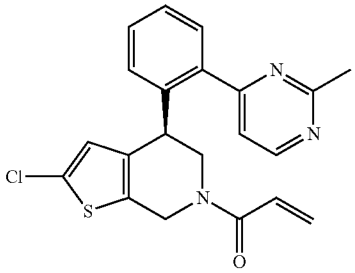
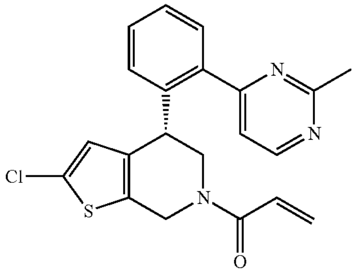

TABLE 1-continued
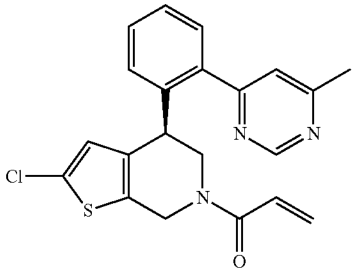
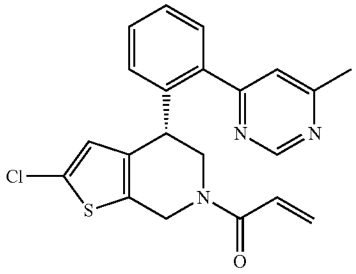
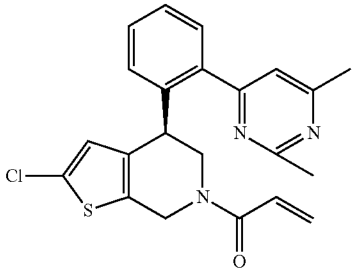
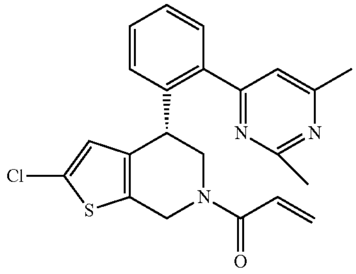
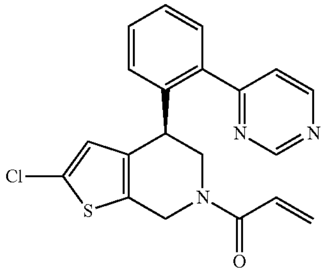
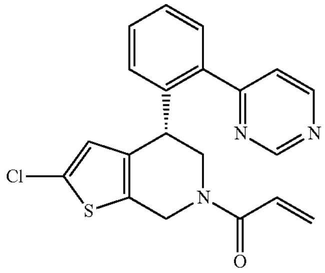
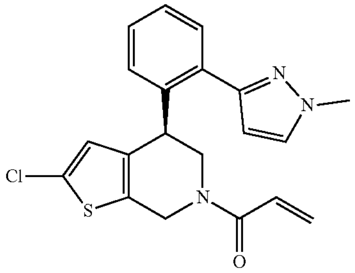
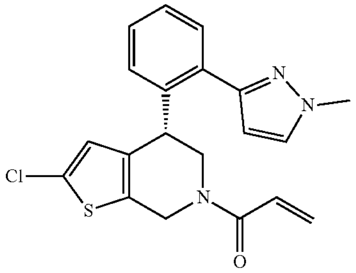
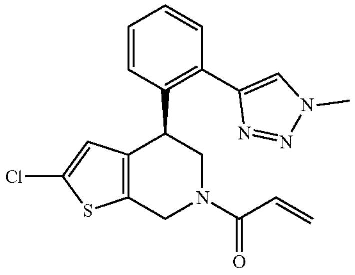
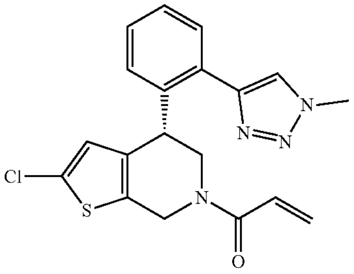

TABLE 1-continued
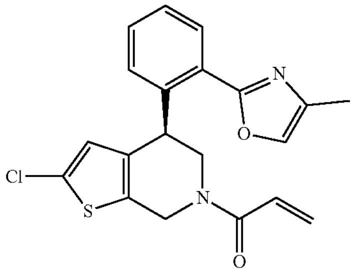
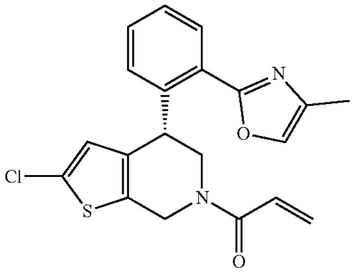
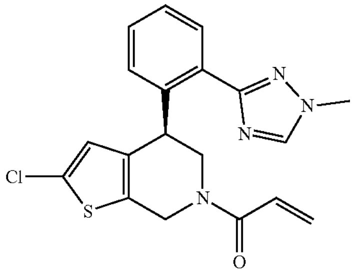
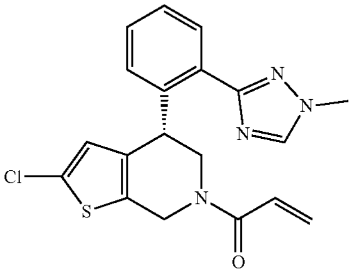
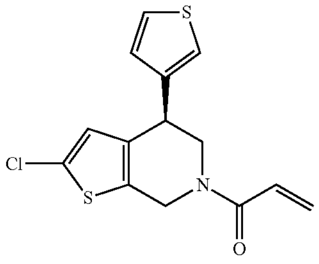
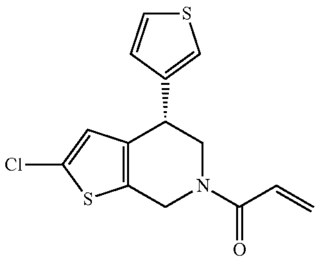
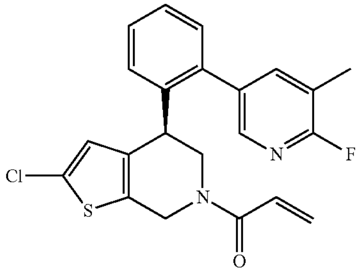
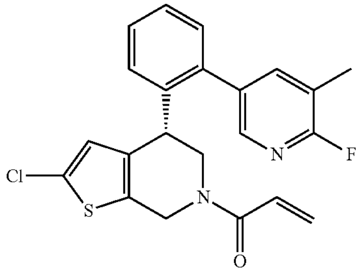
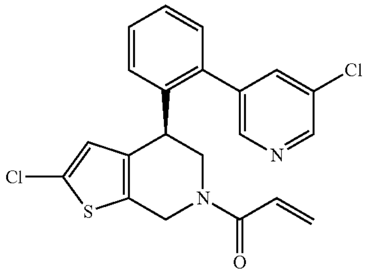
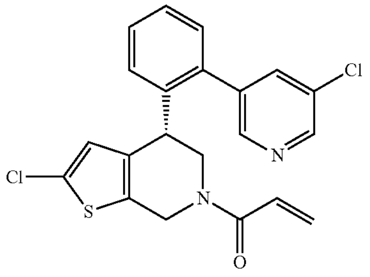

TABLE 1-continued
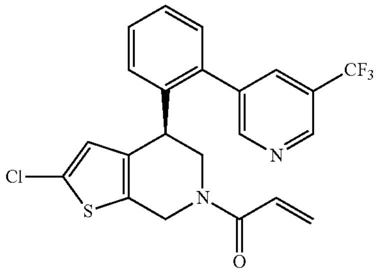
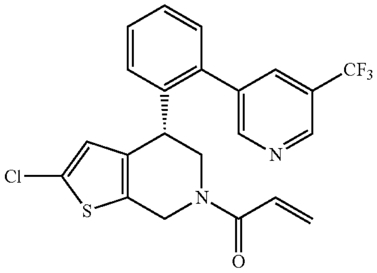
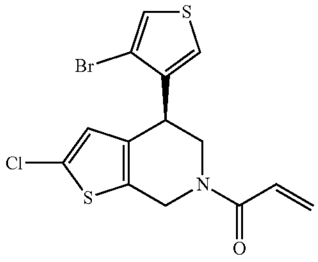
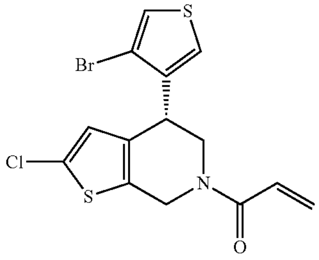
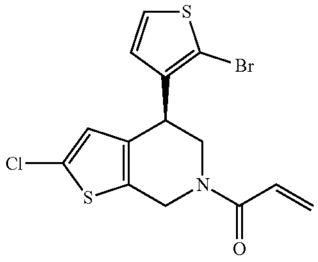
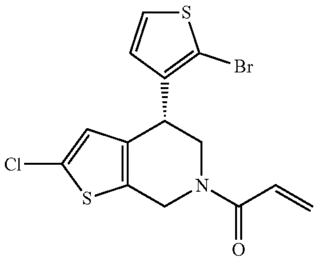
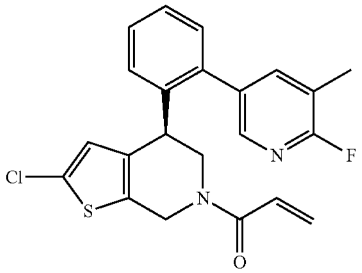
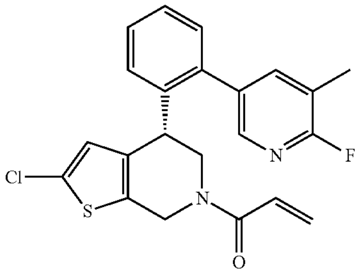
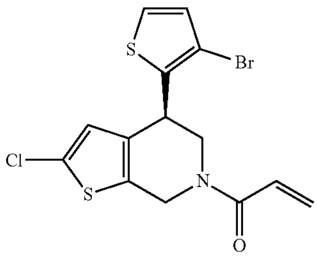
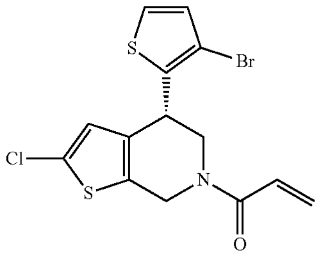
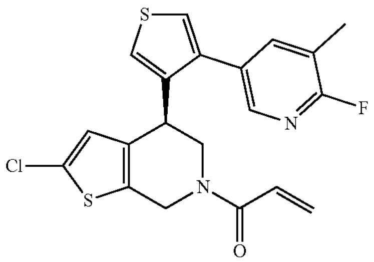
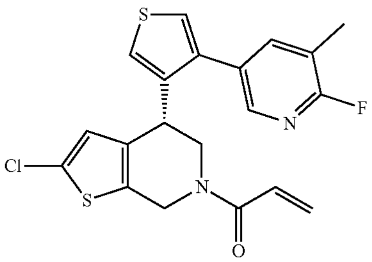

TABLE 1-continued
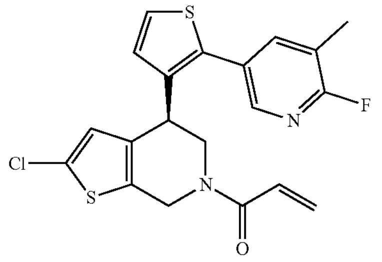 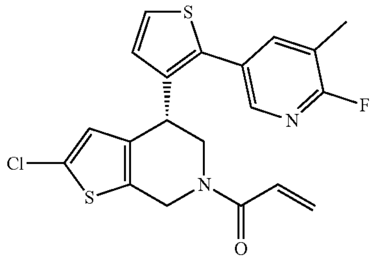
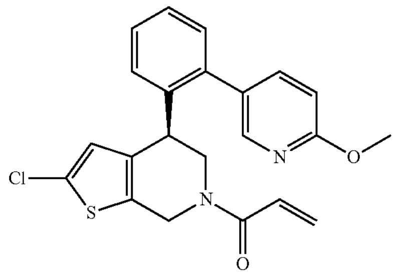 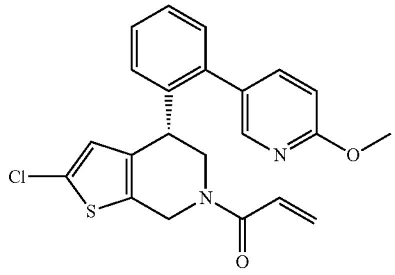
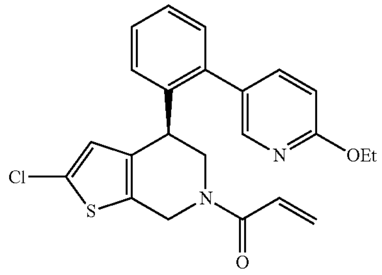 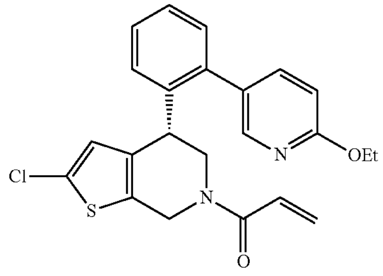
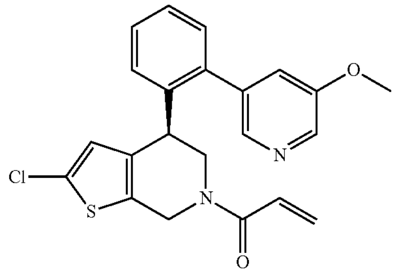 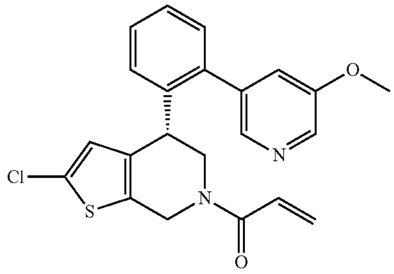
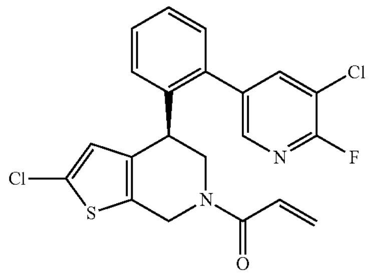 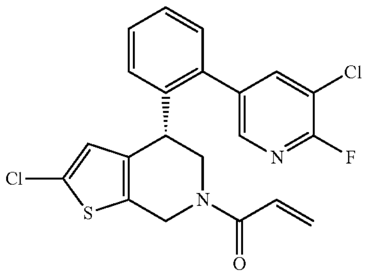

TABLE 1-continued
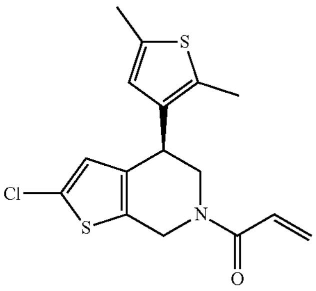 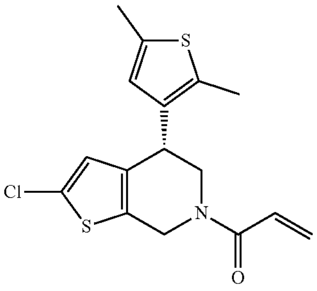
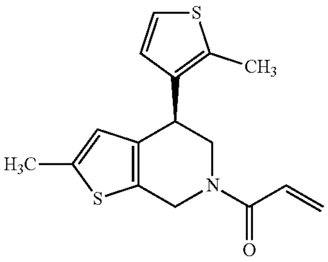 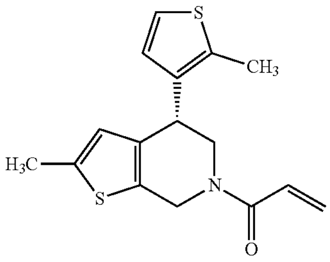
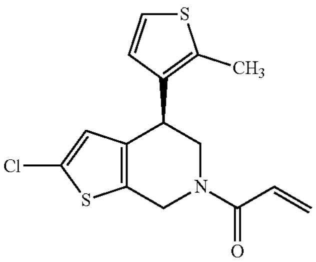 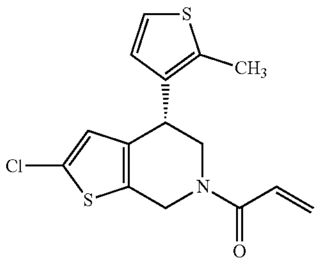
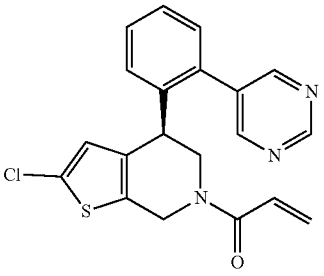 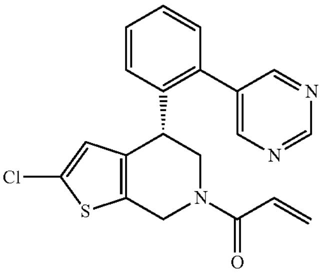
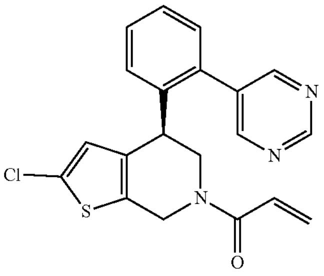 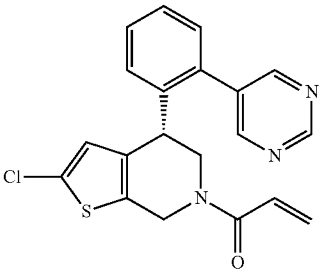

TABLE 1-continued
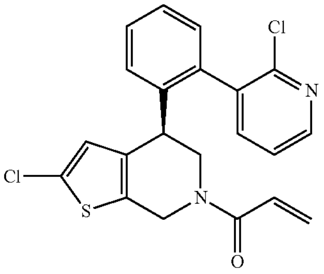
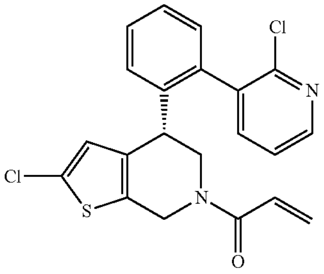
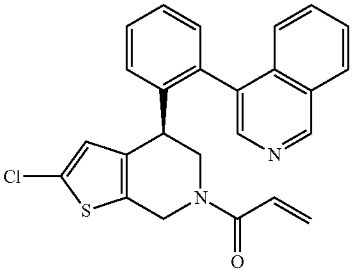
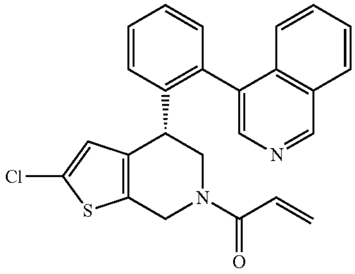
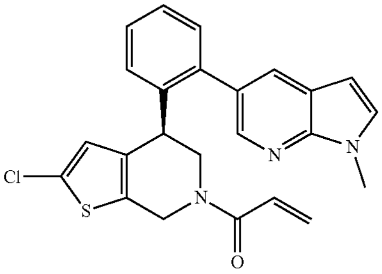
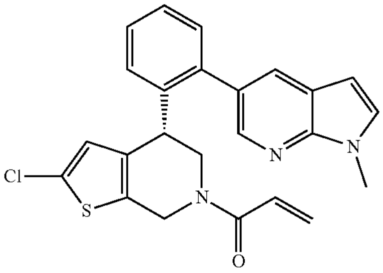
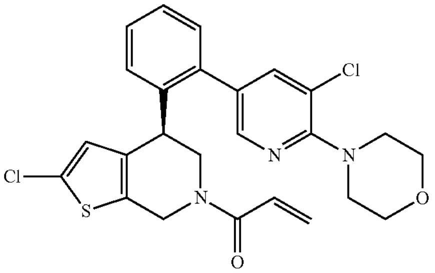
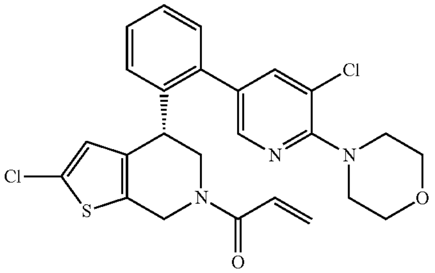
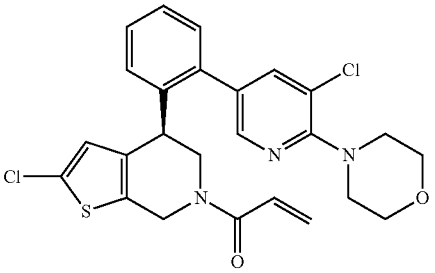
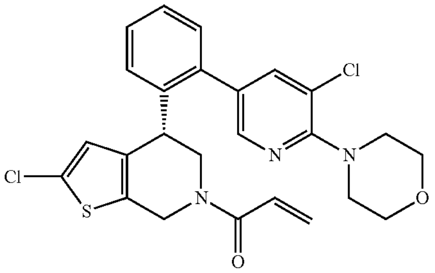

TABLE 1-continued
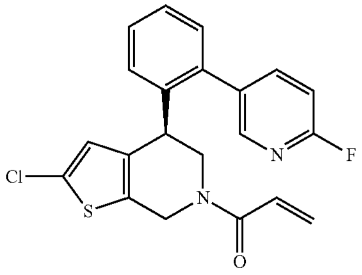
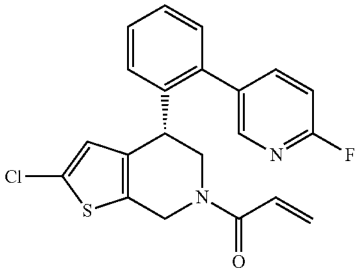
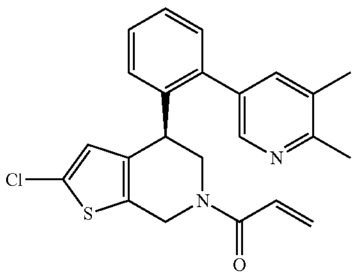
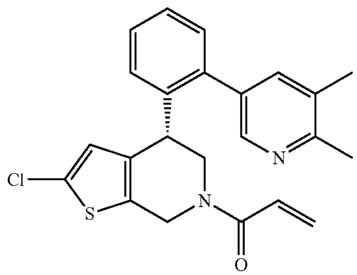
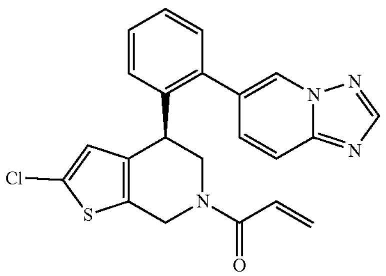
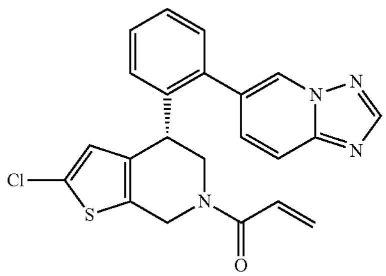
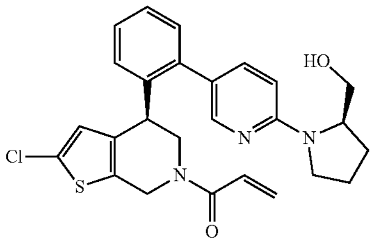
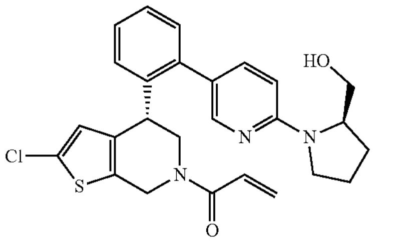
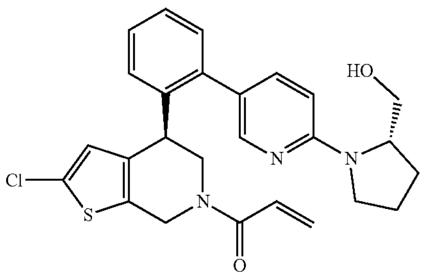
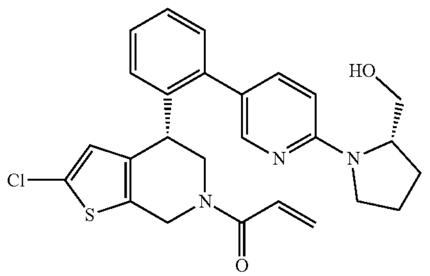
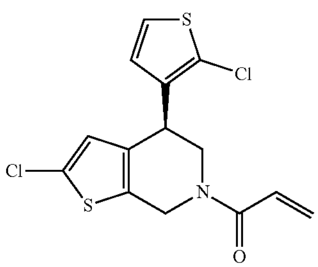
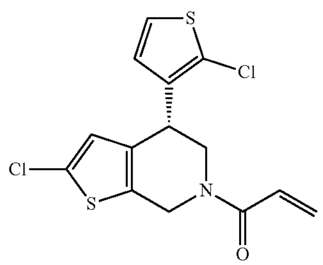

TABLE 1-continued
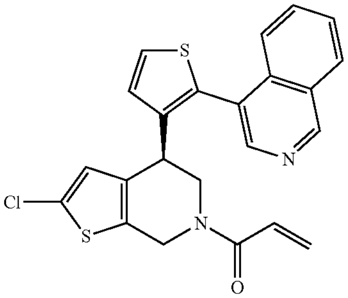
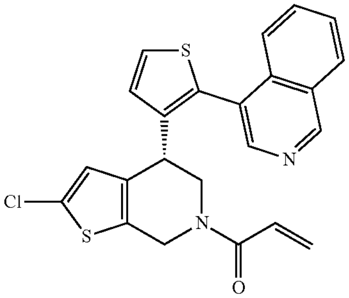
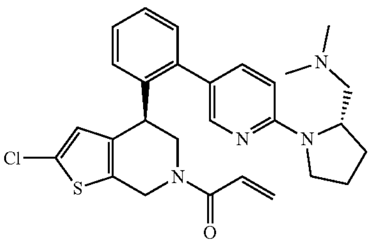
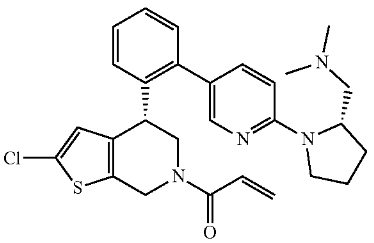
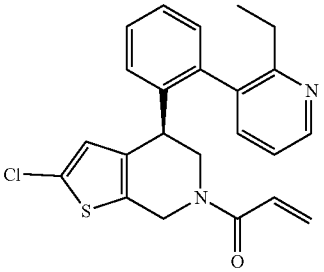
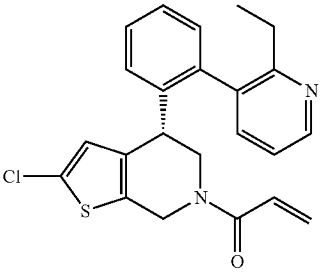
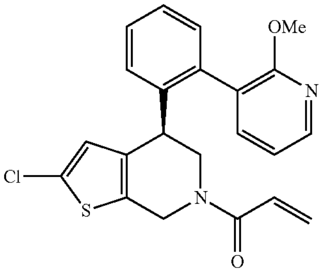
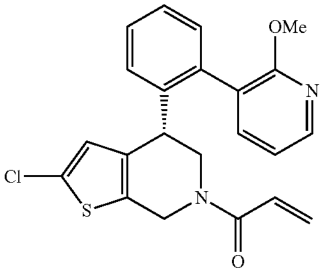
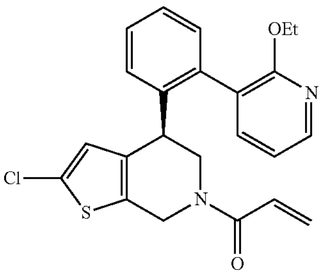
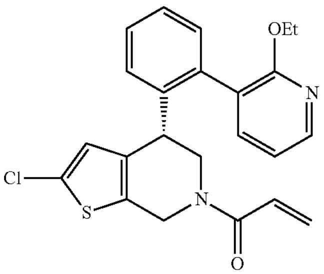

TABLE 1-continued
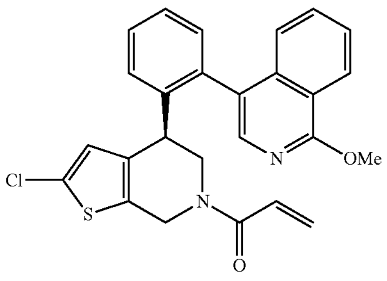
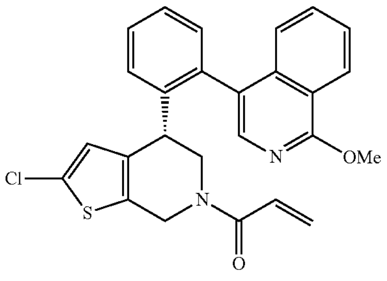
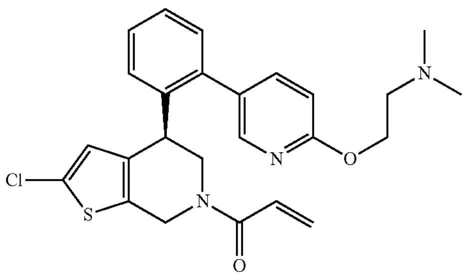
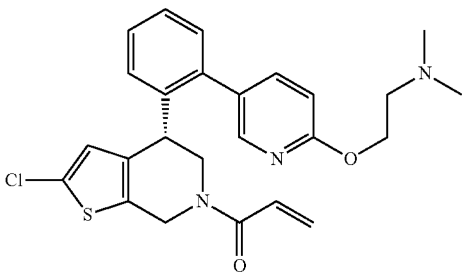
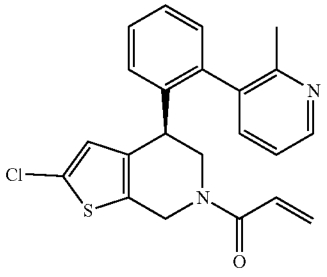
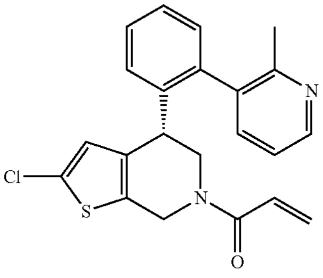
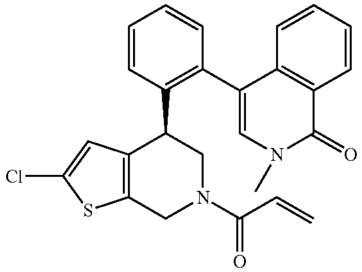
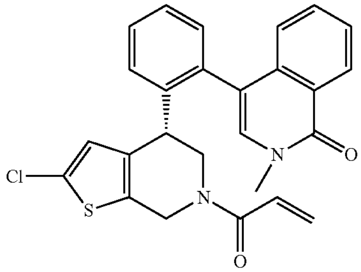
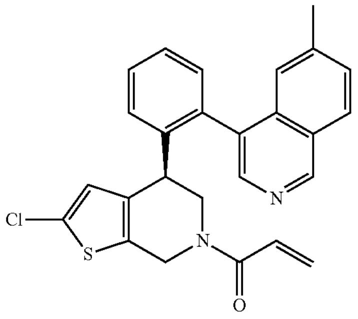
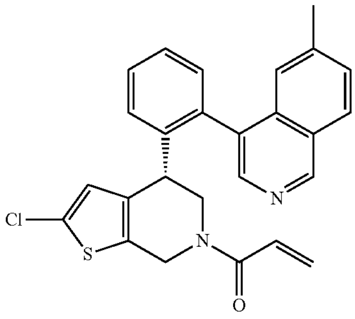

TABLE 1-continued
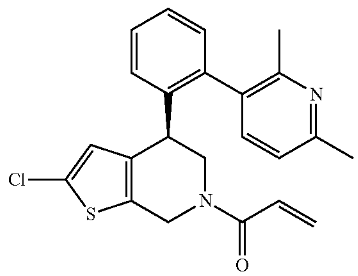
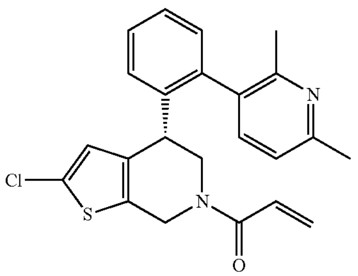
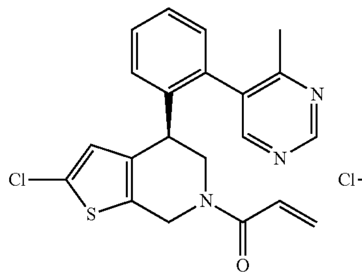
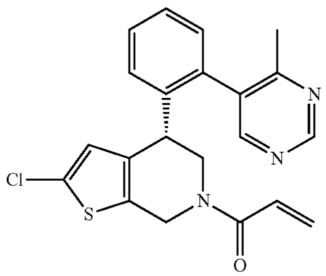
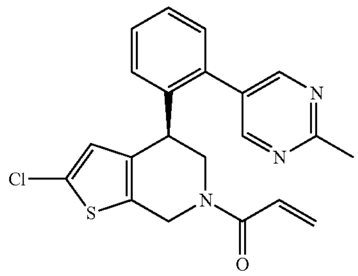
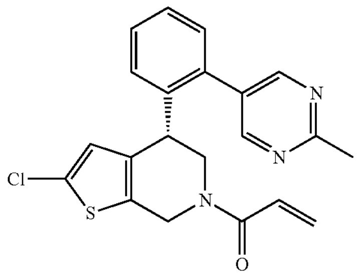
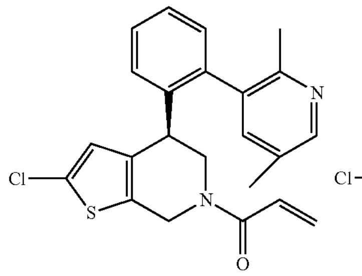
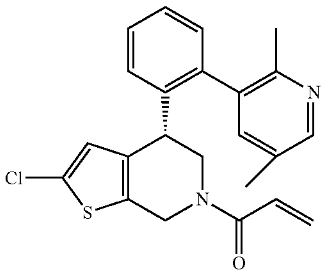
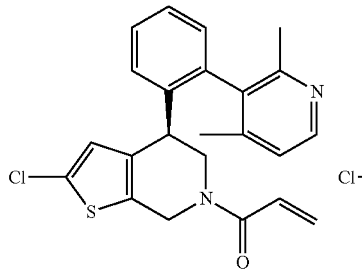
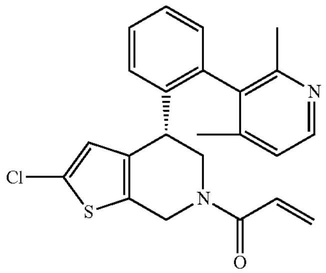

TABLE 1-continued
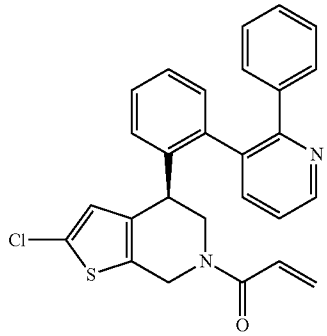
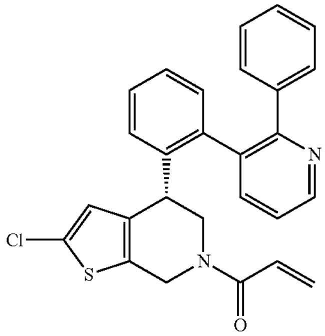
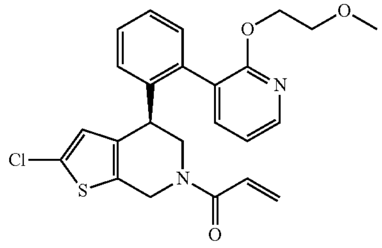
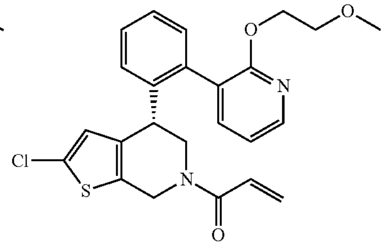
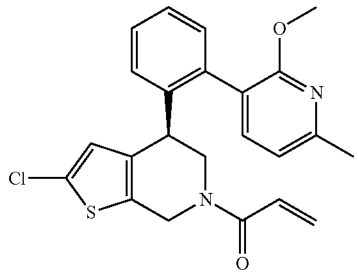
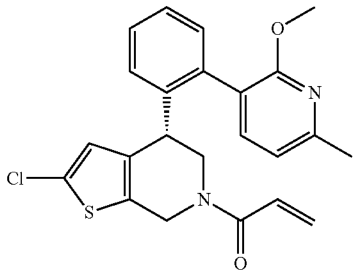
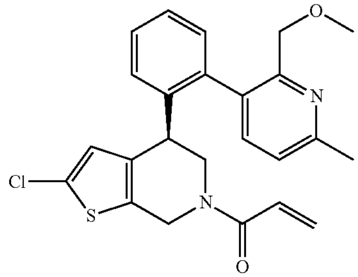
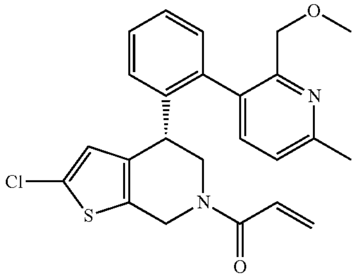
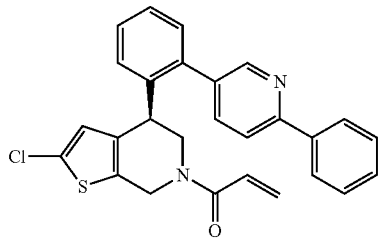
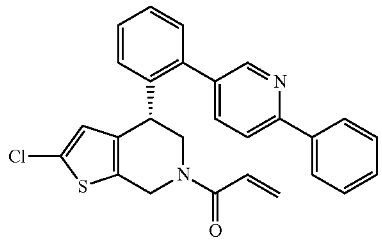

TABLE 1-continued
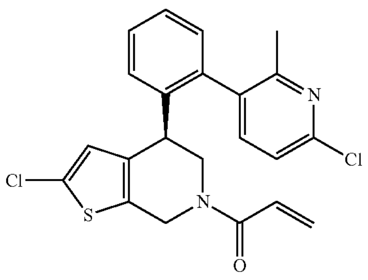
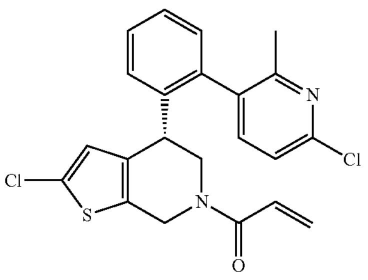
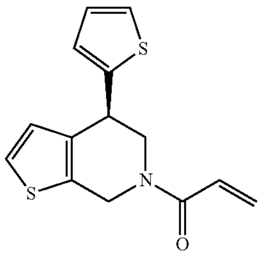
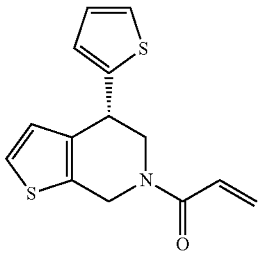
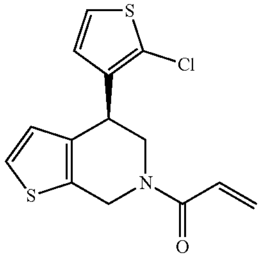
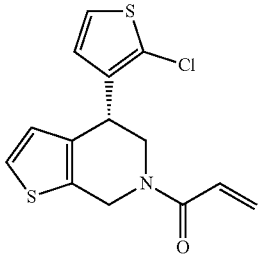
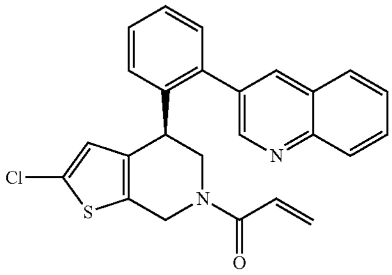
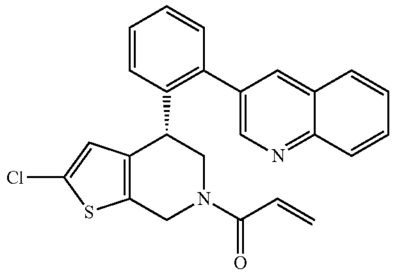
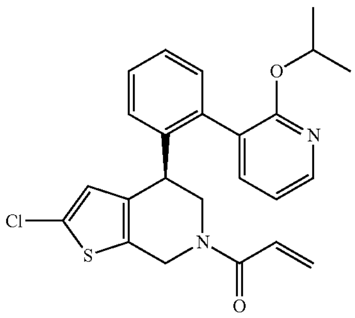
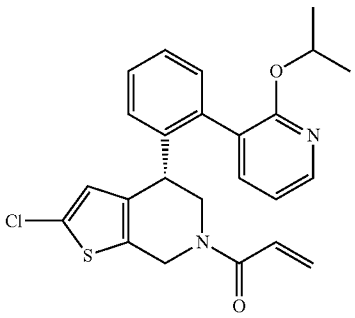

TABLE 1-continued
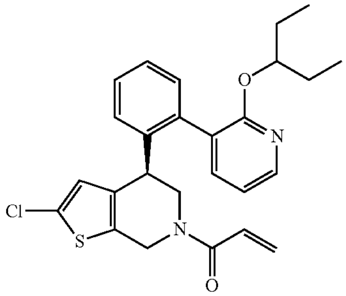
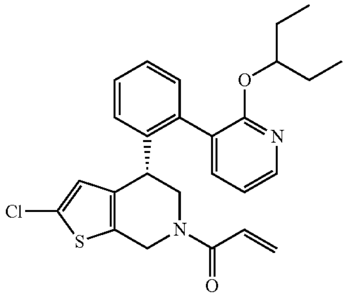
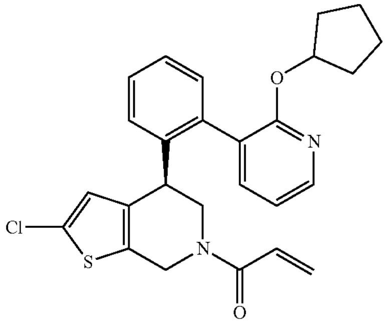
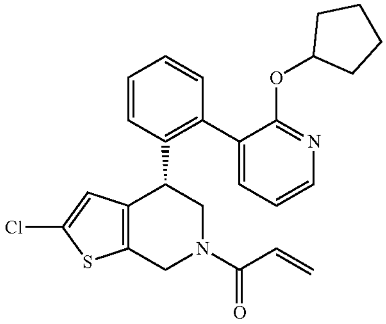
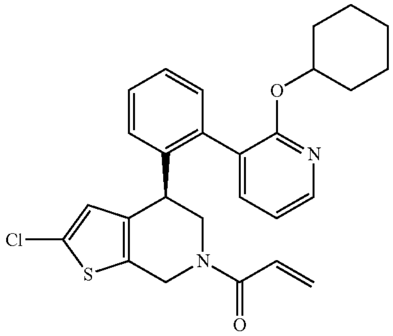
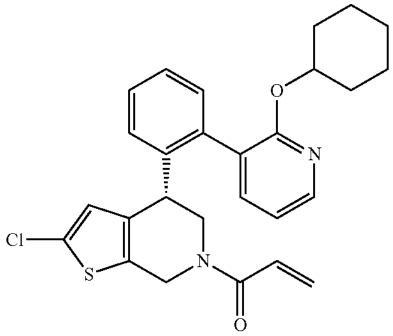
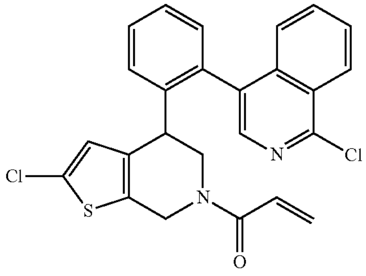
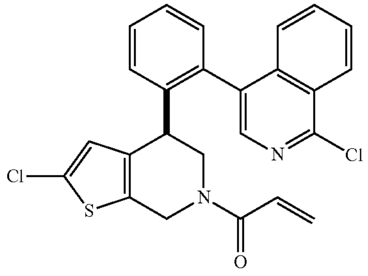
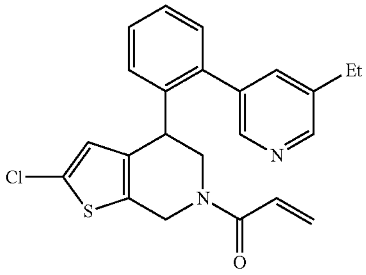
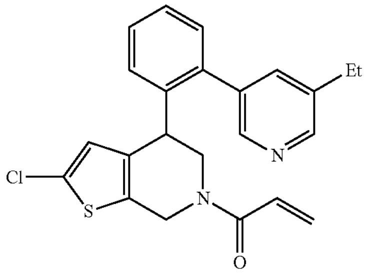

TABLE 1-continued
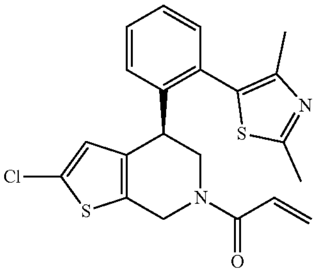
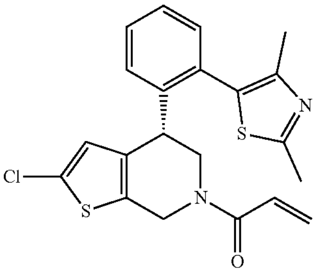
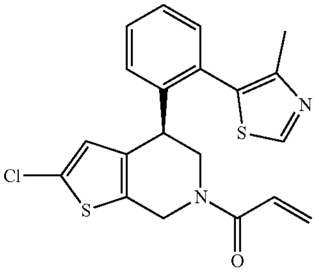
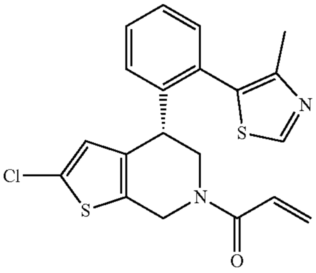
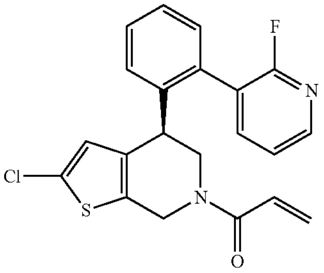
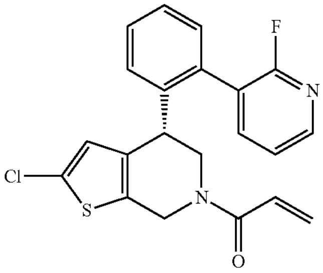
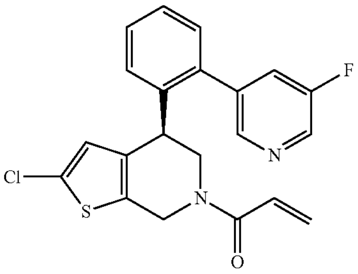
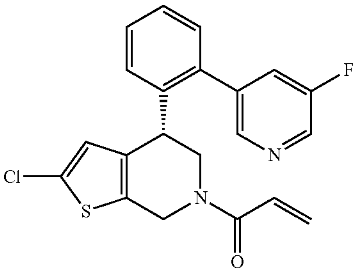
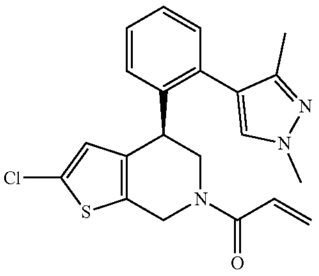
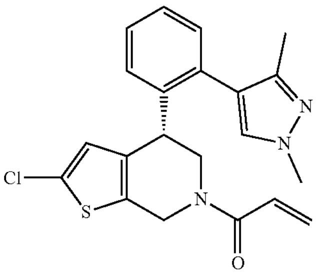

TABLE 1-continued
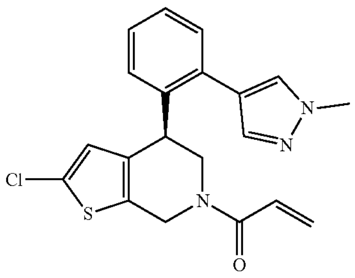
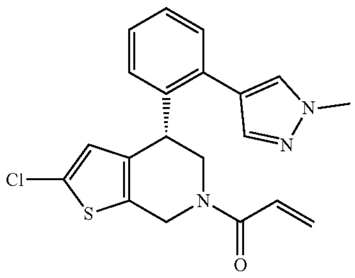
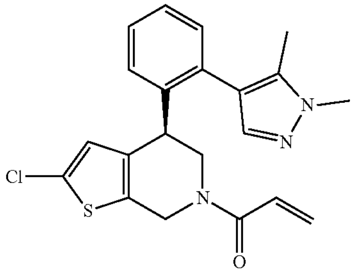
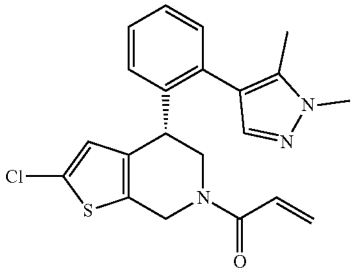
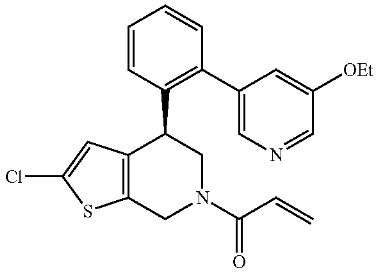
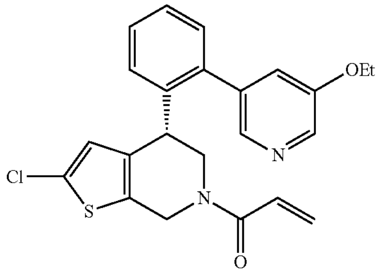
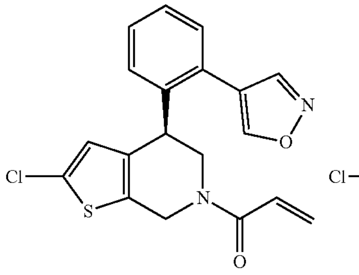
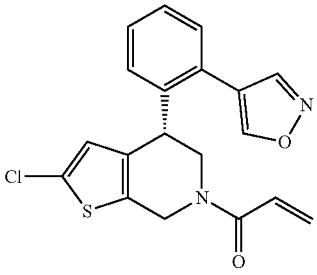
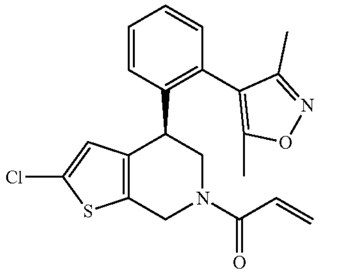
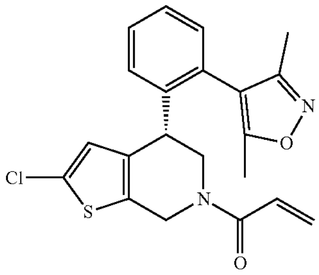

TABLE 1-continued
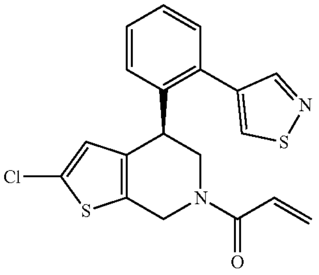 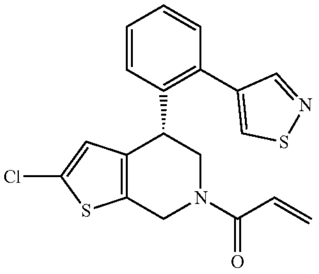
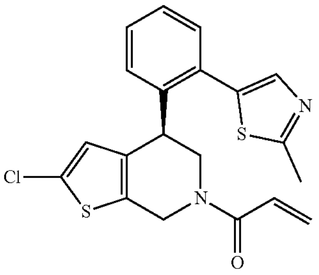 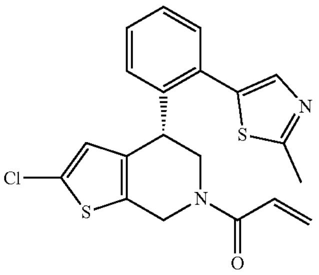
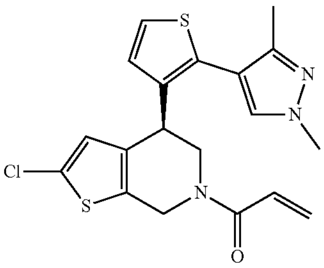 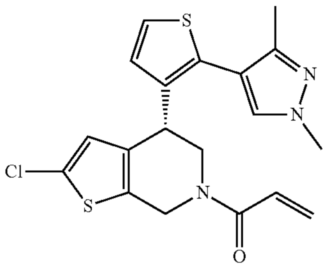
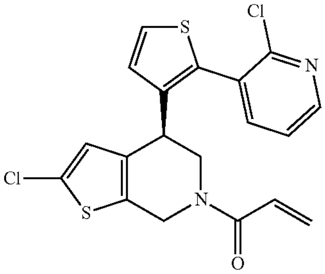 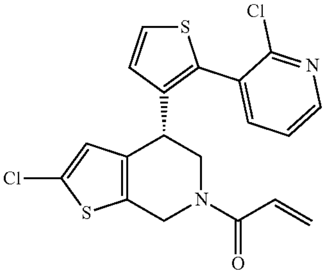
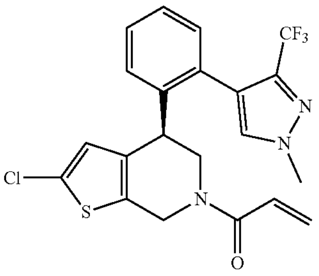 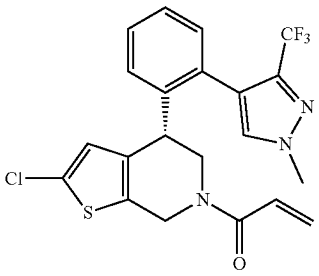

TABLE 1-continued
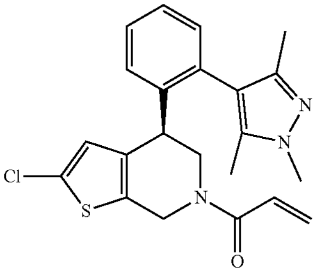
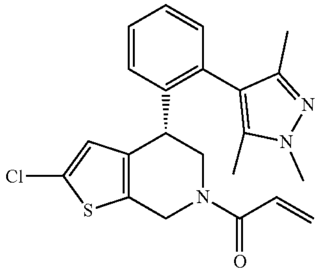
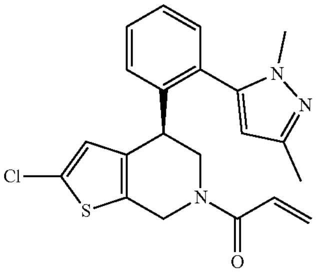
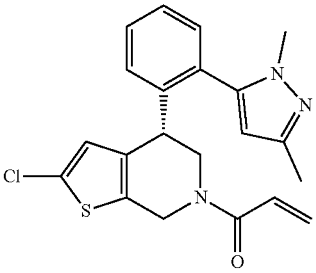
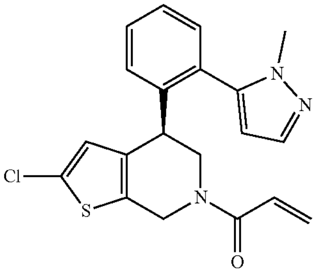
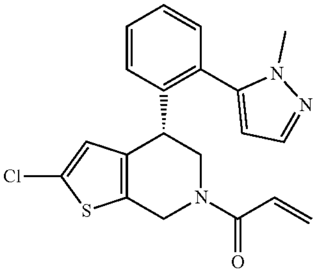
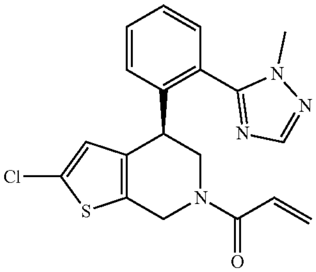
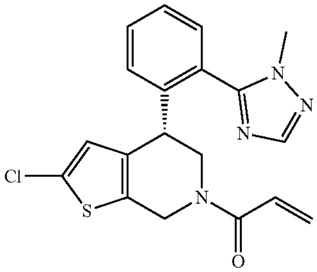
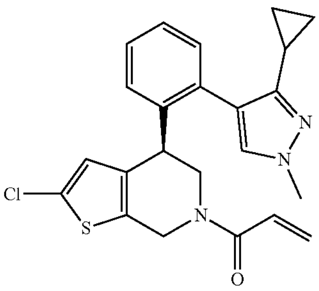
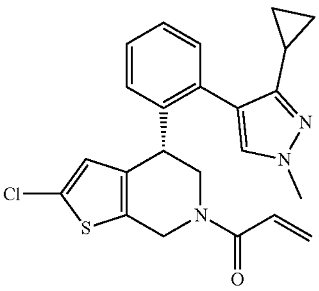

TABLE 1-continued
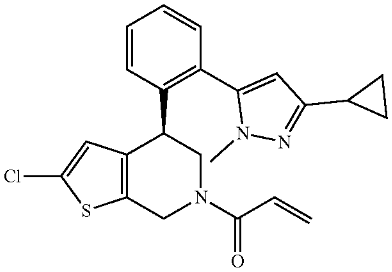 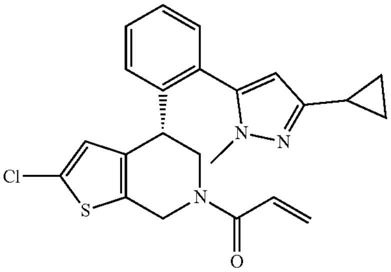
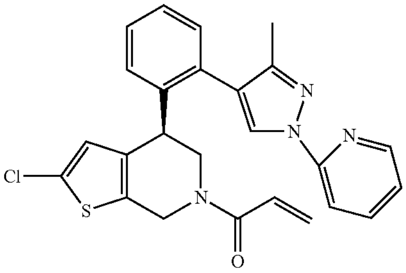 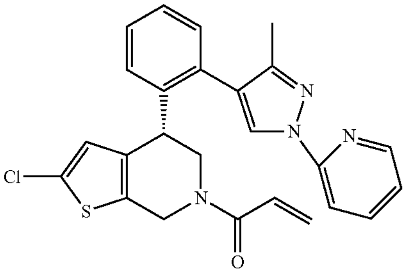
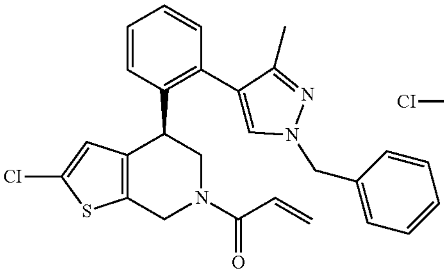 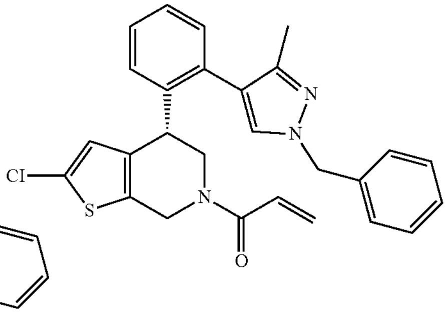
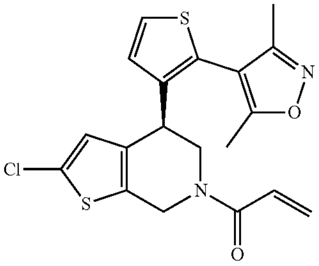 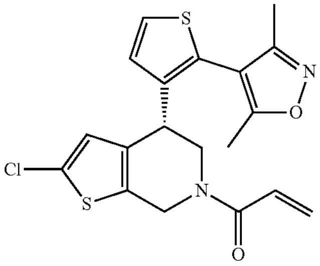
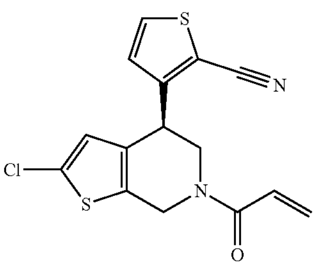 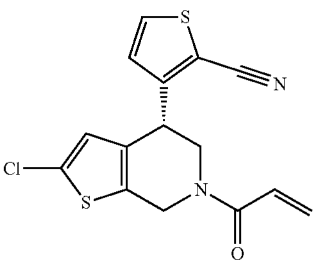

TABLE 1-continued
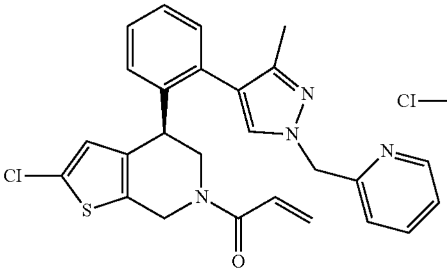
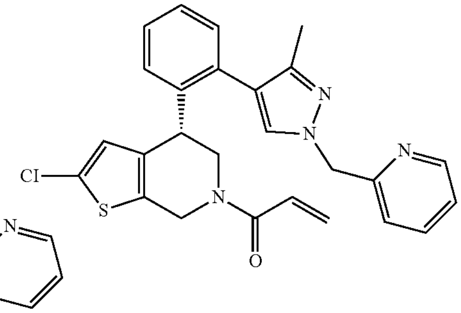
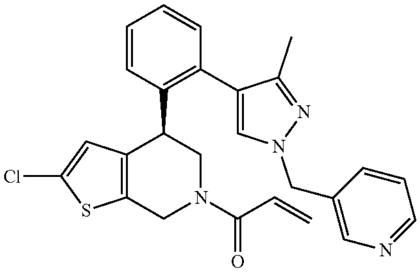
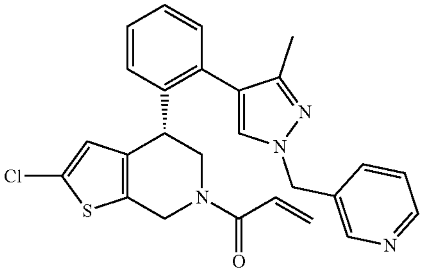
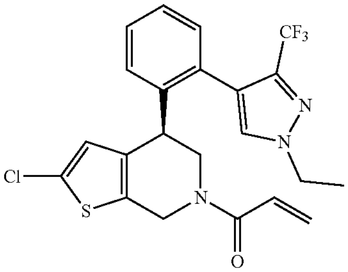
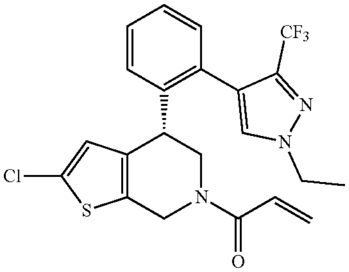
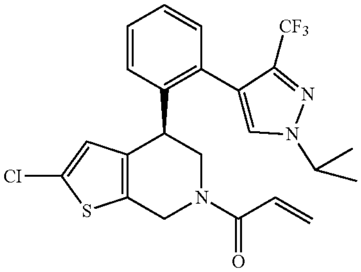
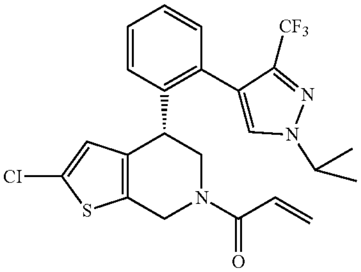
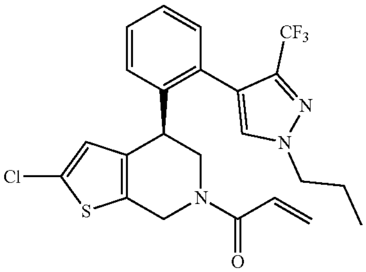
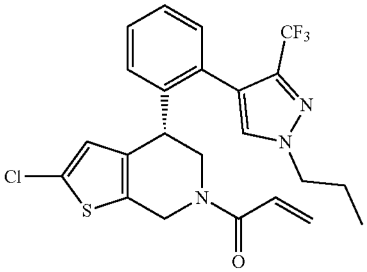

TABLE 1-continued
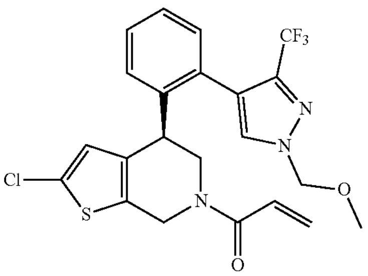
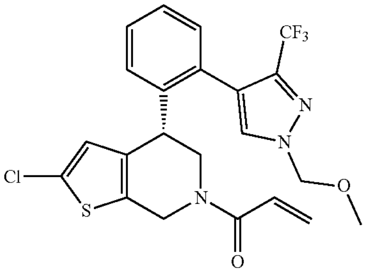
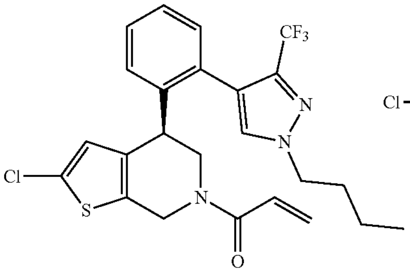
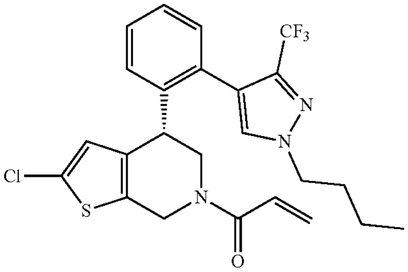
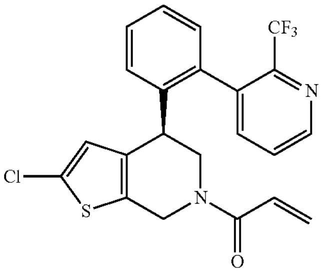
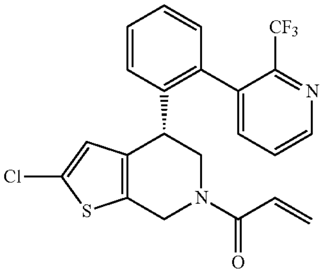
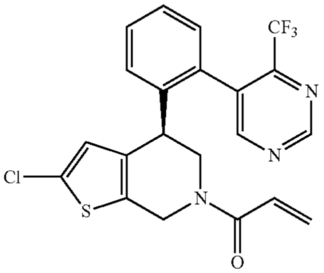
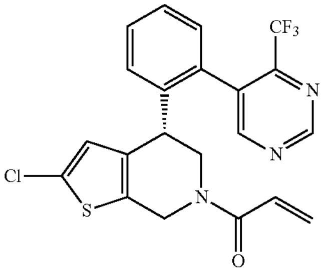
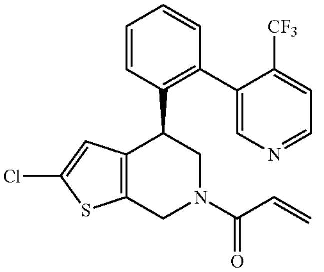
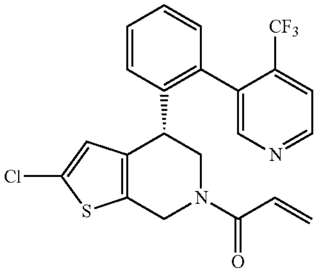

In one embodiment, the compound is selected from
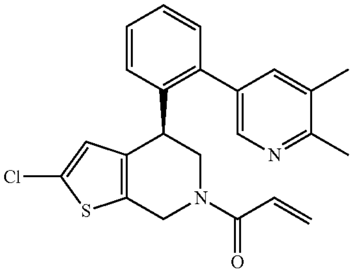
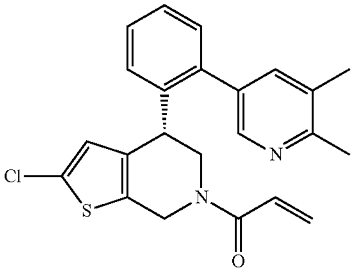
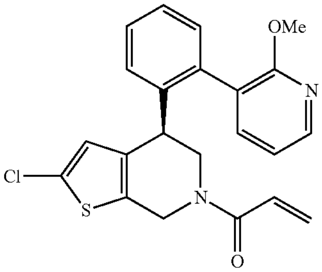
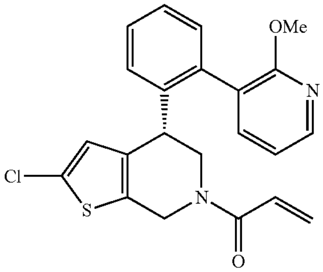
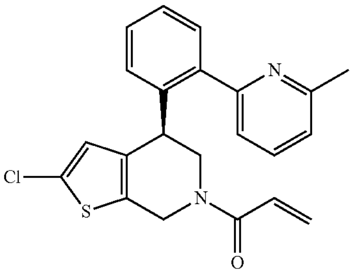
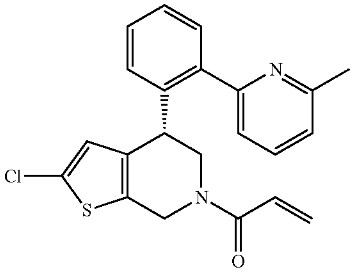
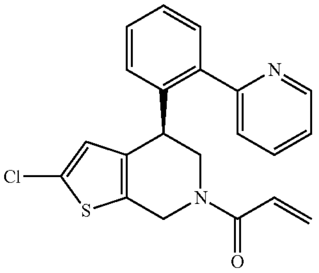
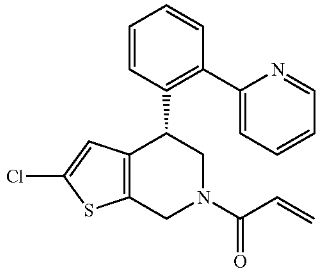
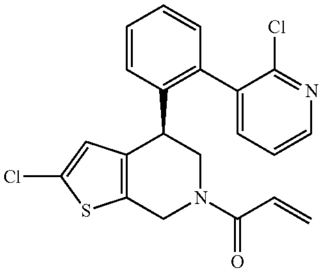
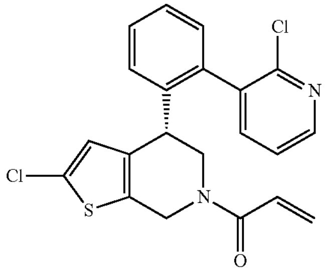

-continued
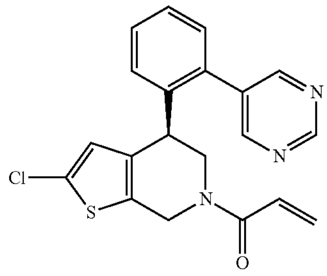
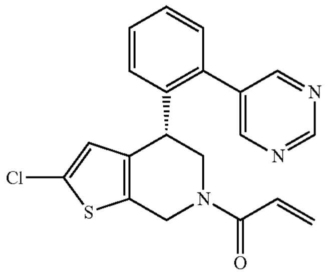
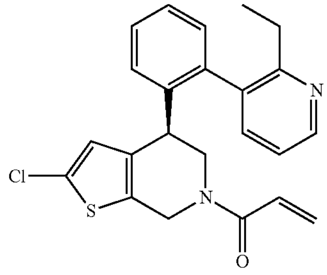
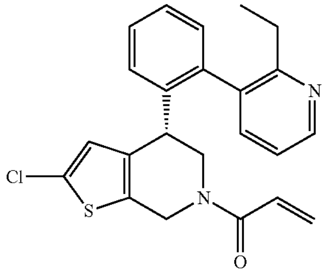
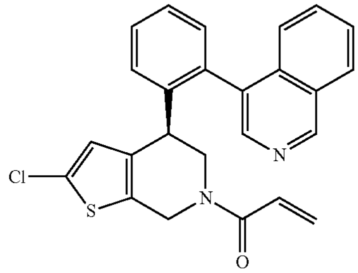
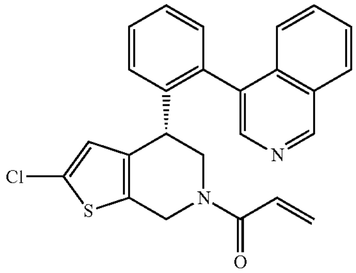
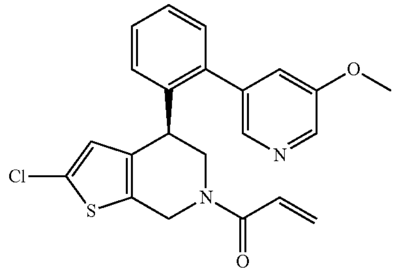
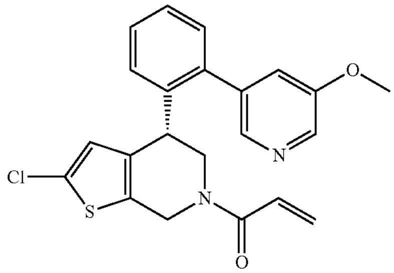
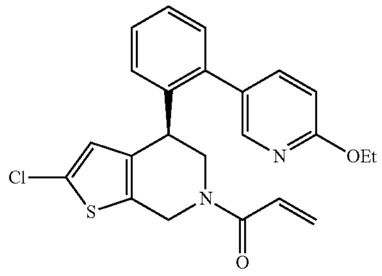
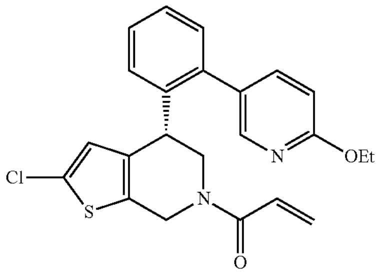

-continued
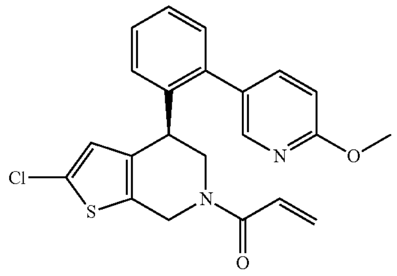 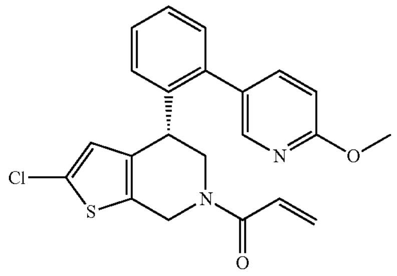
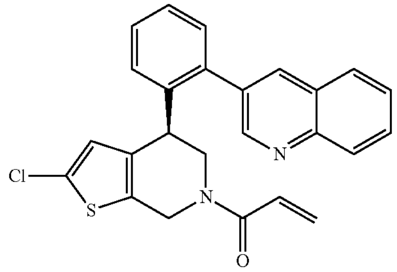 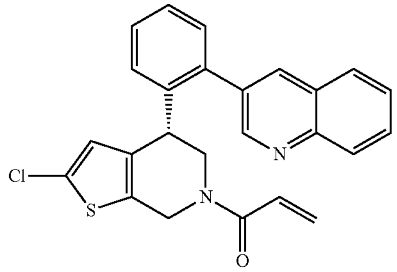
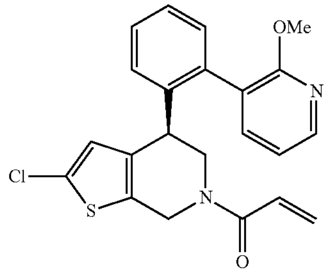 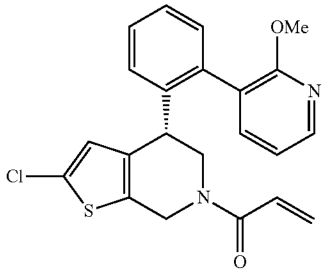
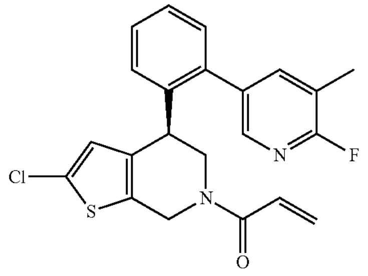 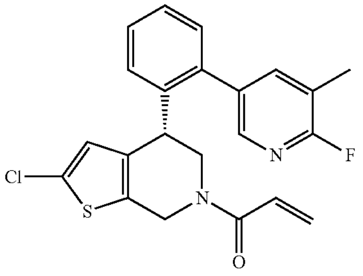
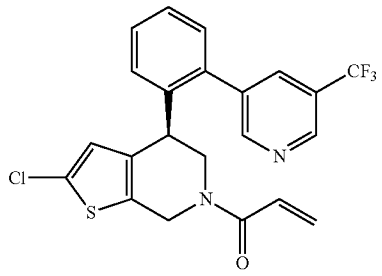 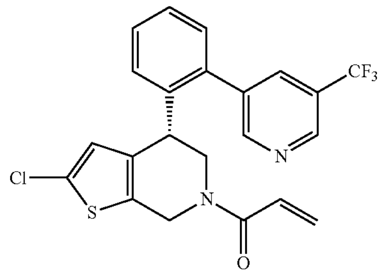

-continued
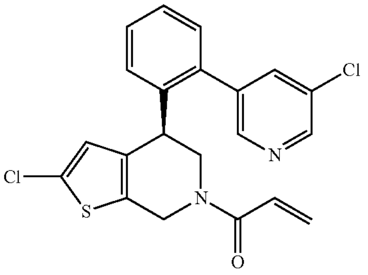
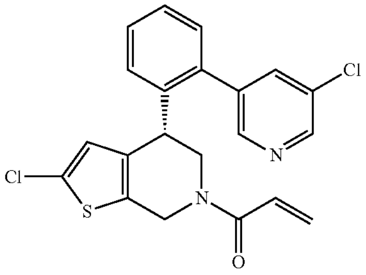
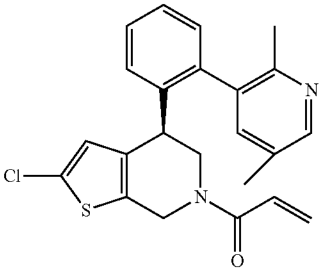
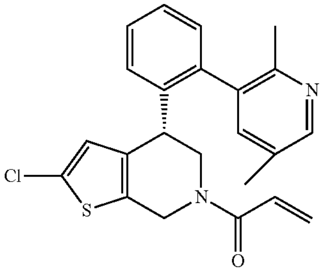
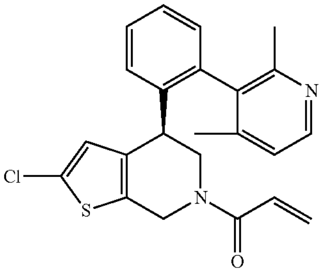
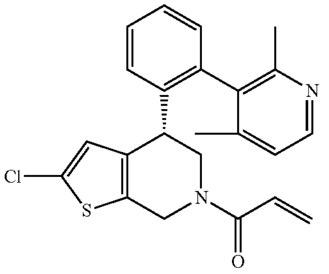
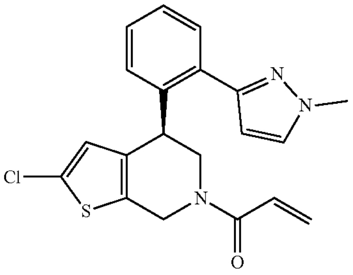
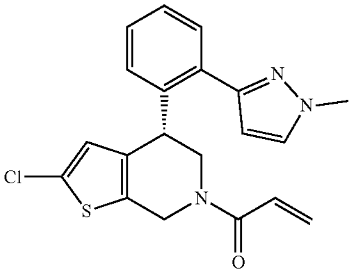
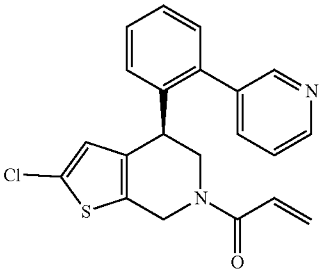
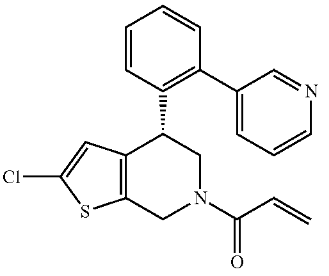

-continued
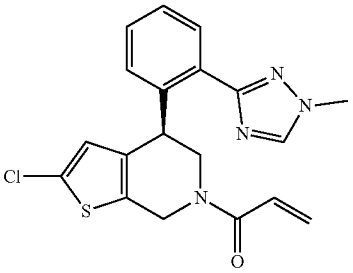
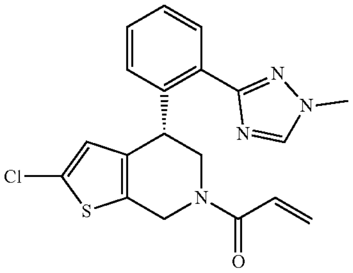
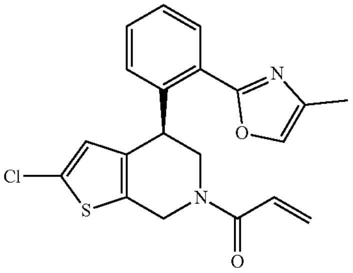
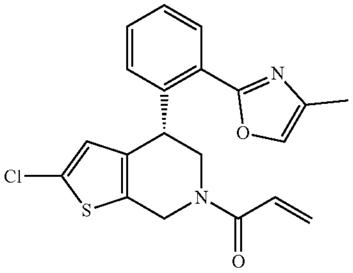
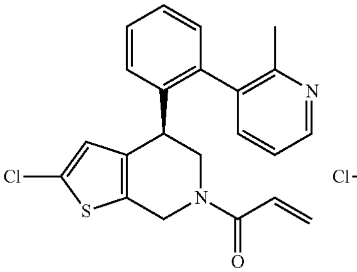
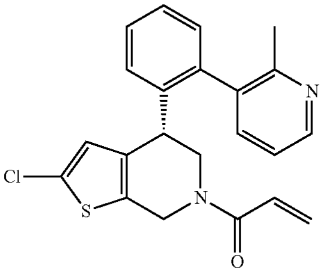
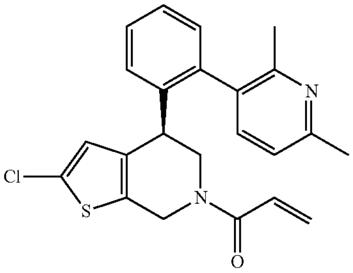
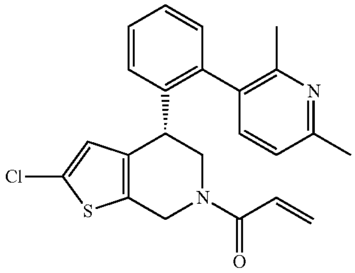
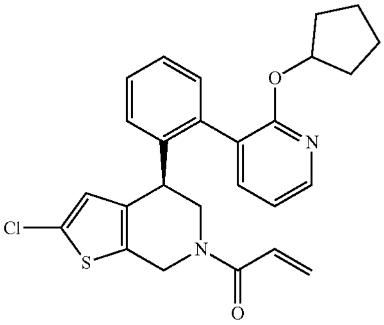
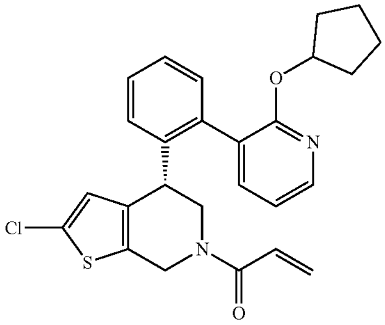

-continued
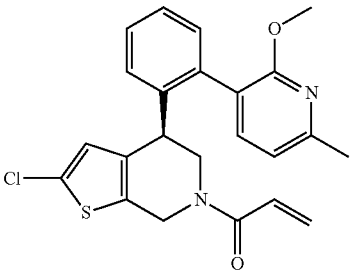
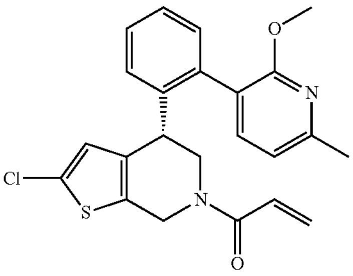
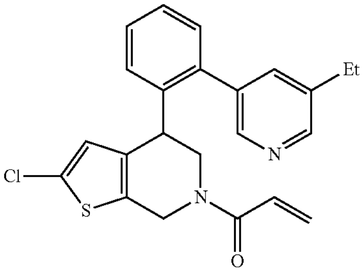
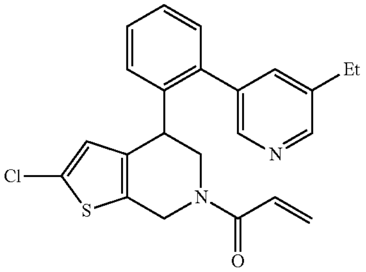
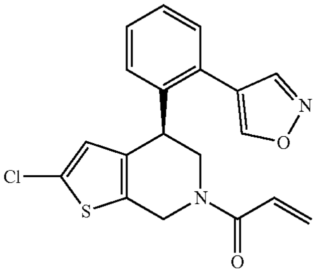
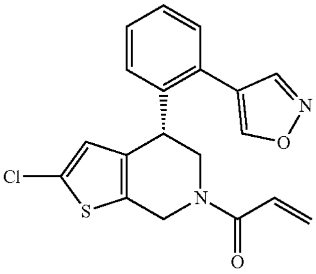
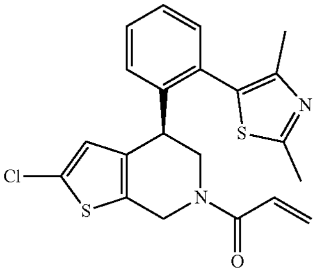
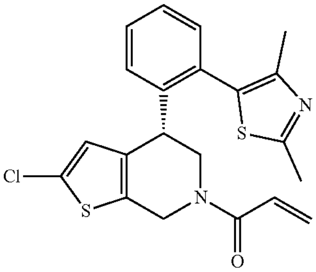
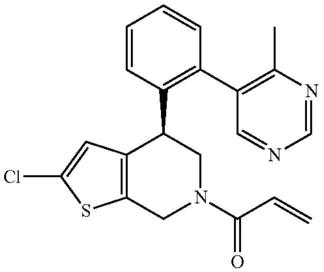
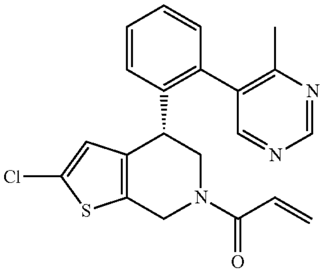

-continued
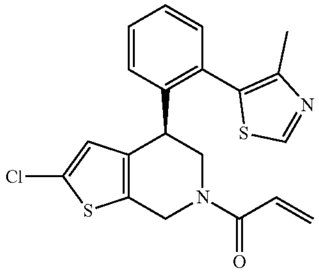
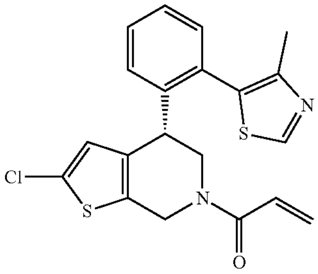
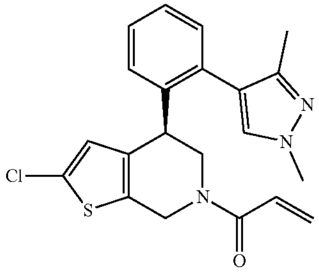
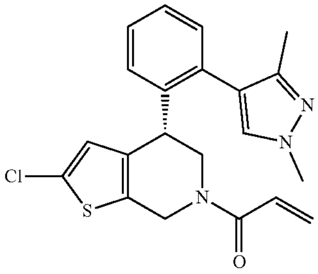
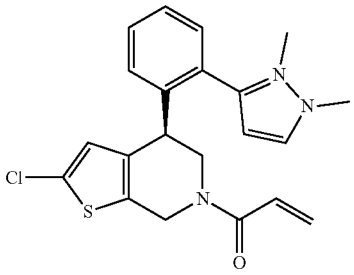
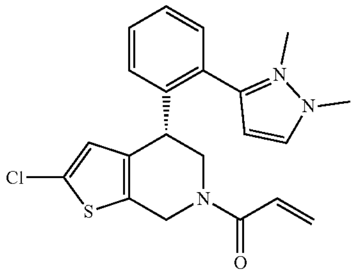
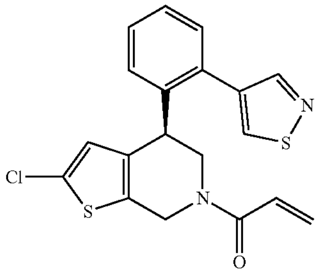
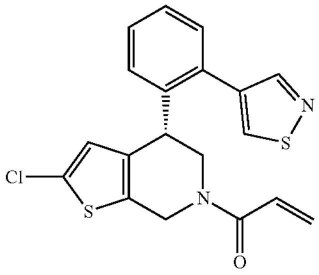
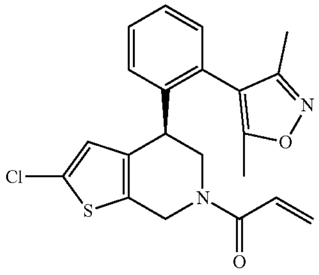
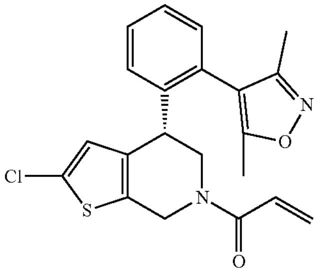

-continued
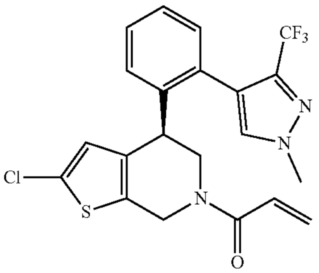
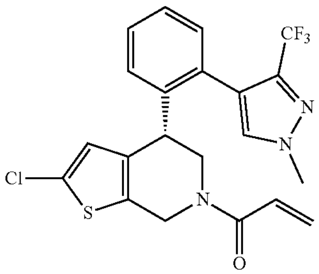
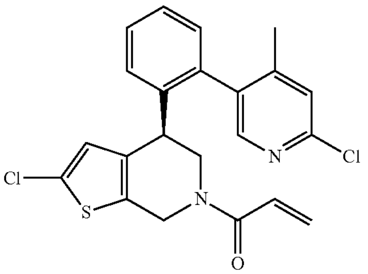
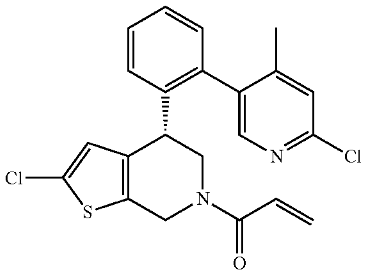
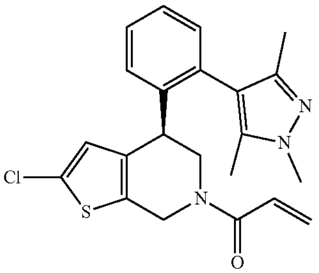
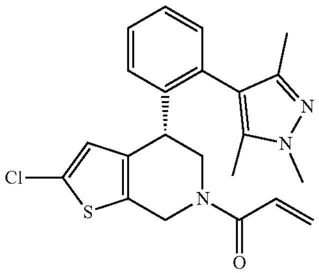
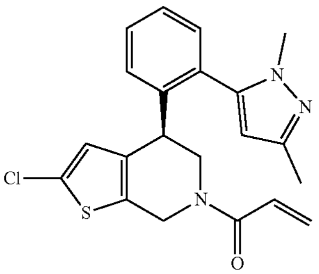
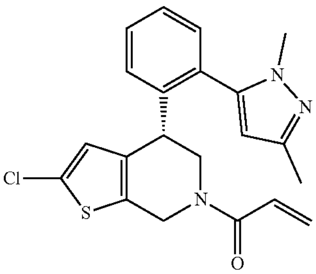
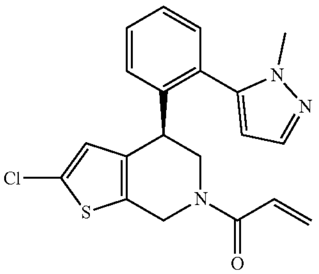
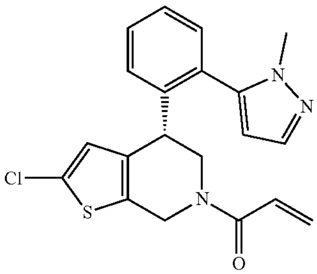

-continued
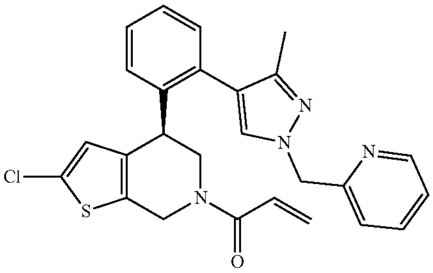
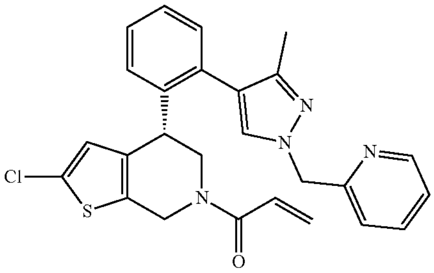
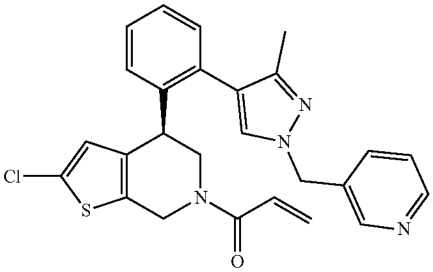
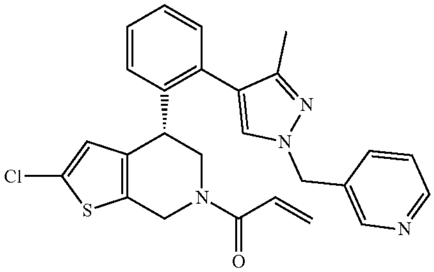
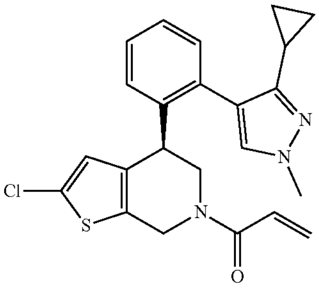
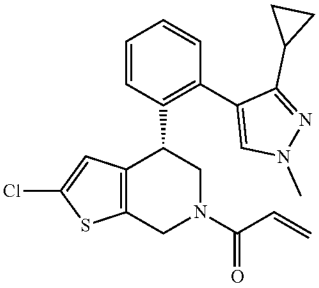
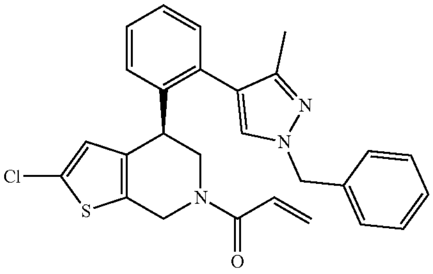
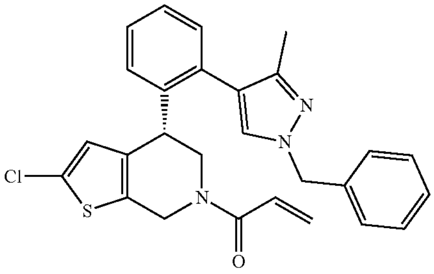
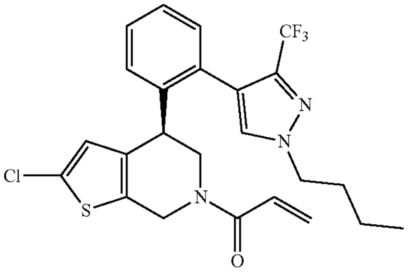
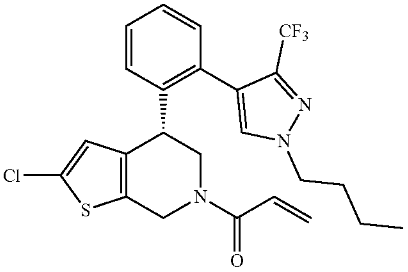

-continued
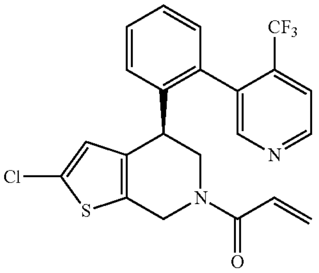
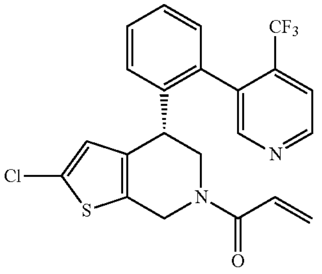
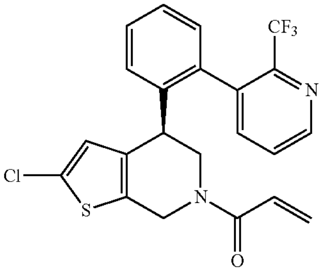
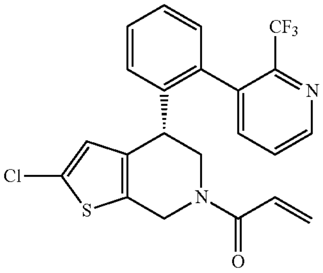
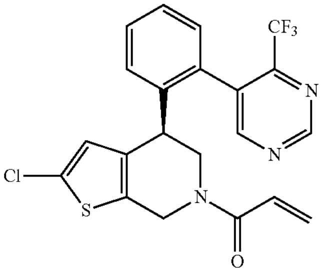
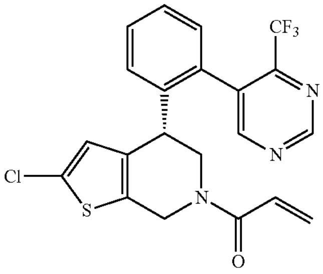
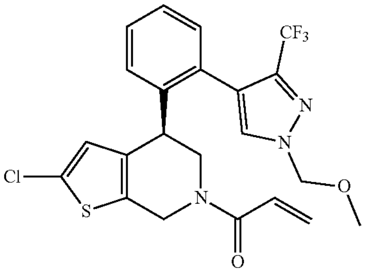
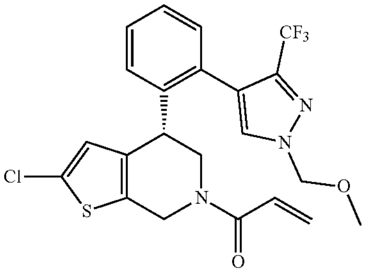
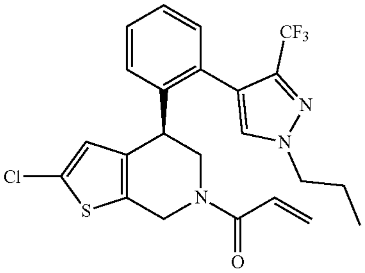
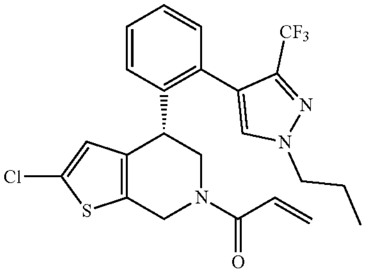

-continued
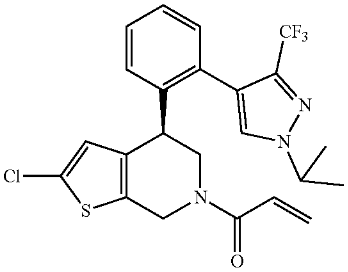
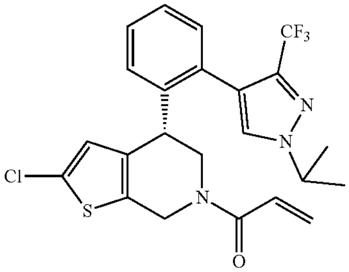
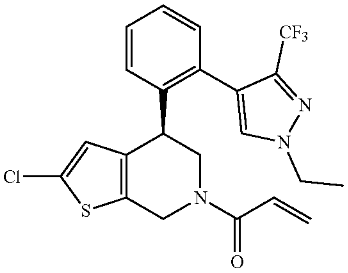
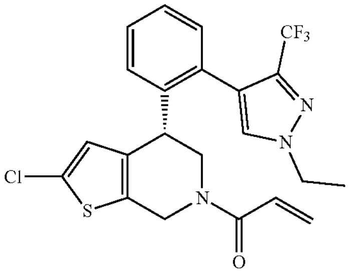
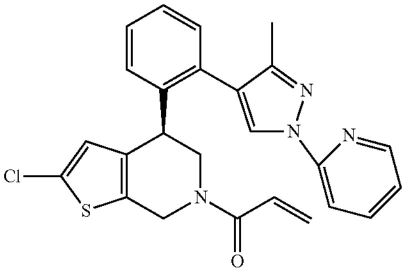
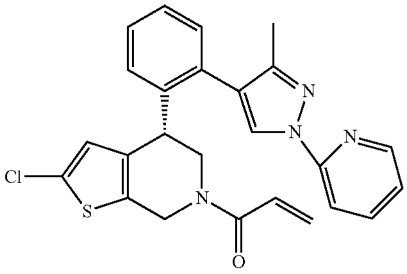
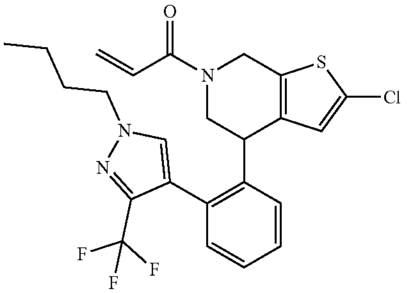 [SMILES: C=CC(=O)N1Cc2sc(Cl)cc2C(c2ccccc2-c2cn(CCCC)nc2C(F)(F)F)C1]
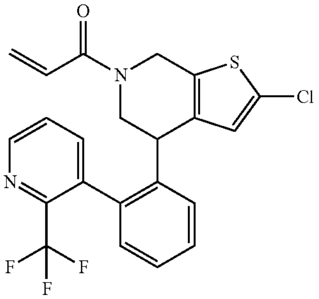

-continued
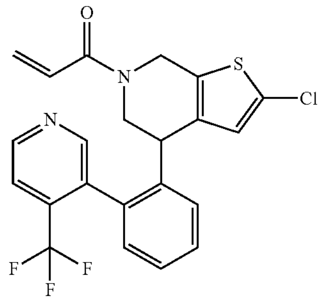 [SMILES: C=CC(=O)N1Cc2sc(Cl)cc2C(c2ccccc2-c2cnccc2C(F)(F)F)C1]
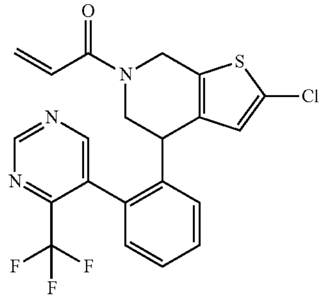
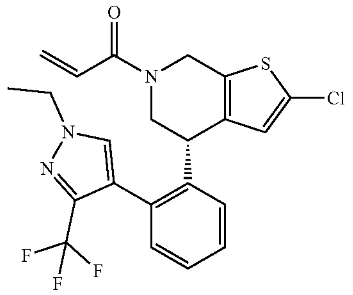
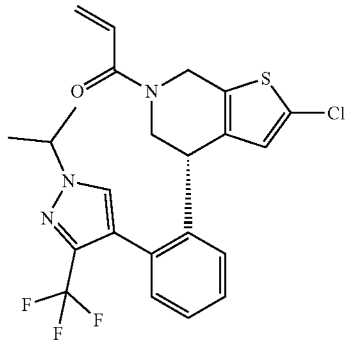 [SMILES: C=CC(=O)N1Cc2sc(Cl)cc2[C@H](c2ccccc2-c2cn(C(C)C)nc2C(F)(F)F)C1]
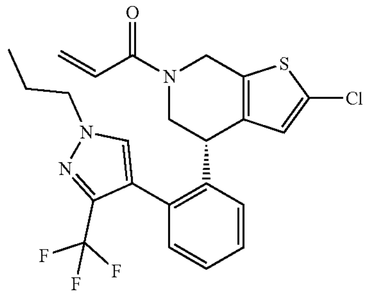 [SMILES: C=CC(=O)N1Cc2sc(Cl)cc2[C@H](c2ccccc2-c2cn(CCC)nc2C(F)(F)F)C1]

-continued
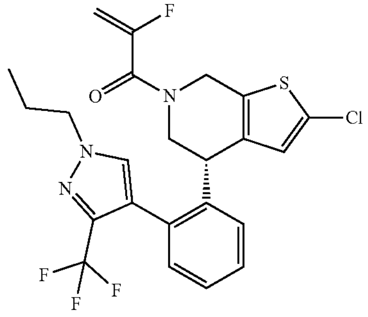 [SMILES: C=C(F)C(=O)N1Cc2sc(Cl)cc2[C@H](c2ccccc2-c2cn(CCC)nc2C(F)(F)F)C1]
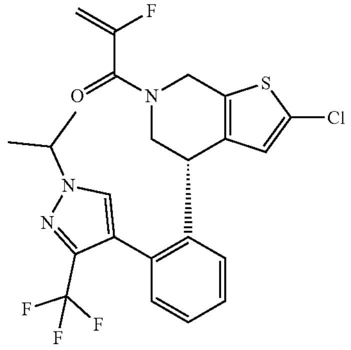 [SMILES: C=C(F)C(=O)N1Cc2sc(Cl)cc2[C@H](c2ccccc2-c2cn(C(C)C)nc2C(F)(F)F)C1]
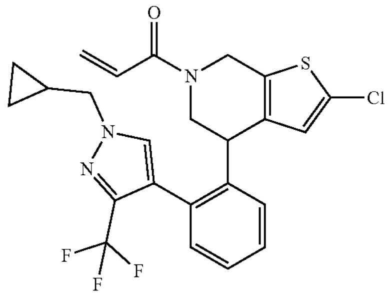 [SMILES: C=CC(=O)N1Cc2sc(Cl)cc2C(c2ccccc2-c2cn(CC3CC3)nc2C(F)(F)F)C1]
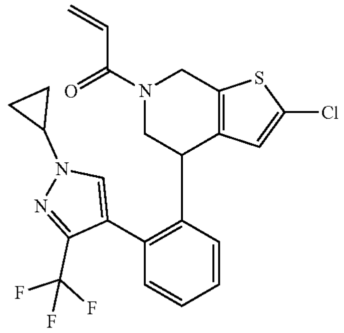 [SMILES: C=CC(=O)N1Cc2sc(Cl)cc2C(c2ccccc2-c2cn(C3CC3)nc2C(F)(F)F)C1]
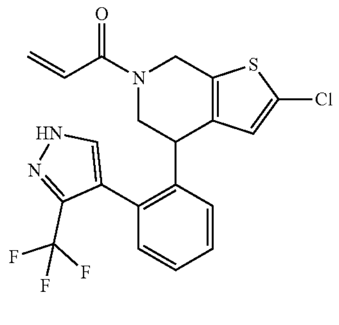

-continued
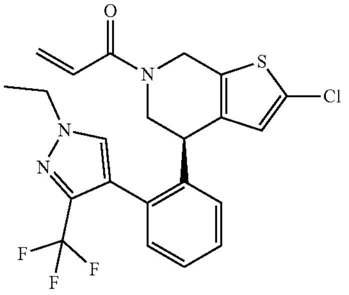 [SMILES: C=CC(=O)N1Cc2sc(Cl)cc2[C@@H](c2ccccc2-c2cn(CC)nc2C(F)(F)F)C1]
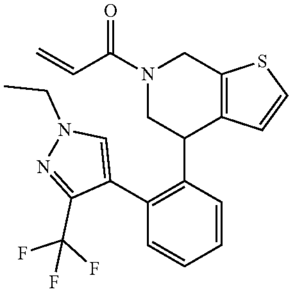 [SMILES: C=CC(=O)N1Cc2sccc2C(c2ccccc2-c2cn(CC)nc2C(F)(F)F)C1]
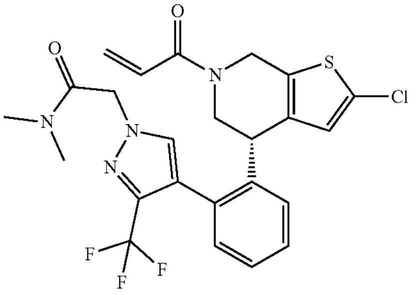 [SMILES: C=CC(=O)N1Cc2sc(Cl)cc2[C@H](c2ccccc2-c2cn(CC(=O)N(C)C)nc2C(F)(F)F)C1]
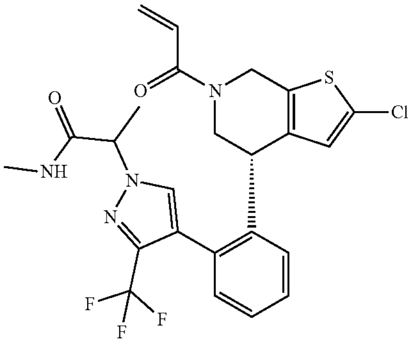 [SMILES: C=CC(=O)N1Cc2sc(Cl)cc2[C@H](c2ccccc2-c2cn(C(C)C(=O)NC)nc2C(F)(F)F)C1]
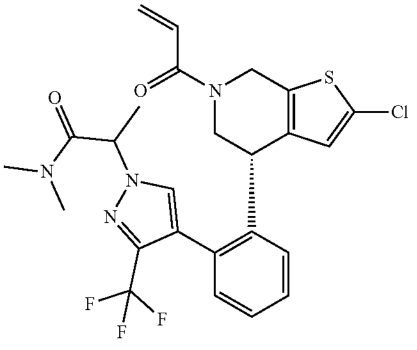 [SMILES: C=CC(=O)N1Cc2sc(Cl)cc2[C@H](c2ccccc2-c2cn(C(C)C(=O)N(C)C)nc2C(F)(F)F)C1]

-continued
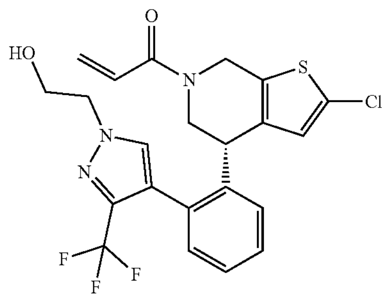 [SMILES: C=CC(=O)N1Cc2sc(Cl)cc2[C@H](c2ccccc2-c2cn(CCO)nc2C(F)(F)F)C1]
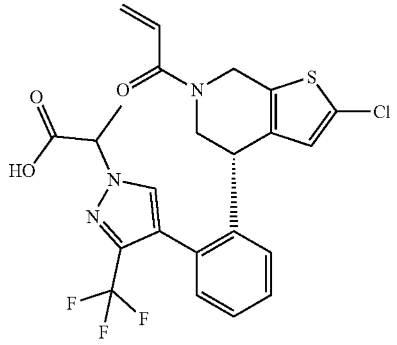 [SMILES: C=CC(=O)N1Cc2sc(Cl)cc2[C@H](c2ccccc2-c2cn(C(C)C(=O)O)nc2C(F)(F)F)C1]
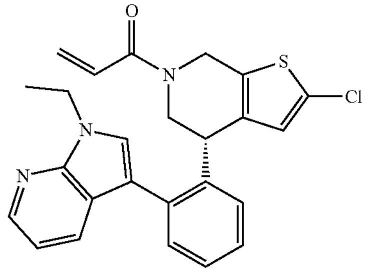 [SMILES: C=CC(=O)N1Cc2sc(Cl)cc2[C@H](c2ccccc2-c2cn(CC)c3ncccc23)C1]
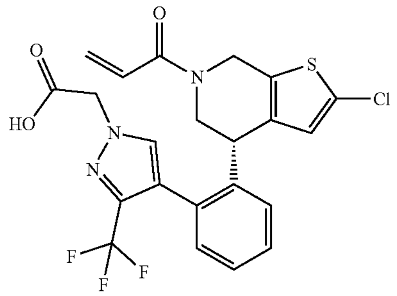 [SMILES: C=CC(=O)N1Cc2sc(Cl)cc2[C@H](c2ccccc2-c2cn(CC(=O)O)nc2C(F)(F)F)C1]
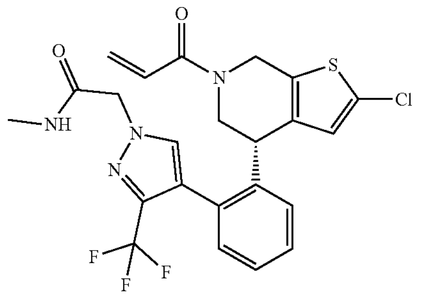 [SMILES: C=CC(=O)N1Cc2sc(Cl)cc2[C@H](c2ccccc2-c2cn(CC(=O)NC)nc2C(F)(F)F)C1]

-continued
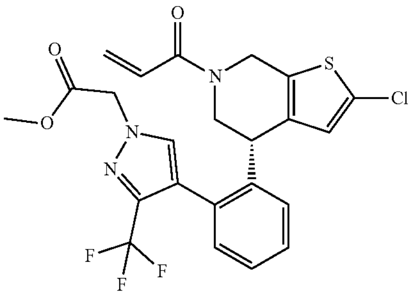 [SMILES: C=CC(=O)N1Cc2sc(Cl)cc2[C@H](c2ccccc2-c2cn(CC(=O)OC)nc2C(F)(F)F)C1]
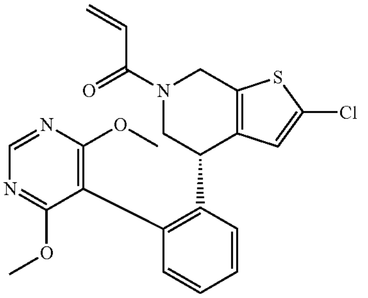 [SMILES: C=CC(=O)N1Cc2sc(Cl)cc2[C@H](c2ccccc2-c2c(OC)ncnc2OC)C1]
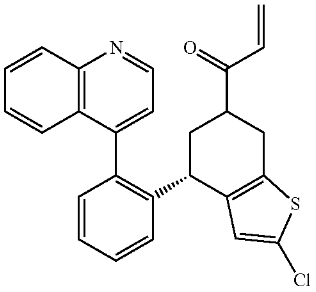
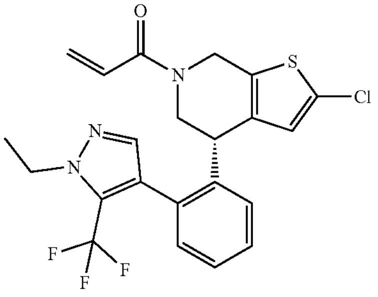 [SMILES: C=CC(=O)N1Cc2sc(Cl)cc2[C@H](c2ccccc2-c2cnn(CC)c2C(F)(F)F)C1]
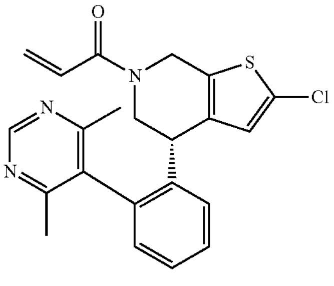 [SMILES: C=CC(=O)N1Cc2sc(Cl)cc2[C@H](c2ccccc2-c2c(C)ncnc2C)C1]

-continued
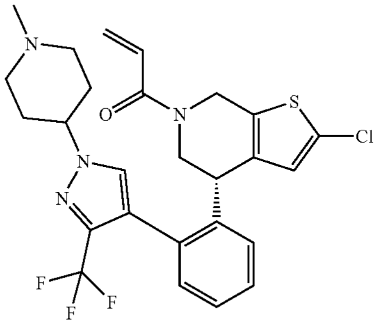 [SMILES: C=CC(=O)N1Cc2sc(Cl)cc2[C@H](c2ccccc2-c2cn(C3CCN(C)CC3)nc2C(F)(F)F)C1]
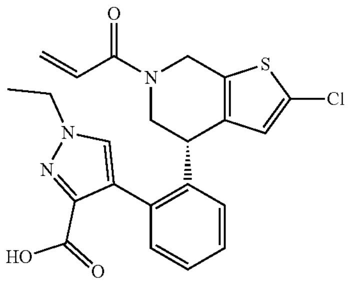 [SMILES: C=CC(=O)N1Cc2sc(Cl)cc2[C@H](c2ccccc2-c2cn(CC)nc2C(=O)O)C1]
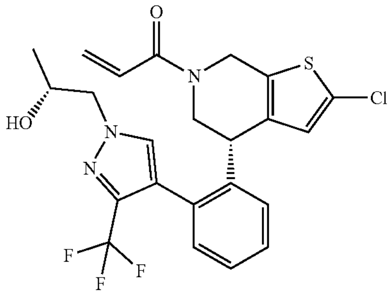 [SMILES: C=CC(=O)N1Cc2sc(Cl)cc2[C@H](c2ccccc2-c2cn(C[C@@H](C)O)nc2C(F)(F)F)C1]
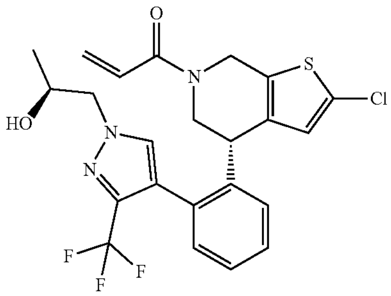 [SMILES: C=CC(=O)N1Cc2sc(Cl)cc2[C@H](c2ccccc2-c2cn(C[C@H](C)O)nc2C(F)(F)F)C1]
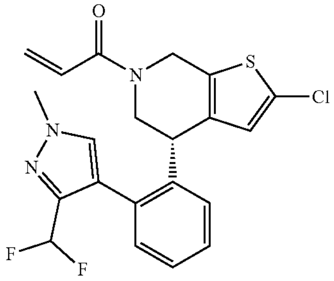 [SMILES: C=CC(=O)N1Cc2sc(Cl)cc2[C@H](c2ccccc2-c2cn(C)nc2C(F)F)C1]

-continued
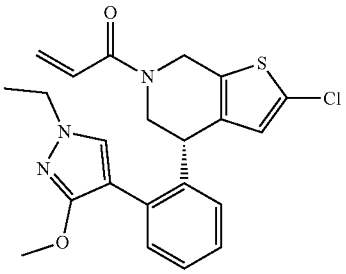 [SMILES: C=CC(=O)N1Cc2sc(Cl)cc2[C@H](c2ccccc2-c2cn(CC)nc2OC)C1]
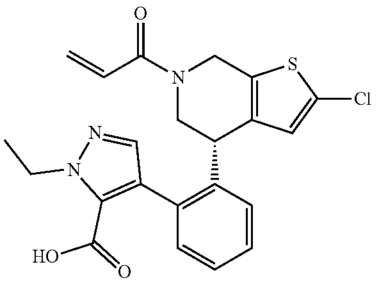 [SMILES: C=CC(=O)N1Cc2sc(Cl)cc2[C@H](c2ccccc2-c2cnn(CC)c2C(=O)O)C1]
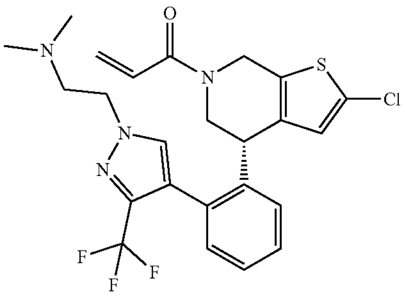 [SMILES: C=CC(=O)N1Cc2sc(Cl)cc2[C@H](c2ccccc2-c2cn(CCN(C)C)nc2C(F)(F)F)C1]
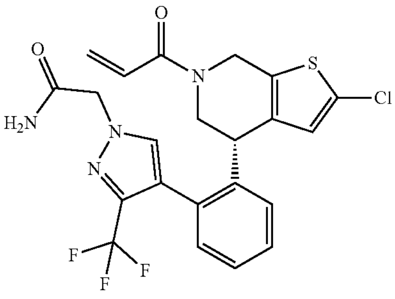 [SMILES: C=CC(=O)N1Cc2sc(Cl)cc2[C@H](c2ccccc2-c2cn(CC(N)=O)nc2C(F)(F)F)C1]
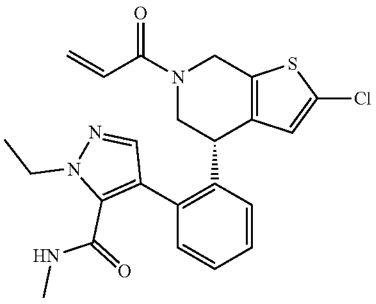 [SMILES: C=CC(=O)N1Cc2sc(Cl)cc2[C@H](c2ccccc2-c2cnn(CC)c2C(=O)NC)C1]

-continued
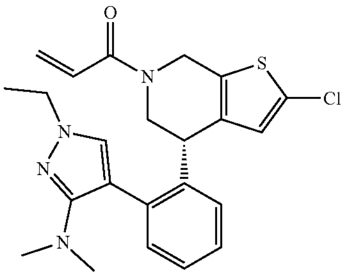 [SMILES: C=CC(=O)N1Cc2sc(Cl)cc2[C@H](c2ccccc2-c2cn(CC)nc2N(C)C)C1]
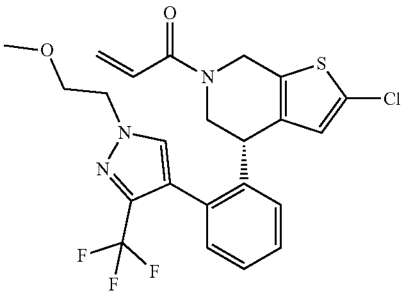 [SMILES: C=CC(=O)N1Cc2sc(Cl)cc2[C@H](c2ccccc2-c2cn(CCOC)nc2C(F)(F)F)C1]
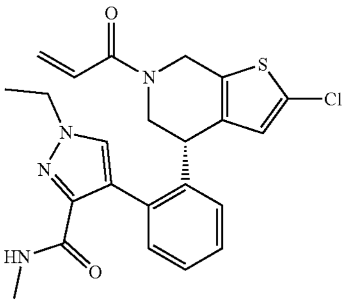 [SMILES: C=CC(=O)N1Cc2sc(Cl)cc2[C@H](c2ccccc2-c2cn(CC)nc2C(=O)NC)C1]
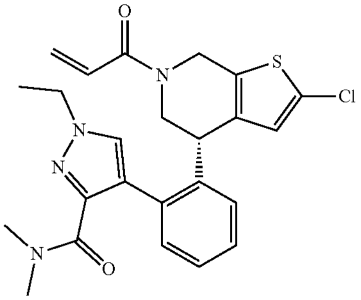 [SMILES: C=CC(=O)N1Cc2sc(Cl)cc2[C@H](c2ccccc2-c2cn(CC)nc2C(=O)N(C)C)C1]
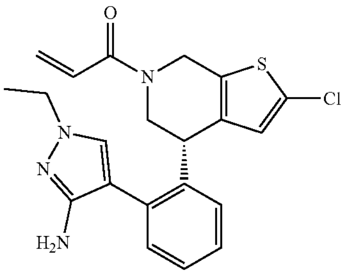 [SMILES: C=CC(=O)N1Cc2sc(Cl)cc2[C@H](c2ccccc2-c2cn(CC)nc2N)C1]

-continued
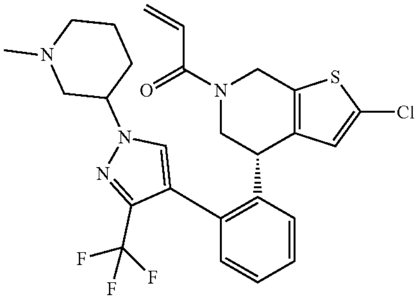 [SMILES: C=CC(=O)N1Cc2sc(Cl)cc2[C@H](c2ccccc2-c2cn(C3CCCN(C)C3)nc2C(F)(F)F)C1]
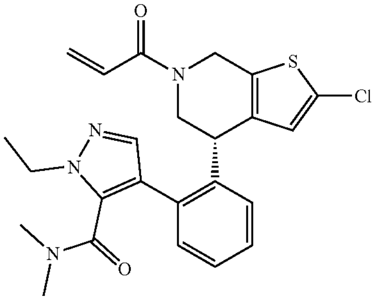 [SMILES: C=CC(=O)N1Cc2sc(Cl)cc2[C@H](c2ccccc2-c2cnn(CC)c2C(=O)N(C)C)C1]
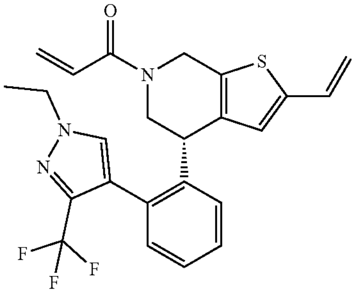 [SMILES: C=CC(=O)N1Cc2sc(C=C)cc2[C@H](c2ccccc2-c2cn(CC)nc2C(F)(F)F)C1]
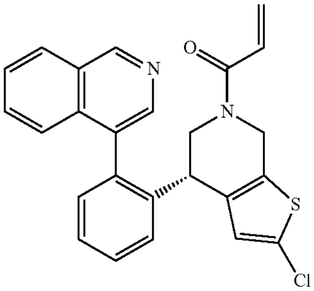 [SMILES: C=CC(=O)N1Cc2sc(Cl)cc2[C@H](c2ccccc2-c2cncc3ccccc23)C1]
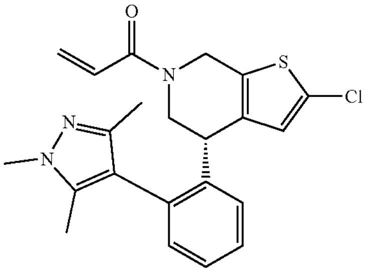 [SMILES: C=CC(=O)N1Cc2sc(Cl)cc2[C@H](c2ccccc2-c2c(C)nn(C)c2C)C1]

-continued
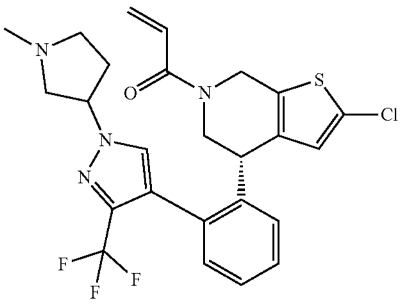 [SMILES: C=CC(=O)N1Cc2sc(Cl)cc2[C@H](c2ccccc2-c2cn(C3CCN(C)C3)nc2C(F)(F)F)C1]
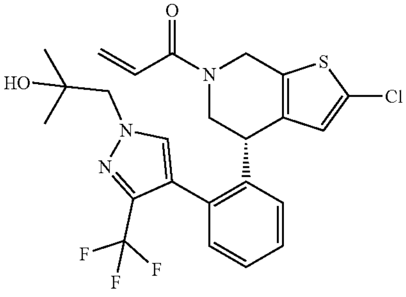 [SMILES: C=CC(=O)N1Cc2sc(Cl)cc2[C@H](c2ccccc2-c2cn(CC(C)(C)O)nc2C(F)(F)F)C1]
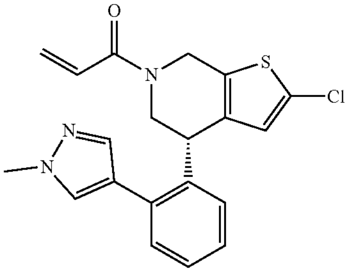 [SMILES: C=CC(=O)N1Cc2sc(Cl)cc2[C@H](c2ccccc2-c2cnn(C)c2)C1]
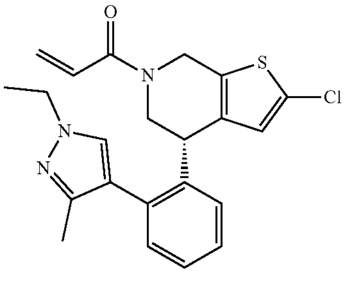
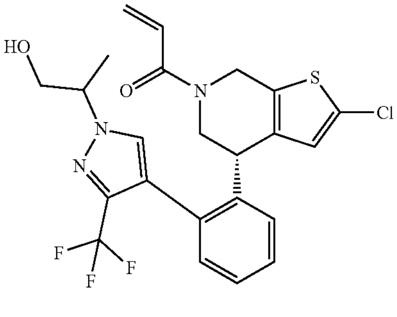 [SMILES: C=CC(=O)N1Cc2sc(Cl)cc2[C@H](c2ccccc2-c2cn(C(C)CO)nc2C(F)(F)F)C1]

-continued
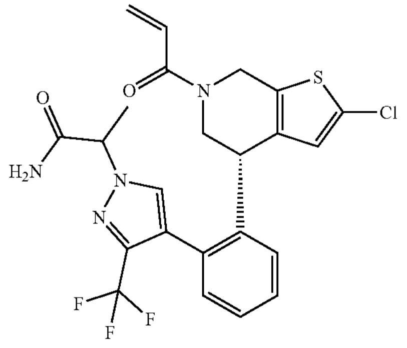 [SMILES: C=CC(=O)N1Cc2sc(Cl)cc2[C@H](c2ccccc2-c2cn(C(C)C(N)=O)nc2C(F)(F)F)C1]
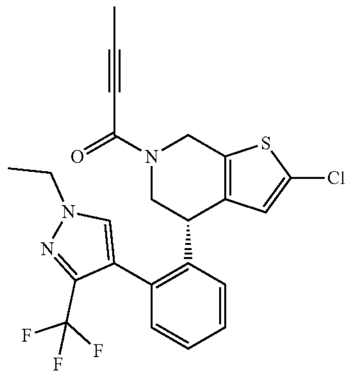 [SMILES: CC#CC(=O)N1Cc2sc(Cl)cc2[C@H](c2ccccc2-c2cn(CC)nc2C(F)(F)F)C1]
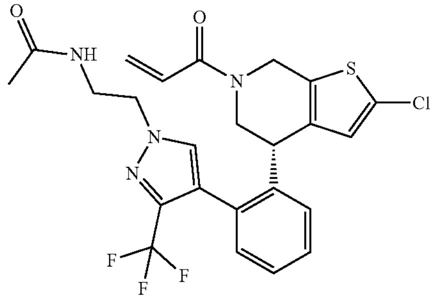 [SMILES: C=CC(=O)N1Cc2sc(Cl)cc2[C@H](c2ccccc2-c2cn(CCNC(C)=O)nc2C(F)(F)F)C1]
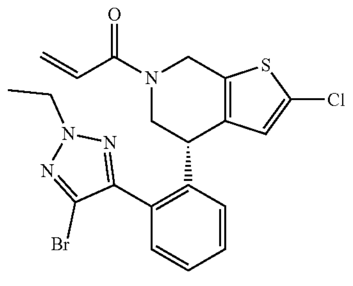
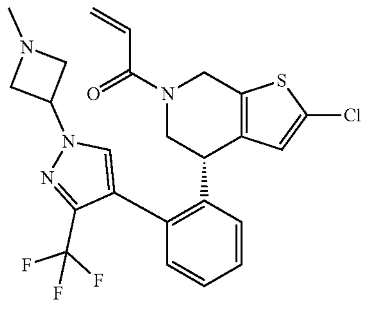 [SMILES: C=CC(=O)N1Cc2sc(Cl)cc2[C@H](c2ccccc2-c2cn(C3CN(C)C3)nc2C(F)(F)F)C1]

-continued
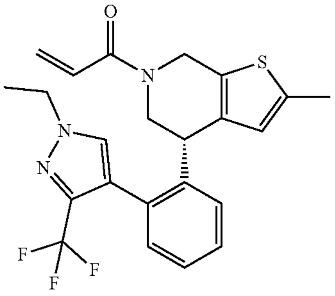 [SMILES: C=CC(=O)N1Cc2sc(C)cc2[C@H](c2ccccc2-c2cn(CC)nc2C(F)(F)F)C1]
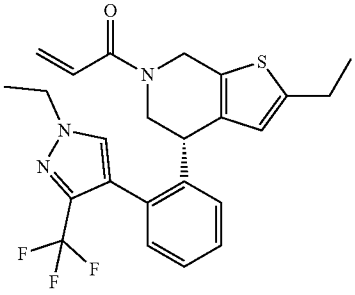 [SMILES: C=CC(=O)N1Cc2sc(CC)cc2[C@H](c2ccccc2-c2cn(CC)nc2C(F)(F)F)C1]
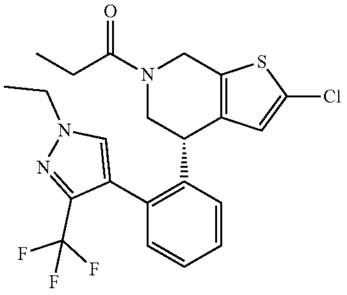
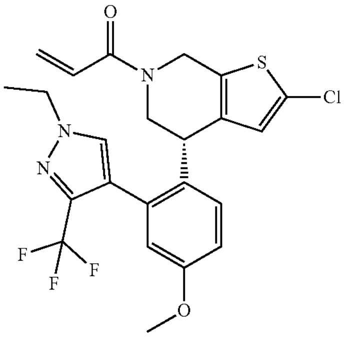 [SMILES: C=CC(=O)N1Cc2sc(Cl)cc2[C@H](c2ccc(OC)cc2-c2cn(CC)nc2C(F)(F)F)C1]
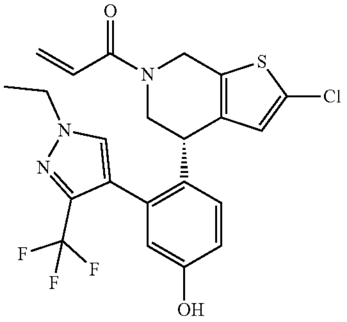

-continued
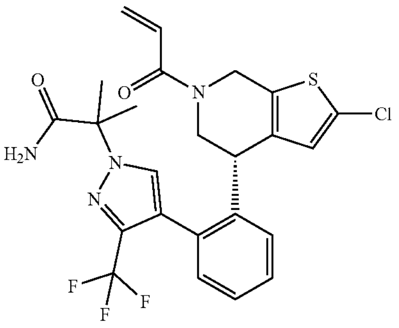 [SMILES: C=CC(=O)N1Cc2sc(Cl)cc2[C@H](c2ccccc2-c2cn(C(C)(C)C(N)=O)nc2C(F)(F)F)C1]
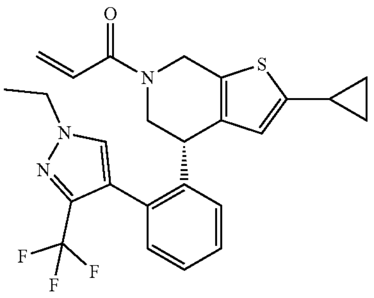 [SMILES: C=CC(=O)N1Cc2sc(C3CC3)cc2[C@H](c2ccccc2-c2cn(CC)nc2C(F)(F)F)C1]
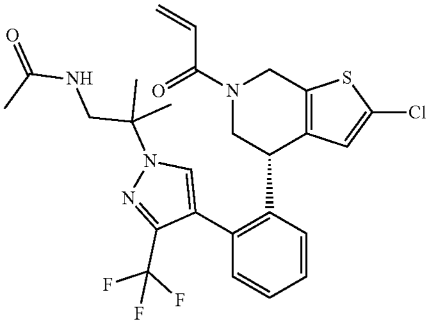 [SMILES: C=CC(=O)N1Cc2sc(Cl)cc2[C@H](c2ccccc2-c2cn(C(C)(C)CNC(C)=O)nc2C(F)(F)F)C1]
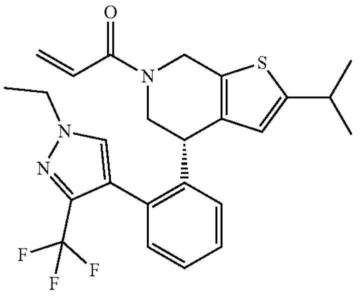 [SMILES: C=CC(=O)N1Cc2sc(C(C)C)cc2[C@H](c2ccccc2-c2cn(CC)nc2C(F)(F)F)C1]
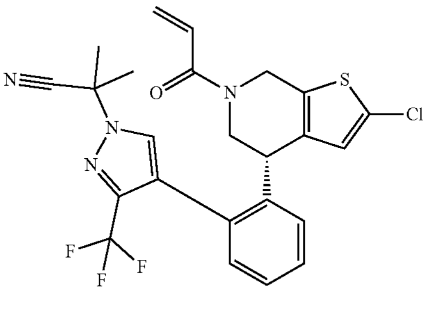 [SMILES: C=CC(=O)N1Cc2sc(Cl)cc2[C@H](c2ccccc2-c2cn(C(C)(C)C#N)nc2C(F)(F)F)C1]

-continued
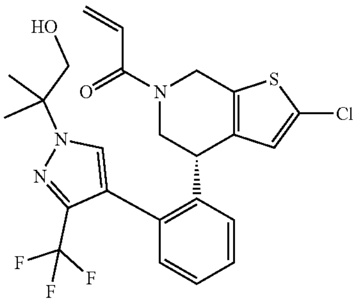 [SMILES: C=CC(=O)N1Cc2sc(Cl)cc2[C@H](c2ccccc2-c2cn(C(C)(C)CO)nc2C(F)(F)F)C1]
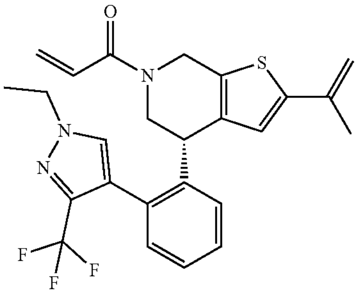 [SMILES: C=CC(=O)N1Cc2sc(C(=C)C)cc2[C@H](c2ccccc2-c2cn(CC)nc2C(F)(F)F)C1]
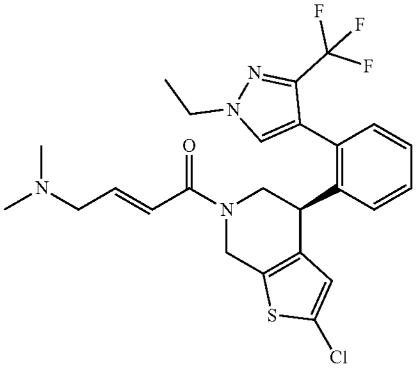 [SMILES: CCn1cc(-c2ccccc2[C@@H]2CN(C(=O)/C=C/CN(C)C)Cc3sc(Cl)cc32)c(C(F)(F)F)n1]
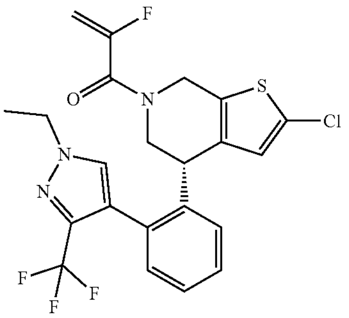 [SMILES: C=C(F)C(=O)N1Cc2sc(Cl)cc2[C@H](c2ccccc2-c2cn(CC)nc2C(F)(F)F)C1]

In one embodiment, the compound is selected from:
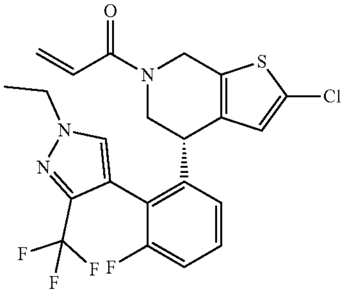
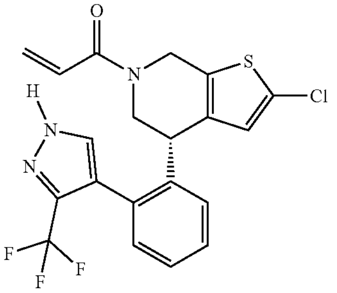 [SMILES: C=CC(=O)N1Cc2sc(Cl)cc2[C@H](c2ccccc2-c2c[nH]nc2C(F)(F)F)C1]
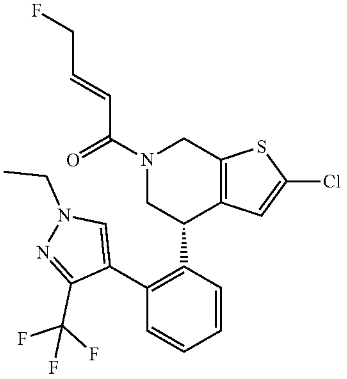 [SMILES: CCn1cc(-c2ccccc2[C@@H]2CN(C(=O)/C=C/CF)Cc3sc(Cl)cc32)c(C(F)(F)F)n1]
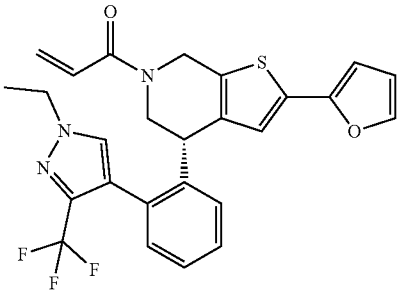 [SMILES: C=CC(=O)N1Cc2sc(-c3ccco3)cc2[C@H](c2ccccc2-c2cn(CC)nc2C(F)(F)F)C1]
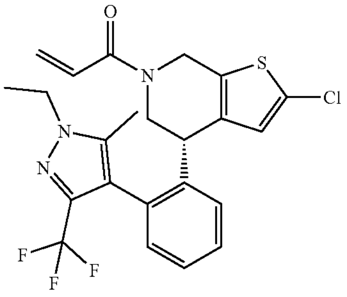
-continued
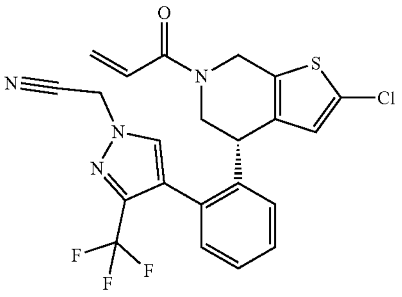 [SMILES: C=CC(=O)N1Cc2sc(Cl)cc2[C@H](c2ccccc2-c2cn(CC#N)nc2C(F)(F)F)C1]
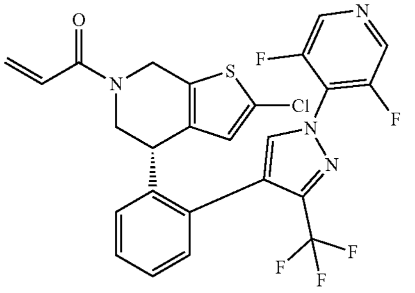 [SMILES: C=CC(=O)N1Cc2sc(Cl)cc2[C@H](c2ccccc2-c2cn(-c3c(F)cncc3F)nc2C(F)(F)F)C1]
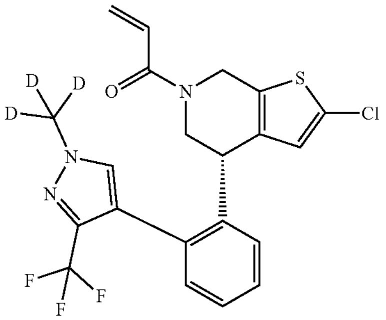 [SMILES: [2H]C([2H])([2H])n1cc(-c2ccccc2[C@@H]2CN(C(=O)C=C)Cc3sc(Cl)cc32)c(C(F)(F)F)n1]
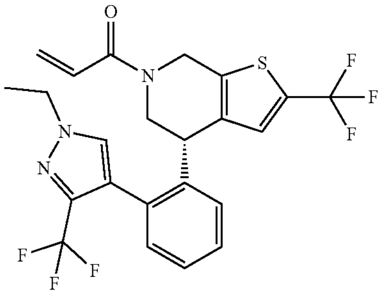 [SMILES: C=CC(=O)N1Cc2sc(C(F)(F)F)cc2[C@H](c2ccccc2-c2cn(CC)nc2C(F)(F)F)C1]
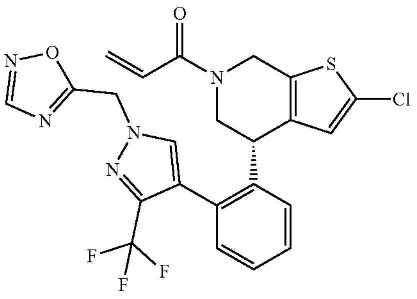 [SMILES: C=CC(=O)N1Cc2sc(Cl)cc2[C@H](c2ccccc2-c2cn(Cc3ncno3)nc2C(F)(F)F)C1]

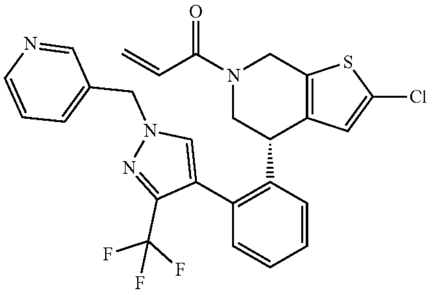 [SMILES: C=CC(=O)N1Cc2sc(Cl)cc2[C@H](c2ccccc2-c2cn(Cc3cccnc3)nc2C(F)(F)F)C1]
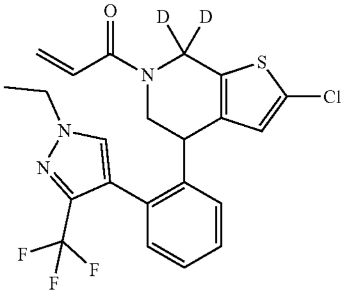
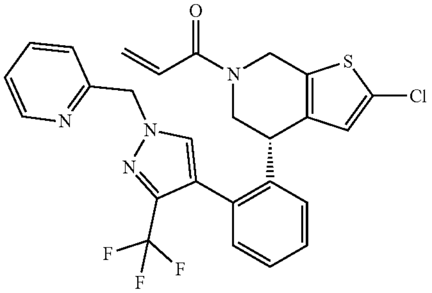 [SMILES: C=CC(=O)N1Cc2sc(Cl)cc2[C@H](c2ccccc2-c2cn(Cc3ccccn3)nc2C(F)(F)F)C1]
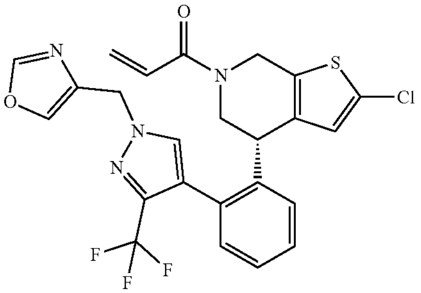 [SMILES: C=CC(=O)N1Cc2sc(Cl)cc2[C@H](c2ccccc2-c2cn(Cc3cocn3)nc2C(F)(F)F)C1]
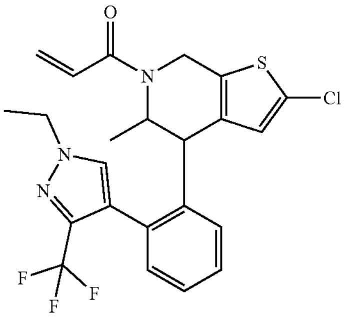 [SMILES: C=CC(=O)N1Cc2sc(Cl)cc2C(c2ccccc2-c2cn(CC)nc2C(F)(F)F)C1C]
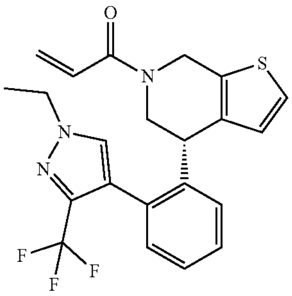 [SMILES: C=CC(=O)N1Cc2sccc2[C@H](c2ccccc2-c2cn(CC)nc2C(F)(F)F)C1]
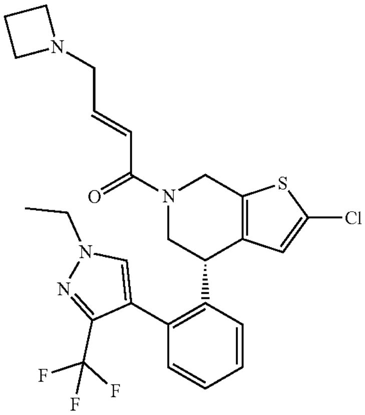 [SMILES: CCn1cc(-c2ccccc2[C@@H]2CN(C(=O)/C=C/CN3CCC3)Cc3sc(Cl)cc32)c(C(F)(F)F)n1]
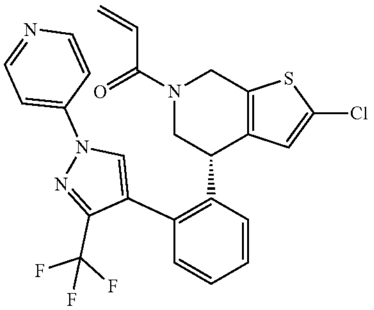 [SMILES: C=CC(=O)N1Cc2sc(Cl)cc2[C@H](c2ccccc2-c2cn(-c3ccncc3)nc2C(F)(F)F)C1]
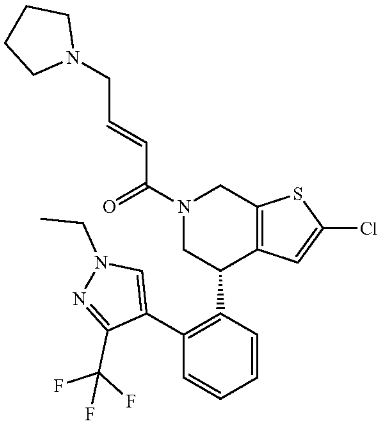 [SMILES: CCn1cc(-c2ccccc2[C@@H]2CN(C(=O)/C=C/CN3CCCC3)Cc3sc(Cl)cc32)c(C(F)(F)F)n1]

-continued
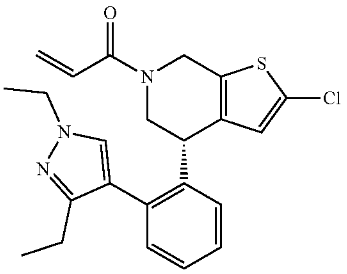
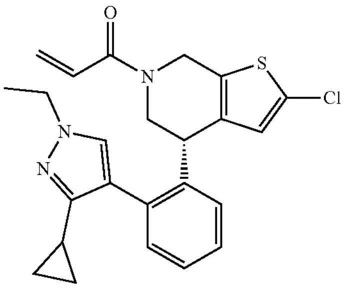 [SMILES: C=CC(=O)N1Cc2sc(Cl)cc2[C@H](c2ccccc2-c2cn(CC)nc2C2CC2)C1]
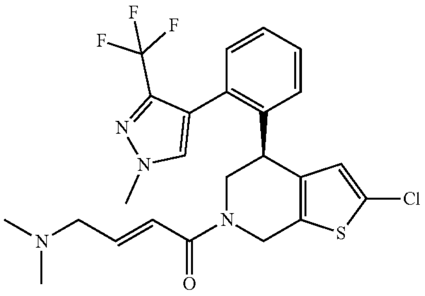 [SMILES: CN(C)C/C=C/C(=O)N1Cc2sc(Cl)cc2[C@H](c2ccccc2-c2cn(C)nc2C(F)(F)F)C1]
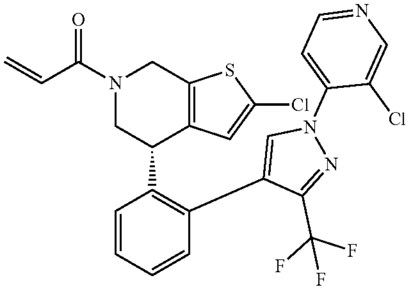 [SMILES: C=CC(=O)N1Cc2sc(Cl)cc2[C@H](c2ccccc2-c2cn(-c3ccncc3Cl)nc2C(F)(F)F)C1]
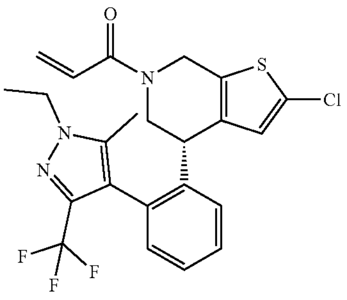 [SMILES: C=CC(=O)N1Cc2sc(Cl)cc2[C@H](c2ccccc2-c2c(C(F)(F)F)nn(CC)c2C)C1]
-continued
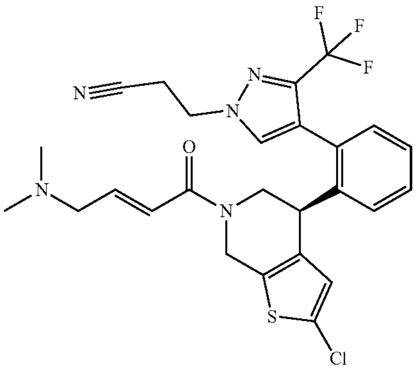 [SMILES: CN(C)C/C=C/C(=O)N1Cc2sc(Cl)cc2[C@H](c2ccccc2-c2cn(CCC#N)nc2C(F)(F)F)C1]
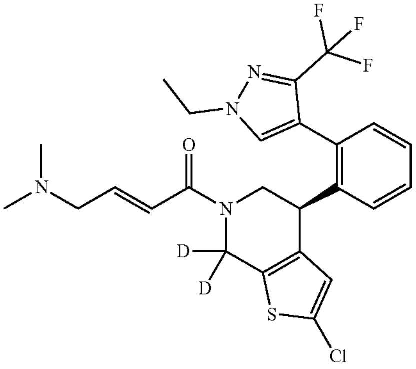 [SMILES: [2H]C1([2H])c2sc(Cl)cc2[C@H](c2ccccc2-c2cn(CC)nc2C(F)(F)F)CN1C(=O)/C=C/CN(C)C]
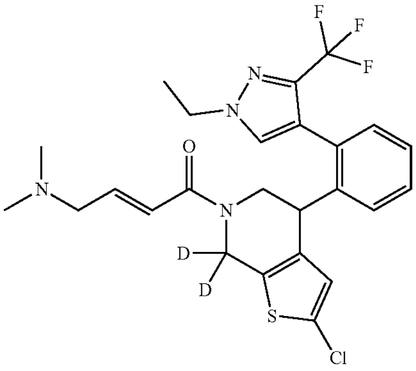 [SMILES: [2H]C1([2H])c2sc(Cl)cc2C(c2ccccc2-c2cn(CC)nc2C(F)(F)F)CN1C(=O)/C=C/CN(C)C]
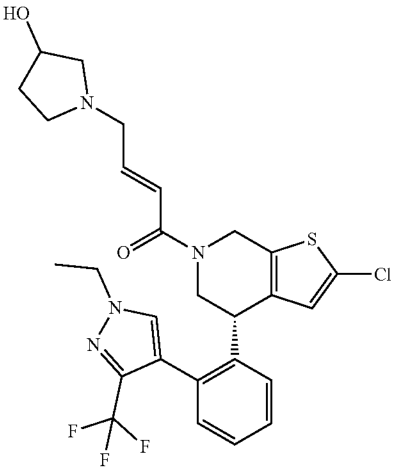 [SMILES: CCn1cc(-c2ccccc2[C@@H]2CN(C(=O)/C=C/CN3CCC(O)C3)Cc3sc(Cl)cc32)c(C(F)(F)F)n1]

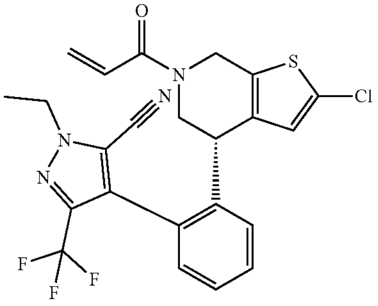 [SMILES: C=CC(=O)N1Cc2sc(Cl)cc2[C@H](c2ccccc2-c2c(C(F)(F)F)nn(CC)c2C#N)C1]
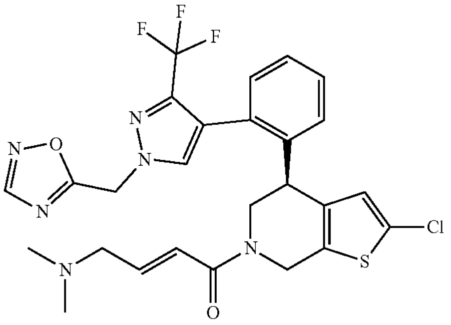 [SMILES: CN(C)C/C=C/C(=O)N1Cc2sc(Cl)cc2[C@H](c2ccccc2-c2cn(Cc3ncno3)nc2C(F)(F)F)C1]
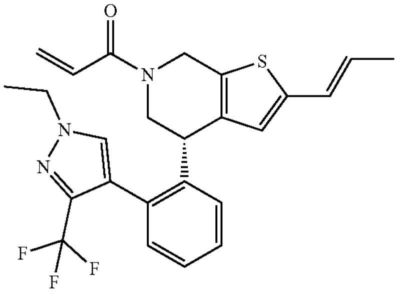 [SMILES: C=CC(=O)N1Cc2sc(/C=C/C)cc2[C@H](c2ccccc2-c2cn(CC)nc2C(F)(F)F)C1]
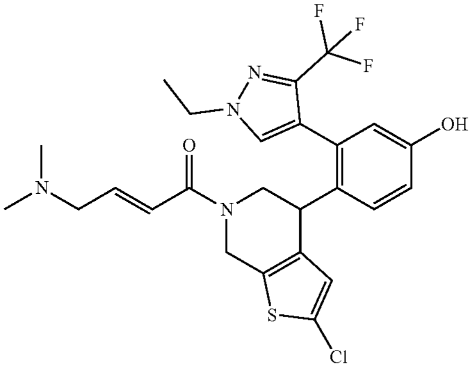 [SMILES: CCn1cc(-c2cc(O)ccc2C2CN(C(=O)/C=C/CN(C)C)Cc3sc(Cl)cc32)c(C(F)(F)F)n1]
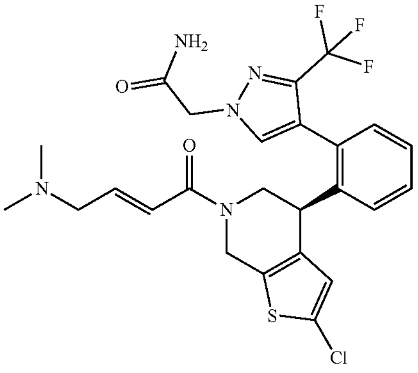 [SMILES: CN(C)C/C=C/C(=O)N1Cc2sc(Cl)cc2[C@H](c2ccccc2-c2cn(CC(N)=O)nc2C(F)(F)F)C1]
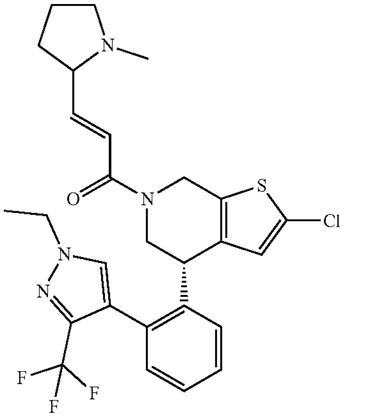 [SMILES: CCn1cc(-c2ccccc2[C@@H]2CN(C(=O)/C=C/C3CCCN3C)Cc3sc(Cl)cc32)c(C(F)(F)F)n1]
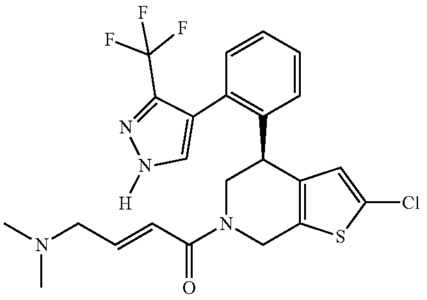 [SMILES: CN(C)C/C=C/C(=O)N1Cc2sc(Cl)cc2[C@H](c2ccccc2-c2c[nH]nc2C(F)(F)F)C1]
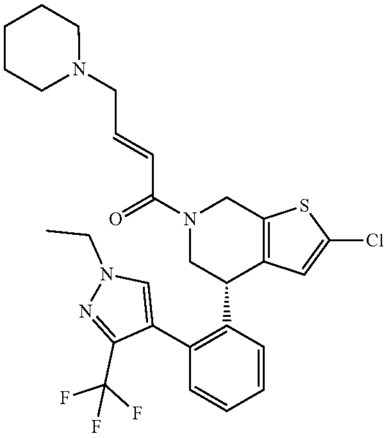 [SMILES: CCn1cc(-c2ccccc2[C@@H]2CN(C(=O)/C=C/CN3CCCCC3)Cc3sc(Cl)cc32)c(C(F)(F)F)n1]

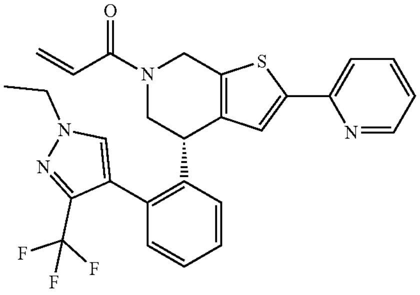 [SMILES: C=CC(=O)N1Cc2sc(-c3ccccn3)cc2[C@H](c2ccccc2-c2cn(CC)nc2C(F)(F)F)C1]
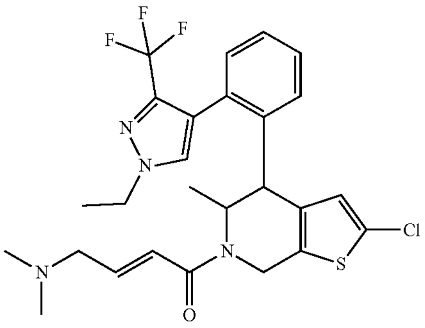 [SMILES: CCn1cc(-c2ccccc2C2c3cc(Cl)sc3CN(C(=O)/C=C/CN(C)C)C2C)c(C(F)(F)F)n1]
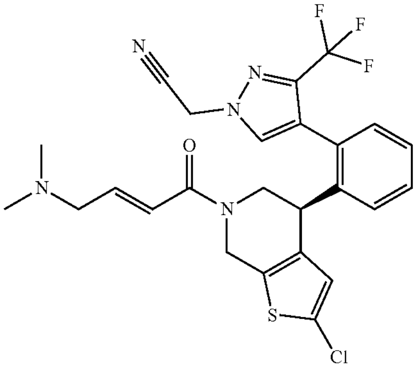 [SMILES: CN(C)C/C=C/C(=O)N1Cc2sc(Cl)cc2[C@H](c2ccccc2-c2cn(CC#N)nc2C(F)(F)F)C1]
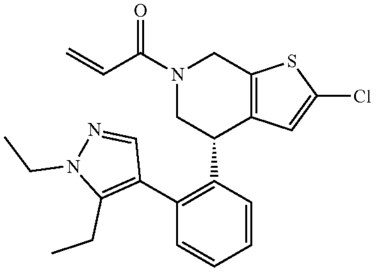 [SMILES: C=CC(=O)N1Cc2sc(Cl)cc2[C@H](c2ccccc2-c2cnn(CC)c2CC)C1]
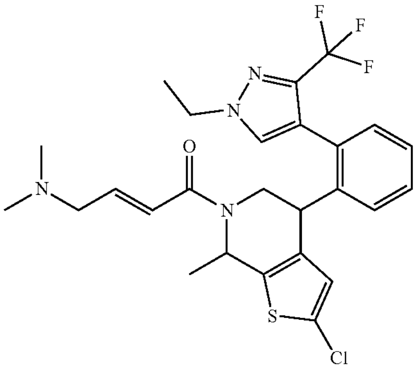 [SMILES: CCn1cc(-c2ccccc2C2CN(C(=O)/C=C/CN(C)C)C(C)c3sc(Cl)cc32)c(C(F)(F)F)n1]
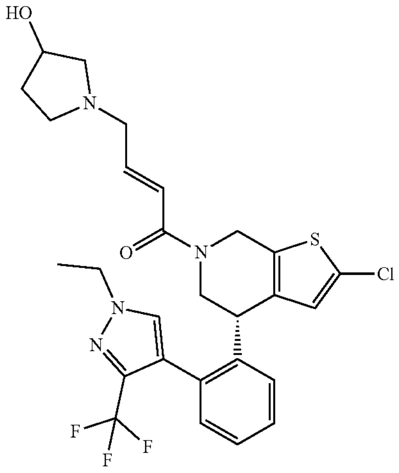 [SMILES: CCn1cc(-c2ccccc2[C@@H]2CN(C(=O)/C=C/CN3CCC(O)C3)Cc3sc(Cl)cc32)c(C(F)(F)F)n1]
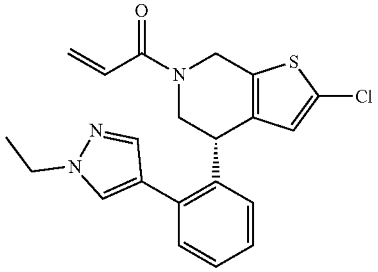 [SMILES: C=CC(=O)N1Cc2sc(Cl)cc2[C@H](c2ccccc2-c2cnn(CC)c2)C1]
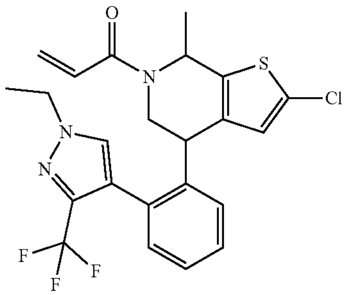 [SMILES: C=CC(=O)N1CC(c2ccccc2-c2cn(CC)nc2C(F)(F)F)c2cc(Cl)sc2C1C]
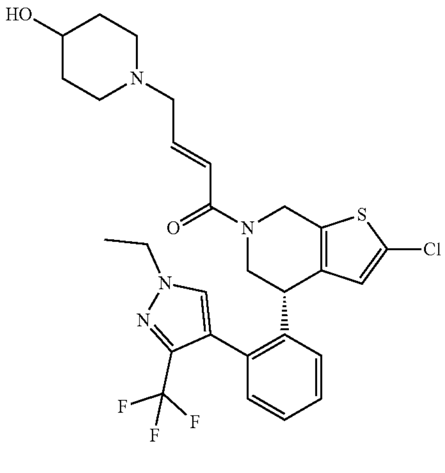 [SMILES: CCn1cc(-c2ccccc2[C@@H]2CN(C(=O)/C=C/CN3CCC(O)CC3)Cc3sc(Cl)cc32)c(C(F)(F)F)n1]

-continued
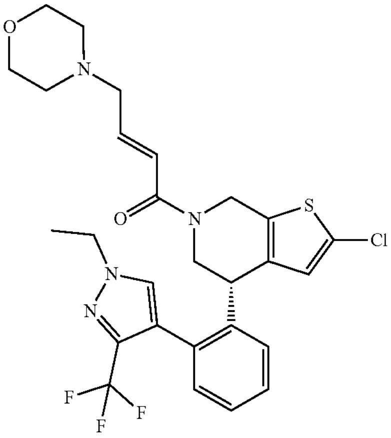 [SMILES: CCn1cc(-c2ccccc2[C@@H]2CN(C(=O)/C=C/CN3CCOCC3)Cc3sc(Cl)cc32)c(C(F)(F)F)n1]
In one embodiment, the compound is selected from
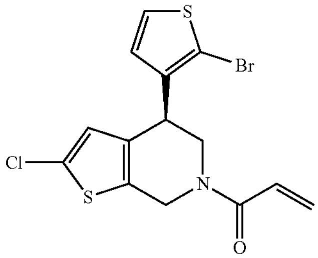
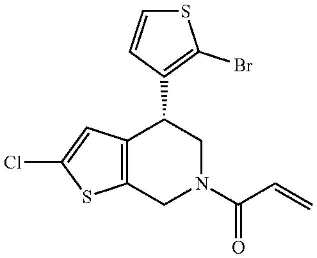
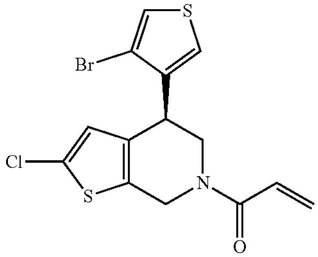
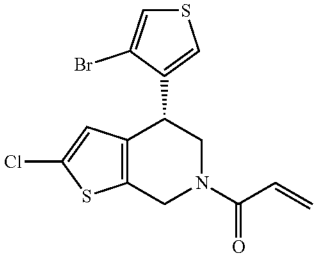
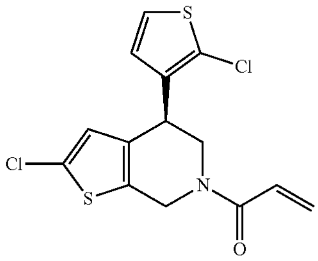
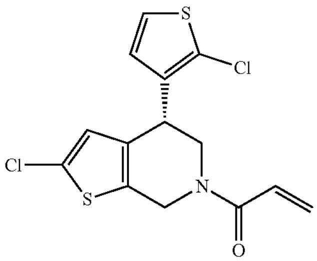
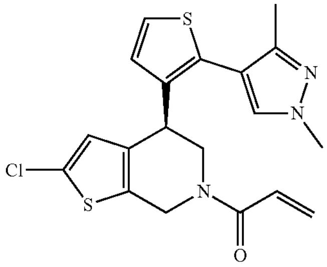
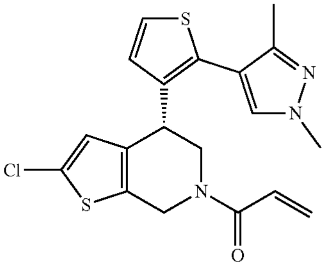

-continued
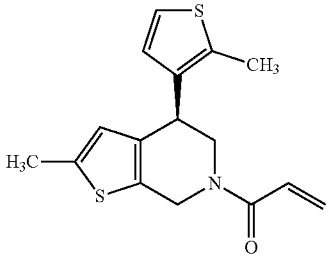
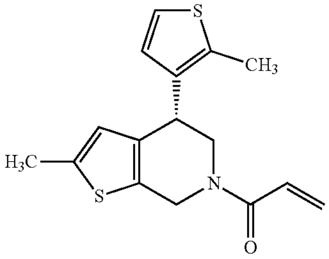
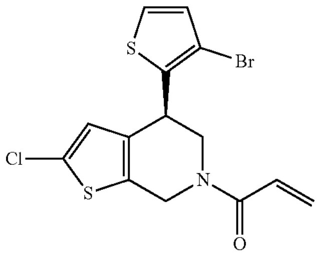
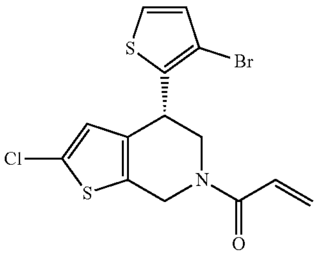
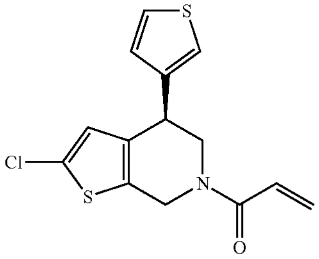
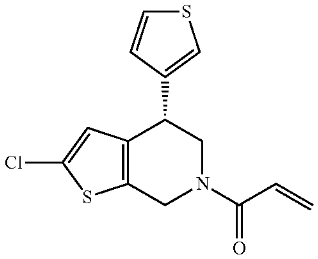
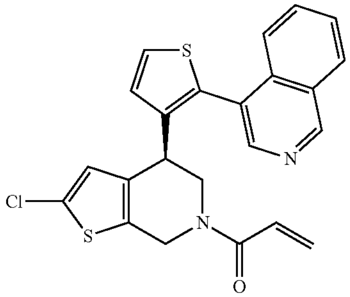
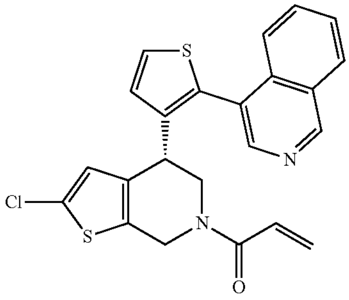
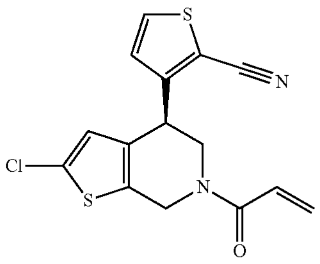
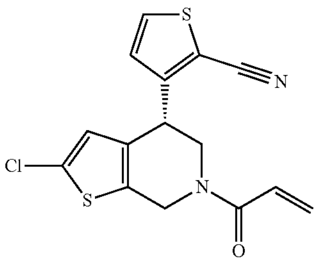
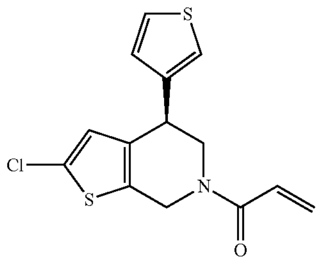
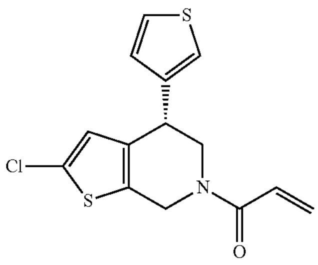

-continued
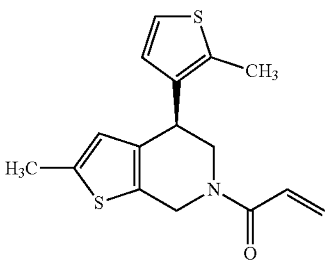
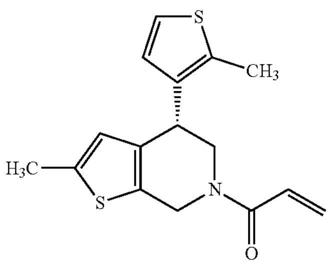
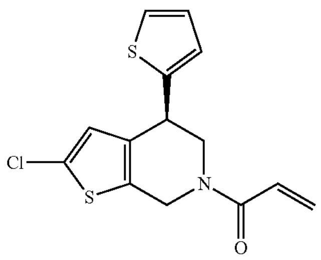
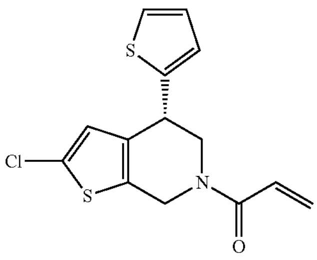
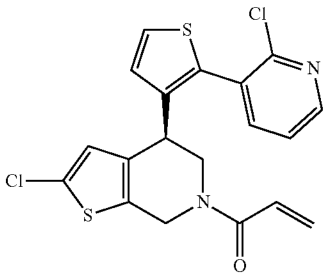
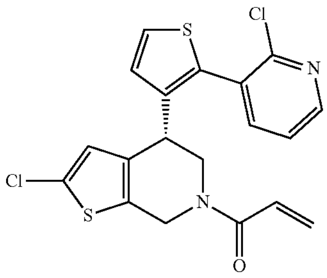
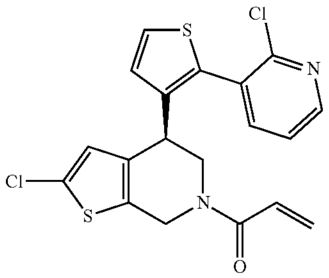
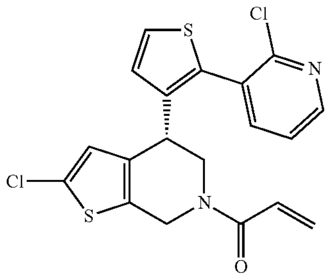
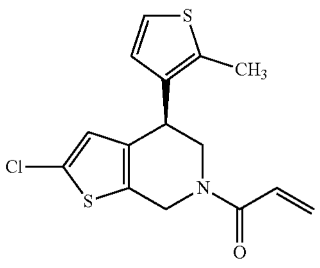
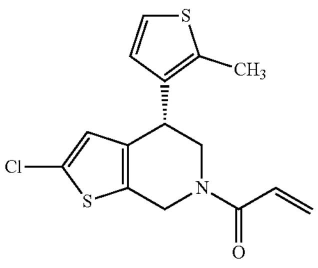

In some embodiments, the compound is covalently attached to an E1 cysteine amino acid corresponding to Cys30 of Uba2 subunit 2. In embodiments, E contains an electrophilic moiety. In embodiments, the electron-withdrawing moieties are sufficiently electron withdrawing to allow the compound to covalently bind to an E1 cysteine amino acid corresponding to Cys30 of Uba2 subunit 2.

Method of Inhibition

In embodiments, the compounds of Formulas XI-XV covalently bind to an E1 cysteine amino acid corresponding to Cys30 of Uba2 subunit 2.

In embodiments, the method includes allowing the compound to covalently bind an E1 enzyme. In embodiments, the method includes allowing the compound to covalently bind an E1 cysteine amino acid corresponding to Cys30 of Uba2 subunit 2.

In an aspect is provided a method of inhibiting cell proliferation, the method including contacting the cell with a compound described herein. In embodiments, the method includes contacting the cell with an effective amount of the compound. In embodiments, the compound is administered at a rate approximately equal to the half-life of an E1 enzyme.

In an aspect is provided a method of inhibiting an E1 enzyme, the method including contacting an E1 enzyme with a compound described herein, thereby inhibiting the E1 enzyme. In embodiments, the method includes allowing the compound to covalently bind the E1 enzyme. In embodiments, the method includes allowing the compound to covalently bind an E1 cysteine amino acid corresponding to Cys30 of Uba2 subunit 2.

In an aspect is provided a pharmaceutical composition including a compound described herein, or pharmaceutically acceptable salt thereof, and a pharmaceutically acceptable excipient.

In an aspect is provided a method of treating cancer, the method including administering to a subject in need thereof an effective amount of a compound described herein.

In an aspect is provided a method of inhibiting cell proliferation, the method including contacting the cell with a compound described herein.

Definitions

The abbreviations used herein have their conventional meaning within the chemical and biological arts. The chemical structures and formulae set forth herein are constructed according to the standard rules of chemical valency known in the chemical arts.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds referred to as "alkenyl" or "alkynyl" groups. Examples of unsaturated alkyl groups or alkenyl or alkynyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, $—CH_2CH_2CH_2CH_2$. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, S, B, As, or Si), and wherein the nitrogen and sulfur atoms may optionally be oxidized, and the nitrogen heteroatom may optionally be quaternized. The heteroatom(s) (e.g., O, N, P, S, B, As, or Si) may be placed at any interior position of the heteroalkyl group or at the position at which the alkyl group is attached to the remainder of the molecule. Heteroalkyl is an uncyclized chain. Examples include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2$, $—S(O)—CH_3$, $—CH_2—CH_2—S(O)_2—CH_3$, $—CH{=}CH—O—CH_3$, $—Si(CH_3)_3$, $—CH_2—CH{=}N—OCH_3$, $—CH{=}CH—N(CH_3)—CH_3$, $—O—CH_3$, $—O—CH_2—CH_3$, and —CN. Up to two or three heteroatoms may be consecutive, such as, for example, $—CH_2—NH—OCH_3$ and $—CH_2—O—Si(CH_3)_3$.

Similarly, the term "heteroalkylene," by itself or as part of another substituent, means, unless otherwise stated, a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$. As described above, heteroalkyl groups, as used herein, include those groups that are attached to the remainder of the molecule through a heteroatom, such as —C(O)R', —C(O)NR', —NR'R", —OR', —SR', and/or $—SO_2R'$.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A heteroaryl group can be attached to the remainder of the molecule through a carbon or heteroatom. An "arylene" and a "heteroarylene," alone or as part of another substituent, mean a divalent radical derived from an aryl and heteroaryl, respectively.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "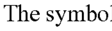" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

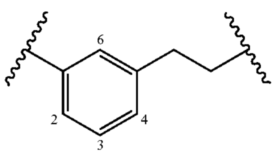

or

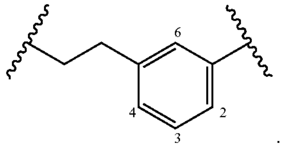

.

Each of the above terms (e.g., "alkyl," "heteroalkyl," "cycloalkyl," "heterocycloalkyl," "aryl," and "heteroaryl") includes both substituted and unsubstituted forms of the indicated radical.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R'', —SR', -halogen, —SiR'R''R''', —OC(O)R', —C(O)R', —$CO_2$R', —CONR'R'', —OC(O)NR'R'', —NR''C(O)R', —NR'—C(O)NR''R''', —NR''C(O)$_2$R', —NR—C(NR'R''R''')=NR'''', —NR—C(NR'R'')=NR''', —S(O)R', —S(O)$_2$R', —S(O)$_2$NR'R'', —NRSO$_2$R', —NRNR''R''', —ONR'R'', —NR'C(O)NR''NR'''R'''', —CN, —$NO_2$, —NR'SO$_2$R'', —NR'C(O)R'', —NR'C(O)—OR'', —NR'OR'', in a number ranging from zero to (2m'+1), where m' is the total number of carbon atoms in such radical. R, R', R'', R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R'', R''', and R'''' group when more than one of these groups is present. When R' and R'' are attached to the same nitrogen atom, they can be combined with the nitrogen atom to form a 4-, 5-, 6-, or 7-membered ring. For example, —NR'R'' includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R'', —SR', -halogen, —SiR'R''R''', —OC(O)R', —C(O)R', —$CO_2$R', —CONR'R'', —OC(O)NR'R'', —NR''C(O)R', —NR'—C(O)NR''R''', —NR''C(O)$_2$R', —NR—C(NR'R''R''')=NR'''', —NR—C(NR'R'')=NR''', —S(O)R', —S(O)$_2$R', —S(O)$_2$NR'R'', —NRSO$_2$R', —NR'NR''R''', —ONR'R'', —NR'C(O)NR''NR'''R'''', —CN, —$NO_2$, —R', —$N_3$, —CH(Ph)$_2$, fluoro($C_1$-$C_4$)alkoxy, fluoro($C_1$-$C_4$)alkyl, —NR'SO$_2$R'', —NR'C(O)R'', —NR'C(O)—OR'', —NR'OR'', in a number ranging from zero to the total number of open valences on the aromatic ring system; and where R', R'', R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R'', R''', and R'''' groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

As used herein, the terms "heteroatom" or "ring heteroatom" are meant to include oxygen (O), nitrogen (N), sulfur (S), phosphorus (P), Boron (B), and silicon (Si).

A "substituent group," as used herein, means a group selected from the following moieties:

(A) halogen, oxo, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2F$, $—OCH_2I$, $—N_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered), and (B) alkyl (e.g., $C_1$-$C_{20}$, $C_1$-$C_{12}$, $C_1$-$C_8$, $C_1$-$C_6$, $C_1$-$C_4$, or $C_1$-$C_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., $C_3$-$C_{10}$, $C_3$-$C_8$, $C_3$-$C_6$, $C_4$-$C_6$, or $C_5$-$C_6$), heterocycloalkyl (e.g., 3 to 10 membered, 3 to 8 membered, 3 to 6 membered, 4 to 6 membered, 4 to 5 membered, or 5 to 6 membered), aryl (e.g., $C_6$-$C_{12}$, $C_6$-$C_{10}$, or phenyl), or heteroaryl (e.g., 5 to 12 membered, 5 to 10 membered, 5 to 9 membered, or 5 to 6 membered), substituted with at least one substituent selected from:

(i) oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2F$, $—OCH_2I$, $—N_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered), and (ii) alkyl (e.g., $C_1$-$C_{20}$, $C_1$-$C_{12}$, $C_1$-$C_8$, $C_1$-$C_6$, $C_1$-$C_4$, or $C_1$-$C_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., $C_3$-$C_{10}$, $C_3$-$C_8$, $C_3$-$C_6$, $C_4$-$C_6$, or $C_5$-$C_6$), heterocycloalkyl (e.g., 3 to 10 membered, 3 to 8 membered, 3 to 6 membered, 4 to 6 membered, 4 to 5 membered, or 5 to 6 membered), aryl (e.g., $C_6$-$C_{12}$, $C_6$-$C_{10}$, or phenyl), or heteroaryl (e.g., 5 to 12 membered, 5 to 10 membered, 5 to 9 membered, or 5 to 6 membered), substituted with at least one substituent selected from:

(a) oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2F$, $—OCH_2I$, $—N_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered), and (b) alkyl (e.g., $C_1$-$C_{20}$, $C_1$-$C_{12}$, $C_1$-$C_8$, $C_1$-$C_6$, $C_1$-$C_4$, or $C_1$-$C_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., $C_3$-$C_{10}$, $C_3$-$C_8$, $C_3$-$C_6$, $C_4$-$C_6$, or $C_5$-$C_6$), heterocycloalkyl (e.g., 3 to 10 membered, 3 to 8 membered, 3 to 6 membered, 4 to 6 membered, 4 to 5 membered, or 5 to 6 membered), aryl (e.g., $C_6$-$C_{12}$, $C_6$-$C_{10}$, or phenyl), or heteroaryl (e.g., 5 to 12 membered, 5 to 10 membered, 5 to 9 membered, or 5 to 6 membered), substituted with at least one substituent selected from: oxo, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, —NHC(O)H, —NHC(O)OH, —NHOH, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2F$, $-OCH_2I$, $-N_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or"lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be, a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. As used herein and unless otherwise indicated, the term "stereoisomer" or"stereomerically pure" means one stereoisomer of a compound that is substantially free of other stereoisomers of that compound. For example, a stereomerically pure compound having one chiral center will be substantially free of the mirror image enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed. This is not to be confused with a wavy line drawn perpendicular to a bond which indicates the point of attachment of a group to the rest of the molecule. As described above, this invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al. (1997) Tetrahedron 33:2725; Eliel, E. L., Stereochemistry of Carbon Compounds (McGraw-Hill, NY, 1962); and Wilen, S. H., Tables of Resolving Agents and Optical Resolutions p. 268 (E. L. Eliel, Ed., Univ. of Notre Dame Press, Notre Dame, IN, 1972).

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this is selected from invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (XV)), a Roman alphabetic symbol may be used to distinguish each appearance of that particular R group.

The term "pharmaceutically acceptable salts" is meant to include salts of the active compounds that are prepared with relatively nontoxic acids or bases, depending on the particular substituents found on the compounds described herein. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

The terms "disease" or "condition" refer to a state of being or health status of a patient or subject capable of being treated with the compounds or methods provided herein. The disease may be a cancer. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma. As used herein, the term "cancer" refers to all types of cancer, neoplasm or malignant tumors found in mammals (e.g. humans), including leukemia, carcinomas and sarcomas. The term "leukemia" refers broadly to progressive, malignant diseases of the blood-forming organs and is generally characterized by a distorted proliferation and development of leukocytes and their precursors in the blood and bone marrow. The term "sarcoma" generally refers to a tumor which is made up of a substance like the embryonic connective tissue and is generally composed of closely packed cells embedded in a fibrillar or homogeneous substance. The term "melanoma" is taken to mean a tumor arising from the melanocytic system of the skin and other organs.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, Dosage Calculations (1999); and *Remington: The Science and Practice of Pharmacy,* 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

"Co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulator" refers to a composition that increases or decreases the level of a target molecule or the function of a target molecule or the physical state of the target of the molecule.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of a substance or substance activity or function associated with a disease (e.g. a protein associated disease) means that the disease (e.g. cancer) is caused by (in whole or in part), or a symptom of the disease is caused by (in whole or in part) the substance or substance activity or function.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extra-cellular components (e.g. proteins, nucleic acids, small molecules, ions, lipids) that conveys a change in one component to one or more other components, which in turn may convey a change to additional components, which is optionally propogated to other signaling pathway components.

The present invention comprises a method of treating cancer with a therapeutically effective amount of a compound of any of Formulas XI-XV. In some embodiments the cancer is selected from acute myeloid leukemia, large B-cell lymphoma, lung squamous cell carcinoma, pancreatic adenocarcoma, esophegeal carcinoma, cervical squamous cell carcinoma, endocervical adenocarcoma, stomach adenocarcinomathymoma, renal cell carcinoma, head and neck squamous cell carcinoma, bladder carcinoma, ovarian cystadenocarcinoma and mesothelioma.

In certain embodiments, a compound of any of Formulas XI-XV is administered at a rate approximately equal to the half-life of an E1 enzyme.

The present invention comprises a method of treating cancer with a therapeutically-effective amount of a compound of any of Formulas XI-XV.

The present invention comprises a method of inhibiting E1 with a therapeutically-effective amount of a compound of any of Formulas XI-XV.

In embodiments, the compound is covalently attached to an E1 cysteine amino acid corresponding to Cys30 of Uba2 subunit 2. In embodiments, E contains an electrophilic moiety. In embodiments, the electron-withdrawing moieties are sufficiently electron withdrawing to allow the compound to covalently bind to an E1 cysteine amino acid corresponding to Cys30 of Uba2 subunit 2.

In a certain embodiment, the method includes allowing the compound to covalently bind an E1 enzyme.

In embodiments, the method includes allowing the compound to covalently bind an E1 cysteine amino acid corresponding to Cys30 of Uba2 subunit 2. In embodiments, the method includes allowing the E1 cysteine amino acid to bind to carbon attached to R" and $R^{18}$.

In an aspect is provided a method of inhibiting cell proliferation, the method including contacting the cell with a compound described herein. In embodiments, the method includes contacting the cell with an effective amount of the compound. In embodiments, the compound is administered at a rate approximately equal to the half-life of an E1 enzyme.

In an aspect is provided a method of inhibiting an E1 enzyme, the method including contacting an E1 enzyme with a compound described herein, thereby inhibiting the E1 enzyme. In embodiments, the method includes allowing the compound to covalently bind the E1 enzyme. In embodiments, the method includes allowing the compound to covalently bind an E1 cysteine amino acid corresponding to Cys30 of Uba2 subunit 2. In embodiments, the method includes allowing the E1 cysteine amino acid to bind to carbon attached to R" and $R^{19}$.

GENERAL SYNTHETIC SCHEMES

The compounds of this invention can be synthesized according to the procedures described in WO2020/191151. In addition, the compounds of this invention can be synthesized according to the following procedure of Scheme I, wherein the substituents are as defined for Formulas XI-XV, above, except where further noted.

Scheme I

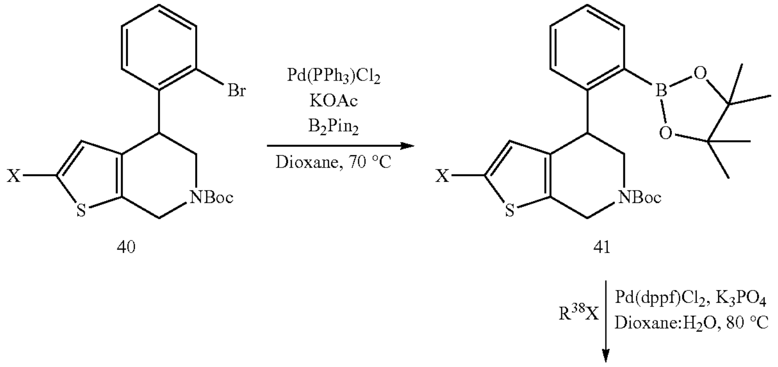

40

41

-continued

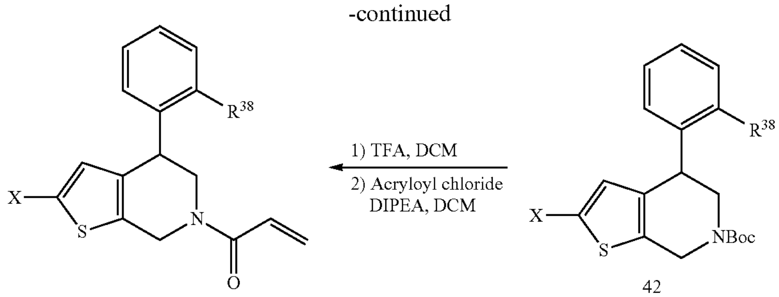

43 42

The compounds of the invention can also be synthesized according to Scheme I. In step A, bromo compound 40 is converted to the boronic ether 41. Coupling with the halide, such as in the presence of Pd(dppf)$Cl_2$ gives compound 42. Compound 42 is deprotected and acylated, such as with acryloyl chloride to provide the desired compounds 43.

The following examples contain detailed descriptions of the methods of preparation of compounds of Formulas XI-XV. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated.

EXAMPLES

Comparative Example 1

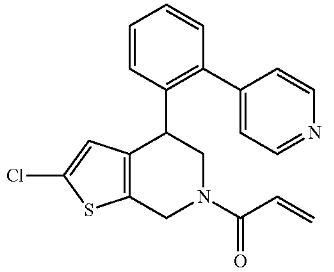 [SMILES: C=CC(=O)N1Cc2sc(Cl)cc2C(c2ccccc2-c2ccncc2)C1]

1-(2-chloro-4-(2-(pyridin-4-yl)phenyl)-4,7-dihydrothieno[2,3-c]pyridin-6(5H)-yl)prop-2-en-1-one

Step A—Preparation of (E)-1-(2-bromophenyl)-2-(((5-chlorothiophen-2-yl)methylene)amino)ethan-1-ol

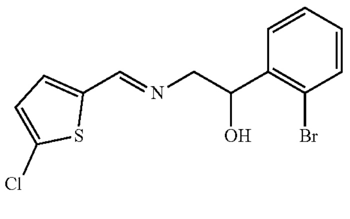 [SMILES: OC(C/N=C/c1ccc(Cl)s1)c1ccccc1Br]

2-Amino-1-(2-bromophenyl)ethan-1-ol (5 g, 23 mmol), 5-chlorothiophene-2-carbaldehyde (4 g, 27 mmol), $MgSO_4$ (11 g, 92 mmol) were mixed in dichloromethane and heated at 50° C. for 3 hours under argon. The mixture was filtered and the filtrate was concentrated in vacuo to give a crude compound.

Step B—Preparation of 1-(2-bromophenyl)-2-(((5-chlorothiophen-2-yl)methyl)amino)ethan-1-ol

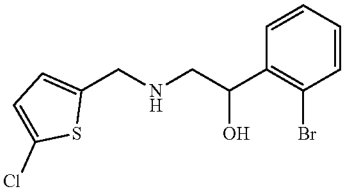 [SMILES: OC(CNCc1ccc(Cl)s1)c1ccccc1Br]

Crude (E)-1-(2-bromophenyl)-2-(((5-chlorothiophen-2-yl)methylene)amino)ethan-1-ol (23 mmol) was dissolved in methanol (50 mL), then sodium borohydride (870 mg, 23 mmol) was added and the mixture was left at room temperature for 30 min. After removal of the solvent, the mixture was partitioned between ethyl acetate (100 mL) and saturated $NaHCO_3$ solution (100 mL, aq.). The organic phase was dried over $MgSO_4$, then concentrated. Flash chromatography on silica gel yielded 6 g (17.3 mmol, 75% two steps) of the title compound as white solid. MS (ES+): 345.7, 347.7 (M+H).

Step C—Preparation of 4-(2-bromophenyl)-2-chloro-4,5,6,7-tetrahydrothieno[2,3-c]pyridine

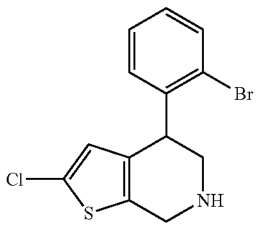 [SMILES: Clc1cc2c(s1)CNCC2c1ccccc1Br]

1-(2-Bromophenyl)-2-(((5-chlorothiophen-2-yl)methyl)amino)ethan-1-ol (6 g, 17.3 mmol) was mixed with methanesulfonic acid (11.6 g, 120 mmol) and the mixture was heated at 95° C. for 2 h. The mixture was cooled to 0° C. and quenched with saturated sodium bicarbonate aqueous solution saturated until pH>8. The mixture was extracted with ethyl acetate. The organic layer was dried with anhydrous magnesium sulfate, then concentrated in vacuo. The mixture was purified with silica gel flash chromatography to give 1.7 g (5.2 mmol, 30%) of the desired compound. MS (ES+): 327.7, 329.7 (M+H).

Step D—Preparation of tert-butyl 4-(2-bromophenyl)-2-chloro-4,7-dihydrothieno[2,3-c]pyridine-6(5H)-carboxylate

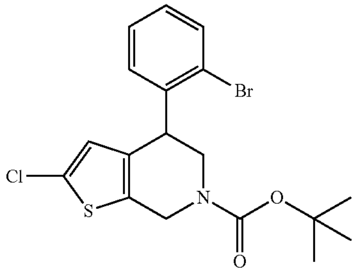 [SMILES: CC(C)(C)OC(=O)N1Cc2sc(Cl)cc2C(c2ccccc2Br)C1]

4-(2-Bromophenyl)-2-chloro-4,5,6,7-tetrahydrothieno[2,3-c]pyridine (1.7 g, 5.2 mmol) was mixed with Boc anhydride (4.9 g, 22.4 mol) and triethylamine (1.6 g, 15.5 mmol) in dichloromethane (100 mL). The mixture was stirred under argon overnight, then concentrated in vacuo. Silica gel flash chromatography was performed to isolate 2 g (4.7 mmol, 89%) of the desired compound.

Step E—Preparation of tert-butyl 2-chloro-4-(2-(pyridin-4-yl)phenyl)-4,7-dihydrothieno[2,3-c]pyridine-6(5H)-carboxylate

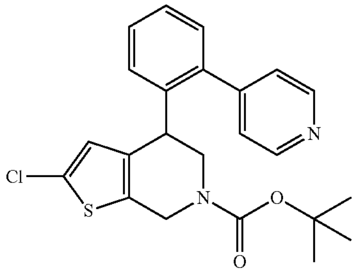 [SMILES: CC(C)(C)OC(=O)N1Cc2sc(Cl)cc2C(c2ccccc2-c2ccncc2)C1]

tert-Butyl 4-(2-bromophenyl)-2-chloro-4,7-dihydrothieno[2,3-c]pyridine-6(5H)-carboxylate (428 mg, 1 mmol), pyridin-4-ylboronic acid (135 mg, 1.1 mmol), $K_3PO_4$ (700 mg, 3.3 mmol) and PdCl2(dppf) (74 mg, 0.1 mmol) were mixed in dioxane (15 mL) and water (5 mL) and the mixture was heated at 80° C. under argon overnight. Silica gel flash chromatography was performed to isolate 140 mg (0.33 mmol, 33%) of the desired compound.

Step F—Preparation of 2-chloro-4-(2-(pyridin-4-yl)phenyl)-4,5,6,7-tetrahydrothieno[2,3-c]pyridine

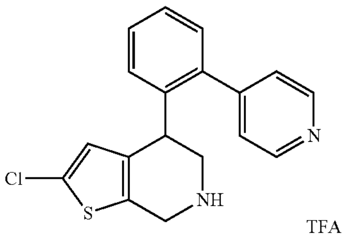 [SMILES: Clc1cc2c(s1)CNCC2c1ccccc1-c1ccncc1]

TFA tert-Butyl 2-chloro-4-(2-(pyridin-4-yl)phenyl)-4,7-dihydrothieno[2,3-c]pyridine-6(5H)-carboxylate (140 mg, 0.33 mmol), was dissolved in 10 mL dichloromethane, then 4 mL TFA was added and the mixture was stirred at room temperature for 10 min. The mixture was concentrated under high vacuum and the resulting crude compound was used directly for next step.

Step G—Preparation of 1-(2-chloro-4-(2-(pyridin-4-yl)phenyl)-4,7-dihydrothieno[2,3-c]pyridin-6(5H)-yl)prop-2-en-1-one To a mixture of 2-chloro-4-(2-(pyridin-4-yl)phenyl)-4,5,6,7-tetrahydrothieno[2,3-c]pyridine TFA salt (40 mg, 0.09 mmol), N,N-diisopropylethylamine (35 mg, 0.27 mmol) in dichloromethane (10 mL) was added acryloyl chloride (8 mg, 0.09 mmol). After 5 min, the mixture was quenched with saturated sodium bicarbonate aqueous solution and extracted with ethyl acetate. The organic layer was dried with anhydrous magnesium sulfate, then concentrated in vacuo. The crude was purified with preparative thin-layer chromatography to give 8 mg (0.02 mmol) of the desired product. MS (ES+): 381.0, 383.0 (M+H).

Example 1

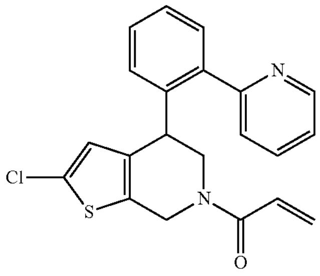 [SMILES: C=CC(=O)N1Cc2sc(Cl)cc2C(c2ccccc2-c2ccccn2)C1]

1-(2-chloro-4-(2-(pyridin-2-yl)phenyl)-4,7-dihydrothieno[2,3-c]pyridin-6(5H)-yl)prop-2-en-1-one Step A—Preparation of tert-butyl 2-chloro-4-(2-(4,4,5,5-tetramethyl-1,3,2-dioxaborolan-2-yl)phenyl)-4,7-dihydrothieno[2,3-c]pyridine-6(5H)-carboxylate

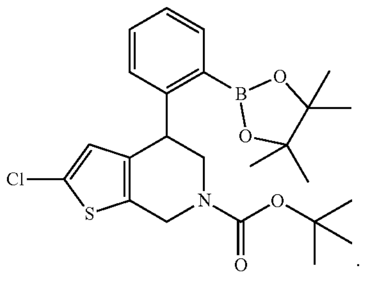 [SMILES: CC(C)(C)OC(=O)N1Cc2sc(Cl)cc2C(c2ccccc2B2OC(C)(C)C(C)(C)O2)C1]

tert-Butyl 4-(2-bromophenyl)-2-chloro-4,7-dihydrothieno[2,3-c]pyridine-6(5H)-carboxylate (1.00 g, 2.33 mmol, 1.00 eq) was dissolved in 1,4-dioxane (10.0 mL), then $B_2pin_2$ (711 mg, 2.80 mmol, 1.20 eq), KOAc (458 mg, 4.66 mmol, 2.00 eq) and $Pd(PPh_3)_2Cl_2$ (164 mg, 233 umol, 0.10 eq) were added. The mixture was stirred at 70° C. for 24 hrs under $N_2$ atmosphere. LCMS (ET27187-12-R1, Product: RT=1.46 min) indicated the reaction was complete, and desired compound was detected. The mixture was cooled to 25° C., diluted with $H_2O$ 15.0 mL and extracted with EtOAc (15.0 mL×3). The combined organic layers were washed with brine 10.0 mL, dried over $Na_2SO_4$, filtered and concentrated under reduced pressure to give a residue. The residue was purified by column chromatography ($SiO_2$, Petroleum ether/Ethyl acetate=50/1 to 5/1). Desired compound (500 mg, 1.05 mmol, 45.0% yield) was obtained as yellow oil.

Step B—Preparation of tert-butyl 2-chloro-4-(2-(pyridin-2-yl)phenyl)-4,7-dihydrothieno[2,3-c]pyridine-6(5H)-carboxylate

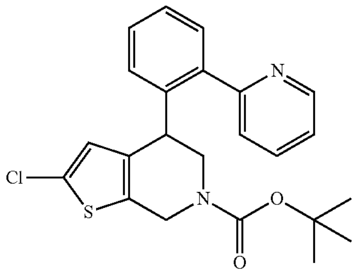 [SMILES: CC(C)(C)OC(=O)N1Cc2sc(Cl)cc2C(c2ccccc2-c2ccccn2)C1]

tert-Butyl 2-chloro-4-(2-(4,4,5,5-tetramethyl-1,3,2-dioxaborolan-2-yl)phenyl)-4,7-dihydrothieno[2,3-c]pyridine-6(5H)-carboxylate (120 mg, 252 umol, 1.00 eq) was dissolved in 1,4-dioxane (1.20 mL) and $H_2O$ (120 uL), then 2-bromopyridine (43.8 mg, 277 umol, 1.10 eq), $K_3PO_4$ (107 mg, 504 umol, 2.00 eq) and $Pd(dppf)Cl_2$ (18.4 mg, 25.2 umol, 0.10 eq) were added. The reaction was degassed and purged with $N_2$ for 3 times. The mixture was stirred at 80° C. for 12 hrs under $N_2$ atmosphere. TLC (Petroleum ether: Ethyl acetate=10:1, $R_f$=0.15) indicated the reaction was complete. The reaction mixture was cooled to 25° C., filtered and concentrated under reduced pressure to give a residue. The residue was purified by pre-TLC ($SiO_2$, Petroleum ether/Ethyl acetate=10/1). The title compound (50.0 mg, 117 umol, 46.4% yield) was obtained as yellow oil.

Step C—Preparation of 2-chloro-4-(2-(pyridin-2-yl)phenyl)-4,5,6,7-tetrahydrothieno[2,3-c]pyridine

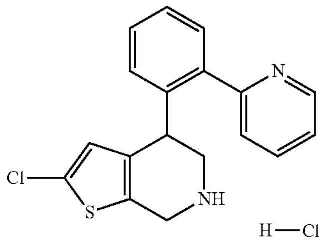 [SMILES: Clc1cc2c(s1)CNCC2c1ccccc1-c1ccccn1 ; Cl]

A solution of tert-butyl 2-chloro-4-(2-(pyridin-2-yl)phenyl)-4,7-dihydrothieno[2,3-c]pyridine-6(5H)-carboxylate (50.0 mg, 117 umol, 1.00 eq) in HCl/EtOAc (4M) (500 μL) was stirred at 25° C. for 3 hrs. TLC (Petroleum ether:Ethyl acetate=10:1, $R_f$=0.01) indicated the reaction was complete. The mixture was concentrated under reduced pressure to give a residue. Title compound (40.0 mg, 110 umol, 94.0% yield, HCl salt) was obtained as a white solid.

Step D—Preparation of 1-(2-chloro-4-(2-(pyridin-2-yl)phenyl)-4,7-dihydrothieno[2,3-c]pyridin-6(5H)-yl)prop-2-en-1-one To a solution of acrylic acid (11.9 mg, 165 umol, 11.3 uL, 1.50 eq), 2-chloro-4-(2-(pyridin-2-yl)phenyl)-4,5,6,7-tetrahydrothieno[2,3-c]pyridine (40.0 mg, 110 umol, 1.00 eq, HCl salt) and HATU (62.8 mg, 165 umol, 1.50 eq) in DMF (400 μL) was added DIPEA (42.7 mg, 330 umol, 57.5 uL, 3.00 eq). The reaction was stirred at 25° C. for 12 hrs. The mixture was filtered and concentrated under reduced pressure to give a residue. Prep-HPLC was used to isolate 9 mg target compound as a light yellow solid. MS (ES+): 381.0, 383.0 (M+H).

Example 2

1-(4-(2-Bromothiophen-3-yl)-2-chloro-4,7-dihydrothieno[2,3-c]pyridin-6(5H)-yl)prop-2-en-1-one

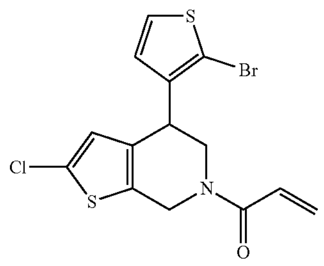 [SMILES: C=CC(=O)N1Cc2sc(Cl)cc2C(c2ccsc2Br)C1]

Step A—Preparation of 1-(2-bromothiophen-3-yl)-2-nitroethan-1-ol

A solution of 2-bromothiophene-3-carbaldehyde (5 g, 26.3 mmol) and nitromethane (1.76 g, 28.9 mmol) in methanol (30 mL) was cooled to 0° C. NaOH (1.16 g, 28.9 mmol) in 50 mL of water was added slowly and the mixture was stirred at 0° C. for 30 min. 1N HCl (28.9 mL) was added slowly to the mixture, then the mixture was extracted with EtOAc (100 mL). The layers were separated and the organic extracts were washed with brine, dried over sodium sulfate, filtered, and concentrated. The crude was purified by silica gel chromatography to afford 5.5 g titled compound as a colorless oil.

Step B—Preparation of (1-(2-bromothiophen-3-yl)-2-nitroethoxy)(tert-butyl)dimethylsilane To a solution of 1-(2-bromothiophen-3-yl)-2-nitroethan-1-ol (5.5 g, 22 mmol) in DMF (50 mL) were added TBSCl (4 g, 26.4 mmol) and imidazole (3.75 g, 55 mmol). The resulting mixture was stirred under argon atmosphere for 5 hours. The mixture was mixed with water then extracted with ethyl acetate. The organic extracts were washed with brine, dried over sodium sulfate, filtered, and concentrated. The crude was purified by silica gel chromatography to afford 7 g titled compound as a colorless oil.

Step C—Preparation of 2-(2-bromothiophen-3-yl)-2-((tert-butyldimethylsilyl)oxy)ethan-1-amine To a solution of (1-(2-bromothiophen-3-yl)-2-nitroethoxy)(tert-butyl)dimethylsilane (7 g, 19 mmol) in ethanol (50 mL) and water (50 mL) were added iron powder (11 g, 190 mmol) and $NH_4Cl$ (10 g, 190 mmol). This mixture was stirred vigorously at 80° C. for 2 hours. The mixture was cooled to room temperature, filtered through Celite® bed, and concentrated. The residue was then partitioned between aqueous sodium carbonate solution (200 mL) and ethyl acetate (200 mL). The organic extracts were isolated, washed with brine, dried over sodium sulfate, filtered, and concentrated. The crude was purified by silica gel chromatography to afford 4.1 g titled compound as a colorless oil. MS (ES+): 336.0, 338.0 (M+H).

Step D—Preparation of 2-(2-bromothiophen-3-yl)-2-((tert-butyldimethylsilyl)oxy)-N-((5-chlorothiophen-2-yl)methyl)ethan-1-amine A mixture of 5-chlorothiophene-2-carbaldehyde (2.13 g, 14.6 mmol) and 2-(2-bromothiophen-3-yl)-2-((tert-butyldimethylsilyl)oxy)ethan-1-amine (4.1 g, 12.2 mol) in ethanol (50 mL) was heated at 90° C. for 3 hours then cooled to 0° C. $NaBH_4$ (12.2, 462 mg) in methanol (50 mL) was added slowly to the mixture. The mixture was warmed up to room temperature for 30 min, then the solvents were removed in vacuo. The residue was extracted between aqueous sodium bicarbonate and ethyl acetate. The organic extracts were dried over $MgSO_4$ and concentrated. The crude was purified by silica gel chromatography to afford 5 g titled compound as a yellow oil. MS (ES+): 465.9, 467.9 (M+H).

Step E—Preparation of 1-(2-bromothiophen-3-yl)-2-(((5-chlorothiophen-2-yl)methyl)amino)ethan-1-ol To a mixture of 2-(2-bromothiophen-3-yl)-2-((tert-butyldimethylsilyl)oxy)-N-((5-chlorothiophen-2-yl)methyl)ethan-1-amine (5 g, 10.75 mmol) in THF (50 mL) was added tetra-n-butyl-ammonium fluoride (TBAF, 5.6 g, 21.5 mmol). After stirring at room temperature for 3 hours, the solvents were evaporated and the residue was purified by silica gel chromatography to afford 3.5 g titled compound as a yellow solid. MS (ES+): 351.8, 353.9 (M+H).

Step F—Preparation of 4-(2-bromothiophen-3-yl)-2-chloro-4,5,6,7-tetrahydrothieno[2,3-c]pyridine To a mixture of of 1-(2-bromothiophen-3-yl)-2-(((5-chlorothiophen-2-yl)methyl)amino)ethan-1-ol (3.5 g, 10 mmol) in DCM (30 mL) was added methanesulfonic acid (6.7 g, 70 mmol). After stirring at room temperature overnight, the mixture was quenched with aqueous sodium bicarbonate then extracted with EtOAc. The organic extracts were dried over $MgSO_4$ and then concentrated. The residue was purified by silica gel chromatography to afford 1.4 g titled compound as a colorless gum. MS (ES+): 333.9, 335.9 (M+H).

Step G—Preparation of 1-(4-(2-bromothiophen-3-yl)-2-chloro-4,7-dihydrothieno[2,3-c]pyridin-6(5H)-yl)prop-2-en-1-one To a mixture of 4-(2-bromothiophen-3-yl)-2-chloro-4,5,6,7-tetrahydrothieno[2,3-c]pyridine (100 mg, 0.3 mmol), N,N-diisopropylethylamine (0.9 mmol) in dichloromethane (5 mL) was added acryloyl chloride (0.3 mmol). After 1 min, the mixture was quenched with saturated sodium bicarbonate aqueous solution and extracted with ethyl acetate. The organic layer was dried with anhydrous magnesium sulfate and concentrated in vacuo. The crude mixture was purified with preparative thin-layer chromatography to give 60 mg of the desired product as a colorless gum. MS (ES+): 387.9, 389.9 (M+H). HNMR (d6-DMSO), δ: 7.6 (m, 1.5H), 6.9 (m, 0.5H), 6.7 (m, 1.5H), 6.6 (s, 0.5H), 6.4 (m, 2H), 6.2 (d, 0.5H), 6.0 (d, 1H), 5.8 (d, 0.5H), 5.6 (d, 1H), 5.0-4.8 (m, 2H), 4.6 (m, 1H), 4.2-4.1 (m, 2H), 4.0-3.8 (m, 2H), 3.9 (m, 0.5H).

Example 3

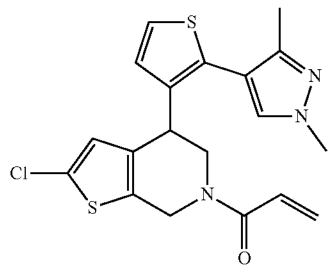 [SMILES: C=CC(=O)N1Cc2sc(Cl)cc2C(c2ccsc2-c2cn(C)nc2C)C1]

1-(2-chloro-4-(2-(1,3-dimethyl-1H-pyrazol-4-yl)thiophen-3-yl)-4,7-dihydrothieno[2,3-c]pyridin-6(5H)-yl)prop-2-en-1-one Step A—Preparation of tert-butyl 4-(2-bromothiophen-3-yl)-2-chloro-4,7-dihydrothieno[2,3-c]pyridine-6(5H)-carboxylate

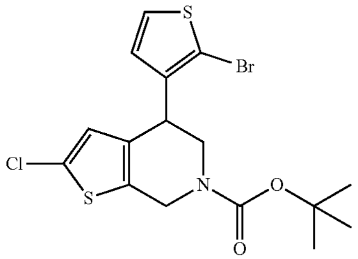 [SMILES: CC(C)(C)OC(=O)N1Cc2sc(Cl)cc2C(c2ccsc2Br)C1]

To a mixture of of 4-(2-bromothiophen-3-yl)-2-chloro-4,5,6,7-tetrahydrothieno[2,3-c]pyridine (1.4 g, 4.2 mmol) in THF (50 mL) was added triethylamine (1.3 g, 12.6 mmol) and di-tert-butyl dicarbonate (1.05 g, 4.8 mmol). The mixture was stirred at room temperature overnight then the solvents were evaporated in vacuo. The residue was purified by silica gel chromatography to afford 1.8 g titled compound as a colorless oil.

Step B—Preparation of tert-butyl 2-chloro-4-(2-(1,3-dimethyl-1H-pyrazol-4-yl)thiophen-3-yl)-4,7-dihydrothieno[2,3-c]pyridine-6(5H)-carboxylate To a mixture of of tert-butyl 4-(2-bromothiophen-3-yl)-2-chloro-4,7-dihydrothieno[2,3-c]pyridine-6(5H)-carboxylate (433 mg, 1 mmol) in THF (15 mL) and water (5 mL) was added (1,3-dimethyl-1H-pyrazol-4-yl)boronic acid (182 mg, 1.3 mmol) and $K_3PO_4$ (637 mg, 3 mmol). The mixture was degassed then saturated with argon. $PdCl_2$(dppf) (146 mg, 0.2 mmol) was added and the resulting mixture was heated at 80° C. under argon for 3 hours. The mixture was then extracted with EtOAc and the organic layer was washed with brine then dried over $MgSO_4$. After evaporation in vacuo, the residue was purified by silica gel chromatography to afford 165 mg titled compound. The Boc group was removed with 20% TFA in DCM. After concentration the residue (2-chloro-4-(2-(1,3-dimethyl-1H-pyrazol-4-yl)thiophen-3-yl)-4,5,6,7-tetrahydro-thieno[2,3-c]pyridine) was use for next step without further purification. MS (ES+): 350.0, 351.9 (M+H).

Step C—Preparation of 1-(2-chloro-4-(2-(1,3-dimethyl-1H-pyrazol-4-yl)thiophen-3-yl)-4,7-dihydrothieno[2,3-c]pyridin-6(5H)-yl)prop-2-en-1-one To a mixture of (2-chloro-4-(2-(1,3-dimethyl-1H-pyrazol-4-yl)thiophen-3-yl)-4,5,6,7-tetrahydro-thieno[2,3-c]pyridine) (100 mg, 0.286 mmol), N,N-diisopropylethylamine (0.86 mmol) in dichloromethane (5 mL) was added acryloyl chloride (0.286 mmol). After 1 min, the mixture was quenched with saturated sodium bicarbonate aqueous solution and then extracted with ethyl acetate. The organic layer was dried with anhydrous magnesium sulfate and then concentrated in vacuo. The crude mixture was purified with preparative thin-layer chromatography to give 23 mg of the desired product as a colorless gum. MS (ES+): 404.1, 406.0 (M+H).

Example 4

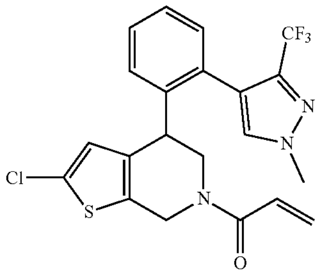 [SMILES: C=CC(=O)N1Cc2sc(Cl)cc2C(c2ccccc2-c2cn(C)nc2C(F)(F)F)C1]

1-(2-Chloro-4-{o-[1-methyl-3-(trifluoromethyl)-1H-pyrazol-4-yl]phenyl}-1-thia-6-aza-4,5,6,7-tetrahydroinden-6-yl)-2-propen-1-one Step A—Preparation of 6-Boc-2-[o-(2-chloro-1-thia-6-aza-4,5,6,7-tetrahydroinden-4-yl)phenyl]-4,4,5,5-tetramethyl-1,3,2-dioxaborolane

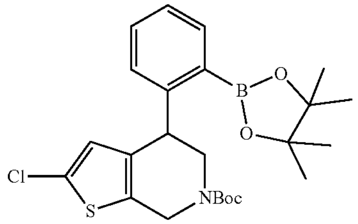 [SMILES: CC(C)(C)OC(=O)N1Cc2sc(Cl)cc2C(c2ccccc2B2OC(C)(C)C(C)(C)O2)C1]

6-Boc-4-(o-bromophenyl)-2-chloro-1-thia-6-aza-4,5,6,7-tetrahydroindene (3.36 g, 7.82 mmol), $Pd(PPh_3)Cl_2$ (0.55 g, 0.78 mmol), KOAc (1.54 g, 15.6 mmol), and $B_2Pin_2$ (2.98 g, 11.7 mmol) were suspended in dioxane (30 mL). The reaction was flushed with Ar three times, stirred, and heated to 70° C. for 16 h. Upon completion, the mixture was cooled to RT and diluted with $H_2O$ (25 mL). The crude was extracted with EtOAc (30 mL), separated and dried over $MgSO_4$. The mixture was purified by silica flash column chromatography (0-50% EtOAc/Hexanes) to give the borolane as a yellow foam (1.67 g). LC-MS Calc'd for $C_{24}H_{32}BClNO_4S$, 476.19 $[M+H]^+$, found 476.1 $[M+H]^+$.

Step B—Preparation of Boc-4-[o-(2-chloro-1-thia-6-aza-4,5,6,7-tetrahydroinden-4-yl)phenyl]-1-methyl-3-(trifluoromethyl)-1H-pyrazole

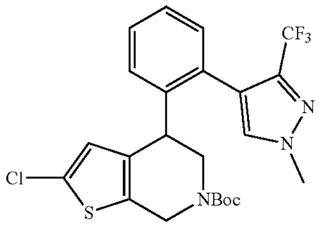 [SMILES: Cn1cc(-c2ccccc2C2CN(C(=O)OC(C)(C)C)Cc3sc(Cl)cc32)c(C(F)(F)F)n1]

The borolane from Step A (50.0 mg, 0.11 mmol), 4-bromo-1-methyl-3-(trifluoromethyl)pyrazole (26.0 mg, 0.16 mmol), Pd(dppf)$Cl_2$ (4.00 mg, 5.00 gmol), and $K_3PO_4$ (67.0 mg, 0.32 mmol) were added to a 4 mL reaction vial and suspended in a 3:1 dioxane:$H_2O$ mixture (2 mL). The reaction was flushed with Ar three times, stirred, and heated to 80° C. for 14 h. Upon completion, the mixture was cooled to RT and diluted with sat. $NaHCO_3$ (2 mL). The crude was extracted with EtOAc (5 mL), dried over $MgSO_4$, and purified by silica flash column chromatography (0-100% EtOAc/Hexanes) to give the pyrazole as a yellow oil. The compound was used immediately in the next reaction. LC-MS Calcd for $C_{18}H_{15}ClF_3N_3S$, 397.06 $[M]^+$, found 397.6 $[M]^+$.

Step C: Preparation of 1-(2-Chloro-4-{o-[1-methyl-3-(trifluoromethyl)-1H-pyrazol-4-yl]phenyl}-1-thia-6-aza-4,5,6,7-tetrahydroinden-6-yl)-2-propen-1-one

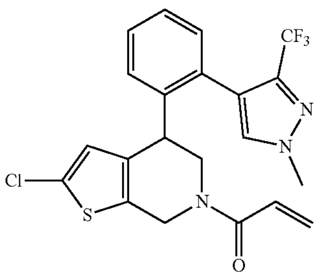 [SMILES: C=CC(=O)N1Cc2sc(Cl)cc2C(c2ccccc2-c2cn(C)nc2C(F)(F)F)C1]

The pyrazole from Step B was dissolved in a 1:1 TFA: DCM mixture (2 mL) and stirred at RT for 3 h. The reaction was concentrated in vacuo. The mixture was dissolved in THF (2 mL) and concentrated in vacuo. The mixture was dissolved in THF (1 mL) and $Et_3N$ (0.07 mL, (0.53 mmol). Acryloyl chloride (0.02 mL, 0.21 mmol) was diluted in THF (1 mL) and added to the reaction dropwise. The mixture was stirred for 10 min then quenched with sat. $NaHCO_3$ (3 mL). The crude was extracted with EtOAc (5 mL). The organic layer was separated and washed with 1 N HCl (5 mL). The organic layer was separated and neutralized with $NaHCO_3$. The organic layer was separated and dried over $MgSO_4$. The crude was purified by Prep TLC (1% MeOH/EtOAc) to give the product as a yellow oil (9.87 mg) LC-MS Calcd for $C_{21}H_{17}ClF_3N_3OS$ 453.07 $[M+H]^+$, found 453.1 $[M+H]^+$.

Example 5

Step a: Preparation of 1-(2-bromophenyl)-2-nitro-1-ethanol

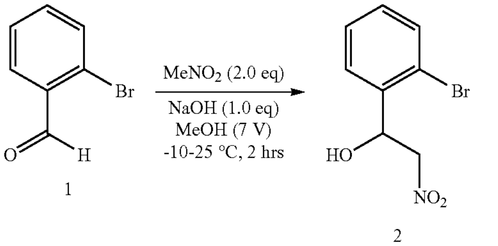 [SMILES: O=Cc1ccccc1Br ; O=[N+]([O-])CC(O)c1ccccc1Br]

1 2

To a solution of 2-bromobenzaldehyde (470 g, 2.54 mol) and nitromethane (310 g, 5.08 mol) in MeOH (3.29 L) was added a solution of NaOH (102 g, 2.54 mol) in $H_2O$ (500.0 mL) at −10° C., and the mixture was stirred at 25° C. for 2 hrs. The reaction mixture was quenched by water (2.00 L), adjust to pH 5 with 4M HCl, extracted with DCM (2.0 L×2), the combined organic phase was dried over $Na_2SO_4$, filtered and concentrated under reduced pressure to give a residue. The residue was purified by column chromatography ($SiO_2$, Petroleum ether/Ethyl acetate=20/1 to 3/1), to afford the nitro compound (510 g, 2.07 mol, 81.5% yield) as a yellow oil.

Step b: Preparation of 2-amino-1-(2-bromophenyl)-ethanol

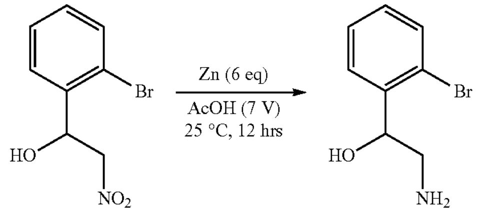

2 3

Two reactions were carried out parallel. To a solution of 1-(2-bromophenyl)-2-nitro-1-ethanol (230 g, 935 mmol) in AcOH (1.60 L) was added Zn (367 g, 5.61 mol) at 25° C., then the mixture was stirred at 25° C. for 12 hrs. Two reactions were combined for work-up. The reaction mixture was filtered and the filtrate was concentrated under reduced pressure to give a residue. The residue was diluted with EtOAc (1.00 L) and water (2.00 L), extracted with EtOAc (1.00 L×2), the aqueous phase was adjust to pH 10 with 4 M NaOH, extracted with EtOAc (1.00 L×3), the combined organic was dried with $Na_2SO_4$, filtered and concentrated under reduced pressure to give a residue, to afford the amine (230 g, 1.06 mol, 56.9% yield) as a yellow oil. LCMS $(M+H)^+$ 216.1.

Step c: Preparation of 1-(2-bromophenyl)-2-{[(5-chloro-2-thienyl)methyl]amino}-1-ethanol

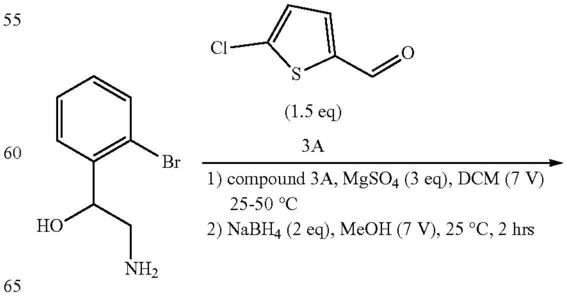

3

-continued

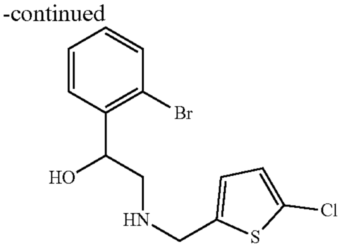

4

To a solution of 2-amino-1-(2-bromophenyl)-ethanol (230 g, 1.06 mol) in DCM (1.60 L) was added 5-chloro-2-thenaldehyde (234 g, 1.60 mol) and $MgSO_4$ (384 g, 3.19 mol) at 25° C., then the mixture was stirred at 50° C. for 3 hrs. The reaction mixture was filtered and the filtrate was concentrated under reduced pressure to give a residue. The residue was dissolved with MeOH (1.60 L), and $NaBH_4$ (80.5 g, 2.13 mol) was added and the mixture was stirred at 25° C. for 2 hrs. The reaction mixture was diluted with water (1.50 L), extracted with EtOAc (1.00 L×3), the combined organic phase was washed with brine (1.00 L), dried over $Na_2SO_4$, filtered and concentrated under reduced pressure to give a residue. The residue was purified by column chromatography ($SiO_2$, Petroleum ether/Ethyl acetate=10/1 to 1/1), to afford the desired compound (185 g, 534 mmol, 50.1% yield) as a yellow oil.

Step d: Preparation of 4-(2-bromophenyl)-2-chloro-4,5,6,7-tetrahydro-1-thia-6-azaindene

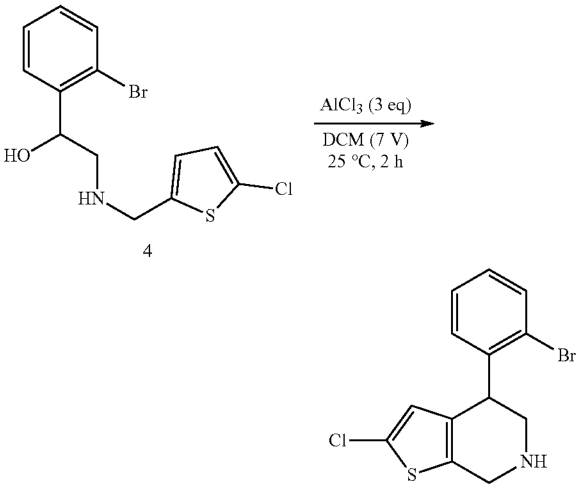

4

5

To a solution of 1-(2-bromophenyl)-2-{[(5-chloro-2-thienyl)methyl]amino}-1-ethanol (185 g, 534 mmol) in DCM (1.29 L) was added $AlCl_3$ (213 g, 1.60 mol), the mixture was stirred at 25° C. for 2 hrs. The reaction mixture was quenched by water (1.00 L), the mixture was adjusted to pH 13 with NaOH, separated and the aqueous phase was extracted with DCM (500 mL×2), the combined organic phase was washed with brine (400 mL), dried over $Na_2SO_4$, filtered and concentrated under reduced pressure to afford the thia-azaindane (110 g, crude) as a yellow oil.

Step e: Preparation of 4-(2-bromophenyl)-2-chloro-6-Boc-4,5,6,7-tetrahydro-1-thia-6-azaindene

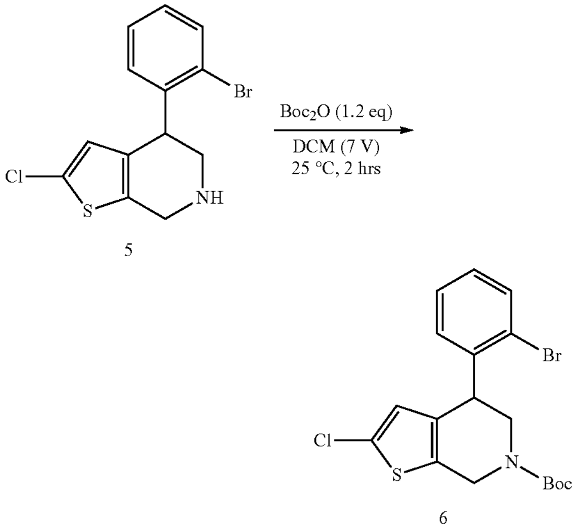

5

6

To a solution of 4-(2-bromophenyl)-2-chloro-4,5,6,7-tetrahydro-1-thia-6-azaindene (110 g, 335 mmol) in DCM (770 mL) was added $Boc_2O$ (87.6 g, 402 mmol), and the mixture was stirred at 25° C. for 2 hrs. The reaction mixture was quenched by water (500 mL), separated with DCM (300 mL×2), the combined organic phase was washed with brine (200 mL), dried over $Na_2SO_4$, filtered and concentrated under reduced pressure to give a residue. The residue was purified by column chromatography ($SiO_2$, Petroleum ether/Ethyl acetate=50/1 to 10/1), to afford the Boc-protected compound (80.0 g, 187 mmol, 55.7% yield) as a white solid.

Step f: Separation of 4-(o-bromophenyl)-2-chloro-6-Boc-4,5,6,7-tetrahydro-1-thia-6-azaindene isomers

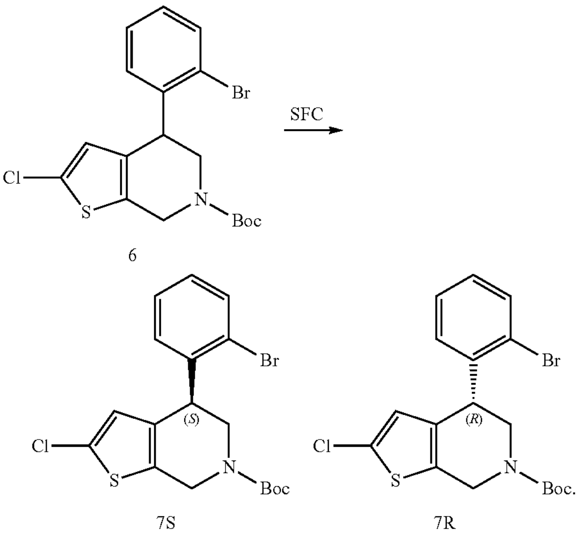

6

7S 7R

The 4-(2-bromophenyl)-2-chloro-6-Boc-4,5,6,7-tetrahydro-1-thia-6-azaindene was separated by SFC with a Waters SFC350 preparative SFC (column: DAICEL CHIRALPAK AD (250 mm×50 mm, 10 μm); mobile phase: [0.1% $NH_3H_2O$ IPA]; B %: 70%-70%, 6 min). The fractions were concentrated under reduced pressure below 40° C. to afford the S form (20.3 g, 46.1 mmol, 39.5% yield, 97.3% purity) as a light yellow solid and R form (20.1 g, 46.9 mmol, 40.2% yield, 100% purity) as a light yellow solid.

Example 6

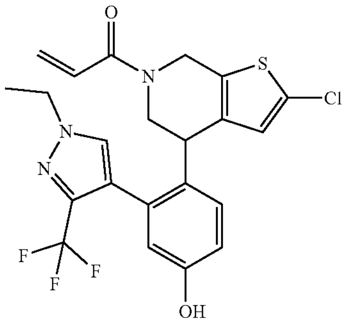

1-(2-Chloro-4-(2-(1-ethyl-3-(trifluoromethyl)-1*H*-pyrazol-4-yl)-4-hydroxyphenyl)-4,7-dihydrothieno[2,3-*c*]pyridin-6(5*H*)-yl)prop-2-en-1-one Step a: Preparation of 2-bromo-1-(2-bromo-4-methoxyphenyl)ethan-1-one Bromine (0.25 mL, 4.36 mmol) was added dropwise to a solution containing 1-(2-bromo-4-methoxyphenyl)ethan-1-one (1.00 g, 4.36 mmol) dissolved in THE (20 mL). The mixture was stirred at r.t. for 2 h. The mixture was diluted with sat. sodium thiosulfate (20 mL) and extracted with EtOAc (20 mL). The organic layer was separated, dried over $MgSO_4$, and concentrated in vacuo. The crude compound was then purified by silica column chromatography (0-100% EtOAc in hexanes) to give the desired compound mixed with the starting material as a colorless oil (0.42 g, 31%). The mixture was taken into the next step without further purification. LC-MS calcd for $C_9H_8Br_2O_2$ 308.98 $[M+H]^+$, found 308.9 $[M+H]^+$.

Step b: Preparation of 1-(2-bromo-4-methoxyphenyl)-2-(((5-chlorothiophen-2-yl)methyl)amino) ethan-1-ol (5-Chlorothiophen-2-yl)methanamine (0.15 mL, 1.36 mmol) was added to a mixture of 2-bromo-1-(2-bromo-4-methoxyphenyl)ethan-1-one (0.42 g, 1.36 mmol) and $K_2CO_3$ (0.58 g, 4.09 mmol) in MeCN (14 mL) and stirred at r.t. for 16 h. The mixture was diluted with MeOH (10 mL). $NaBH_4$ (0.10 g, 2.72 mmol) was slowly added to the mixture and stirred for 1 h. The mixture was then diluted with sat. aq. $NaHCO_3$ (20 mL) and extracted with EtOH (3×30 mL). The organic layers were combined, dried over $MgSO_4$, and concentrated in vacuo. The crude product was then purified by silica gel column chromatography (0-100% EtOAc in hexanes) to give the desired compound as a yellow oil (0.16 g, 31%). LC-MS calcd for $C_{14}H_{15}BrClNO_2S$, 375.98 [M+H]), found 376.0 $[M+H]^+$.

Step c: Preparation of tert-butyl 4-(2-bromo-4-methoxyphenyl)-2-chloro-4,7-dihydrothieno[2,3-c] pyridine-6(5H)-carboxylate 1-(2-Bromo-4-methoxyphenyl)-2-(((5-chlorothiophen-2-yl)methyl)amino)ethan-1-ol (0.16 g, 0.48 mmol) was dissolved in DCM (10 mL) and dropwise added to a suspension of $AlCl_3$ (0.19 g, 1.44 mmol) in DCM (10 mL) at 0° C. The suspension was warmed to r.t. over 30 min. Sat. aq. Rochelle's salt solution (20 mL) was added the suspension. The mixture was then extracted with DCM (3×20 mL), combined, dried over $MgSO_4$, and concentrated in vacuo. The crude organic material was then dissolved in DCM (20 mL). $Boc_2O$ (0.22 mL, 0.96 mmol) and $Et_3N$ (0.25 mL, 1.44 mmol) were added to the mixture and stirred overnight. The mixture was then washed with 1 M citric acid (20 mL) and separated. The organic layer was then dried over $MgSO_4$ and concentrated in vacuo. The crude product was then purified by silica gel column chromatography (0-100% EtOAc in hexanes) to give the desired compound as a yellow oil (78.5 mg, 36%). LC-MS calcd for $C_{19}H_{21}BrClNO_3S$, 480.01 $[M+Na]^+$, found 480.1 $[M+Na]^+$.

Step d—Preparation of tert-butyl 2-chloro-4-(2-(1-ethyl-3-(trifluoromethyl)-1H-pyrazol-4-yl)-4-methoxyphenyl)-4,7-dihydrothieno[2,3-c]pyridine-6 (5H)-carboxylate tert-Butyl 4-(2-bromo-4-methoxyphenyl)-2-chloro-4,7-dihydrothieno[2,3-c]pyridine-6(5H)-carboxylate (78.5 mg, 0.17 mmol), $Pd(dppf)Cl_2$ (13.0 mg, 0.020 mmol), $K_3PO_4$ (0.11 g, 0.51 mmol), and (1-ethyl-3-(trifluoromethyl)-1H-pyrazol-4-yl)boronic acid (43.0 mg, 0.21 mmol) was placed in a vial and 4:1 dioxane:$H_2O$ (2.0 mL) was added. The vial was then purged with Argon and heated to 80° C. The mixture was then stirred for 24 h. The mixture was cooled to r.t. and diluted with EtOAc (5 mL). The mixture as then washed with sat. aq. $NaHCO_3$ (2 mL) and separated. The organic layer was then dried over $MgSO_4$ and concentrated in vacuo. The crude was then purified by silica gel column chromatography (0-100% EtOAc in hexanes) to give the desired compound as a yellow oil (38.3 mg, 41%). LC-MS calcd for $C_{25}H_{27}ClF_3N_3O_3S$, 564.01 $[M+Na]^+$, found 564.2 $[M+Na]^+$.

Step e—Preparation of 1-(2-chloro-4-(2-(1-ethyl-3-(trifluoromethyl)-1H-pyrazol-4-yl)-4-hydroxyphenyl)-4,7-dihydrothieno[2,3-c]pyridin-6(5H)-yl)prop-2-en-1-one tert-Butyl 2-chloro-4-(2-(1-ethyl-3-(trifluoromethyl)-1H-pyrazol-4-yl)-4-methoxyphenyl)-4,7-dihydrothieno[2,3-c] pyridine-6(5H)-carboxylate (10.0 mg, 18.4 mol) in DCM (1 mL) was stirred at 0° C. $BBr_3$ (0.06 mL, 55.2 μmol) was added to the mixture slowly and stirred. The mixture was warmed to r.t. over an hour. The mixture was diluted with DCM (5 mL) and then quenched with sat. aq. $NaHCO_3$ (5 mL). The organic layer was separated, dried over $MgSO_4$, concentrated in vacuo. The concentrate was then dissolved in THF (1 mL). DIPEA (5.0 μL, 55 mol) was added to the mixture. Acryloyl chloride (1.50 μL, 18.4 mol) in THF (0.10 mL) was added to the mixture slowly and stirred for 15 min. 1 M NaOH (0.50 mL) was added the mixture and stirred vigorously for 1 h. The mixture was extracted with EtOAc (5 mL). The organic layer was washed with 1 M citric acid (5 mL), separated, and then washed with sat. aq. $NaHCO_3$ (5 mL). The organic layer was separated, dried over $MgSO_4$, and concentrated in vacuo. The crude was purified by silica gel column chromatography (0-100% EtOAc in hexanes) to give the desired product as a white solid (5.0 mg, 56%). LC-MS calcd for $C_{22}H_{19}ClF_3N_3O_2S$, 482.09 $[M+H]^+$, found 482.1 $[M+H]^+$.

Example 7

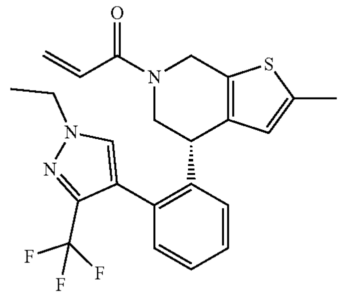

1-(4-{o-[1-Ethyl-3-(trifluoromethyl)-1H-pyrazol-4-yl]phenyl}-2-methyl-4,5,6,7-tetrahydro-1-thia-6-aza-6-indenyl)-2-propen-1-one Step a: Preparation of 4-bromo-1-ethyl-3-(trifluoromethyl)-1H-pyrazole To a solution of 4-bromo-3-(trifluoromethyl)-1H-pyrazole (1.00 g, 4.67 mmol) in N,N-dimethylformate (10.0 mL) at room temperature were added iodoethane (1.46 g, 9.34 mmol) and $K_2CO_3$ (1.93 g, 14.0 mmol). The reaction mixture was heated to 65° C. and stirred at the same temperature overnight. After cooled to room temperature, water (20 mL) was added and the mixture was extracted with ethyl acetate (20 mL×3). The combined organic layers were washed with water (20 mL×3), dried over anhydrous $Na_2SO_4$, filtered and concentrated under vacuum to give a residue which was purified by silica gel chromatography to give 4-bromo-1-ethyl-3-(trifluoromethyl)-1H-pyrazole as a colorless oil (900 mg, 80% yield). LCMS: $(M+H)^+$=244.9.

Step b: Preparation of tert-butyl (S)-2-chloro-4-(2-(4,4,5,5-tetramethyl-1,3,2-dioxaborolan-2-yl)phenyl)-4,7-dihydrothieno[2,3-c]pyridine-6(5H)-carboxylate To a solution of (R)-tert-butyl 4-(2-bromophenyl)-2-chloro-4,5-dihydrothieno[2,3-c]pyridine-6(7H)-carboxylate (427 mg, 1.0 mmol) in 1,4-dioxane (7 mL) were added $B_2pin_2$ (305 mg, 1.2 mmol), KOAc (196 mg, 2 mmol) and $Pd(PPh_3)_2Cl_2$ (70.2 mg, 0.1 mmol) and the reaction mixture was stirred at 70° C. overnight under $N_2$ atmosphere. The reaction mixture was cooled to room temperature, diluted with $H_2O$ (20 mL) and extracted with EtOAc (10 mL×3). The combined organic layers were washed with brine (10 mL), dried over $Na_2SO_4$, filtered and concentrated under reduced pressure to give a residue. The residue was purified by silica gel chromatography (petroleum:ethyl acetate=0%~3%) to give tert-butyl (S)-2-chloro-4-(2-(4,4,5,5-tetramethyl-1,3,2-dioxaborolan-2-yl)phenyl)-4,7-dihydrothieno[2,3-c]pyridine-6(5H)-carboxylate (365 mg, 76.8% yield) as a colorless solid. LCMS: $(M\text{-}Boc+1)^+$=376.0.

Step c: Preparation of tert-butyl (S)-2-chloro-4-(2-(1-ethyl-3-(trifluoromethyl)-1H-pyrazol-4-yl)phenyl)-4,7-dihydrothieno[2,3-c]pyridine-6(5H)-carboxylate To a solution of tert-butyl (S)-2-chloro-4-(2-(4,4,5,5-tetramethyl-1,3,2-dioxaborolan-2-yl)phenyl)-4,7-dihydrothieno[2,3-c]pyridine-6(5H)-carboxylate (200 mg, 0.421 mmol) in dioxane/$H_2O$ (10:1, 5.00 mL) were added 4-bromo-1-ethyl-3-(trifluoromethyl)-1H-pyrazole (0.112 g, 0.463 mmol), Pd(dppf)$Cl_2$ (0.0308 g, 0.0421 mmol) and $K_3PO_4$ (0.178 g, 0.842 mmol) at room temperature. The reaction mixture was heated to 85° C. and stirred at the same temperature under microwave for 1 hour. The reaction mixture was cooled to room temperature and diluted with water (20 mL). The mixture was extracted with ethyl acetate (10.0 mL×3). The combined organic layers were dried over anhydrous $Na_2SO_4$, filtered and concentrated under vacuum give a residue which was purified by silica gel chromatography (petroleum:ethyl acetate=0%~50%) to give tert-butyl (S)-2-chloro-4-(2-(1-ethyl-3-(trifluoromethyl)-1H-pyrazol-4-yl)phenyl)-4,7-dihydrothieno[2,3-c]pyridine-6(5H)-carboxylate (100 mg, 46.5% yield) as a yellow oil. LCMS: $(M+Na)^*$=534.

Step d: Preparation of tert-butyl (S)-4-(2-(1-ethyl-3-(trifluoromethyl)-1H-pyrazol-4-yl)phenyl)-2-methyl-4,7-dihydrothieno[2,3-c]pyridine-6(5H)-carboxylate To a solution of tert-butyl (S)-2-chloro-4-(2-(1-ethyl-3-(trifluoromethyl)-1H-pyrazol-4-yl)phenyl)-4,7-dihydrothieno[2,3-c]pyridine-6(5H)-carboxylate (150 mg, 0.293 mmol) in dioxane/$H_2O$ (10:1, 5.00 mL) were added 2,4,6-trimethyl-1,3,5,2,4,6-trioxatriborinane (0.0555 g, 0.440 mmol), RuphosPd (0.0239 g, 0.0293 mmol) and $K_3PO_4$ (0.124 g, 0.587 mmol). The reaction mixture was heated to 90° C. and stirred at the same temperature under microwave for 1 hour. The reaction mixture was cooled to room temperature and diluted with water (10 mL). Then the mixture was extracted with ethyl acetate (10 mL×3) and the combined organic layers were dried over anhydrous $Na_2SO_4$, filtered and concentrated under vacuum to give a residue. The residue was purified by silica gel chromatography to give tert-butyl (S)-4-(2-(1-ethyl-3-(trifluoromethyl)-1H-pyrazol-4-yl)phenyl)-2-methyl-4,7-dihydrothieno[2,3-c]pyridine-6(5H)-carboxylate (100 mg, 69.3% yield) as a yellow oil. LCMS: (M+Na)*514.

Step e: Preparation of (S)-4-(2-(1-ethyl-3-(trifluoromethyl)-1H-pyrazol-4-yl)phenyl)-2-methyl-4,5,6,7-tetrahydrothieno[2,3-c]pyridine To a solution of tert-butyl (S)-4-(2-(1-ethyl-3-(trifluoromethyl)-1H-pyrazol-4-yl)phenyl)-2-methyl-4,7-dihydrothieno[2,3-c]pyridine-6(5H)-carboxylate (100 mg, 0.204 mmol) in dioxane (1.00 mL) was added HCl/dioxane (4M, 5 mL) at room temperature, then the mixture was stirred at room temperature for 20 min. The mixture was diluted with dichloromethane (10 mL) and washed with $NaHCO_3$ (20 mL×1). The organic layer was dried over anhydrous $Na_2SO_4$, filtered and concentrated under vacuum to give the crude (S)-4-(2-(1-ethyl-3-(trifluoromethyl)-1H-pyrazol-4-yl)phenyl)-2-methyl-4,5,6,7-tetrahydrothieno[2,3-c]pyridine (80 mg) as a yellow oil which was used directly in the next step reaction without further purification. LCMS: $(M+H)^*$=392.0.

Step f: Preparation of 1-(4-{o-[1-Ethyl-3-(trifluoromethyl)-1H-pyrazol-4-yl]phenyl}-2-methyl-4,5,6,7-tetrahydro-1-thia-6-aza-6-indenyl)-2-propen-1-one To a suspension of (S)-4-(2-(1-ethyl-3-(trifluoromethyl)-1H-pyrazol-4-yl)phenyl)-2-methyl-4,5,6,7-tetrahydrothieno[2,3-c]pyridine (80 mg, crude, ca. 0.972 mmol) in dioxane (5 mL) at 0° C. was added NaOH (10 M, 1 mL) and acryloyl chloride (0.175 g, 1.94 mmol). The reaction mixture was stirred at room temperature for 20 min and LCMS indicated the reaction completed. The reaction mixture was diluted with water (10 mL) and extracted with dichloromethane (10.0 mL×3). The combined organic layers were dried over anhydrous $Na_2SO_4$, filtered, and concentrated to give the crude product which was purified by Prep-HPLC to give the product (29.5 mg, 32.4%) as a white solid. LCMS: $(M+H)^+$= 445.9.

The following compounds were prepared by methods similar to the procedures described above.

| Compound | Structure | M + H |
|---|---|---|
| 250 | 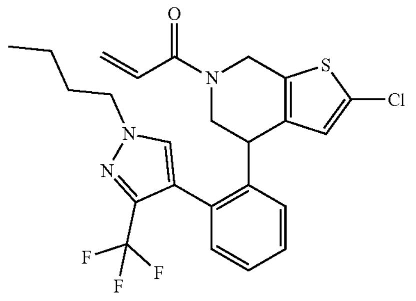 [SMILES: C=CC(=O)N1Cc2sc(Cl)cc2C(c2ccccc2-c2cn(CCCC)nc2C(F)(F)F)C1] | 493.9 |
| 251 | 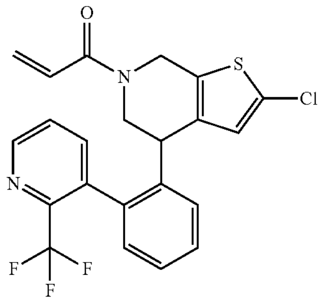 [SMILES: C=CC(=O)N1Cc2sc(Cl)cc2C(c2ccccc2-c2cccnc2C(F)(F)F)C1] | 448.8 |
| 252 | 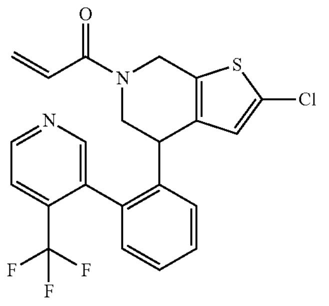 [SMILES: C=CC(=O)N1Cc2sc(Cl)cc2C(c2ccccc2-c2cnccc2C(F)(F)F)C1] | 448.8 |
| 253 | 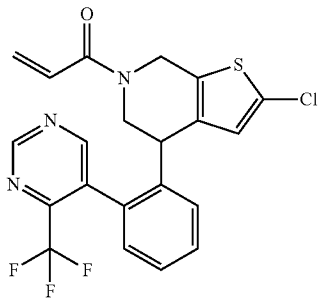 [SMILES: C=CC(=O)N1Cc2sc(Cl)cc2C(c2ccccc2-c2cncnc2C(F)(F)F)C1] | 449.9 |

-continued
| Compound | Structure | M + H |
|---|---|---|
| 254 | 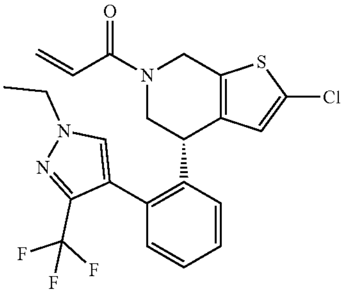 [SMILES: C=CC(=O)N1Cc2sc(Cl)cc2[C@H](c2ccccc2-c2cn(CC)nc2C(F)(F)F)C1] | 466.1 |
| 255 | 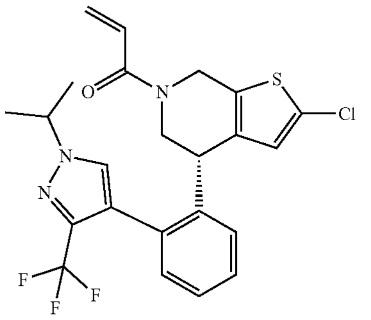 [SMILES: C=CC(=O)N1Cc2sc(Cl)cc2[C@H](c2ccccc2-c2cn(C(C)C)nc2C(F)(F)F)C1] | 480.1 |
| 256 | 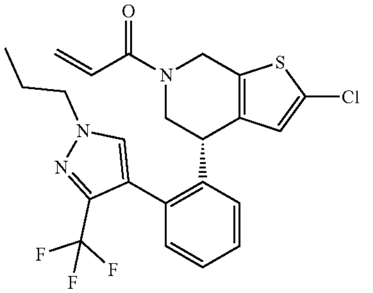 [SMILES: C=CC(=O)N1Cc2sc(Cl)cc2[C@H](c2ccccc2-c2cn(CCC)nc2C(F)(F)F)C1] | 480.1 |
| 257 | 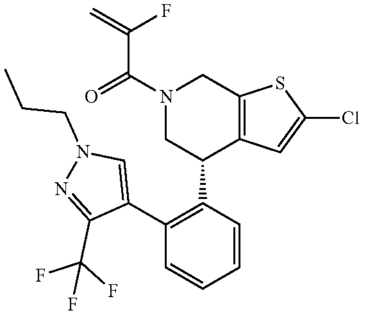 [SMILES: C=C(F)C(=O)N1Cc2sc(Cl)cc2[C@H](c2ccccc2-c2cn(CCC)nc2C(F)(F)F)C1] | 498.8 |
| 258 | 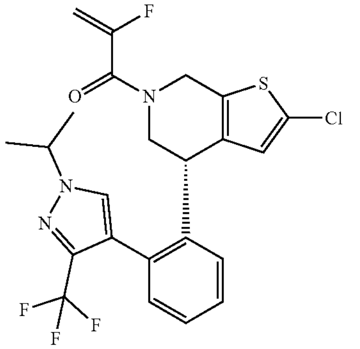 [SMILES: C=C(F)C(=O)N1Cc2sc(Cl)cc2[C@H](c2ccccc2-c2cn(C(C)C)nc2C(F)(F)F)C1] | 497.7 |

-continued
| Compound | Structure | M + H |
|---|---|---|
| 259 | 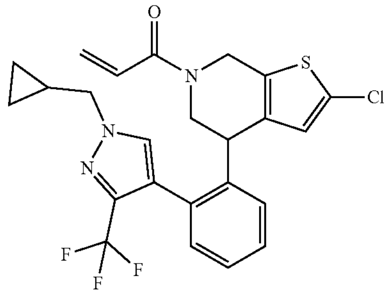 [SMILES: C=CC(=O)N1Cc2sc(Cl)cc2C(c2ccccc2-c2cn(CC3CC3)nc2C(F)(F)F)C1] | 492.0 |
| 260 | 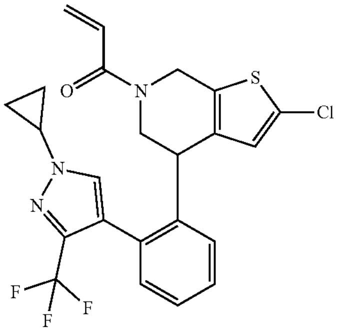 [SMILES: C=CC(=O)N1Cc2sc(Cl)cc2C(c2ccccc2-c2cn(C3CC3)nc2C(F)(F)F)C1] | 477.8 |
| 261 | 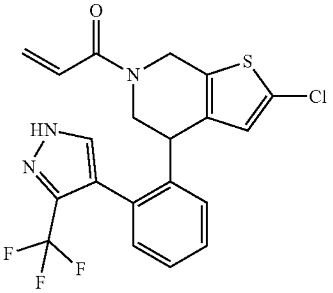 [SMILES: C=CC(=O)N1Cc2sc(Cl)cc2C(c2ccccc2-c2c[nH]nc2C(F)(F)F)C1] | 461.8 [M + Na] |
| 262 | 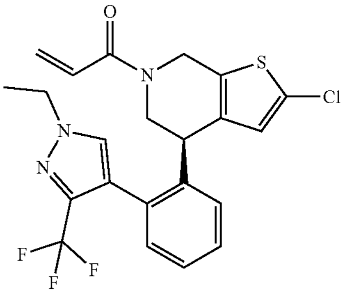 [SMILES: C=CC(=O)N1Cc2sc(Cl)cc2[C@@H](c2ccccc2-c2cn(CC)nc2C(F)(F)F)C1] | 466.1 |
| 263 | 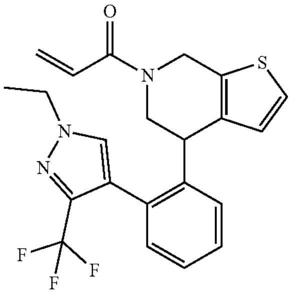 | 432.2 |

-continued
| Compound | Structure | M + H |
|---|---|---|
| 264 | 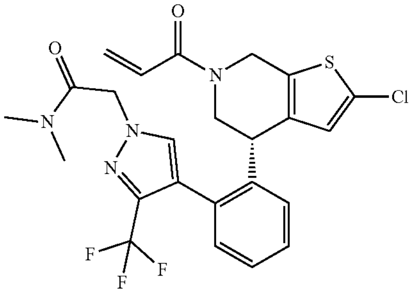 [SMILES: C=CC(=O)N1Cc2sc(Cl)cc2[C@H](c2ccccc2-c2cn(CC(=O)N(C)C)nc2C(F)(F)F)C1] | 523.0 |
| 265 | 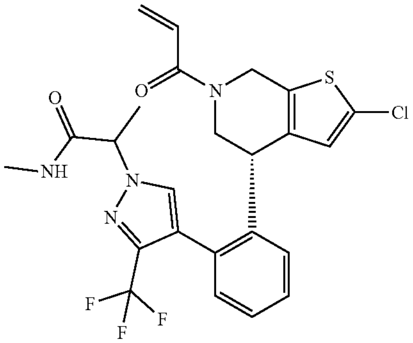 [SMILES: C=CC(=O)N1Cc2sc(Cl)cc2[C@H](c2ccccc2-c2cn(C(C)C(=O)NC)nc2C(F)(F)F)C1] | 523.0 |
| 266 | 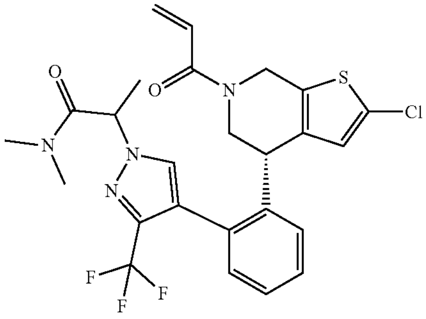 [SMILES: C=CC(=O)N1Cc2sc(Cl)cc2[C@H](c2ccccc2-c2cn(C(C)C(=O)N(C)C)nc2C(F)(F)F)C1] | 536.8 |
| 267 | 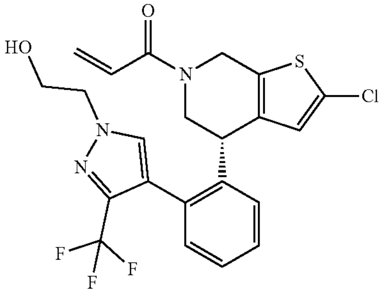 [SMILES: C=CC(=O)N1Cc2sc(Cl)cc2[C@H](c2ccccc2-c2cn(CCO)nc2C(F)(F)F)C1] | 481.8 |
| 268 | 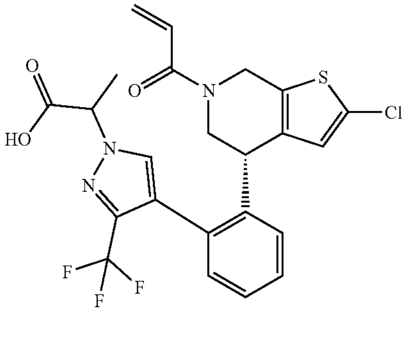 [SMILES: C=CC(=O)N1Cc2sc(Cl)cc2[C@H](c2ccccc2-c2cn(C(C)C(=O)O)nc2C(F)(F)F)C1] | 510.0 |

-continued
| Compound | Structure | M + H |
| --- | --- | --- |
| 269 | 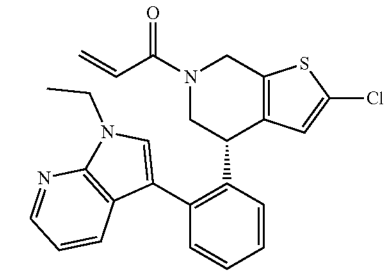 [SMILES: C=CC(=O)N1Cc2sc(Cl)cc2[C@H](c2ccccc2-c2cn(CC)c3ncccc23)C1] | 447.9 |
| 270 | 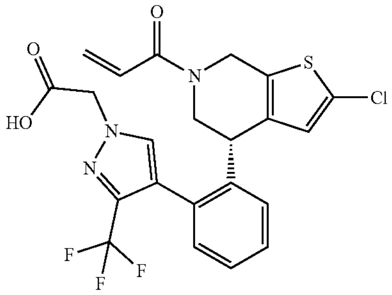 [SMILES: C=CC(=O)N1Cc2sc(Cl)cc2[C@H](c2ccccc2-c2cn(CC(=O)O)nc2C(F)(F)F)C1] | 495.8 |
| 271 | 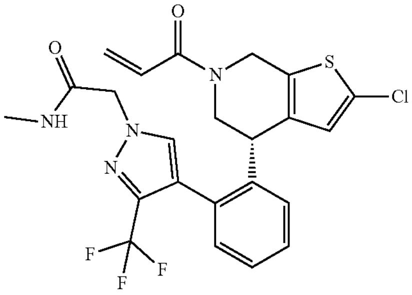 [SMILES: C=CC(=O)N1Cc2sc(Cl)cc2[C@H](c2ccccc2-c2cn(CC(=O)NC)nc2C(F)(F)F)C1] | 508.9 |
| 272 | 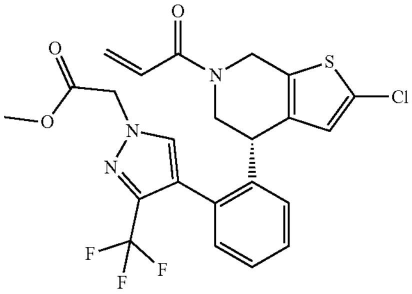 [SMILES: C=CC(=O)N1Cc2sc(Cl)cc2[C@H](c2ccccc2-c2cn(CC(=O)OC)nc2C(F)(F)F)C1] | 509.9 |
| 273 | 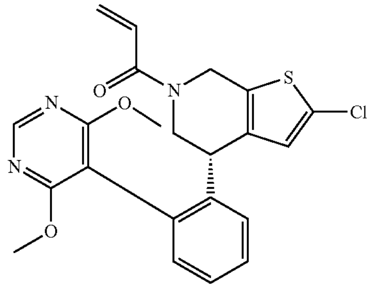 [SMILES: C=CC(=O)N1Cc2sc(Cl)cc2[C@H](c2ccccc2-c2c(OC)ncnc2OC)C1] | 441.9 |

-continued
| Compound | Structure | M + H |
|---|---|---|
| 274 | 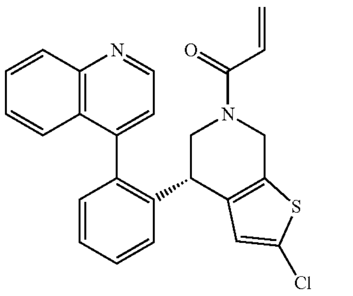 [SMILES: C=CC(=O)N1Cc2sc(Cl)cc2[C@H](c2ccccc2-c2ccnc3ccccc23)C1] | 430.9 |
| 275 | 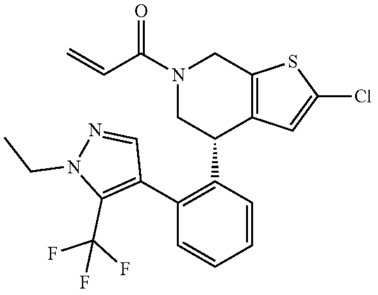 [SMILES: C=CC(=O)N1Cc2sc(Cl)cc2[C@H](c2ccccc2-c2cnn(CC)c2C(F)(F)F)C1] | 465.9 |
| 276 | 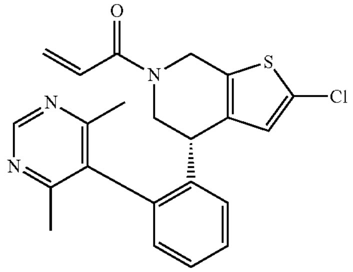 [SMILES: C=CC(=O)N1Cc2sc(Cl)cc2[C@H](c2ccccc2-c2c(C)ncnc2C)C1] | 410.0 |
| 277 | 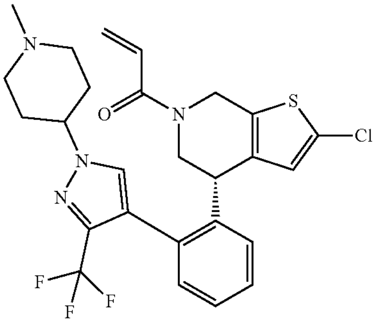 [SMILES: C=CC(=O)N1Cc2sc(Cl)cc2[C@H](c2ccccc2-c2cn(C3CCN(C)CC3)nc2C(F)(F)F)C1] | 535.1 |
| 278 | 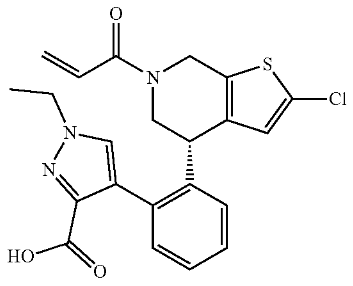 [SMILES: C=CC(=O)N1Cc2sc(Cl)cc2[C@H](c2ccccc2-c2cn(CC)nc2C(=O)O)C1] | 442.0 |

-continued
| Compound | Structure | M + H |
| --- | --- | --- |
| 279 | 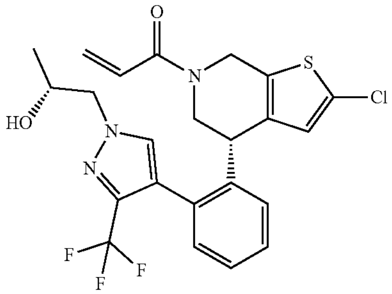 [SMILES: C=CC(=O)N1Cc2sc(Cl)cc2[C@H](c2ccccc2-c2cn(C[C@@H](C)O)nc2C(F)(F)F)C1] | 495.9 |
| 280 | 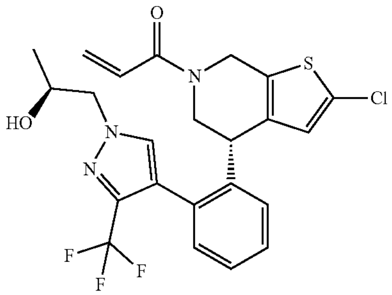 [SMILES: C=CC(=O)N1Cc2sc(Cl)cc2[C@H](c2ccccc2-c2cn(C[C@H](C)O)nc2C(F)(F)F)C1] | 495.9 |
| 281 | 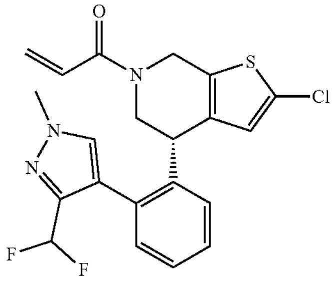 [SMILES: C=CC(=O)N1Cc2sc(Cl)cc2[C@H](c2ccccc2-c2cn(C)nc2C(F)F)C1] | 433.9 |
| 282 | 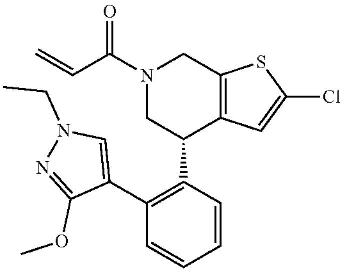 [SMILES: C=CC(=O)N1Cc2sc(Cl)cc2[C@H](c2ccccc2-c2cn(CC)nc2OC)C1] | 428.1 |
| 283 | 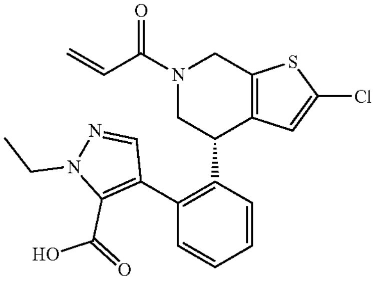 [SMILES: C=CC(=O)N1Cc2sc(Cl)cc2[C@H](c2ccccc2-c2cnn(CC)c2C(=O)O)C1] | 442.0 |

-continued
| Compound | Structure | M + H |
| --- | --- | --- |
| 284 | 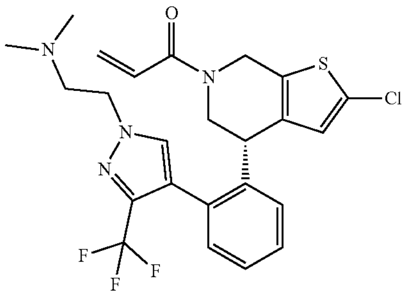 [SMILES: C=CC(=O)N1Cc2sc(Cl)cc2[C@H](c2ccccc2-c2cn(CCN(C)C)nc2C(F)(F)F)C1] | 509.1 |
| 285 | 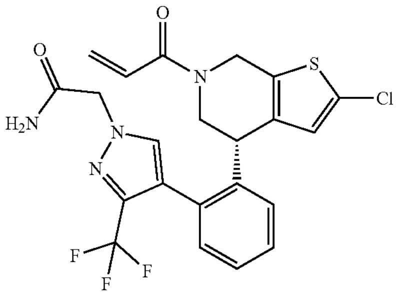 [SMILES: C=CC(=O)N1Cc2sc(Cl)cc2[C@H](c2ccccc2-c2cn(CC(N)=O)nc2C(F)(F)F)C1] | 494.9 |
| 286 | 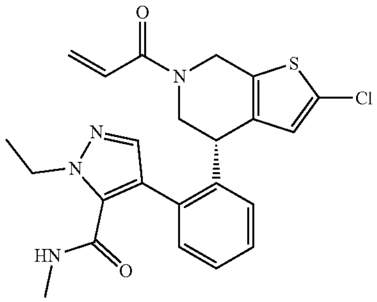 [SMILES: C=CC(=O)N1Cc2sc(Cl)cc2[C@H](c2ccccc2-c2cnn(CC)c2C(=O)NC)C1] | 455.0 |
| 287 | 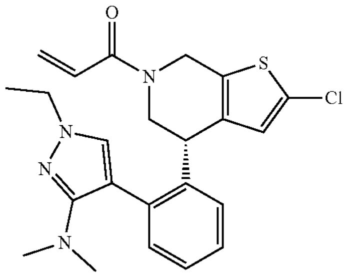 [SMILES: C=CC(=O)N1Cc2sc(Cl)cc2[C@H](c2ccccc2-c2cn(CC)nc2N(C)C)C1] | 441.0 |
| 288 | 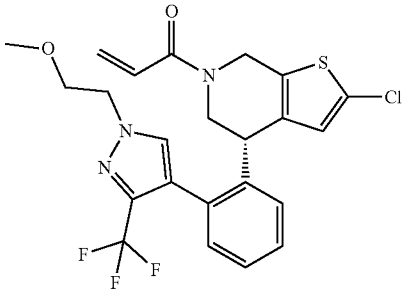 [SMILES: C=CC(=O)N1Cc2sc(Cl)cc2[C@H](c2ccccc2-c2cn(CCOC)nc2C(F)(F)F)C1] | 495.8 |

-continued
| Compound | Structure | M + H |
|---|---|---|
| 289 | 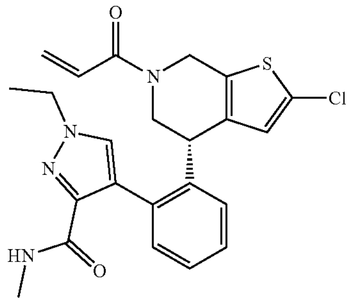 [SMILES: C=CC(=O)N1Cc2sc(Cl)cc2[C@H](c2ccccc2-c2cn(CC)nc2C(=O)NC)C1] | 455.1 |
| 290 | 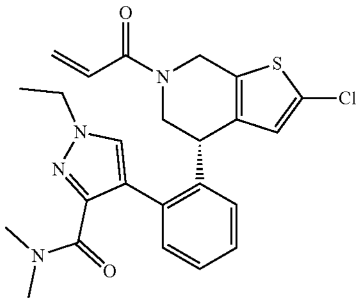 [SMILES: C=CC(=O)N1Cc2sc(Cl)cc2[C@H](c2ccccc2-c2cn(CC)nc2C(=O)N(C)C)C1] | 468.9 |
| 291 | 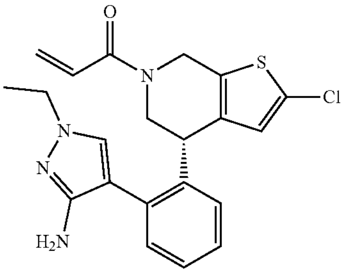 [SMILES: C=CC(=O)N1Cc2sc(Cl)cc2[C@H](c2ccccc2-c2cn(CC)nc2N)C1] | 413.0 |
| 292 | 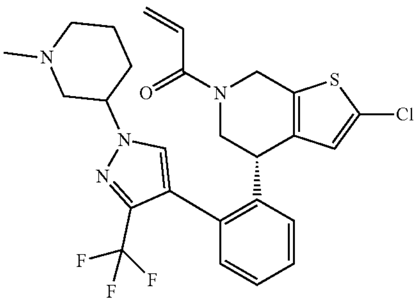 [SMILES: C=CC(=O)N1Cc2sc(Cl)cc2[C@H](c2ccccc2-c2cn(C3CCCN(C)C3)nc2C(F)(F)F)C1] | 534.9 |
| 293 | 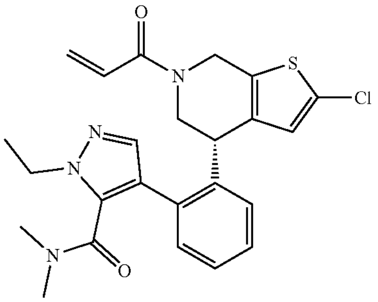 [SMILES: C=CC(=O)N1Cc2sc(Cl)cc2[C@H](c2ccccc2-c2cnn(CC)c2C(=O)N(C)C)C1] | 469.2 |

-continued
| Compound | Structure | M + H |
|---|---|---|
| 294 | 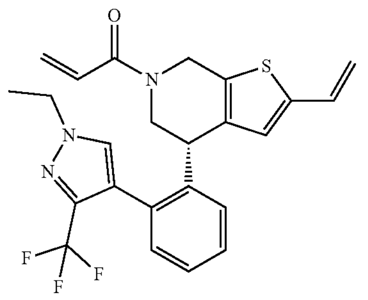 [SMILES: C=CC(=O)N1Cc2sc(C=C)cc2[C@H](c2ccccc2-c2cn(CC)nc2C(F)(F)F)C1] | 457.9 |
| 295 | 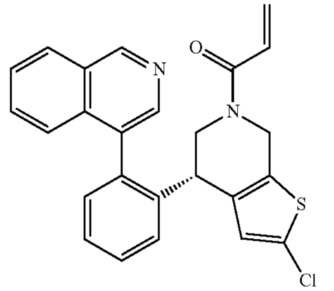 [SMILES: C=CC(=O)N1Cc2sc(Cl)cc2[C@H](c2ccccc2-c2cncc3ccccc23)C1] | 431.1 |
| 296 | 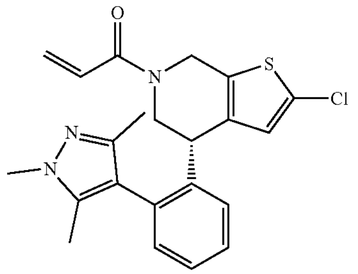 [SMILES: C=CC(=O)N1Cc2sc(Cl)cc2[C@H](c2ccccc2-c2c(C)nn(C)c2C)C1] | 412.1 |
| 297 | 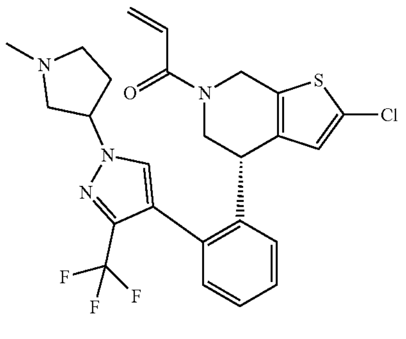 [SMILES: C=CC(=O)N1Cc2sc(Cl)cc2[C@H](c2ccccc2-c2cn(C3CCN(C)C3)nc2C(F)(F)F)C1] | 520.9 |
| 298 | 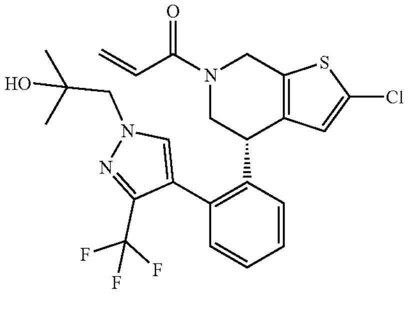 [SMILES: C=CC(=O)N1Cc2sc(Cl)cc2[C@H](c2ccccc2-c2cn(CC(C)(C)O)nc2C(F)(F)F)C1] | 510.2 |

-continued
| Compound | Structure | M + H |
| --- | --- | --- |
| 299 | 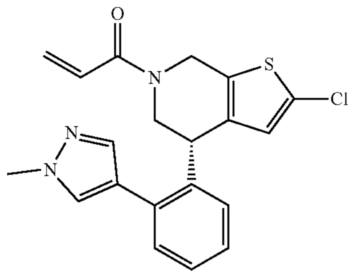 [SMILES: C=CC(=O)N1Cc2sc(Cl)cc2[C@H](c2ccccc2-c2cnn(C)c2)C1] | 384.1 |
| 300 | 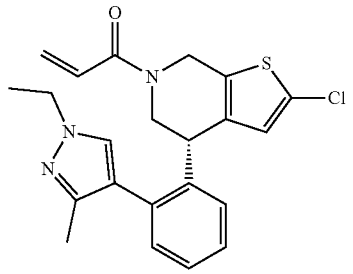 [SMILES: C=CC(=O)N1Cc2sc(Cl)cc2[C@H](c2ccccc2-c2cn(CC)nc2C)C1] | 412.2 |
| 301 | 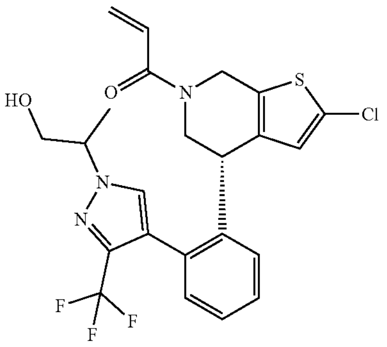 [SMILES: C=CC(=O)N1Cc2sc(Cl)cc2[C@H](c2ccccc2-c2cn(C(C)CO)nc2C(F)(F)F)C1] | 496.0 |
| 302 | 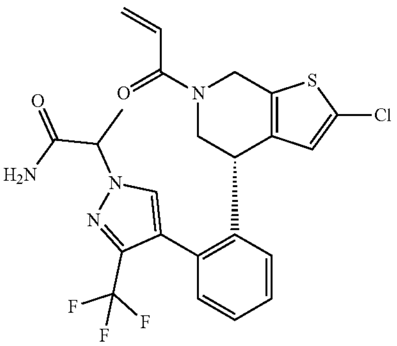 [SMILES: C=CC(=O)N1Cc2sc(Cl)cc2[C@H](c2ccccc2-c2cn(C(C)C(N)=O)nc2C(F)(F)F)C1] | 508.9 |

-continued
| Compound | Structure | M + H |
|---|---|---|
| 303 | 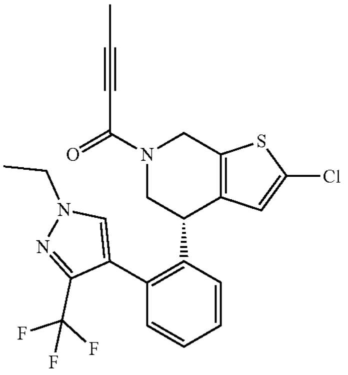 [SMILES: CC#CC(=O)N1Cc2sc(Cl)cc2[C@H](c2ccccc2-c2cn(CC)nc2C(F)(F)F)C1] | 478.1 |
| 304 | 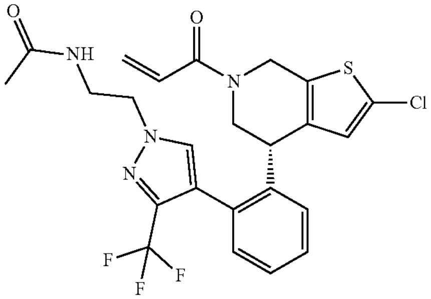 [SMILES: C=CC(=O)N1Cc2sc(Cl)cc2[C@H](c2ccccc2-c2cn(CCNC(C)=O)nc2C(F)(F)F)C1] | 522.8 |
| 305 | 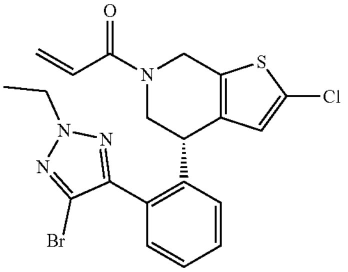 [SMILES: C=CC(=O)N1Cc2sc(Cl)cc2[C@H](c2ccccc2-c2nn(CC)nc2Br)C1] | 479.1 |
| 306 | 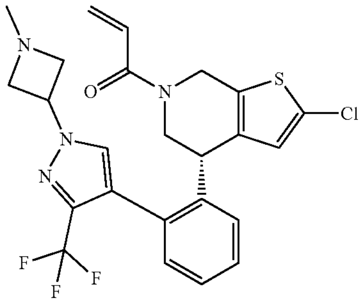 [SMILES: C=CC(=O)N1Cc2sc(Cl)cc2[C@H](c2ccccc2-c2cn(C3CN(C)C3)nc2C(F)(F)F)C1] | 506.9 |
| 307 | 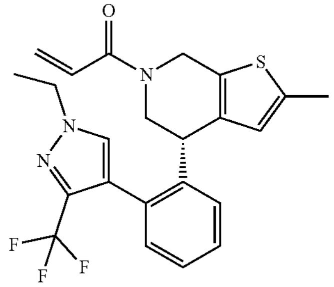 [SMILES: C=CC(=O)N1Cc2sc(C)cc2[C@H](c2ccccc2-c2cn(CC)nc2C(F)(F)F)C1] | 445.9 |

-continued
| Compound | Structure | M + H |
|---|---|---|
| 308 | 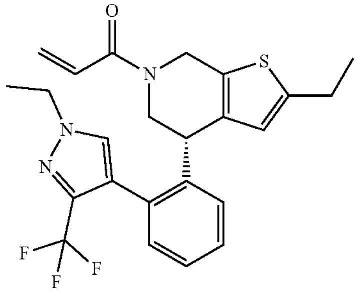 [SMILES: C=CC(=O)N1Cc2sc(CC)cc2[C@H](c2ccccc2-c2cn(CC)nc2C(F)(F)F)C1] | 459.8 |
| 309 | 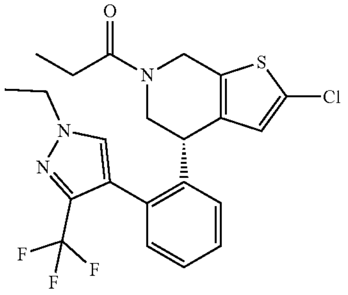 [SMILES: CCC(=O)N1Cc2sc(Cl)cc2[C@H](c2ccccc2-c2cn(CC)nc2C(F)(F)F)C1] | 467.9 |
| 310 | 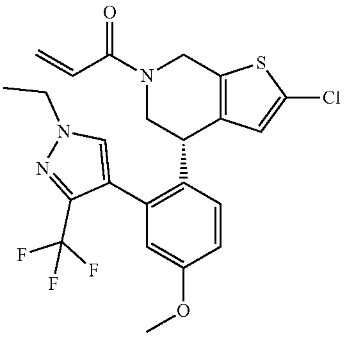 [SMILES: C=CC(=O)N1Cc2sc(Cl)cc2[C@H](c2ccc(OC)cc2-c2cn(CC)nc2C(F)(F)F)C1] | 496.2 |
| 311 | 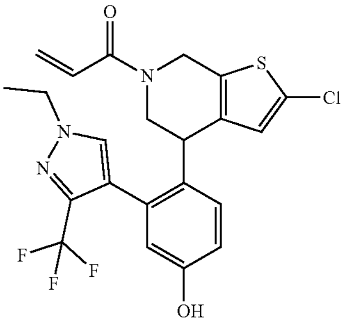 [SMILES: C=CC(=O)N1Cc2sc(Cl)cc2C(c2ccc(O)cc2-c2cn(CC)nc2C(F)(F)F)C1] | 482.1 |
| 312 | 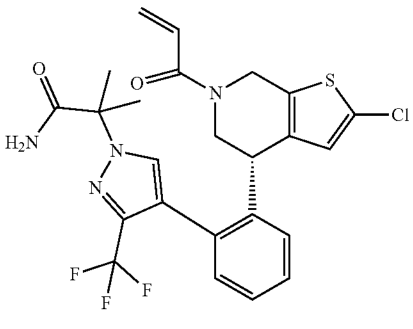 [SMILES: C=CC(=O)N1Cc2sc(Cl)cc2[C@H](c2ccccc2-c2cn(C(C)(C)C(N)=O)nc2C(F)(F)F)C1] | 522.9 |

-continued
| Compound | Structure | M + H |
|---|---|---|
| 313 | 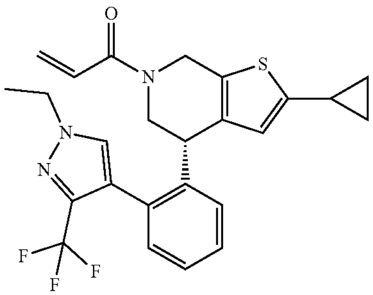 [SMILES: C=CC(=O)N1Cc2sc(C3CC3)cc2[C@H](c2ccccc2-c2cn(CC)nc2C(F)(F)F)C1] | 471.9 |
| 314 | 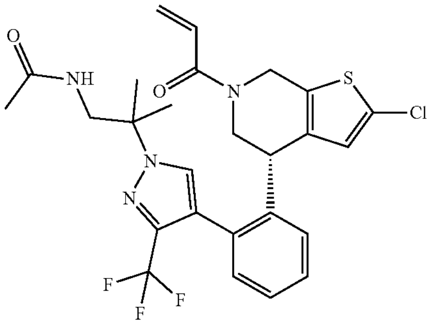 [SMILES: C=CC(=O)N1Cc2sc(Cl)cc2[C@H](c2ccccc2-c2cn(C(C)(C)CNC(C)=O)nc2C(F)(F)F)C1] | 551.2 |
| 315 | 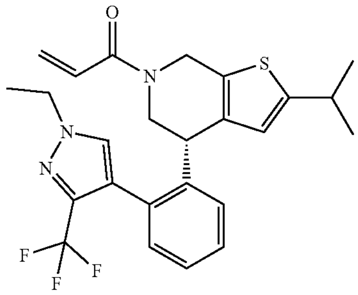 [SMILES: C=CC(=O)N1Cc2sc(C(C)C)cc2[C@H](c2ccccc2-c2cn(CC)nc2C(F)(F)F)C1] | 474.1 |
| 316 | 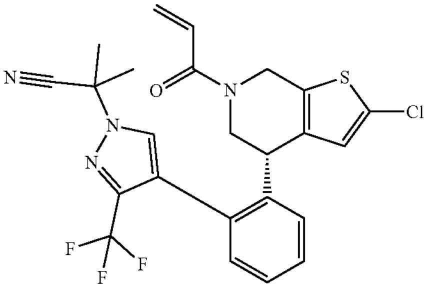 [SMILES: C=CC(=O)N1Cc2sc(Cl)cc2[C@H](c2ccccc2-c2cn(C(C)(C)C#N)nc2C(F)(F)F)C1] | 504.8 |
| 317 | 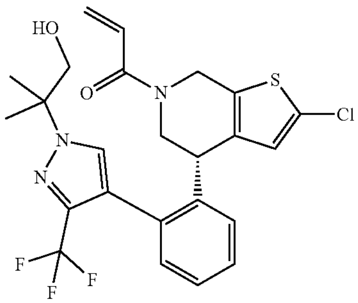 [SMILES: C=CC(=O)N1Cc2sc(Cl)cc2[C@H](c2ccccc2-c2cn(C(C)(C)CO)nc2C(F)(F)F)C1] | 509.8 |

-continued
| Compound | Structure | M + H |
|---|---|---|
| 318 | 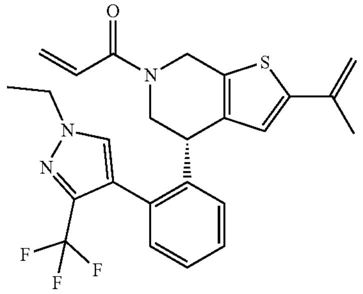 [SMILES: C=CC(=O)N1Cc2sc(C(=C)C)cc2[C@H](c2ccccc2-c2cn(CC)nc2C(F)(F)F)C1] | 472.0 |
| 319 | 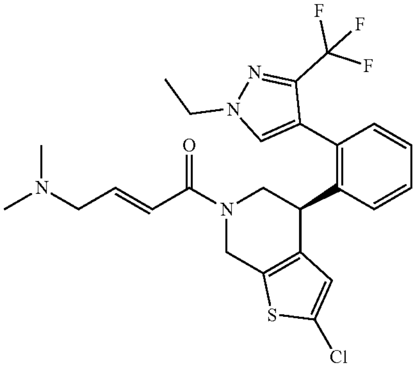 [SMILES: CCn1cc(-c2ccccc2[C@@H]2CN(C(=O)/C=C/CN(C)C)Cc3sc(Cl)cc32)c(C(F)(F)F)n1] | 522.8 |
| 320 | 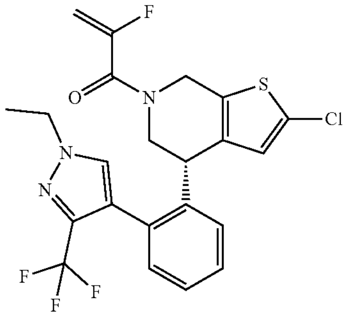 [SMILES: C=C(F)C(=O)N1Cc2sc(Cl)cc2[C@H](c2ccccc2-c2cn(CC)nc2C(F)(F)F)C1] | 483.9 |
| 321 | 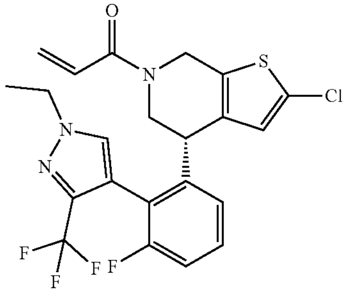 [SMILES: C=CC(=O)N1Cc2sc(Cl)cc2[C@H](c2cccc(F)c2-c2cn(CC)nc2C(F)(F)F)C1] | 484.1 |
| 322 | 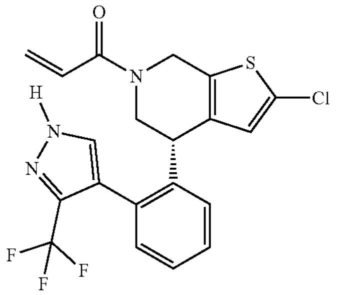 [SMILES: C=CC(=O)N1Cc2sc(Cl)cc2[C@H](c2ccccc2-c2c[nH]nc2C(F)(F)F)C1] | 438.1 |

-continued
| Compound | Structure | M + H |
| --- | --- | --- |
| 323 | 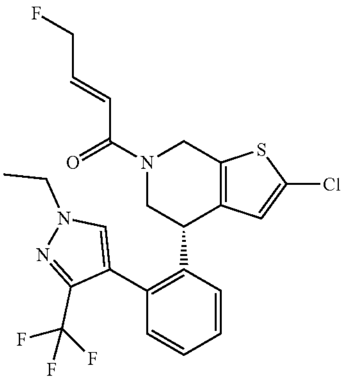 [SMILES: CCn1cc(-c2ccccc2[C@@H]2CN(C(=O)/C=C/CF)Cc3sc(Cl)cc32)c(C(F)(F)F)n1] | 498.0 |
| 324 | 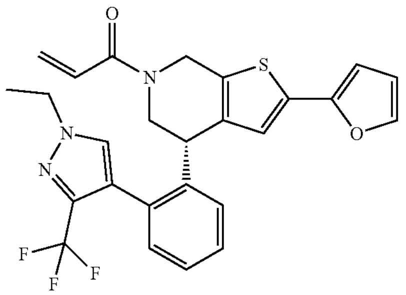 [SMILES: C=CC(=O)N1Cc2sc(-c3ccco3)cc2[C@H](c2ccccc2-c2cn(CC)nc2C(F)(F)F)C1] | 498.1 |
| 325 | 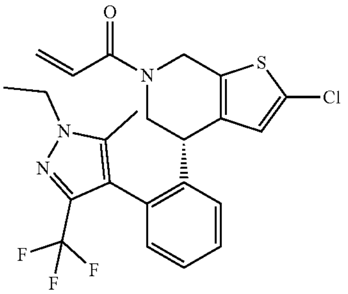 [SMILES: C=CC(=O)N1Cc2sc(Cl)cc2[C@H](c2ccccc2-c2c(C(F)(F)F)nn(CC)c2C)C1] | 480.2 |
| 326 | 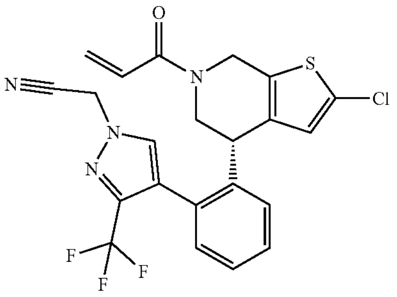 [SMILES: C=CC(=O)N1Cc2sc(Cl)cc2[C@H](c2ccccc2-c2cn(CC#N)nc2C(F)(F)F)C1] | 477.1 |
| 327 | 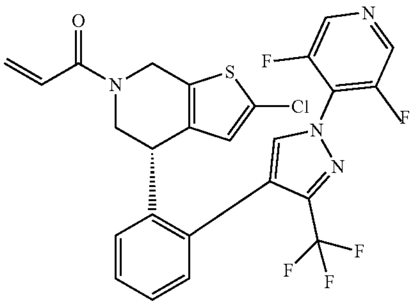 | 550.8 |

-continued
| Compound | Structure | M + H |
|---|---|---|
| 328 | 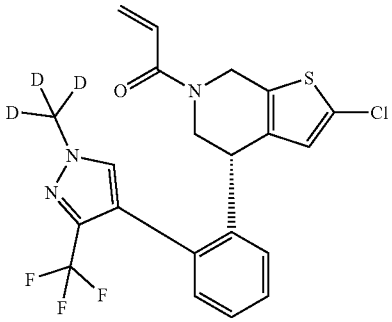 [SMILES: [2H]C([2H])([2H])n1cc(-c2ccccc2[C@@H]2CN(C(=O)C=C)Cc3sc(Cl)cc32)c(C(F)(F)F)n1] | 455.1 |
| 329 | 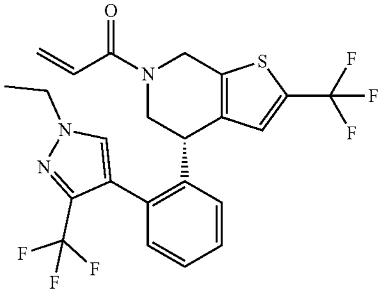 [SMILES: C=CC(=O)N1Cc2sc(C(F)(F)F)cc2[C@H](c2ccccc2-c2cn(CC)nc2C(F)(F)F)C1] | 500.1 |
| 330 | 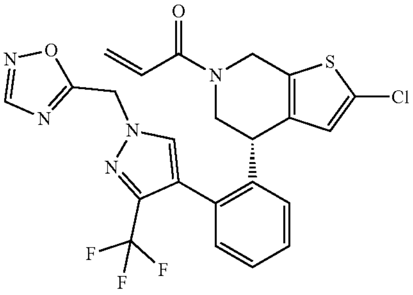 [SMILES: C=CC(=O)N1Cc2sc(Cl)cc2[C@H](c2ccccc2-c2cn(Cc3ncno3)nc2C(F)(F)F)C1] | 520.1 |
| 331 | 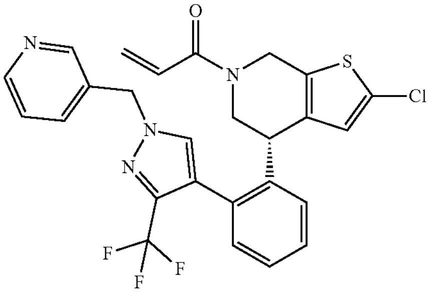 | 529.1 |
| 332 | 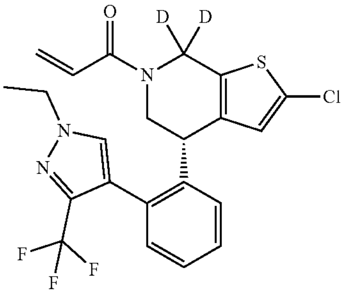 [SMILES: [2H]C1([2H])c2sc(Cl)cc2[C@H](c2ccccc2-c2cn(CC)nc2C(F)(F)F)CN1C(=O)C=C] | 468.1 |

-continued
| Compound | Structure | M + H |
|---|---|---|
| 333 | 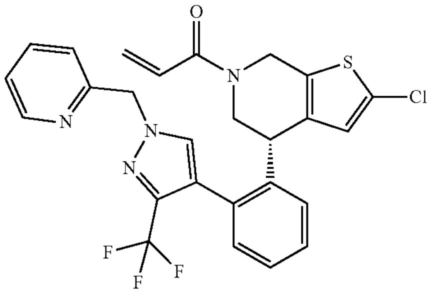 [SMILES: C=CC(=O)N1Cc2sc(Cl)cc2[C@H](c2ccccc2-c2cn(Cc3ccccn3)nc2C(F)(F)F)C1] | 529.1 |
| 334 | 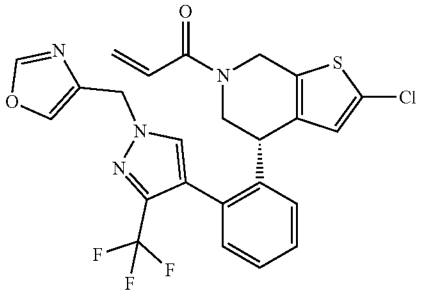 [SMILES: C=CC(=O)N1Cc2sc(Cl)cc2[C@H](c2ccccc2-c2cn(Cc3cocn3)nc2C(F)(F)F)C1] | 519.1 |
| 335 | 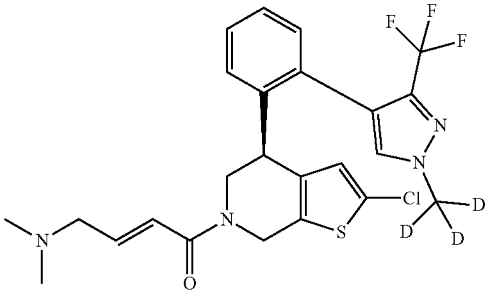 [SMILES: [2H]C([2H])([2H])n1cc(-c2ccccc2[C@@H]2CN(C(=O)/C=C/CN(C)C)Cc3sc(Cl)cc32)c(C(F)(F)F)n1] | 512.2 |
| 336 | 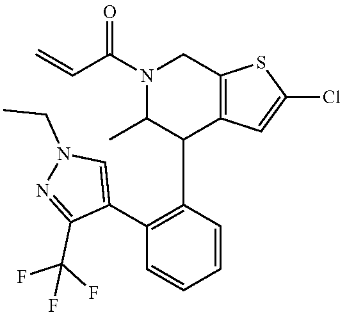 [SMILES: C=CC(=O)N1Cc2sc(Cl)cc2C(c2ccccc2-c2cn(CC)nc2C(F)(F)F)C1C] | 480.1 |
| 337 | 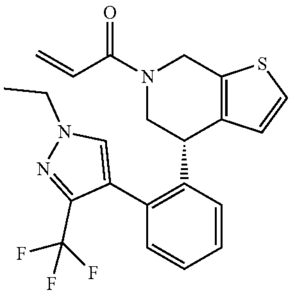 | 432.0 |

-continued
| Compound | Structure | M + H |
|---|---|---|
| 338 | 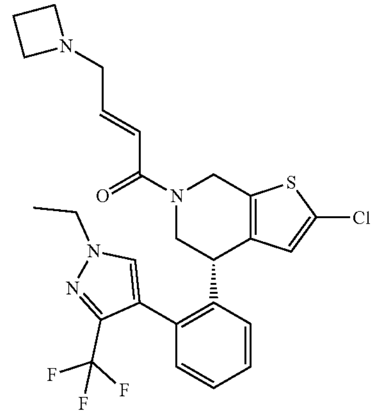 [SMILES: CCn1cc(-c2ccccc2[C@@H]2CN(C(=O)/C=C/CN3CCC3)Cc3sc(Cl)cc32)c(C(F)(F)F)n1] | 534.8 |
| 339 | 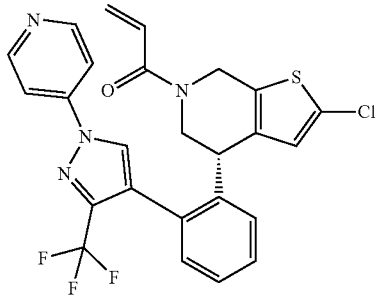 [SMILES: C=CC(=O)N1Cc2sc(Cl)cc2[C@H](c2ccccc2-c2cn(-c3ccncc3)nc2C(F)(F)F)C1] | 514.9 |
| 340 | 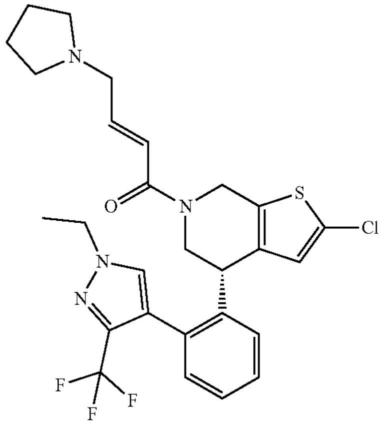 [SMILES: CCn1cc(-c2ccccc2[C@@H]2CN(C(=O)/C=C/CN3CCCC3)Cc3sc(Cl)cc32)c(C(F)(F)F)n1] | 549.0 |
| 341 | 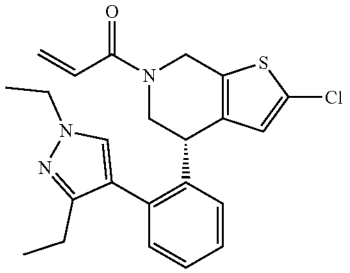 | 426.1 |

-continued
| Compound | Structure | M + H |
|---|---|---|
| 342 | 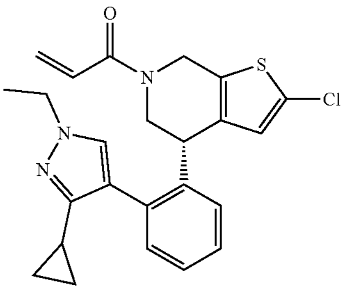 [SMILES: C=CC(=O)N1Cc2sc(Cl)cc2[C@H](c2ccccc2-c2cn(CC)nc2C2CC2)C1] | 437.8 |
| 343 | 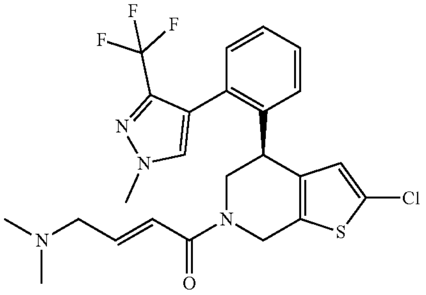 [SMILES: CN(C)C/C=C/C(=O)N1Cc2sc(Cl)cc2[C@H](c2ccccc2-c2cn(C)nc2C(F)(F)F)C1] | 508.9 |
| 344 | 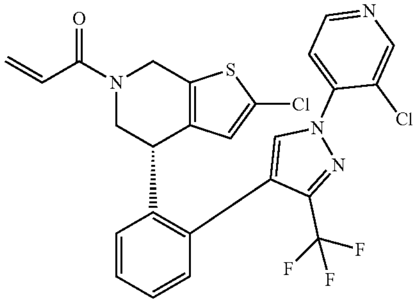 [SMILES: C=CC(=O)N1Cc2sc(Cl)cc2[C@H](c2ccccc2-c2cn(-c3ccncc3Cl)nc2C(F)(F)F)C1] | 508.8 |
| 345 | 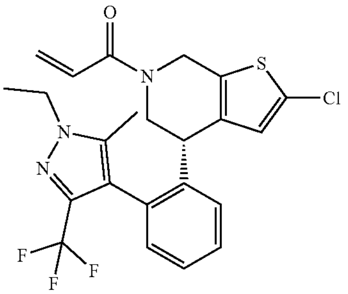 [SMILES: C=CC(=O)N1Cc2sc(Cl)cc2[C@H](c2ccccc2-c2c(C(F)(F)F)nn(CC)c2C)C1] | 480.2 |
| 346 | 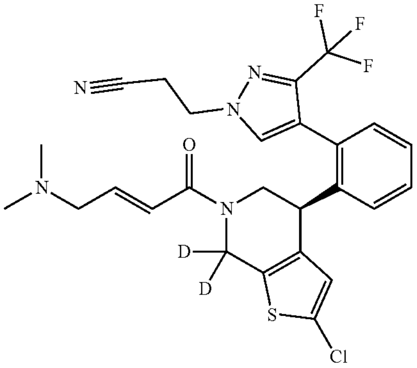 [SMILES: [2H]C1([2H])c2sc(Cl)cc2[C@H](c2ccccc2-c2cn(CCC#N)nc2C(F)(F)F)CN1C(=O)/C=C/CN(C)C] | 548.2 |

-continued
| Compound | Structure | M + H |
|---|---|---|
| 347 | 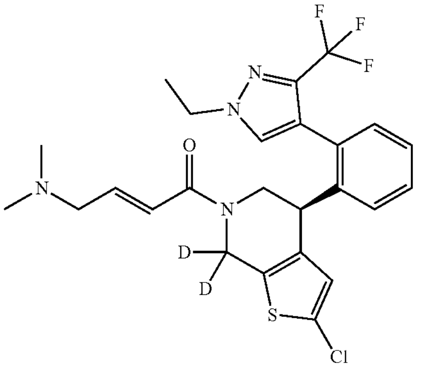 [SMILES: [2H]C1([2H])c2sc(Cl)cc2[C@H](c2ccccc2-c2cn(CC)nc2C(F)(F)F)CN1C(=O)/C=C/CN(C)C] | 525.2 |
| 348 | 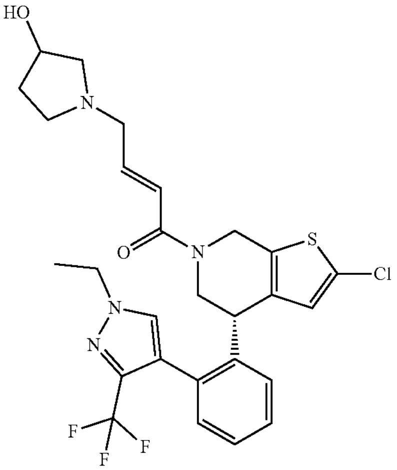 [SMILES: CCn1cc(-c2ccccc2[C@@H]2CN(C(=O)/C=C/CN3CCC(O)C3)Cc3sc(Cl)cc32)c(C(F)(F)F)n1] | 565.0 |
| 349 | 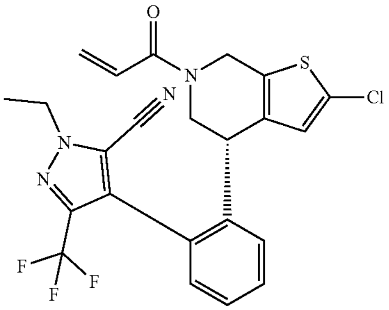 [SMILES: C=CC(=O)N1Cc2sc(Cl)cc2[C@H](c2ccccc2-c2c(C(F)(F)F)nn(CC)c2C#N)C1] | 491.1 |
| 350 | 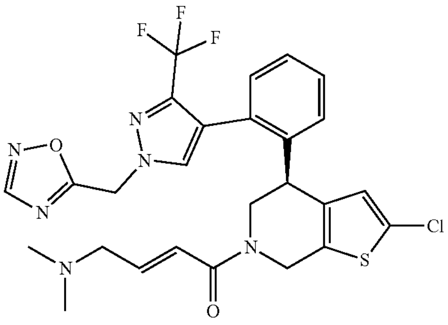 [SMILES: CN(C)C/C=C/C(=O)N1Cc2sc(Cl)cc2[C@H](c2ccccc2-c2cn(Cc3ncno3)nc2C(F)(F)F)C1] | 577.2 |

-continued
| Compound | Structure | M + H |
|---|---|---|
| 351 | 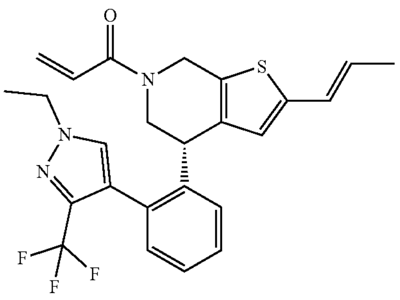 [SMILES: C=CC(=O)N1Cc2sc(/C=C/C)cc2[C@H](c2ccccc2-c2cn(CC)nc2C(F)(F)F)C1] | 471.9 |
| 352 | 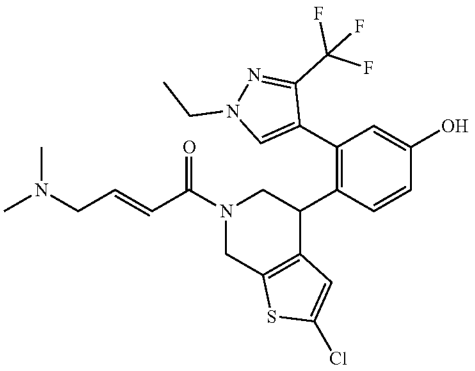 [SMILES: CCn1cc(-c2cc(O)ccc2C2CN(C(=O)/C=C/CN(C)C)Cc3sc(Cl)cc32)c(C(F)(F)F)n1] | 539.2 |
| 353 | 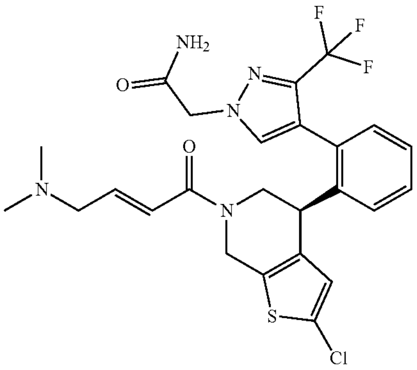 [SMILES: CN(C)C/C=C/C(=O)N1Cc2sc(Cl)cc2[C@H](c2ccccc2-c2cn(CC(N)=O)nc2C(F)(F)F)C1] | 552.2 |
| 354 | 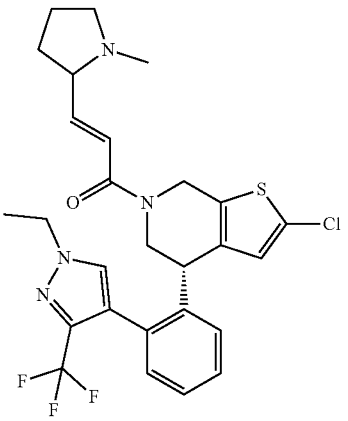 [SMILES: CCn1cc(-c2ccccc2[C@@H]2CN(C(=O)/C=C/C3CCCN3C)Cc3sc(Cl)cc32)c(C(F)(F)F)n1] | 549.2 |

-continued
| Compound | Structure | M + H |
|---|---|---|
| 355 | 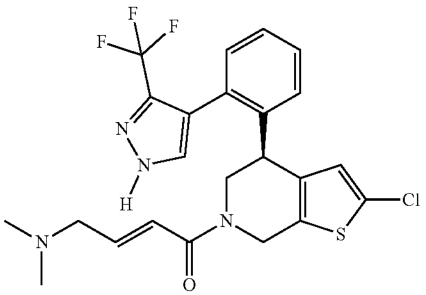 [SMILES: CN(C)C/C=C/C(=O)N1Cc2sc(Cl)cc2[C@H](c2ccccc2-c2c[nH]nc2C(F)(F)F)C1] | 495.2 |
| 356 | 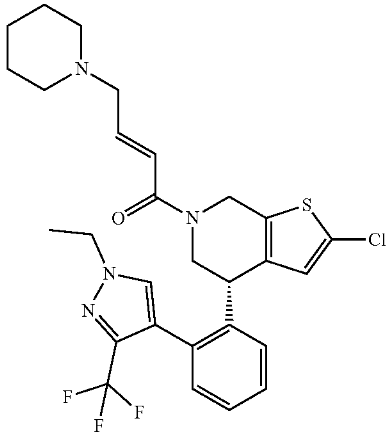 [SMILES: CCn1cc(-c2ccccc2[C@@H]2CN(C(=O)/C=C/CN3CCCCC3)Cc3sc(Cl)cc32)c(C(F)(F)F)n1] | 563.0 |
| 357 | 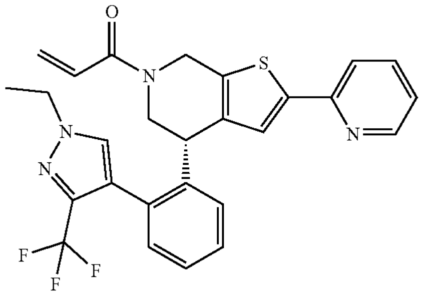 [SMILES: C=CC(=O)N1Cc2sc(-c3ccccn3)cc2[C@H](c2ccccc2-c2cn(CC)nc2C(F)(F)F)C1] | 508.8 |
| 358 | 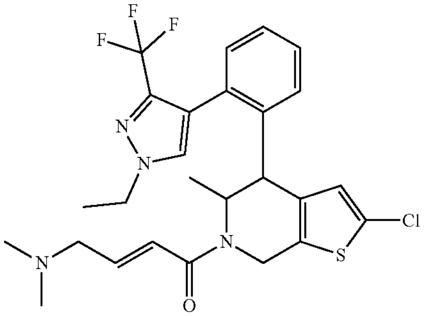 [SMILES: CCn1cc(-c2ccccc2C2c3cc(Cl)sc3CN(C(=O)/C=C/CN(C)C)C2C)c(C(F)(F)F)n1] | 537.2 |

-continued
| Compound | Structure | M + H |
|---|---|---|
| 360 | 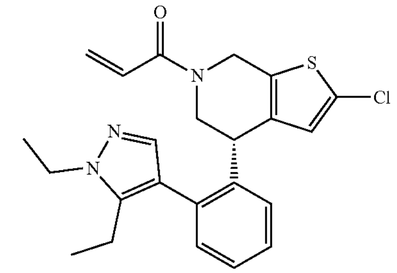 [SMILES: C=CC(=O)N1Cc2sc(Cl)cc2[C@H](c2ccccc2-c2cnn(CC)c2CC)C1] | 426.1 |
| 363 | 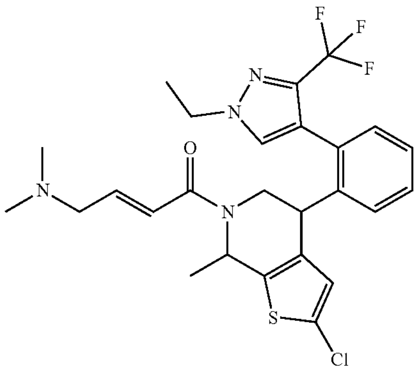 [SMILES: CCn1cc(-c2ccccc2C2CN(C(=O)/C=C/CN(C)C)C(C)c3sc(Cl)cc32)c(C(F)(F)F)n1] | 537.2 |
| 364 | 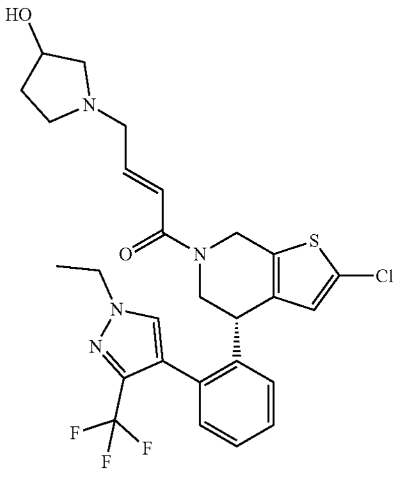 [SMILES: CCn1cc(-c2ccccc2[C@@H]2CN(C(=O)/C=C/CN3CCC(O)C3)Cc3sc(Cl)cc32)c(C(F)(F)F)n1] | 564.9 |
| 365 | 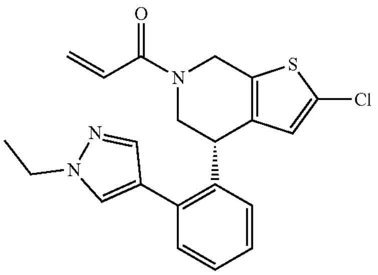 [SMILES: C=CC(=O)N1Cc2sc(Cl)cc2[C@H](c2ccccc2-c2cnn(CC)c2)C1] | 398.1 |

-continued
| Compound | Structure | M + H |
|---|---|---|
| 366 | 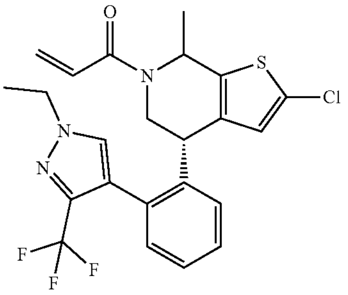 | 480.1 |
| 367 | 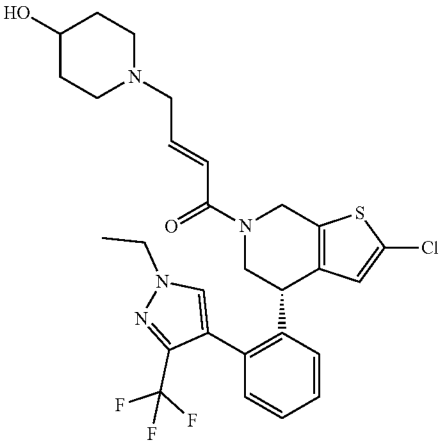 [SMILES: CCn1cc(-c2ccccc2[C@@H]2CN(C(=O)/C=C/CN3CCC(O)CC3)Cc3sc(Cl)cc32)c(C(F)(F)F)n1] | 578.9 |
| 368 | 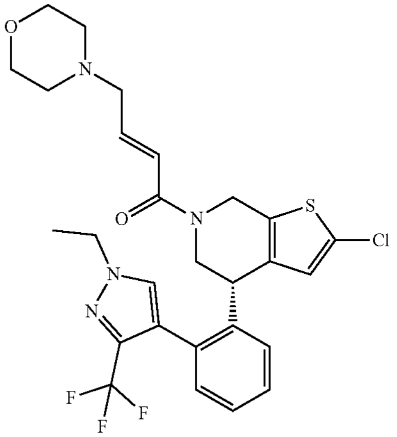 [SMILES: CCn1cc(-c2ccccc2[C@@H]2CN(C(=O)/C=C/CN3CCOCC3)Cc3sc(Cl)cc32)c(C(F)(F)F)n1] | 564.8 |

Example 8

When incubating such compounds with the activating enzymes (E1) of ubiquitin, SUMO, Nedd8, Urm1, ISG15 or Atg7, it forms covalent adducts with the specific Cys residue as depicted below. For the compounds provided herein including embodiments thereof, a covalent adduct may be formed with a cysteine amino acid corresponding to a Cys residue highlighted and in bold from Uba1 (SEQ ID, Uba2, Uba3, Uba4, Uba7 or Atg7 as shown in the sequence alignment below.

| | | |
|---|---|---|
| Uba1 (ubiquitin) | LVGAGAIGCELLK | SEQ ID NO:1 |
| Uba2 (SUMO) | VVGAGGIGCELLK | SEQ ID NO:2 |
| Uba3 (Nedd8) | VIGAGGLGCELLK | SEQ ID NO:3 |
| Uba4 (Urm1) | IVGCGGLGCPLAQ | SEQ ID NO:4 |
| Uba7 (ISG15) | LVGAGAIGCELLK | SEQ ID NO:5 |
| Atg7 (Atg8, Atg12) | LLGAGTLGCNVAR | SEQ ID NO:6 |

Compounds are evaluated for their inhibitory effect on activating enzymes (E1) of ubiquitin, SUMO, Nedd8, Urm1, ISG15 or Atg7 using previously reported methods and protocols. One example is in: Allosteric inhibition of ubiquitin-like modifications by a class of inhibitor of SUMO-activating enzyme. Cell Chemical Biology, 26,1-11, 2019. PMID: 28051857. The enzyme was preincubated with the compounds for 15 minutes. The results are provided in Table 2.

TABLE 2 compounds synthesized and biological activities.

| Compound Structure | | | E1 |
|---|---|---|---|
| 136 | 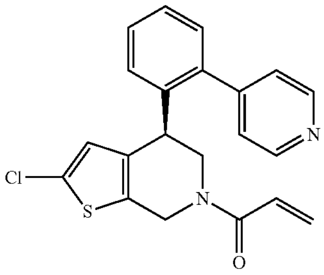 | 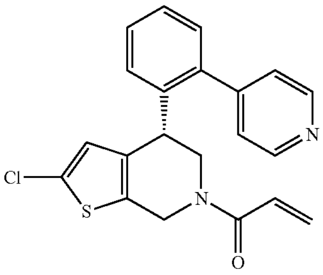 | +++ |
| 141 | 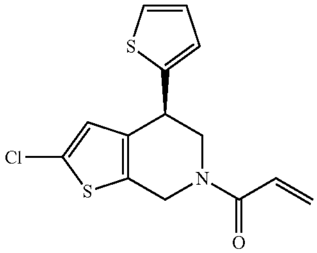 | 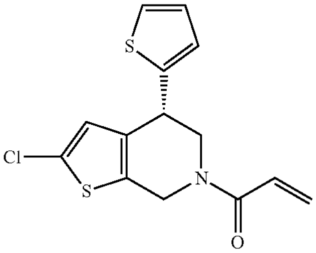 | +++ |

TABLE 2-continued
compounds synthesized and biological activities.
| Compound Structure | | | E1 |
|---|---|---|---|
| 142 | 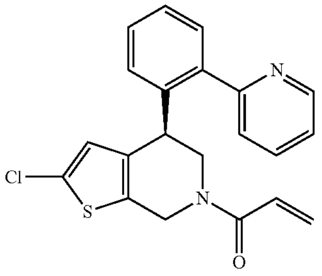 | 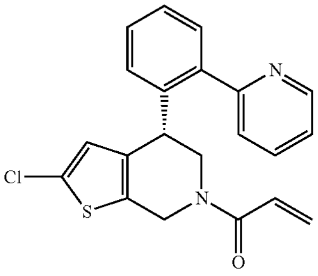 | +++ |
| 143 | 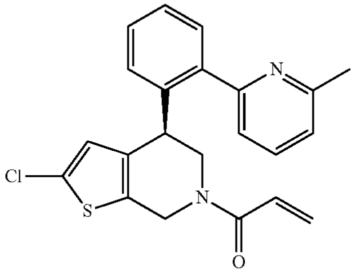 | 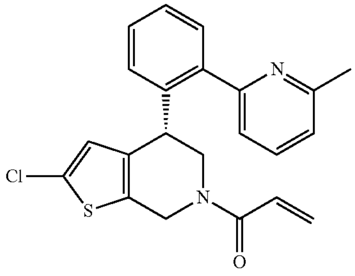 | +++ |
| 144 | 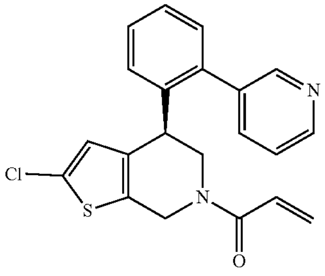 | 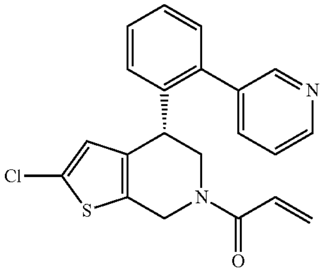 | +++ |
| 145 | 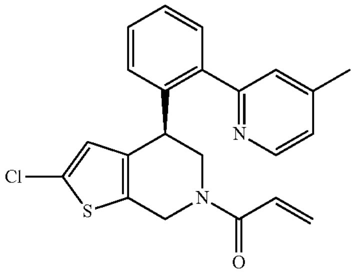 | 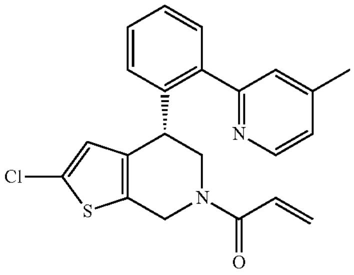 | ++ |
| 146 | 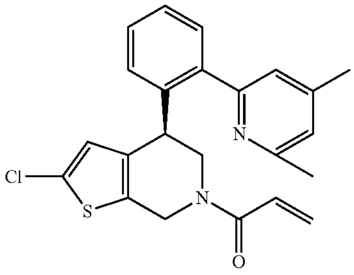 | 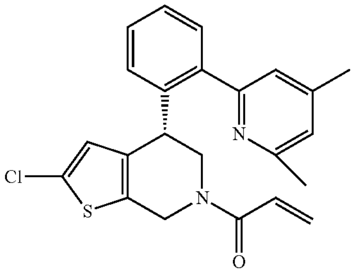 | ++ |

TABLE 2-continued
compounds synthesized and biological activities.
| Compound Structure | | E1 |
|---|---|---|
| 147 | 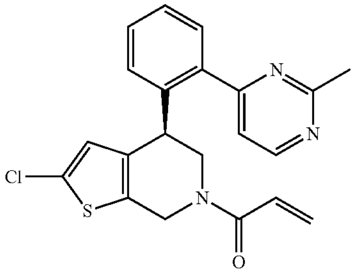 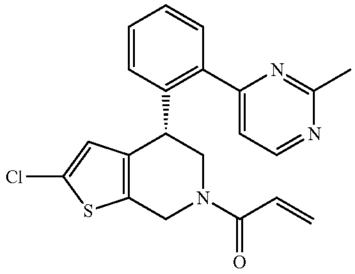 | ++ |
| 148 | 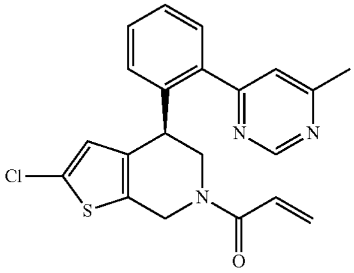 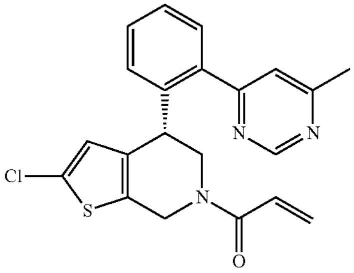 | ++ |
| 149 | 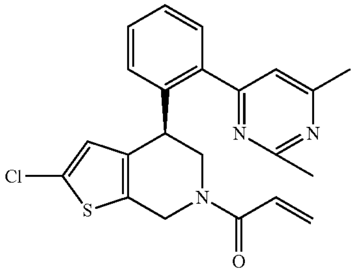 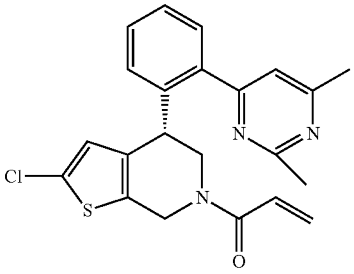 | ++ |
| 150 | 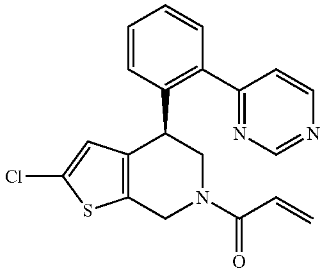 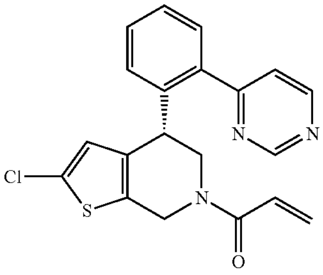 | ++ |
| 151 | 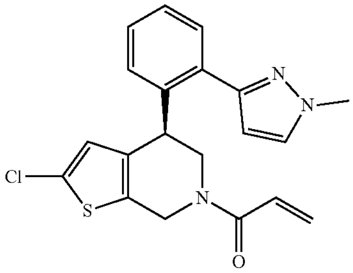 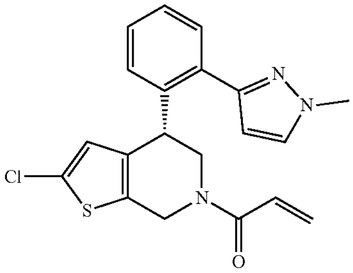 | +++ |

TABLE 2-continued
compounds synthesized and biological activities.
| Compound Structure | | E1 |
|---|---|---|
| 152 | 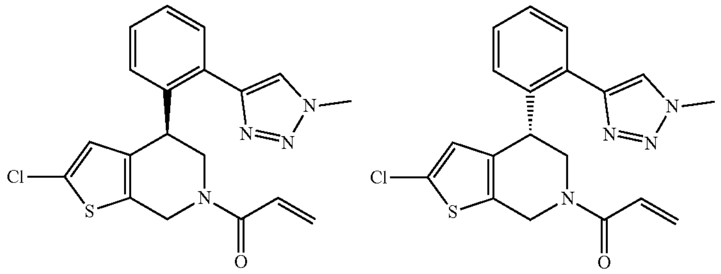 [SMILES: C=CC(=O)N1Cc2sc(Cl)cc2[C@@H](c2ccccc2-c2cn(C)nn2)C1 ; C=CC(=O)N1Cc2sc(Cl)cc2[C@H](c2ccccc2-c2cn(C)nn2)C1] | ++ |
| 153 | 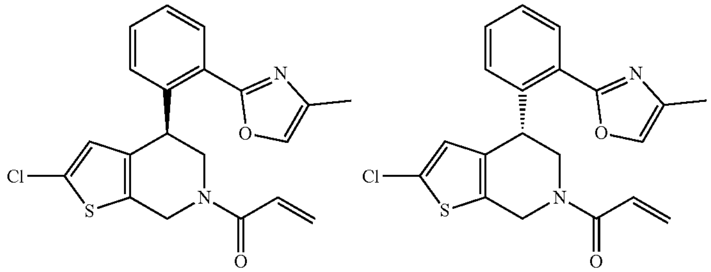 [SMILES: C=CC(=O)N1Cc2sc(Cl)cc2[C@@H](c2ccccc2-c2nc(C)co2)C1 ; C=CC(=O)N1Cc2sc(Cl)cc2[C@H](c2ccccc2-c2nc(C)co2)C1] | |
| 154 | 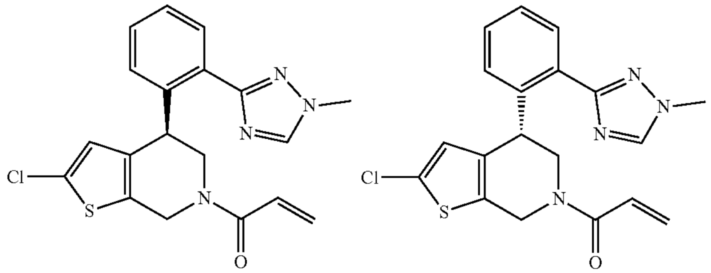 [SMILES: C=CC(=O)N1Cc2sc(Cl)cc2[C@@H](c2ccccc2-c2ncn(C)n2)C1 ; C=CC(=O)N1Cc2sc(Cl)cc2[C@H](c2ccccc2-c2ncn(C)n2)C1] | +++ |
| 155 | 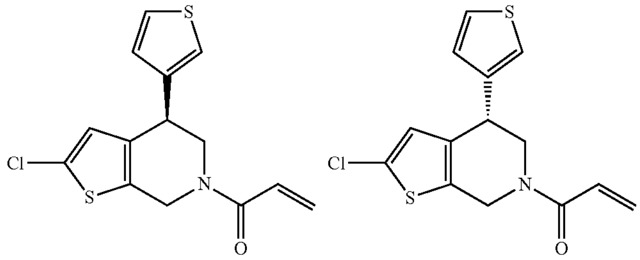 | +++ |
| 156 | 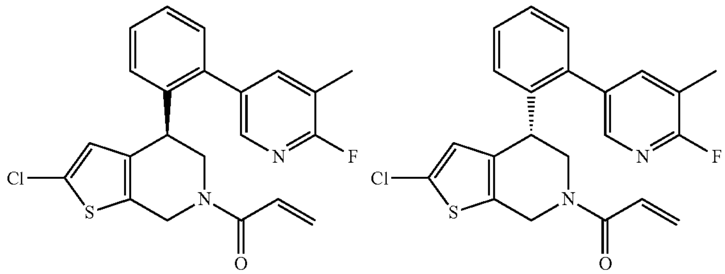 | +++ |

TABLE 2-continued
compounds synthesized and biological activities.
| Compound Structure | | E1 |
| --- | --- | --- |
| 157 | 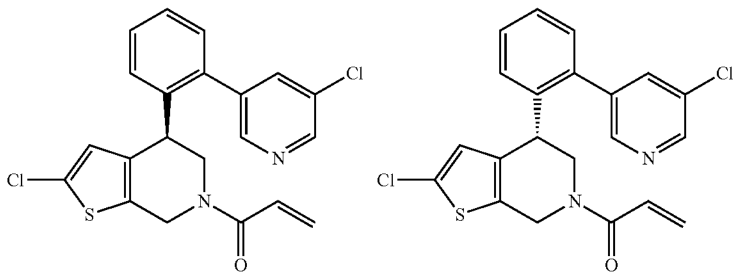 [SMILES: C=CC(=O)N1Cc2sc(Cl)cc2[C@@H](c2ccccc2-c2cncc(Cl)c2)C1 ; C=CC(=O)N1Cc2sc(Cl)cc2[C@H](c2ccccc2-c2cncc(Cl)c2)C1] | +++ |
| 158 | 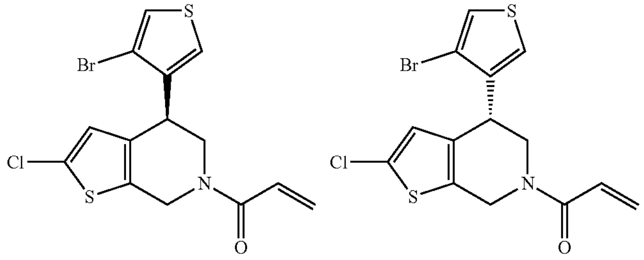 | +++ |
| 159 | 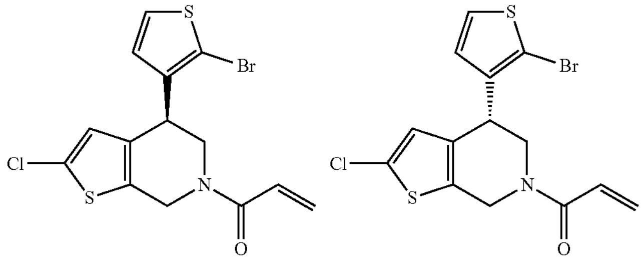 | +++ |
| 160 | 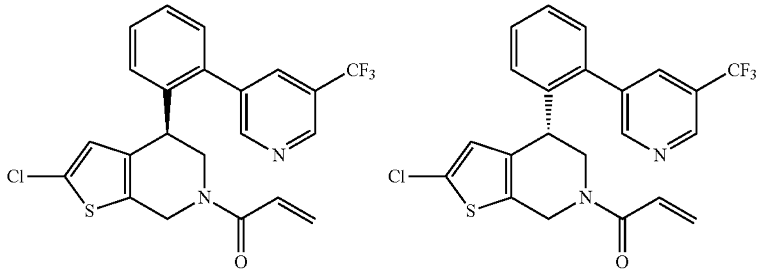 [SMILES: C=CC(=O)N1Cc2sc(Cl)cc2[C@@H](c2ccccc2-c2cncc(C(F)(F)F)c2)C1 ; C=CC(=O)N1Cc2sc(Cl)cc2[C@H](c2ccccc2-c2cncc(C(F)(F)F)c2)C1] | +++ |
| 161 | 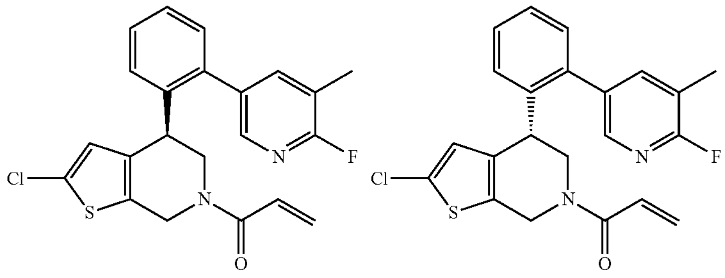 | + |

TABLE 2-continued
compounds synthesized and biological activities.
| Compound Structure | | | E1 |
|---|---|---|---|
| 162 | 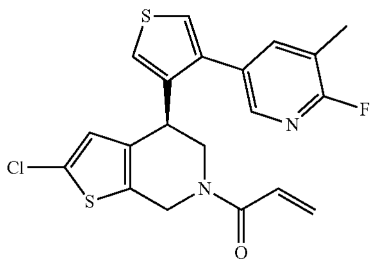 | 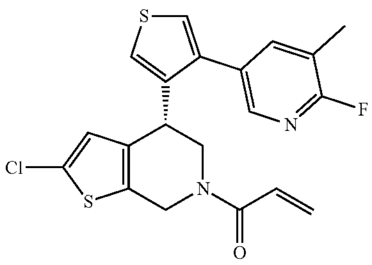 | ++ |
| 163 | 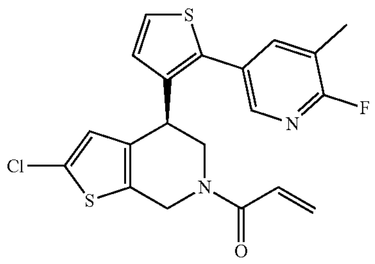 | 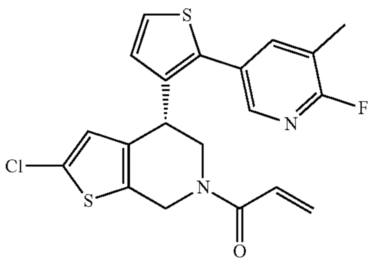 | ++ |
| 164 | 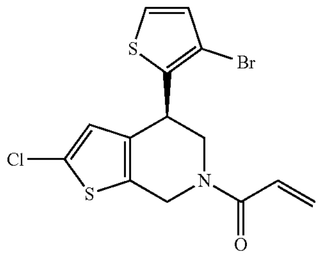 | 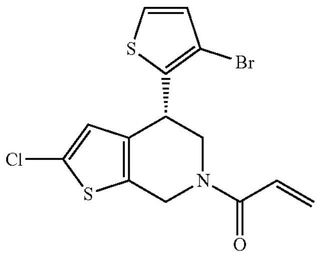 | +++ |
| 165 | 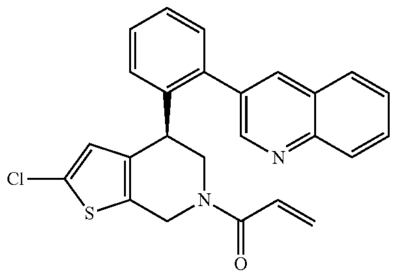 | 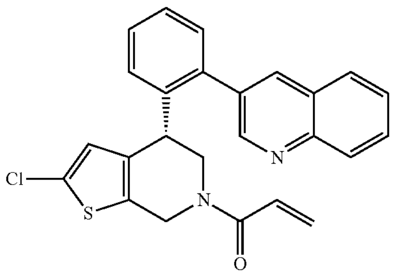 | +++ |
| 166 | 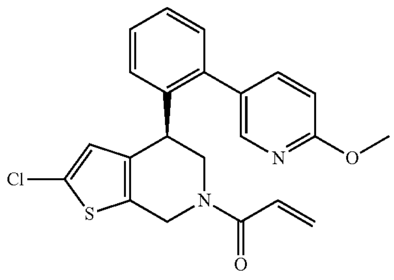 | 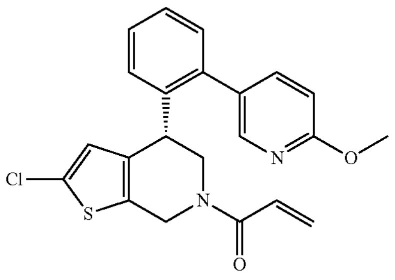 | +++ |

TABLE 2-continued
compounds synthesized and biological activities.
| Compound Structure | | E1 |
|---|---|---|
| 167 | 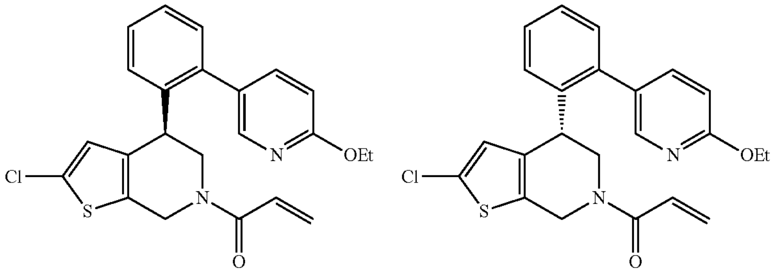 [SMILES: C=CC(=O)N1Cc2sc(Cl)cc2[C@@H](c2ccccc2-c2ccc(OCC)nc2)C1 ; C=CC(=O)N1Cc2sc(Cl)cc2[C@H](c2ccccc2-c2ccc(OCC)nc2)C1] | +++ |
| 168 | 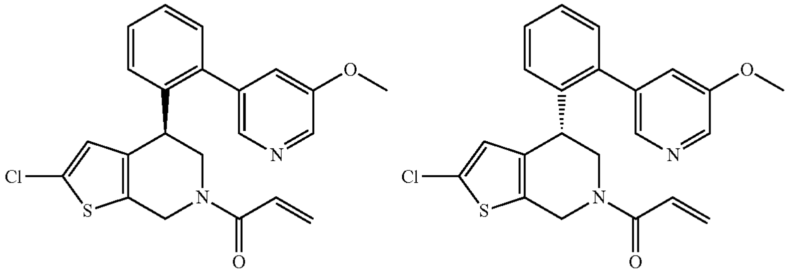 [SMILES: C=CC(=O)N1Cc2sc(Cl)cc2[C@@H](c2ccccc2-c2cncc(OC)c2)C1 ; C=CC(=O)N1Cc2sc(Cl)cc2[C@H](c2ccccc2-c2cncc(OC)c2)C1] | +++ |
| 169 | 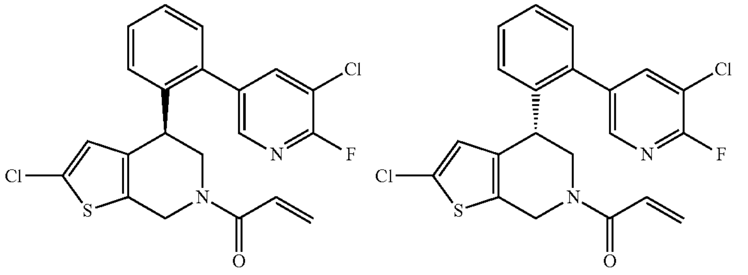 | ++ |
| 170 | 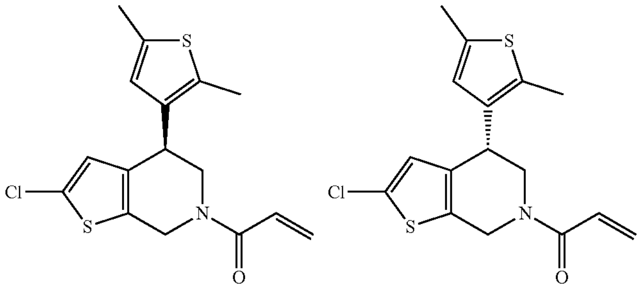 | + |
| 171 | 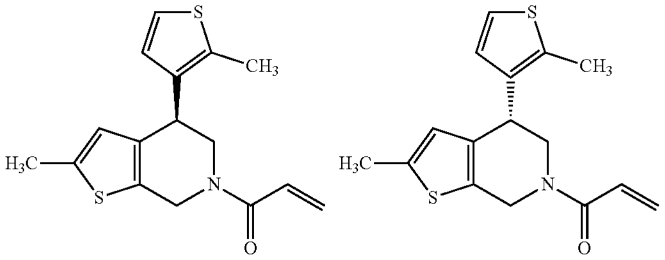 | +++ |

TABLE 2-continued
compounds synthesized and biological activities.
| Compound Structure | | E1 |
| --- | --- | --- |
| 172 | 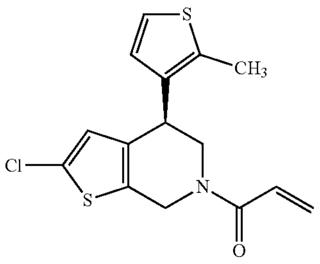 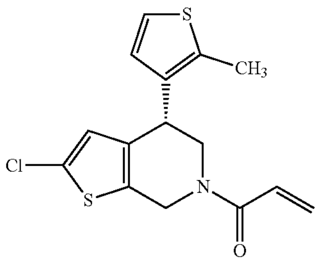 | +++ |
| 173 | 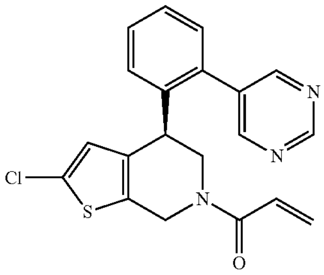 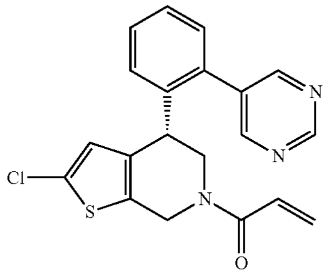 | +++ |
| 174 | 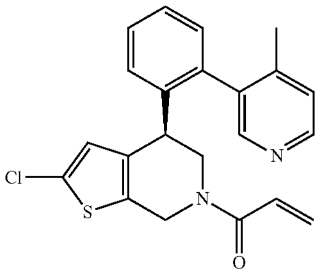 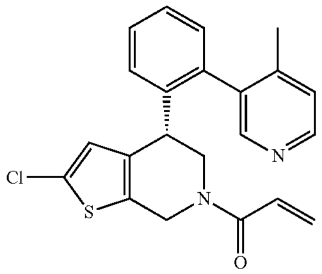 | ++ |
| 175 | 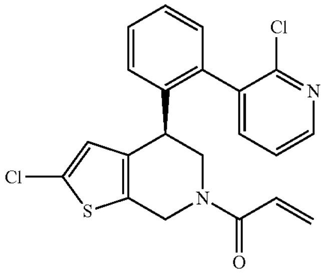 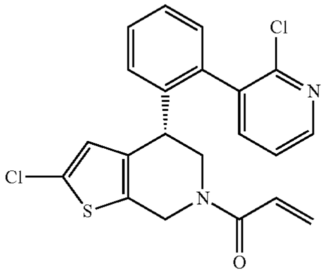 | +++ |
| 176 | 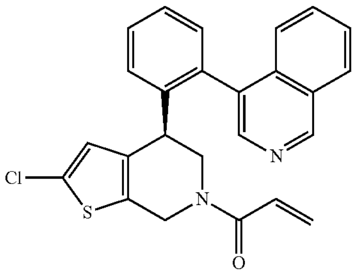 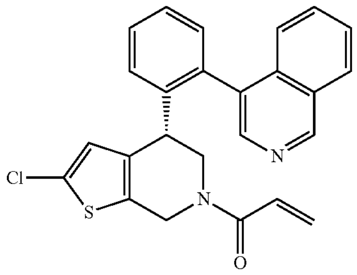 | +++ |

TABLE 2-continued
compounds synthesized and biological activities.
| Compound Structure | | E1 |
|---|---|---|
| 177 | 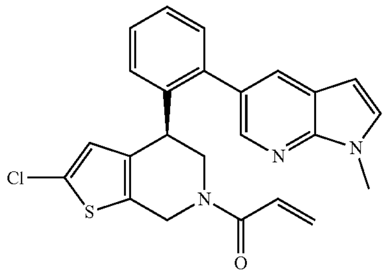 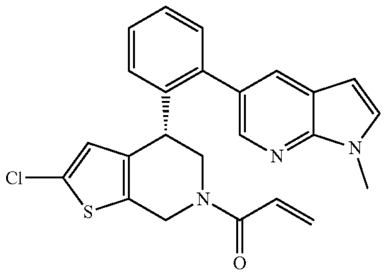 | + |
| 178 | 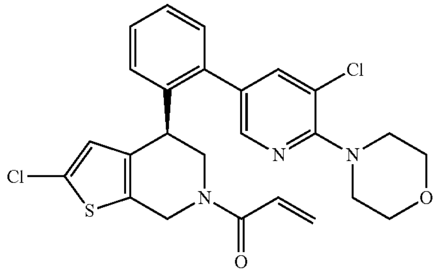 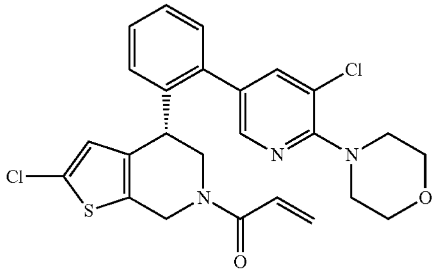 | + |
| 179 | 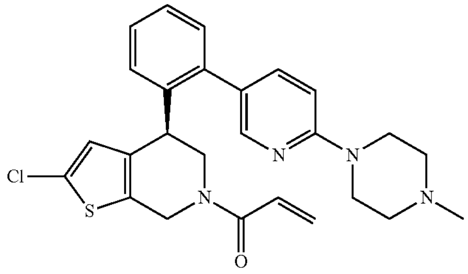 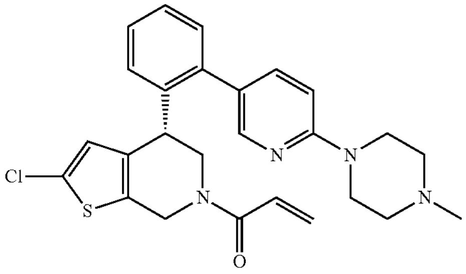 | + |
| 180 | 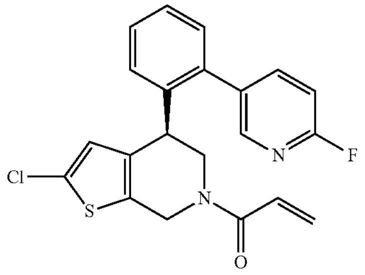 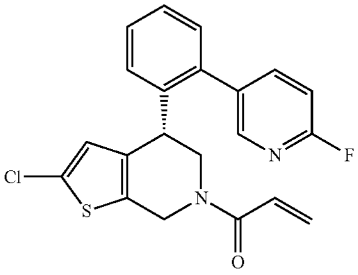 | ++ |
| 181 | 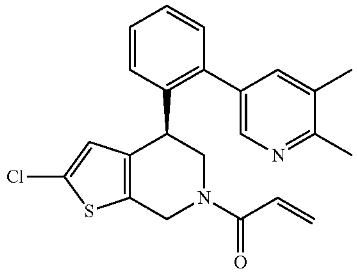 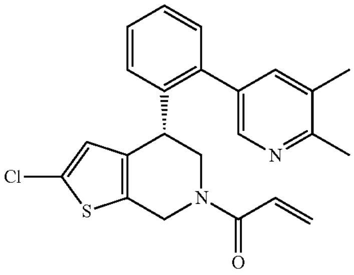 | +++ |

TABLE 2-continued
| compounds synthesized and biological activities. | |
|---|---|
| Compound Structure | E1 |
| 182 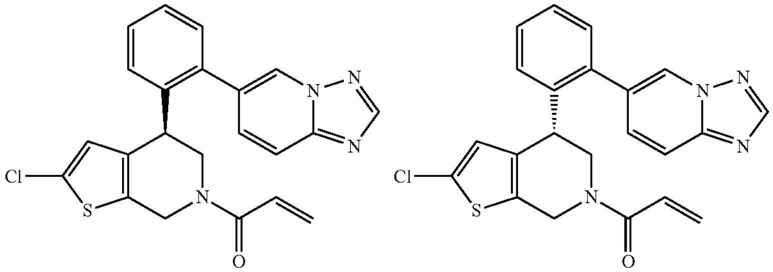 [SMILES: C=CC(=O)N1Cc2sc(Cl)cc2[C@@H](c2ccccc2-c2ccc3ncnn3c2)C1 ; C=CC(=O)N1Cc2sc(Cl)cc2[C@H](c2ccccc2-c2ccc3ncnn3c2)C1] | + |
| 183 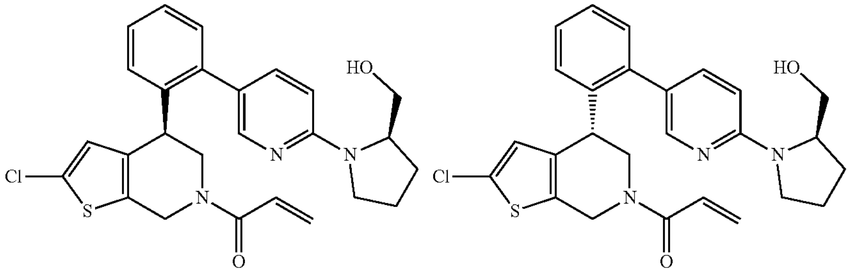 | + |
| 184 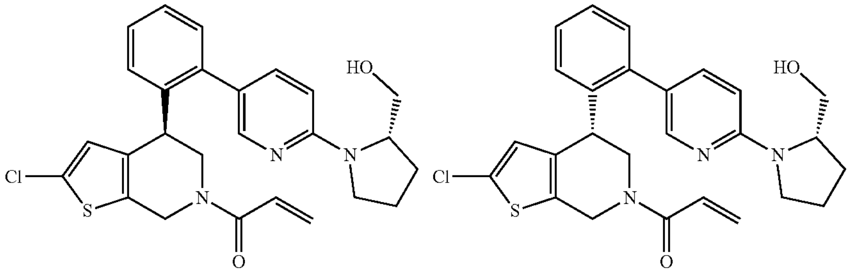 | + |
| 185 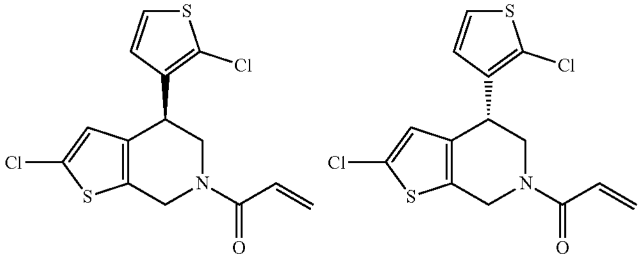 | +++ |
| 186 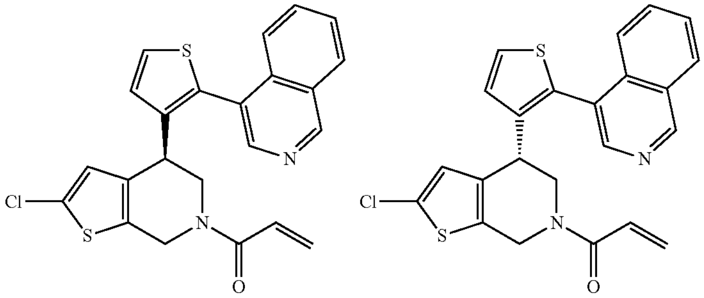 [SMILES: C=CC(=O)N1Cc2sc(Cl)cc2[C@@H](c2ccsc2-c2cncc3ccccc23)C1 ; C=CC(=O)N1Cc2sc(Cl)cc2[C@H](c2ccsc2-c2cncc3ccccc23)C1] | +++ |

TABLE 2-continued
| compounds synthesized and biological activities. | | |
|---|---|---|
| Compound Structure | | E1 |
| 187 | 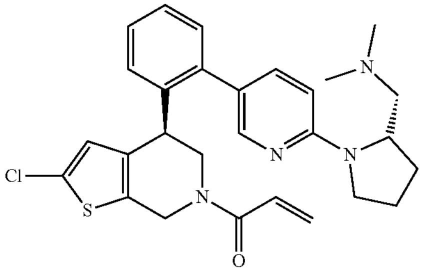 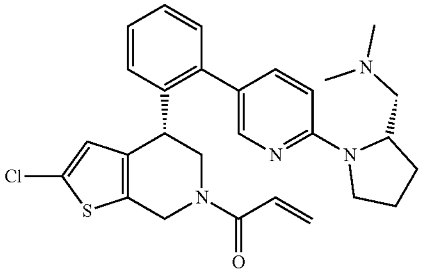 | ++ |
| 188 | 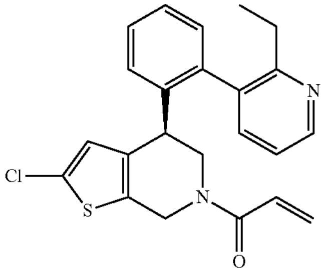 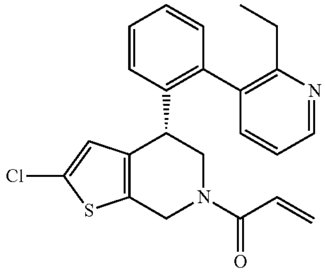 | +++ |
| 189 | 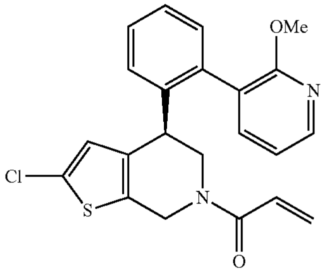 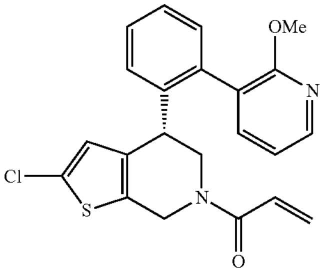 | +++ |
| 190 | 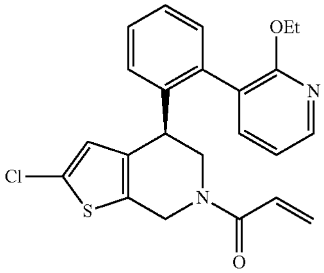 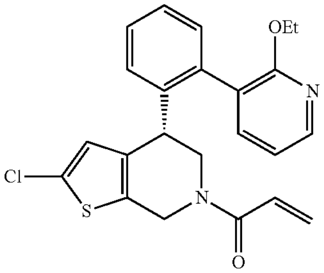 | +++ |
| 191 | 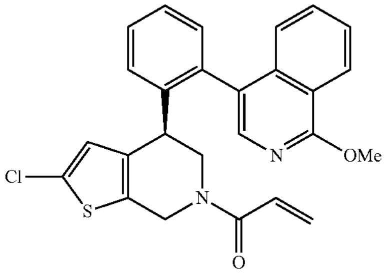 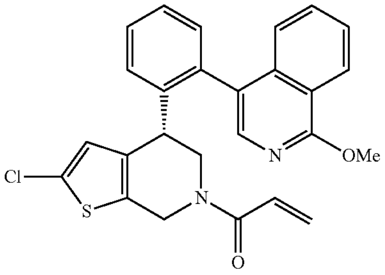 | + |

TABLE 2-continued
| compounds synthesized and biological activities. | | |
|---|---|---|
| Compound Structure | | E1 |
| 192 | 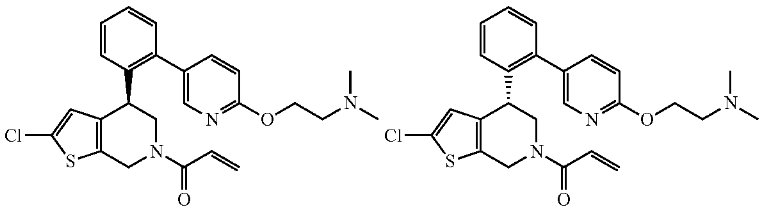 | + |
| 193 | 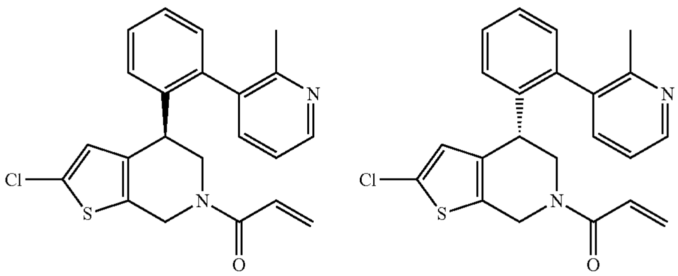 [SMILES: C=CC(=O)N1Cc2sc(Cl)cc2[C@@H](c2ccccc2-c2cccnc2C)C1 ; C=CC(=O)N1Cc2sc(Cl)cc2[C@H](c2ccccc2-c2cccnc2C)C1] | +++ |
| 194 | 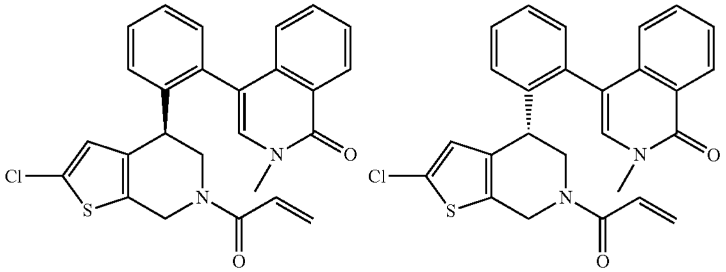 | ++ |
| 195 | 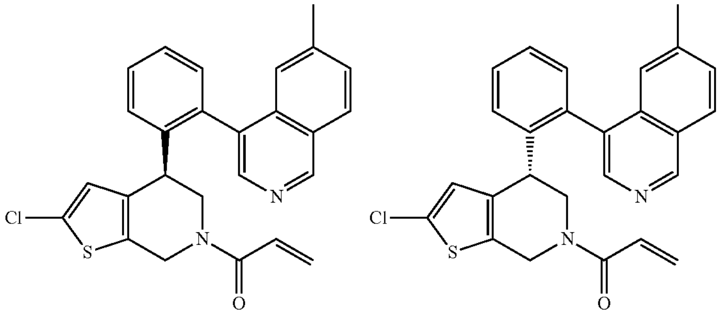 [SMILES: C=CC(=O)N1Cc2sc(Cl)cc2[C@@H](c2ccccc2-c2cncc3ccc(C)cc23)C1 ; C=CC(=O)N1Cc2sc(Cl)cc2[C@H](c2ccccc2-c2cncc3ccc(C)cc23)C1] | ++ |
| 196 | 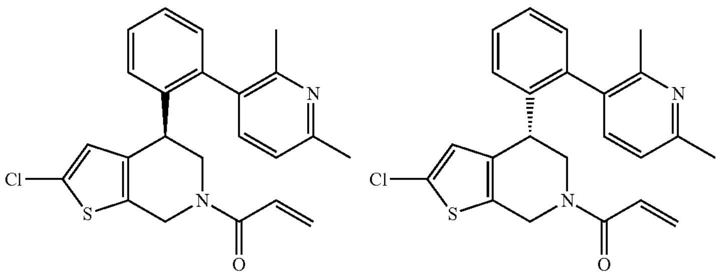 | +++ |

TABLE 2-continued
compounds synthesized and biological activities.
| Compound Structure | E1 |
| --- | --- |
| 197 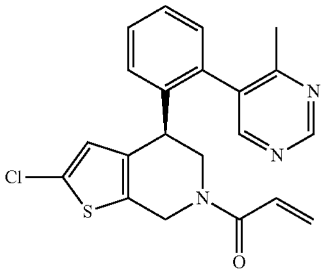 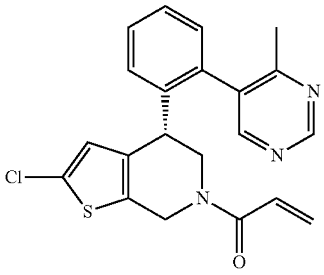 | +++ |
| 198 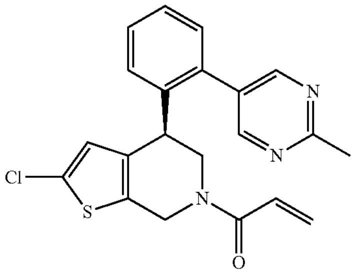 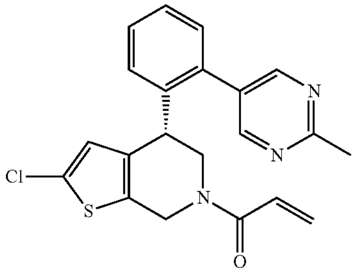 | ++ |
| 199 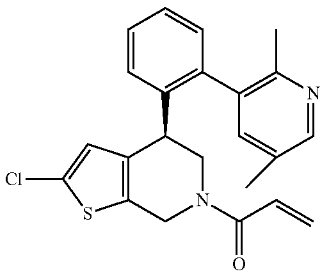 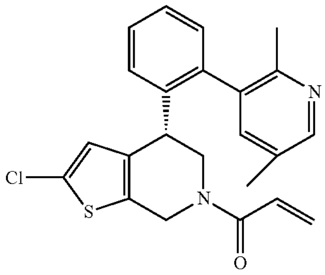 | +++ |
| 200 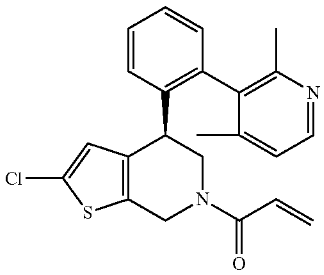 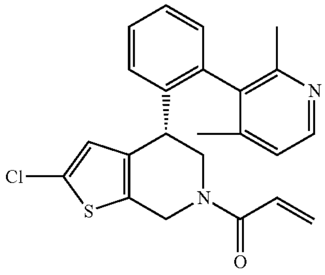 | +++ |
| 201 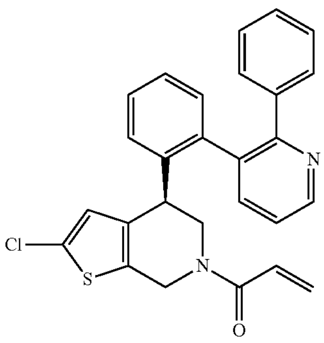 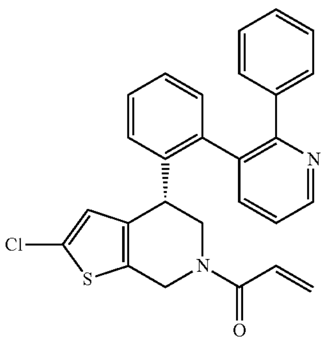 | ++ |

TABLE 2-continued
compounds synthesized and biological activities.
| Compound Structure | | E1 |
|---|---|---|
| 202 | 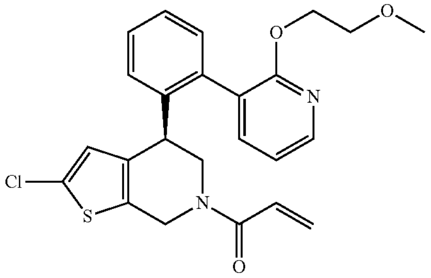 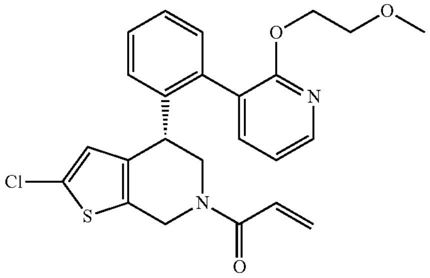 | ++ |
| 203 | 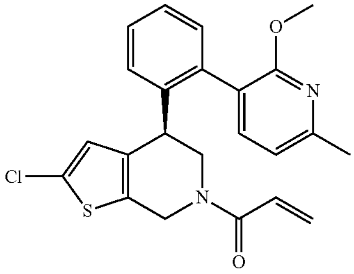 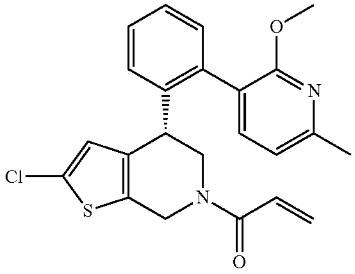 | +++ |
| 204 | 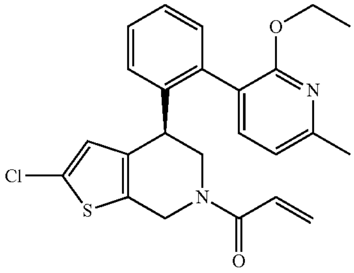 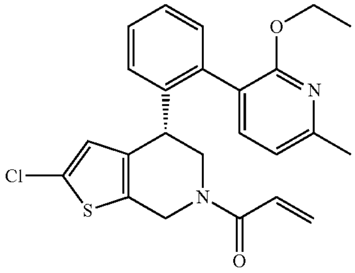 | ++ |
| 205 | 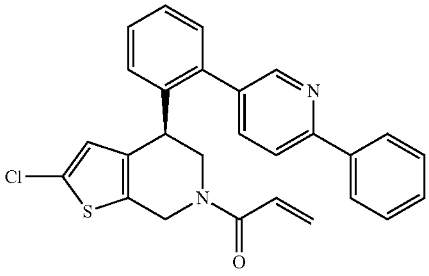 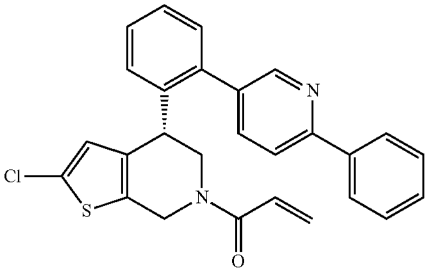 | + |
| 206 | 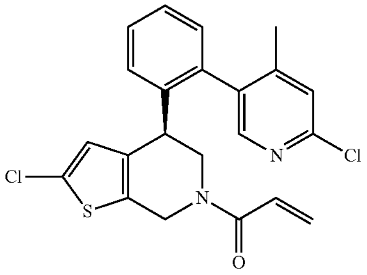 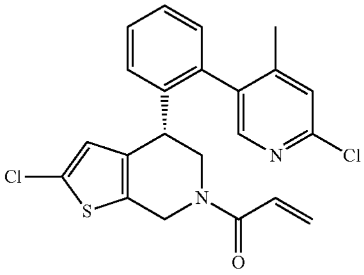 | +++ |

TABLE 2-continued
compounds synthesized and biological activities.
| Compound Structure | | E1 |
|---|---|---|
| 207 | 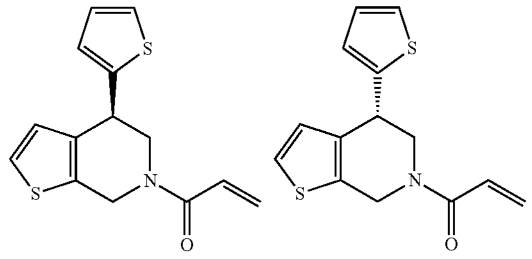 | + |
| 208 | 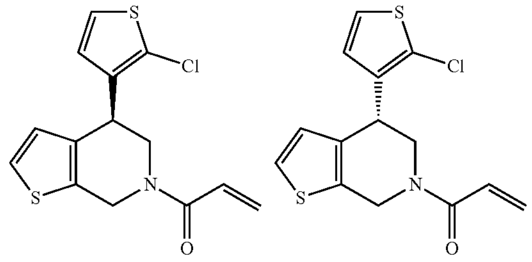 | ++ |
| 209 | 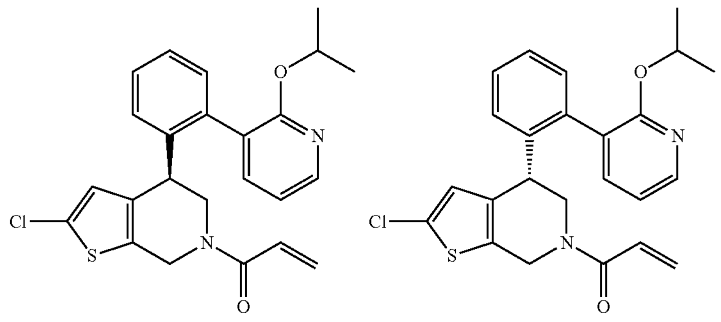 [SMILES: C=CC(=O)N1Cc2sc(Cl)cc2[C@@H](c2ccccc2-c2cccnc2OC(C)C)C1 ; C=CC(=O)N1Cc2sc(Cl)cc2[C@H](c2ccccc2-c2cccnc2OC(C)C)C1] | ++ |
| 210 | 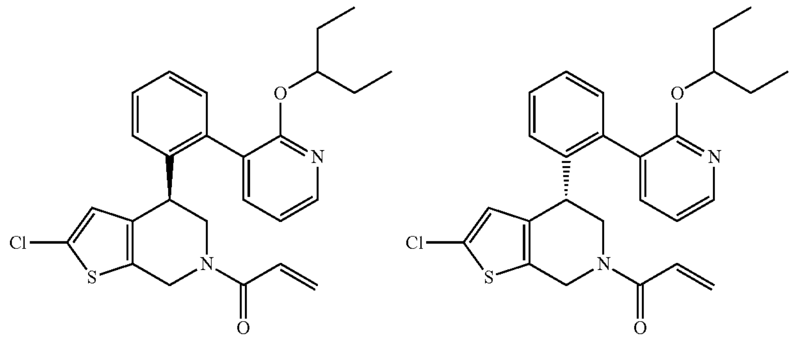 [SMILES: C=CC(=O)N1Cc2sc(Cl)cc2[C@@H](c2ccccc2-c2cccnc2OC(CC)CC)C1 ; C=CC(=O)N1Cc2sc(Cl)cc2[C@H](c2ccccc2-c2cccnc2OC(CC)CC)C1] | + |
| 211 | 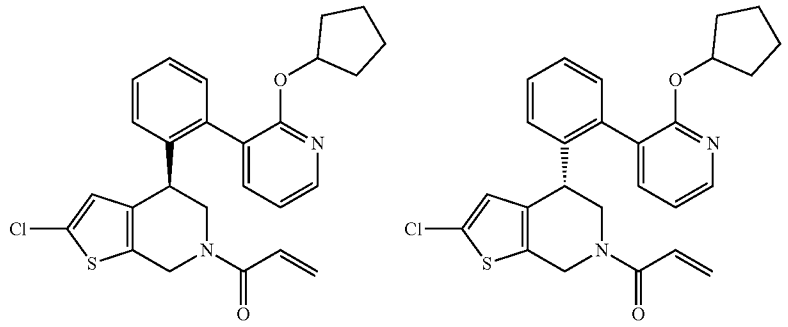 [SMILES: C=CC(=O)N1Cc2sc(Cl)cc2[C@@H](c2ccccc2-c2cccnc2OC2CCCC2)C1 ; C=CC(=O)N1Cc2sc(Cl)cc2[C@H](c2ccccc2-c2cccnc2OC2CCCC2)C1] | +++ |

TABLE 2-continued
compounds synthesized and biological activities.
| Compound Structure | | | E1 |
|---|---|---|---|
| 212 | 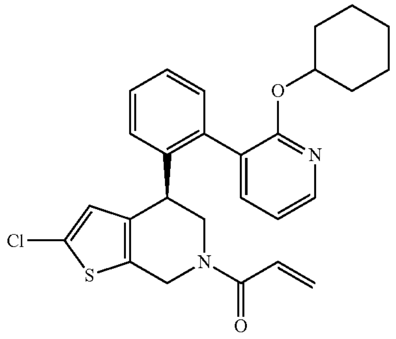 | 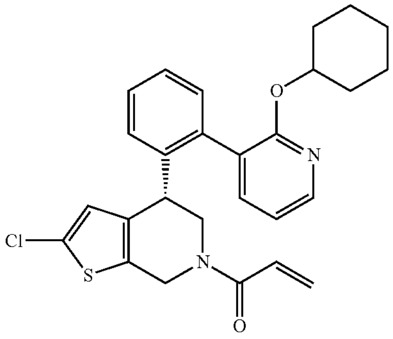 | + |
| 213 | 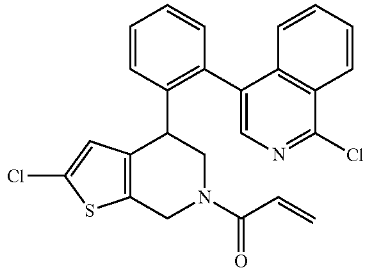 | 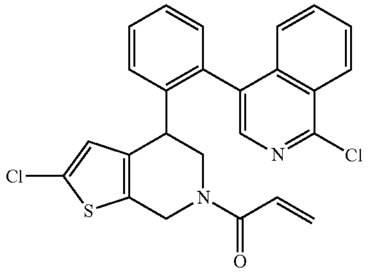 | + |
| 214 | 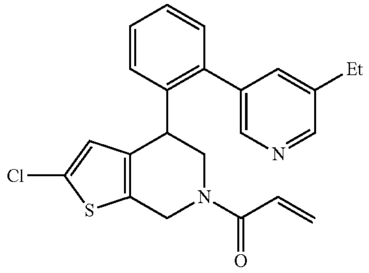 | 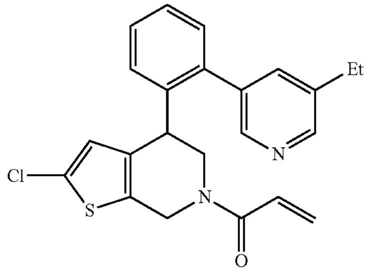 | +++ |
| 215 | 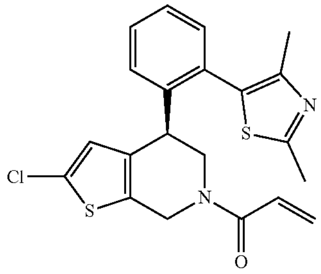 | 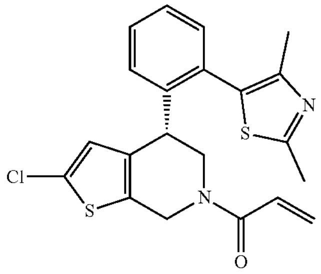 | +++ |
| 216 | 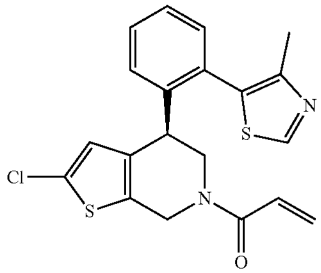 | 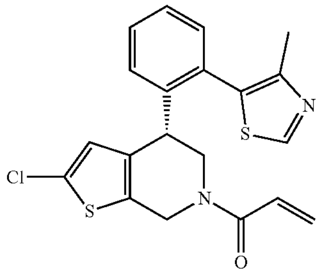 | +++ |

TABLE 2-continued
| compounds synthesized and biological activities. | | |
|---|---|---|
| Compound | Structure | E1 |
| 217 | 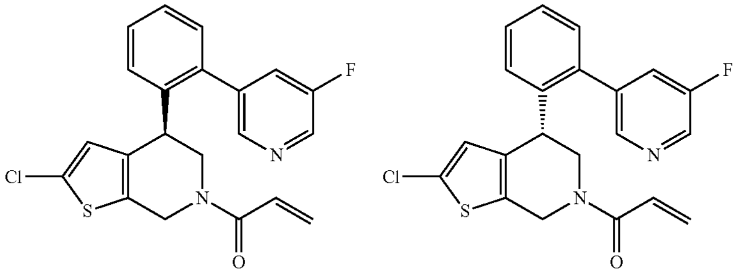 [SMILES: C=CC(=O)N1Cc2sc(Cl)cc2[C@@H](c2ccccc2-c2cncc(F)c2)C1 ; C=CC(=O)N1Cc2sc(Cl)cc2[C@H](c2ccccc2-c2cncc(F)c2)C1] | + |
| 218 | 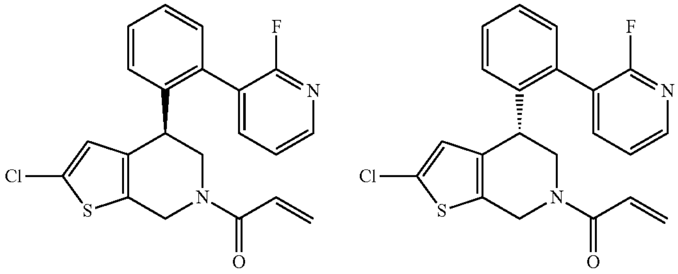 [SMILES: C=CC(=O)N1Cc2sc(Cl)cc2[C@@H](c2ccccc2-c2cccnc2F)C1 ; C=CC(=O)N1Cc2sc(Cl)cc2[C@H](c2ccccc2-c2cccnc2F)C1] | + |
| 219 | 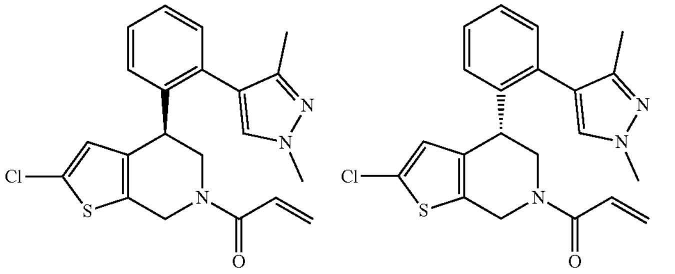 | +++ |
| 220 | 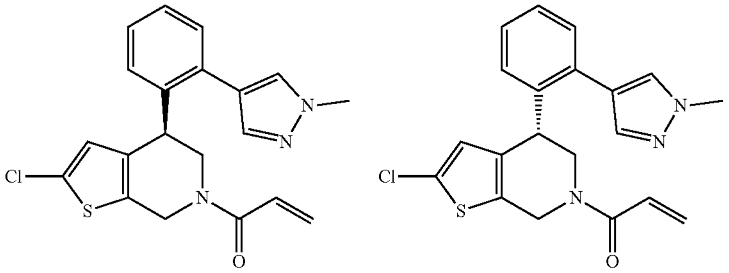 [SMILES: C=CC(=O)N1Cc2sc(Cl)cc2[C@@H](c2ccccc2-c2cnn(C)c2)C1 ; C=CC(=O)N1Cc2sc(Cl)cc2[C@H](c2ccccc2-c2cnn(C)c2)C1] | ++ |
| 221 | 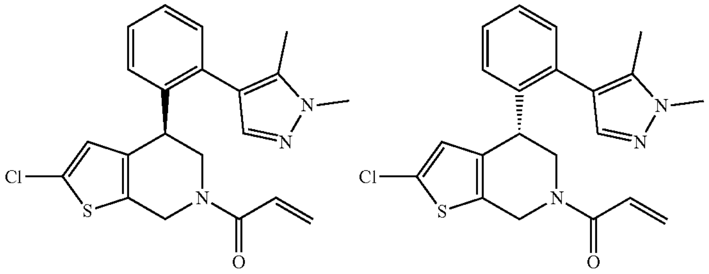 [SMILES: C=CC(=O)N1Cc2sc(Cl)cc2[C@@H](c2ccccc2-c2cnn(C)c2C)C1 ; C=CC(=O)N1Cc2sc(Cl)cc2[C@H](c2ccccc2-c2cnn(C)c2C)C1] | +++ |

TABLE 2-continued
compounds synthesized and biological activities.
| Compound Structure | | E1 |
|---|---|---|
| 222 | 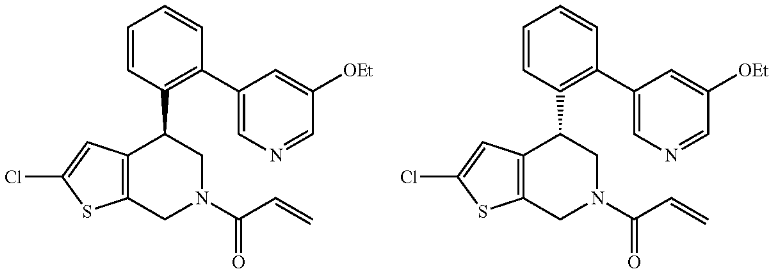 [SMILES: C=CC(=O)N1Cc2sc(Cl)cc2[C@@H](c2ccccc2-c2cncc(OCC)c2)C1 ; C=CC(=O)N1Cc2sc(Cl)cc2[C@H](c2ccccc2-c2cncc(OCC)c2)C1] | ++ |
| 223 | 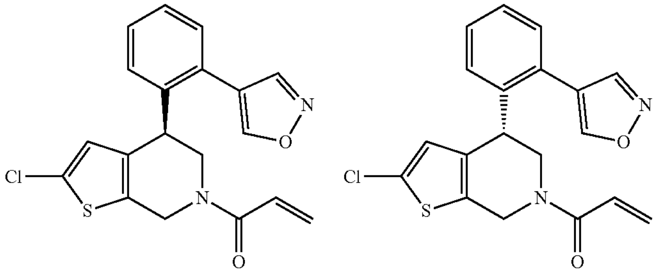 [SMILES: C=CC(=O)N1Cc2sc(Cl)cc2[C@@H](c2ccccc2-c2cnoc2)C1 ; C=CC(=O)N1Cc2sc(Cl)cc2[C@H](c2ccccc2-c2cnoc2)C1] | +++ |
| 224 | 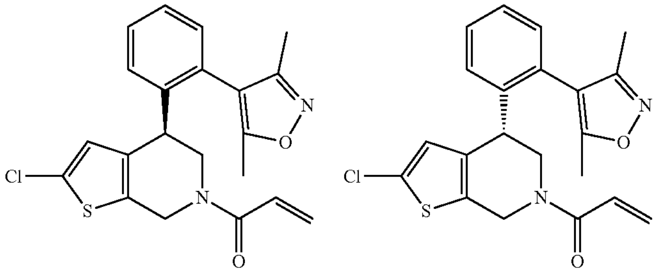 [SMILES: C=CC(=O)N1Cc2sc(Cl)cc2[C@@H](c2ccccc2-c2c(C)noc2C)C1 ; C=CC(=O)N1Cc2sc(Cl)cc2[C@H](c2ccccc2-c2c(C)noc2C)C1] | +++ |
| 225 | 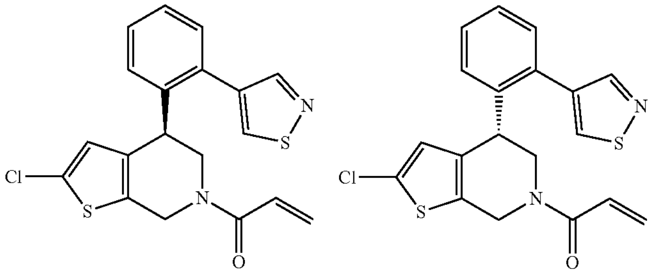 | +++ |
| 226 | 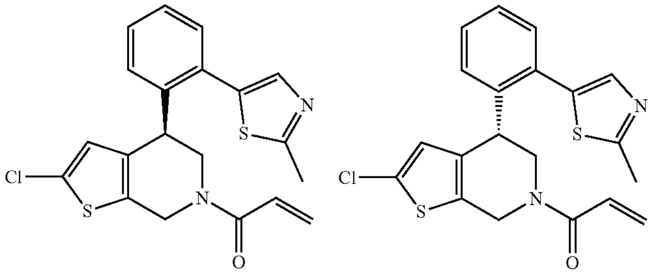 | ++ |

TABLE 2-continued
compounds synthesized and biological activities.
| Compound Structure | | | E1 |
|---|---|---|---|
| 227 | 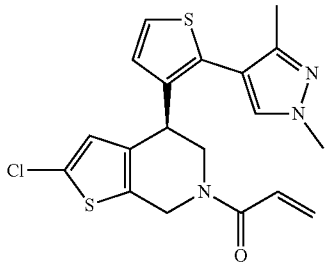 | 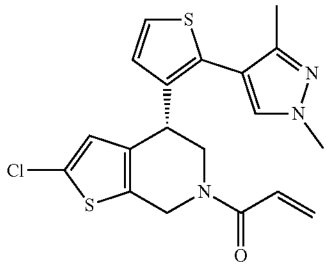 | +++ |
| 228 | 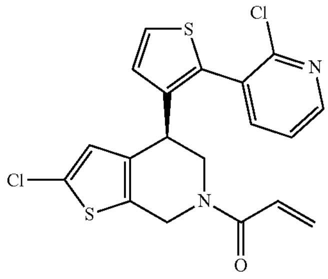 | 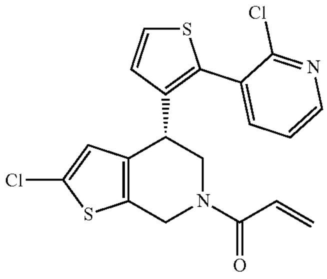 | +++ |
| 229 | 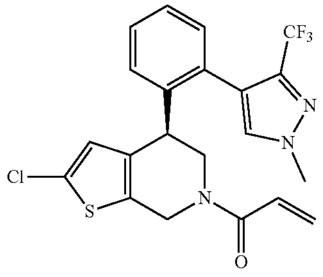 | 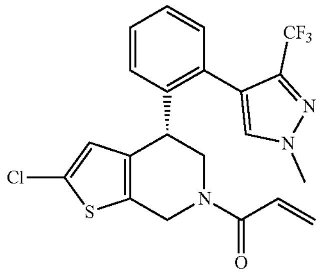 | +++ |
| 230 | 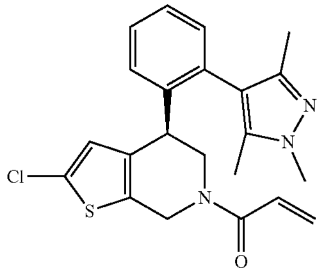 | 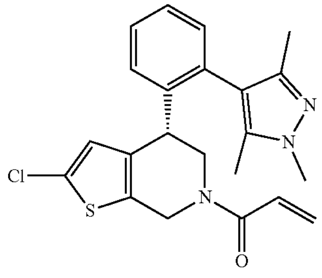 | +++ |
| 231 | 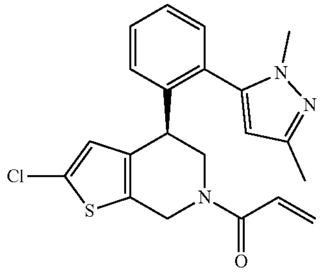 | 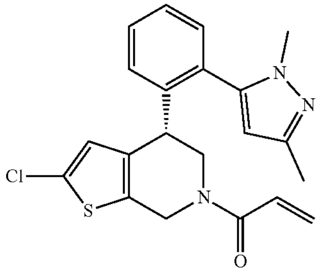 | +++ |

TABLE 2-continued
compounds synthesized and biological activities.
| Compound Structure | | E1 |
|---|---|---|
| 232 | 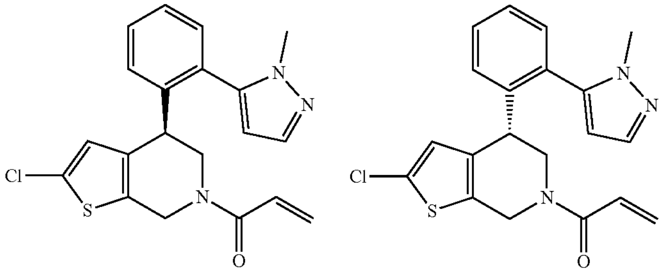 [SMILES: C=CC(=O)N1Cc2sc(Cl)cc2[C@@H](c2ccccc2-c2ccnn2C)C1 ; C=CC(=O)N1Cc2sc(Cl)cc2[C@H](c2ccccc2-c2ccnn2C)C1] | +++ |
| 233 | 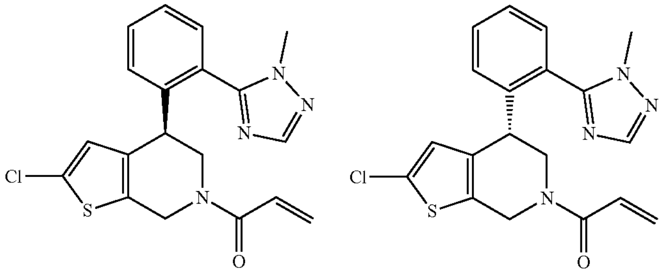 [SMILES: C=CC(=O)N1Cc2sc(Cl)cc2[C@@H](c2ccccc2-c2ncnn2C)C1 ; C=CC(=O)N1Cc2sc(Cl)cc2[C@H](c2ccccc2-c2ncnn2C)C1] | +++ |
| 234 | 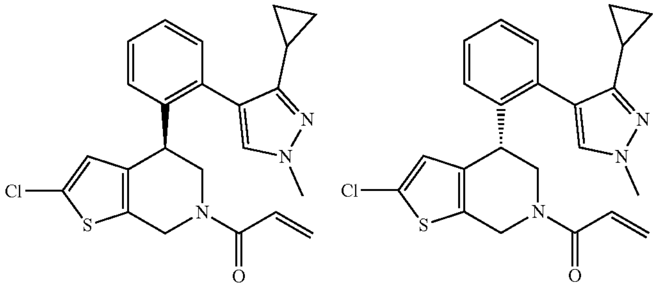 | +++ |
| 235 | 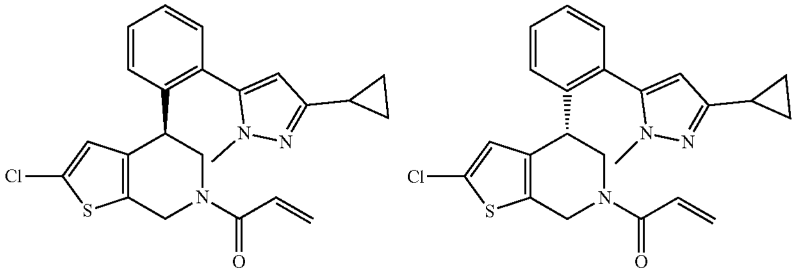 [SMILES: C=CC(=O)N1Cc2sc(Cl)cc2[C@@H](c2ccccc2-c2cc(C3CC3)nn2C)C1 ; C=CC(=O)N1Cc2sc(Cl)cc2[C@H](c2ccccc2-c2cc(C3CC3)nn2C)C1] | ++ |
| 236 | 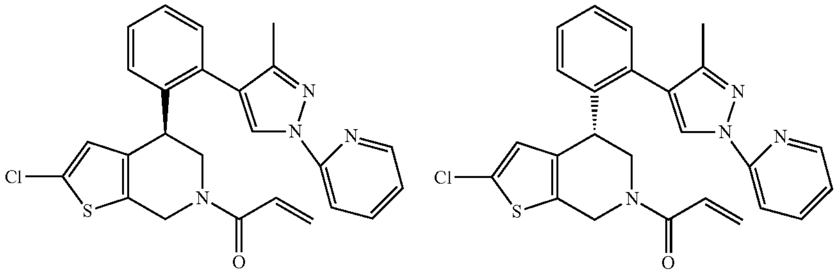 | +++ |

TABLE 2-continued
compounds synthesized and biological activities.
| Compound Structure | | E1 |
|---|---|---|
| 237 | 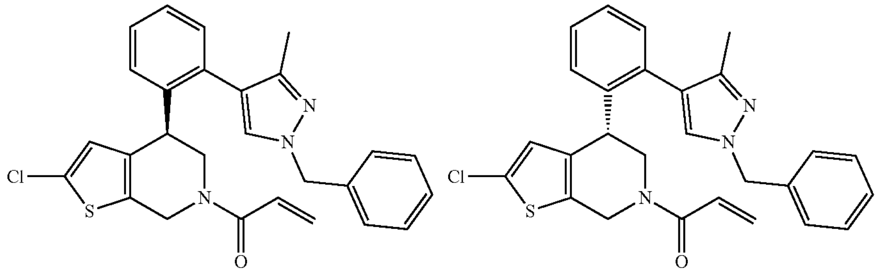 | +++ |
| 238 | 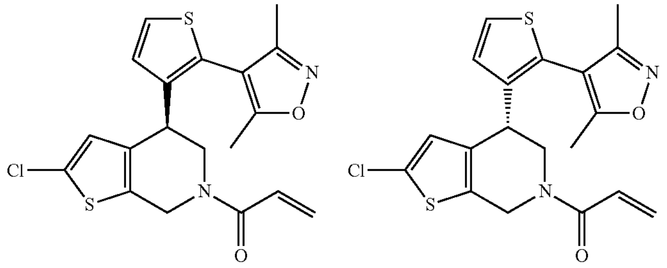 [SMILES: C=CC(=O)N1Cc2sc(Cl)cc2[C@@H](c2ccsc2-c2c(C)noc2C)C1 ; C=CC(=O)N1Cc2sc(Cl)cc2[C@H](c2ccsc2-c2c(C)noc2C)C1] | ++ |
| 239 | 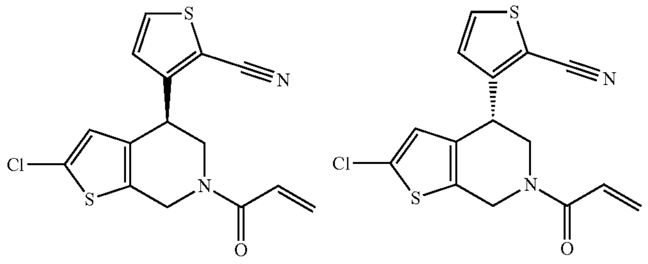 | +++ |
| 240 | 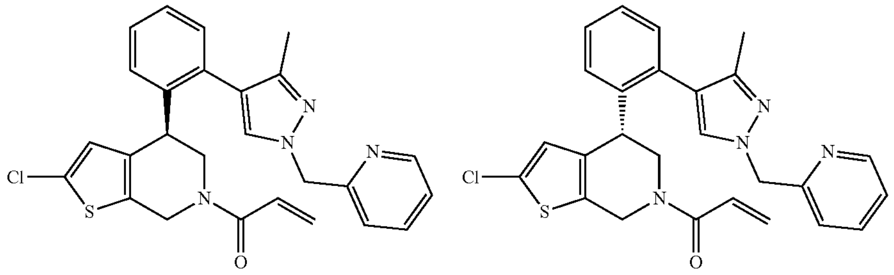 | +++ |
| 241 | 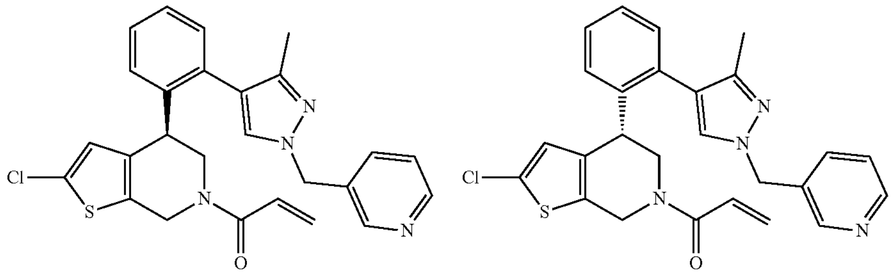 | +++ |

TABLE 2-continued
compounds synthesized and biological activities.
| Compound Structure | | E1 |
|---|---|---|
| 242 | 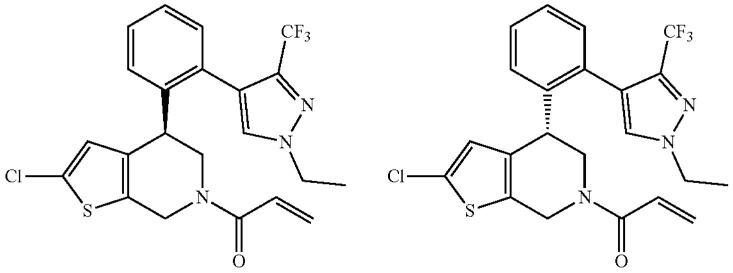 | +++ |
| 243 | 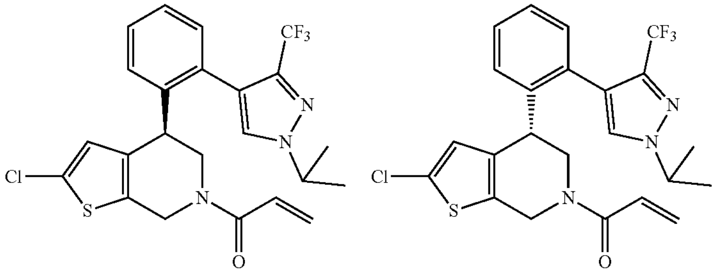 | +++ |
| 244 | 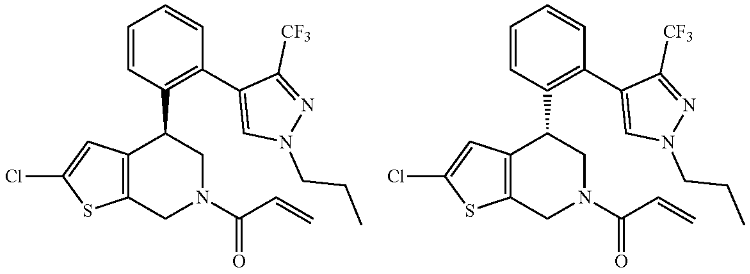 | +++ |
| 245 | 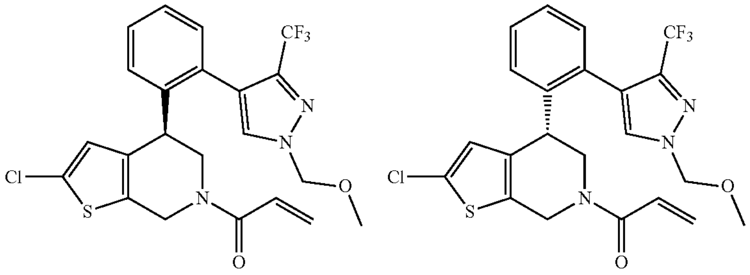 | +++ |
| 246 | 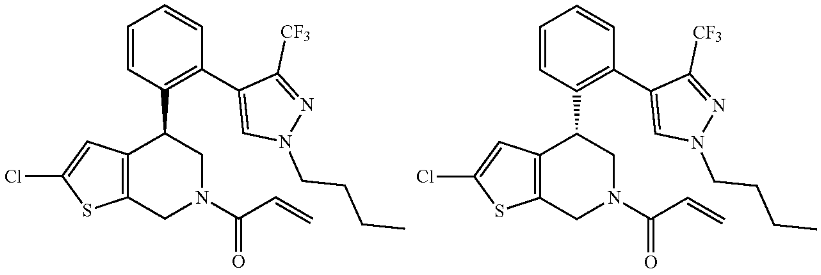 | +++ |

TABLE 2-continued
compounds synthesized and biological activities.
| Compound Structure | | E1 |
|---|---|---|
| 247 | 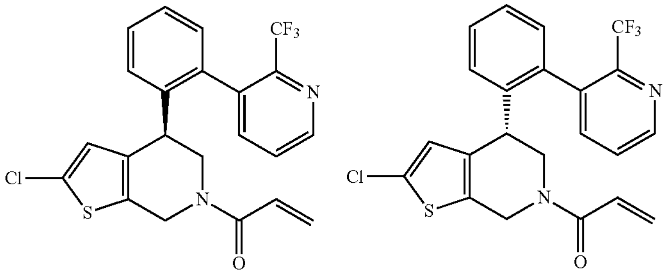 [SMILES: C=CC(=O)N1Cc2sc(Cl)cc2[C@@H](c2ccccc2-c2cccnc2C(F)(F)F)C1 ; C=CC(=O)N1Cc2sc(Cl)cc2[C@H](c2ccccc2-c2cccnc2C(F)(F)F)C1] | +++ |
| 248 | 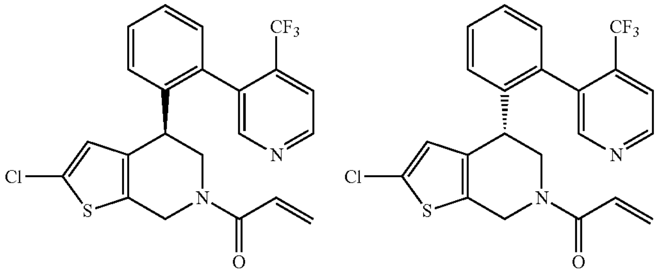 [SMILES: C=CC(=O)N1Cc2sc(Cl)cc2[C@@H](c2ccccc2-c2cnccc2C(F)(F)F)C1 ; C=CC(=O)N1Cc2sc(Cl)cc2[C@H](c2ccccc2-c2cnccc2C(F)(F)F)C1] | +++ |
| 249 | 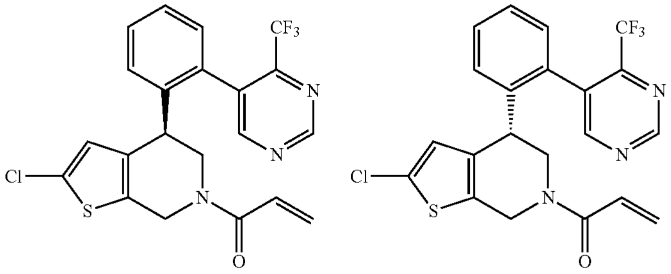 [SMILES: C=CC(=O)N1Cc2sc(Cl)cc2[C@@H](c2ccccc2-c2cncnc2C(F)(F)F)C1 ; C=CC(=O)N1Cc2sc(Cl)cc2[C@H](c2ccccc2-c2cncnc2C(F)(F)F)C1] | +++ |
| 250 | | +++ |
| 251 | | +++ |
| 252 | | +++ |
| 253 | | +++ |
| 254 | | +++ |
| 255 | | +++ |
| 256 | | +++ |
| 257 | | NA |
| 258 | | NA |
| 259 | | +++ |
| 260 | | +++ |
| 261 | | +++ |
| 262 | | + |
| 263 | | +++ |
| 264 | | +++ |
| 265 | | +++ |
| 266 | | +++ |
| 267 | | +++ |
| 268 | | ++ |
| 269 | | + |
| 270 | | +++ |
| 271 | | +++ |
| 272 | | +++ |
| 273 | | + |
| 274 | | + |
| 275 | | ++ |
| 276 | | + |
| 277 | | +++ |
| 278 | | + |
| 279 | | +++ |
| 280 | | +++ |
| 281 | | +++ |
| 282 | | ++ |
| 283 | | + |

TABLE 2-continued

| compounds synthesized and biological activities. | |
|---|---|
| Compound Structure | E1 |
| 284 | +++ |
| 285 | +++ |
| 286 | ++ |
| 287 | ++ |
| 288 | +++ |
| 289 | + |
| 290 | + |
| 291 | + |
| 292 | +++ |
| 293 | ++ |
| 294 | +++ |
| 295 | ++ |
| 296 | +++ |
| 297 | +++ |
| 298 | +++ |
| 299 | ++ |
| 300 | +++ |
| 301 | +++ |
| 302 | +++ |
| 303 | + |
| 304 | +++ |
| 305 | +++ |
| 306 | + |
| 307 | +++ |
| 308 | +++ |
| 309 | + |
| 310 | +++ |
| 311 | +++ |
| 312 | +++ |
| 313 | +++ |
| 314 | +++ |

Activities are listed as
+ (>20 uM),
++ (<20 uM),
+++ (<10 uM)

Example 9

SAE High Throughput Biochemical Assay Protocol

Assay buffer was prepared [50 mM HEPES, pH 7.5, 0.1% BSA and 10 mM $MgCl_2$] as was the Stop Buffer [100 mM HEPES, pH 7.5, 0.05% Tween20, and 410 mM KF]. The 2× Reaction Buffer [80 nM SUMO-GST, 80 nM UBC9-His, 200 μM ATP and diluted in Assay Buffer] and Antibody Reaction Mix [13.34 nM anti-GST XL665, 1.66 nM anti-His EuK and Diluted in Stop Buffer] were also prepared. Compounds were dissolved at 200× in DMSO in a 384-well plate: Serial dilutions were performed in DMSO for each compound, and then each concentration was diluted another 50-fold in Assay Buffer, to 4× the final concentration. 2.5 μL of each concentration was transferred into its own well in a 384-well plate. SAE1 was then diluted to 4× in Assay Buffer, and 2.5 μL of 4×SAE1 was mixed into each compound-containing well. After incubating for 15 minutes at room temperature, 5 μL of 2× Reaction Buffer was mixed into every well. Then after another 45 minutes at room temperature, 10 μL of Antibody Reaction Mix was added and mixed into every well. This plate was then read on an HTRF-compatible plate reader after 2 hours at room temperature, and again after sitting at room temperature overnight. [Final Component Concentrations: SAE1: 12.5 nM; SUMO-GST: 40 nM; UBC9-His: 40 nM; Anti-GST-XL665: 6.67 nM; Anti-His-EuK: 0.83 nM; and ATP: 100 μM] The IC50's are provided in Table 3. Alternatively, the compounds are tested at a single concentration of 25 micromolar and the percent of control is measured. The POC are also provided in Table 3 where appropriate.

Example 10

HCT-116 4 Hour Cell Assay

This protocol describes the procedures used to assess the effects of compounds of interest on sumoylation levels. Immunoblot of SUMO 2/3 conjugates are performed and IC50 curves are generated upon quantification of sumoylations bands. HCT-116 cells are seeded in a 12 well plate (500,000 cells/well). The following day the cells are treated with compounds of interest (resuspended in DMSO) for 4 hours (11 concentrations with a three-fold dilution; starting concentration 25 μM) Following 4 hours of incubation the cells are washed with ice cold PBS 1× and protein extraction is performed with RIPA buffer supplemented with phosphatases and proteases inhibitors, 25 mM of NEM and 50 units/mL of Benzonase.

Samples undergo centrifugation at 13,000 RPM, 4° C., for 10 minutes and the supernatant is collected. Protein quantification is performed using BCA. Non-Reducing Laemmli Buffer is added to the samples. Samples are heated at 75° C. for 10 minutes, and are centrifuged for 3 minutes at 9000 RPM Nupage 4-12% Bis Tris gels and 1×MOPS buffer (Fisher Scientific)+1× NuPAGE Antioxidant (Invitrogen) are used to perform the SDS-PAGE gel electrophoresis (20 to 40 μg of proteins are loaded in the gels). Proteins are then transferred to PVDF membranes and the level of total proteins are measured by staining with Revert Total Protein Stain and the fluorescent bands are acquired using the LI-COR FC (700 nm for 1 min) Membranes are blocked for 5 minutes with Bio-Rad Blocking Buffer and are subsequently incubated over night at 4° C. with Anti-Sumo 2-3 mAb (MBL #M114-3, 1:1000 in Bio-Rad Blocking Buffer, 0.2% Tween 20) Membranes are washed with 1×TBS-T (3 times for 5 minutes) and sumoylation is detected using Li-cor IRDye 800CW Goat anti-Mouse IgG secondary antibody (1:10,000 dilution) upon 1 hour of incubation in blocking buffer with 0.2% Tween 20 and 0.01% SDS. After the incubation, the membranes are washed with 1×TBS-T (3 times for 5 minutes). To visualize the fluorescent bands the membranes are scanned with LI-COR FC (700 nm for 1 min and 800 nM for 2 mins) Sumoylation levels are quantified upon normalization with total protein levels, using the LI-COR Image Studio Lite 5.2 Software. The results are provided in Table 3.

TABLE 3

| Compound | 15 min preincubation HTRF IC50 (uM) Ave | Cell HCT-116 Western SUMO2/3 4 h IC50 (uM) Ave |
|---|---|---|
| 136 | 15.29 POC @ 25 μM | |
| 141 | 1.67 | |
| 142 | 48.53 POC @ 25 μM | |
| 143 | 17.58 POC @ 25 μM | |
| 144 | 34.59 POC @ 25 μM | |
| 145 | 55.54 POC @ 25 μM | |
| 146 | >100 POC @ 25 μM | |
| 147 | 62.81 POC @ 25 μM | |
| 148 | 91.85 POC @ 25 μM | |
| 149 | 14.18 POC @ 25 μM | |
| 150 | 68.77 POC @ 25 μM | |
| 151 | 17.03 POC @ 25 μM | |
| 152 | >100 POC @ 25 μM | |
| 153 | 39.72 POC @ 25 μM | |
| 154 | 88.81 POC @ 25 mM | |
| 155 | 1.56 | |
| 157 | 28.04 POC @ 25 μM | |
| 158 | 11.51 | |
| 159 | 0.76 | |
| 160 | 19.64 POC @ 25 μM | |
| 164 | 2.80 | |
| 172 | 0.94 | |
| 173 | 7.19 POC @ 25 μM | |
| 175 | 13.84 POC @ 25 μM | |
| 176 | 60.9 POC @ 25 μM | |
| 181 | 14.78 POC @ 25 μM | |
| 188 | 5.68 | |
| 189 | 4.52; 14.972 POC @ 25 μM | |
| 190 | 33.75 POC @ 25 μM | |
| 193 | 3.04 | |
| 196 | 3.72 | |
| 197 | 3.92 | |
| 219 | 0.41 | |
| 220 | 27.51 POC @ 25 μM | |
| 221 | 6.24 | |
| 223 | 10.44 | |
| 224 | 3.31; 7.23 POC @ 25 μM | |
| 225 | 12.53 | |
| 227 | 12.64 | |
| 229 | 0.32 | |
| 230 | 0.58; 4.57 POC @ 25 μM | |
| 231 | 1.15; 0 POC @ 25 μM | |
| 232 | 1.00; 10.61 POC @ 25 μM | |
| 233 | 29.39 POC @ 25 μM | |
| 234 | 1.06; 13.76 POC @ 25 mM | |
| 235 | 94.96 POC @ 25 μM | |
| 236 | 4.08; 12.55 POC @ 25 μM | |
| 237 | 20.61; 12.42 POC @ 25 μM | |
| 242 | 0.33 | |
| 243 | 0.39 | |
| 244 | 0.31 | |
| 246 | 0.73; 0.7 POC @ 25 μM | |

TABLE 3-continued

| Compound | 15 min preincubation HTRF IC50 (uM) Ave | Cell HCT-116 Western SUMO2/3 4 h IC50 (uM) Ave |
|---|---|---|
| 247 | 1.28 | |
| 248 | 9.17; 5.81 POC @ 25 μM | |
| 249 | 2.27; 4.68 POC @ 25 μM | |
| 250 | 0.73 | |
| 251 | 1.28 | |
| 252 | 9.17 | |
| 253 | 2.77 | |
| 254 | 0.16 | 0.14 |
| 255 | 0.39 | 0.5 |
| 256 | 0.31 | 0.51 |
| 259 | 1.4 | |
| 260 | 0.61 | |
| 261 | 3 | |
| 262 | >25 | |
| 263 | 4.1 | |
| 264 | 0.05 | 0.64 |
| 265 | 0.07 | 0.56 |
| 266 | 0.17 | 0.19 |
| 267 | 0.05 | 0.9 |
| 271 | 0.24 | 0.77 |
| 272 | 0.06 | 0.3 |
| 275 | >25 | |
| 276 | 12.1 | |
| 277 | 0.13 | 1.1 |
| 279 | 0.14 | 0.4 |
| 280 | 0.07 | 0.26 |
| 281 | 0.29 | 1.5 |
| 284 | 0.13 | 0.86 |
| 285 | 0.1 | 0.24 |
| 288 | 0.32 | 0.27 |
| 289 | >25 | |
| 292 | 0.77 | 2.5 |
| 294 | 0.09 | 0.16 |
| 295 | 1.8 | |
| 296 | 0.22 | >25 |
| 297 | 0.3 | 1.4 |
| 298 | 0.05 | 0.44 |
| 299 | 4.1 | |
| 300 | 0.54 | 6.9 |
| 301 | 0.04 | 0.56 |
| 302 | 0.05 | 0.25 |
| 303 | >25 | |
| 304 | 0.07 | 0.9 |
| 305 | 1.7 | |
| 306 | >25 | |
| 307 | 0.26 | 0.4 |
| 308 | 0.3 | 0.43 |
| 309 | >25 | |
| 310 | 2.1 | 3.5 |
| 311 | 0.09 | 0.13 |
| 312 | 0.23 | 0.28 |
| 313 | 0.53 | 1.7 |
| 314 | 0.1 | 0.56 |
| 315 | 1.71 | |
| 316 | 0.04 | 1.5 |
| 317 | 0.13 | 0.62 |
| 318 | 0.29 | 0.33 |
| 319 | 0.98 | 0.93 |
| 320 | >25 | |
| 321 | 0.03 | 0.24 |
| 322 | 0.10 | 0.34 |
| 323 | 0.13 | 0.39 |
| 324 | 0.14 | 0.34 |
| 325 | 0.23 | 0.32 |
| 326 | 0.24 | 0.87 |
| 327 | 0.25 | 0.85 |
| 328 | 0.26 | 0.58 |
| 329 | 0.41 | 0.72 |
| 330 | 0.41 | 0.35 |
| 331 | 0.46 | |
| 332 | 0.48 | |
| 333 | 0.59 | 2.54 |
| 334 | 0.66 | |
| 335 | 0.83 | 0.94 |
| 336 | 0.87 | 0.65 |
| 337 | 0.88 | |

TABLE 3-continued

| Compound | 15 min preincubation HTRF IC50 (uM) Ave | Cell HCT-116 Western SUMO2/3 4 h IC50 (uM) Ave |
|---|---|---|
| 338 | 0.89 | |
| 339 | 0.91 | |
| 340 | 0.93 | |
| 341 | 0.96 | 2.02 |
| 342 | 0.98 | 1.51 |
| 343 | 1.01 | 1.58 |
| 344 | 1.08 | |
| 345 | 1.13 | 3.02 |
| 346 | 1.18 | |
| 347 | 1.30 | |
| 348 | 1.54 | |
| 349 | 1.54 | |
| 350 | 1.70 | |
| 351 | 1.82 | |
| 352 | 1.94 | 1.56 |
| 353 | 2.56 | 0.89 |
| 354 | 2.59 | 0.96 |
| 355 | 2.95 | 1.97 |
| 356 | 3.02 | 3.92 |
| 357 | 3.17 | |
| 358 | 3.57 | |
| 360 | 4.33 | 13.55 |
| 363 | 8.76 | |
| 364 | 9.23 | |
| 365 | 10.23 | |
| 366 | 11.56 | |
| 367 | 19.48 | |
| 368 | 20.16 | |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound of Formula XI-B

[XI-B]

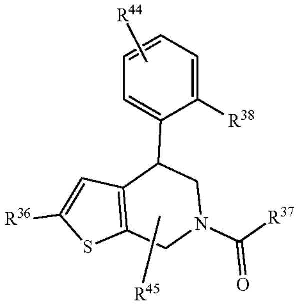

wherein $R^{36}$ is selected from H, halo, $C_1$-$C_4$ alkyl, $C_1$-$C_4$ haloalkyl, $C_2$-$C_4$ alkenyl, substituted or unsubstituted heteroaryl, and $C_3$-$C_6$ cycloalkyl;

$R^{37}$ is substituted or unsubstituted $C_2$-$C_4$ alkenyl or substituted or unsubstituted $C_2$-$C_4$ alkynyl;

$R^{38}$ is selected from substituted or unsubstituted nitrogen containing 5-membered heteroaryl, substituted or unsubstituted nitrogen containing 5- or 6-membered partially unsaturated heterocyclyl and substituted or unsubstituted nitrogen containing 6-10 membered heteroaryl;

$R^{44}$ is one or more substituents selected from H, halo, alkoxy and hydroxy; and $R^{45}$ is one or more substituents selected from H, D and alkyl;

provided $R^{38}$ is not a substituted or unsubstituted 4-pyridyl, unsubstituted 3-pyridyl, or unsubstituted 2-pyridyl;

or a pharmaceutically acceptable salt thereof.

2. The compound of claim 1 wherein $R^{38}$ is selected from substituted or unsubstituted nitrogen containing 5-membered heteroaryl selected from pyrazolyl, isoxazolyl, isothiazolyl, pyrrolyl, thiazolyl, triazolyl and imidazolyl; substituted or unsubstituted nitrogen containing 6-membered heteroaryl selected from pyridinyl, pyrimidinyl and pyrazinyl; substituted or unsubstituted pyrrolinyl, and substituted or unsubstituted dihydropyridinyl; or a pharmaceutically acceptable salt thereof.

3. The compound of claim 1 wherein $R^{38}$ is selected from substituted or unsubstituted 1-pyrrolin-3-yl, and substituted or unsubstituted dihydropyridin-3-yl; or a pharmaceutically acceptable salt thereof.

4. The compound of claim 1 wherein $R^{38}$ is selected from 1-methoxy-4-isoquinolinyl, 1-chloro-4-isoquinolinyl, 6-methyl-4-isoquinolinyl, 1-oxo-2-methyl-4-isoquinolinyl, 5-pyrrolopyridinyl, [1,3,3a]-triazainden-5-yl, 1-ethyl-3-pyrrolopyridinyl, 1-methyl-5-pyrrolopyridinyl, 3-quinolinyl, 4-isoquinolinyl and 4-quinolinyl; or a pharmaceutically acceptable salt thereof.

5. The compound of claim 1 wherein $R^{37}$ is ethenyl, fluoroethenyl, propenyl, fluoropropenyl, propynyl, dialkylaminopropenyl, alkylaminopropenyl, aminopropenyl or nitrogen-containing heterocyclyl-propenyl; or a pharmaceutically acceptable salt thereof.

6. The compound of claim 1 selected from
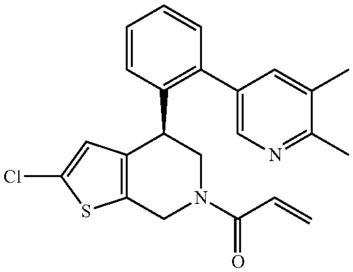
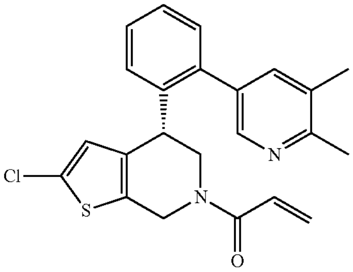
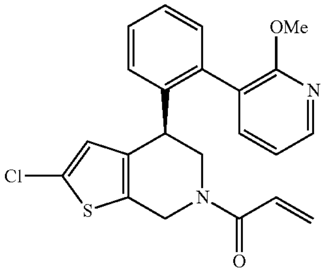
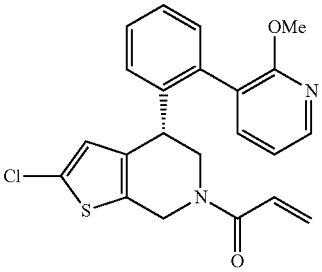
-continued
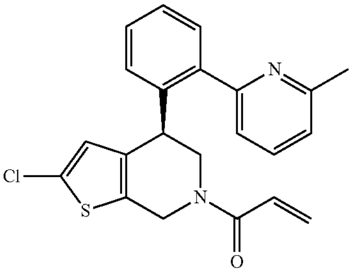
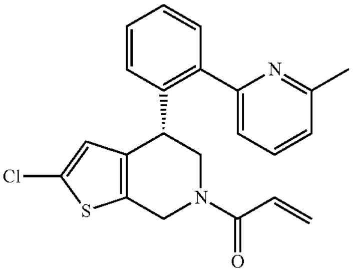
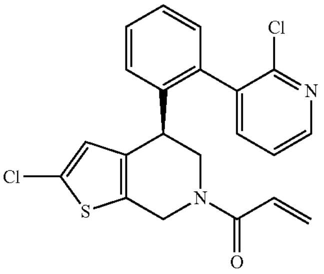
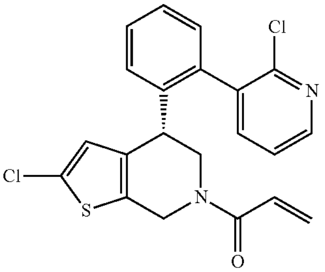

-continued
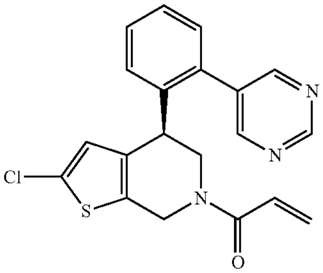
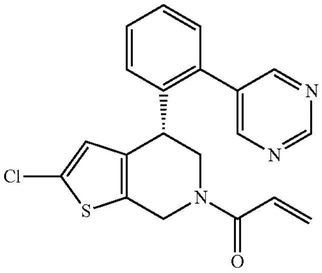
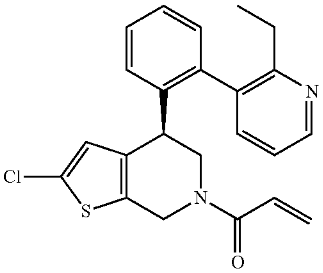
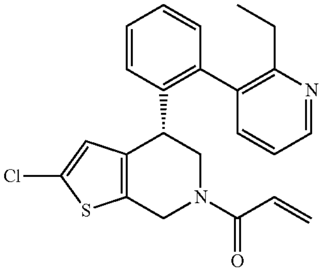
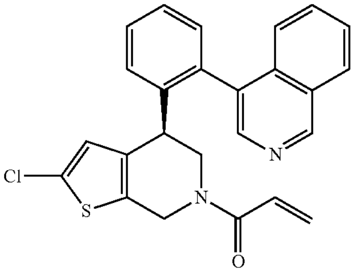
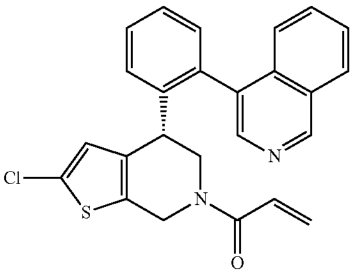
-continued
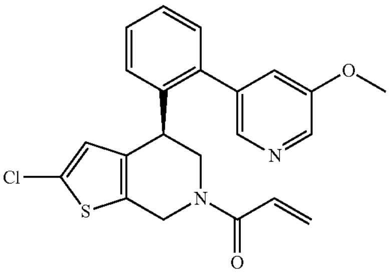
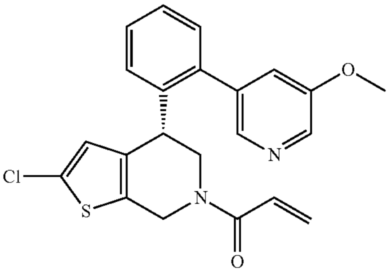
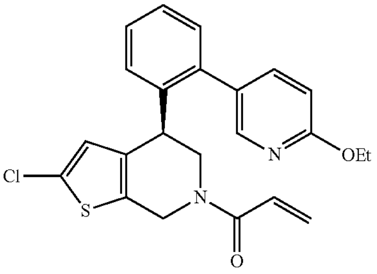
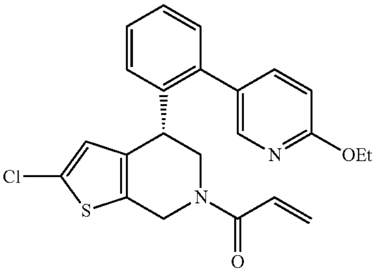

-continued
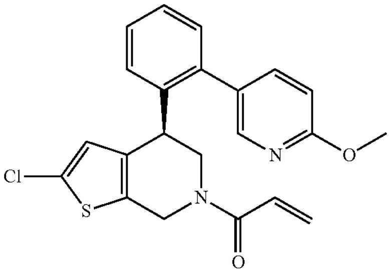
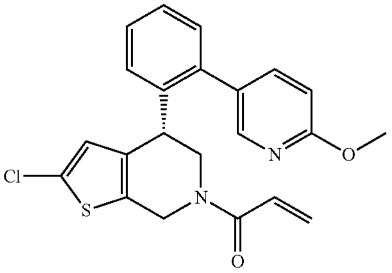
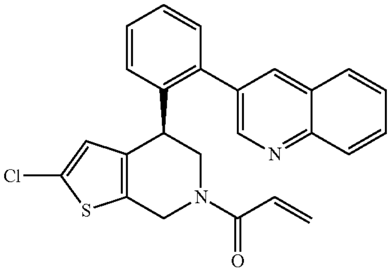
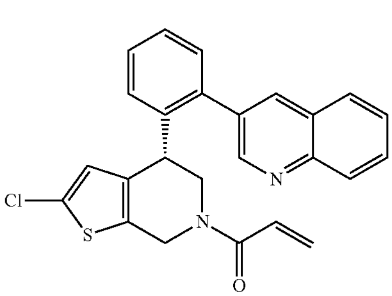
-continued
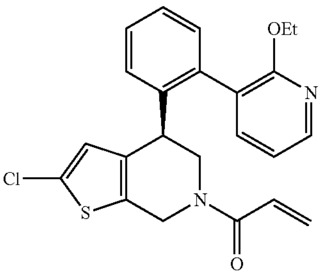
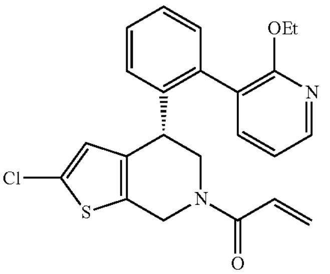
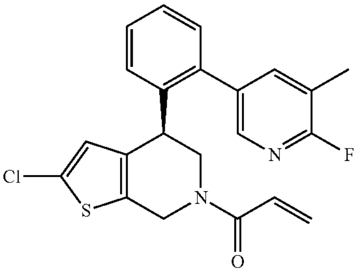
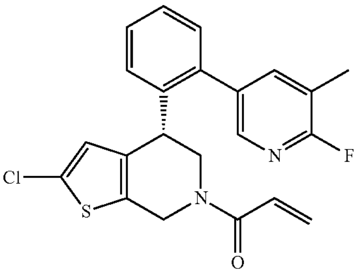

-continued
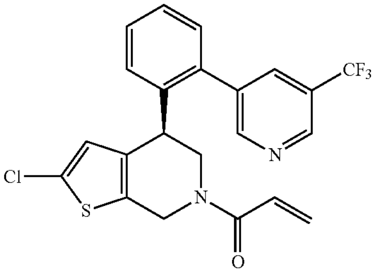
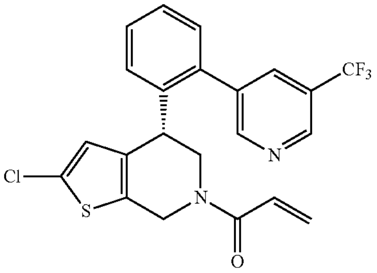
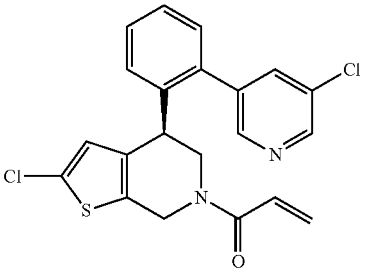
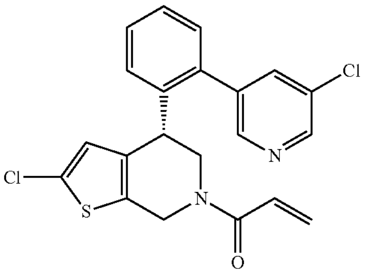
-continued
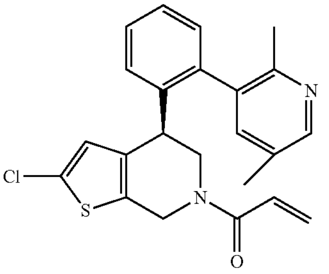
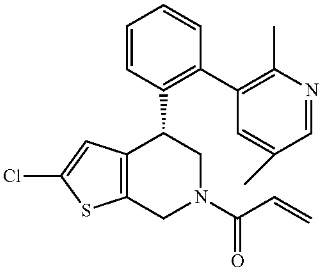
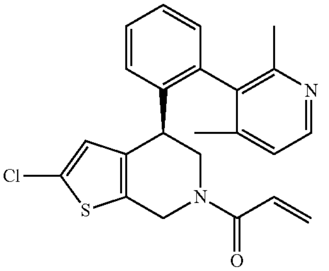
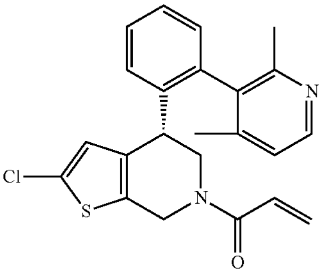

-continued
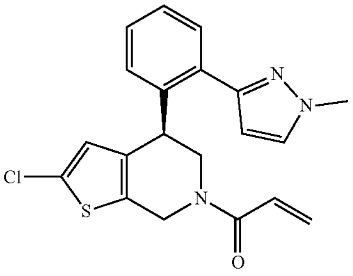
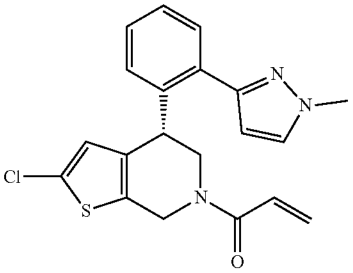
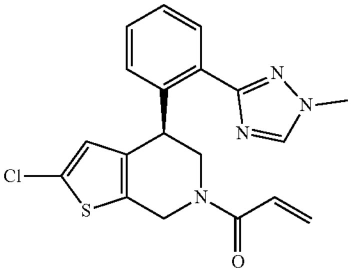
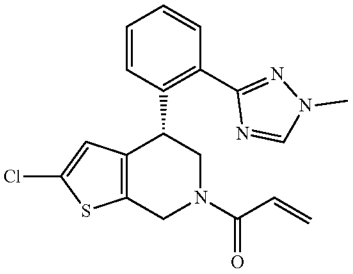
-continued
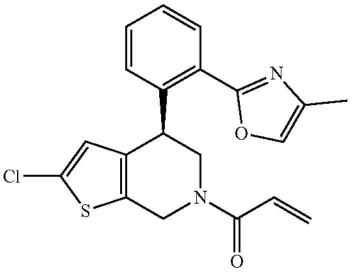
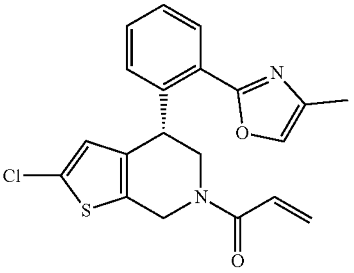
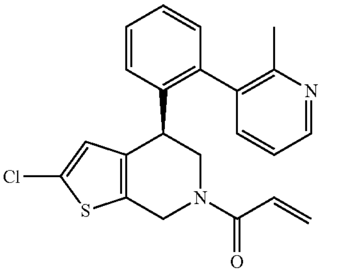
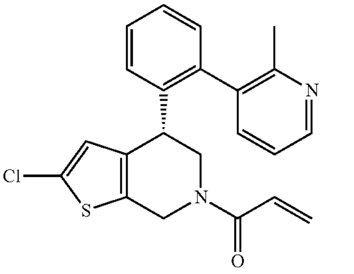

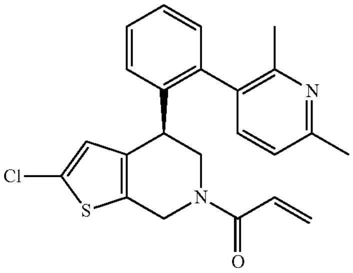
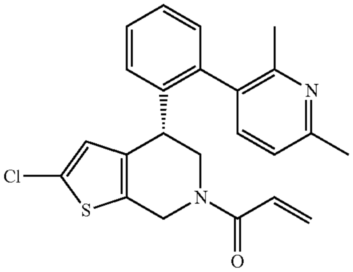
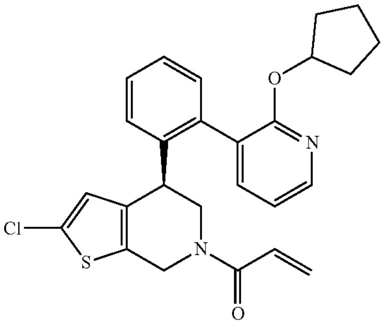
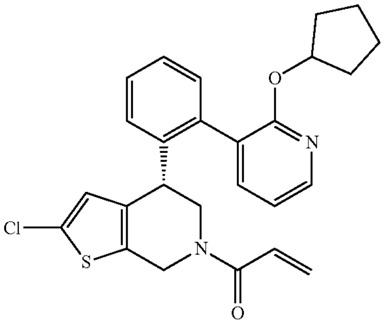
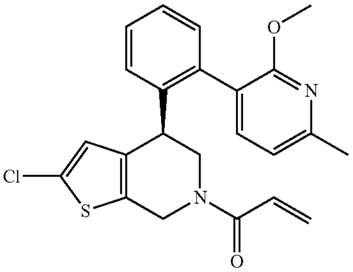
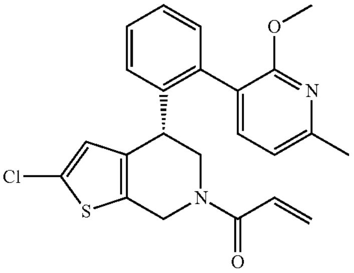
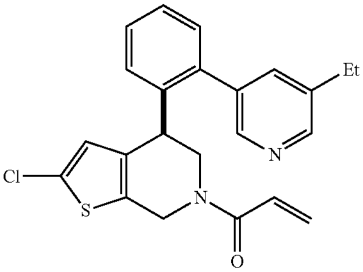
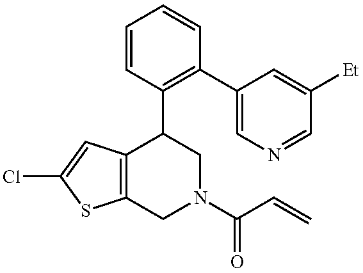

-continued
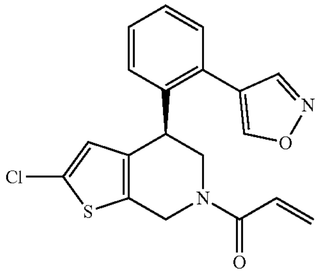
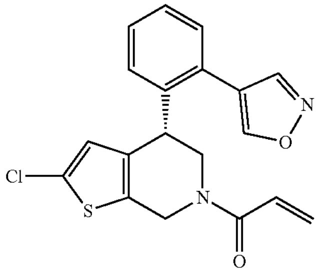
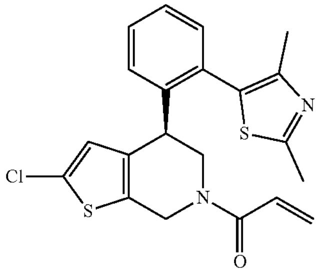
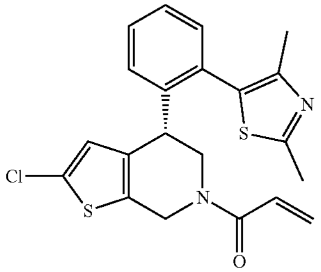
-continued
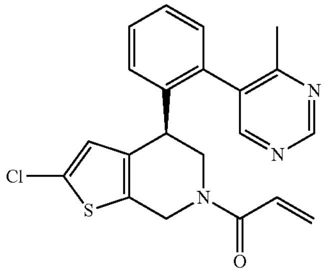
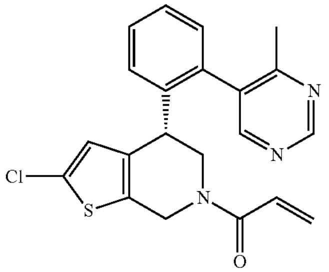
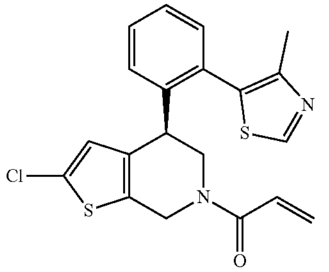
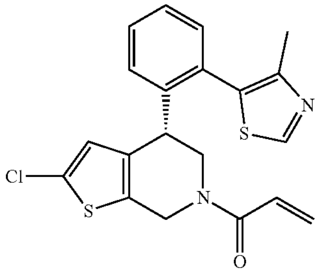

-continued
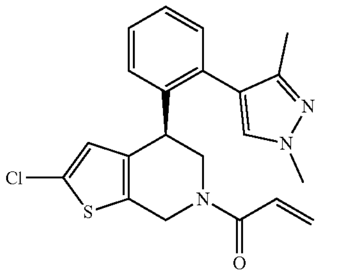
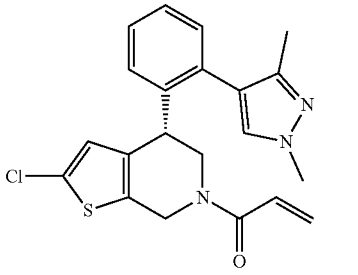
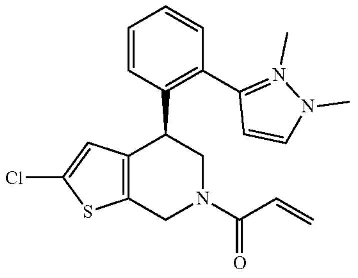
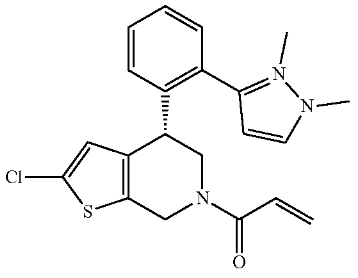
-continued
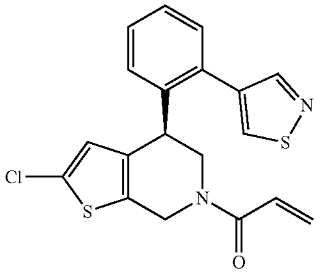
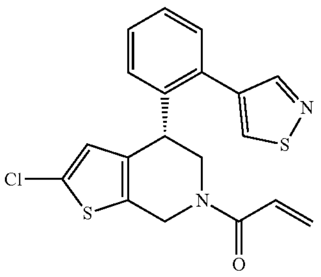
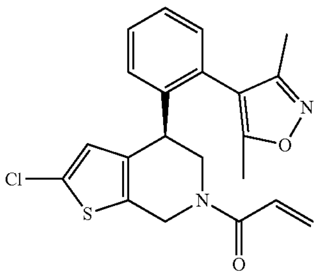
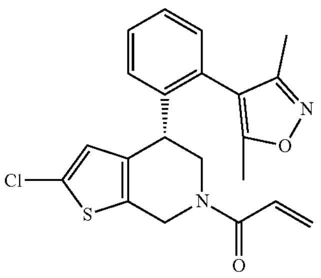

-continued
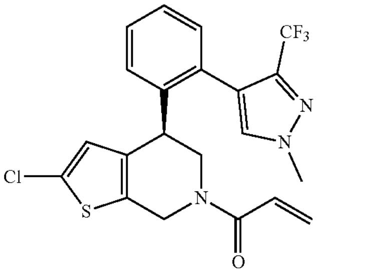
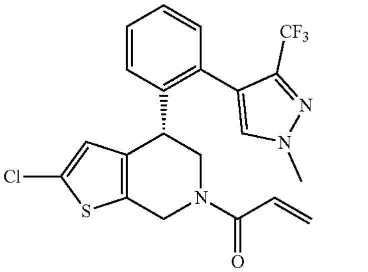
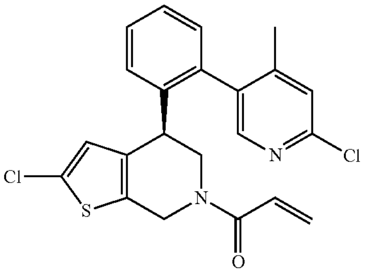
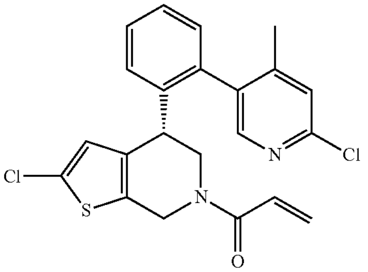
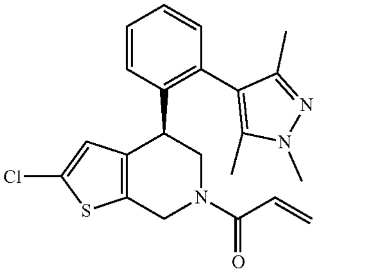
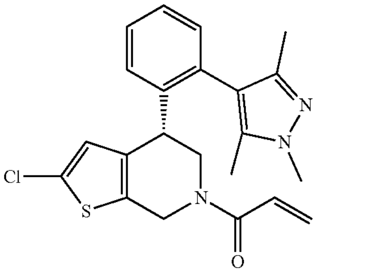
-continued
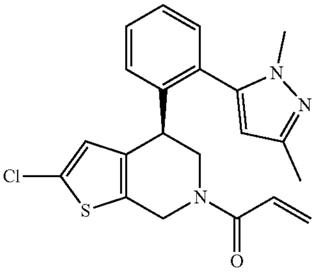
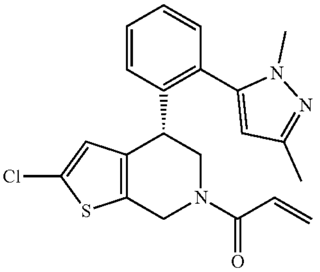
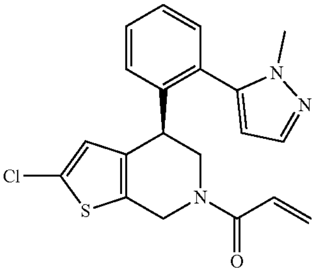
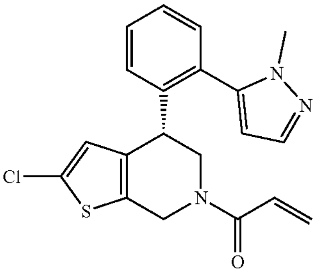

-continued
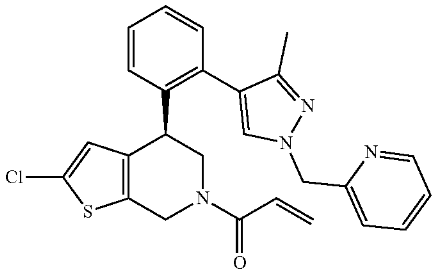
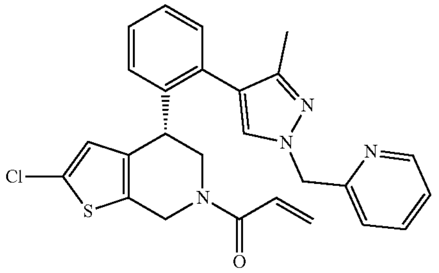
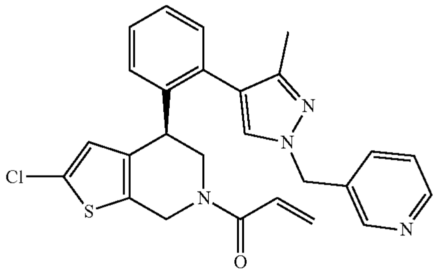
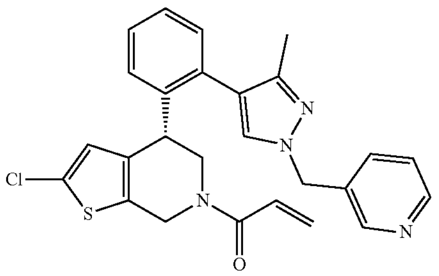
-continued
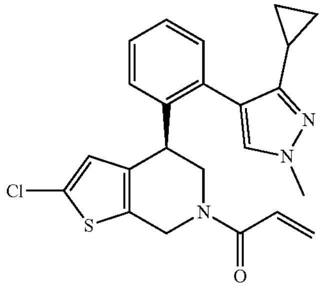
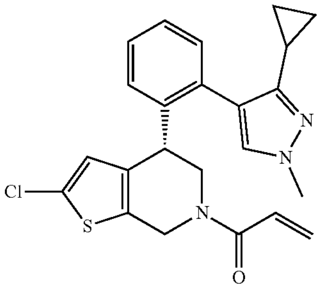
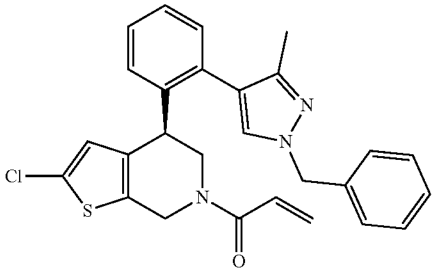
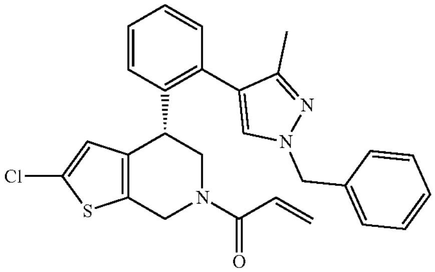

-continued
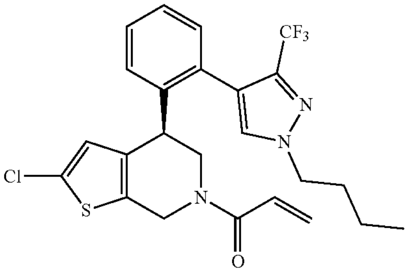
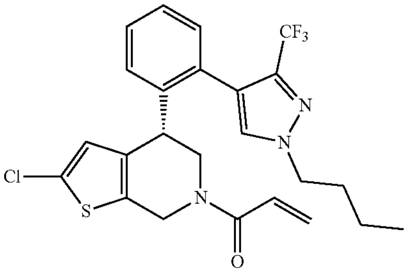
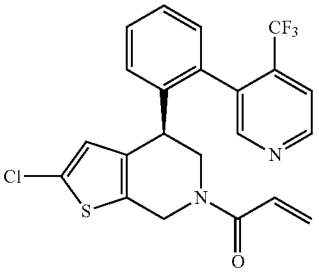
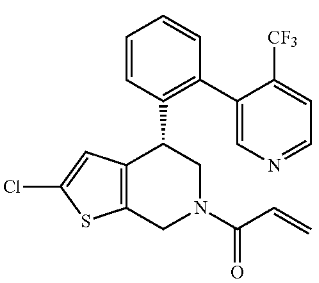
-continued
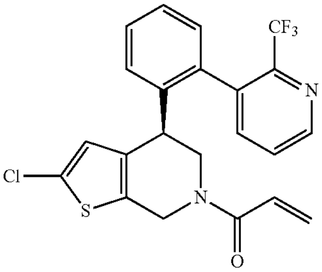
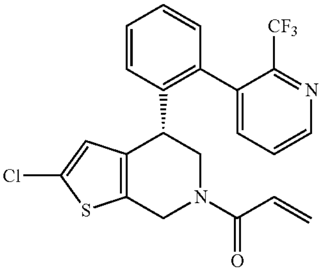
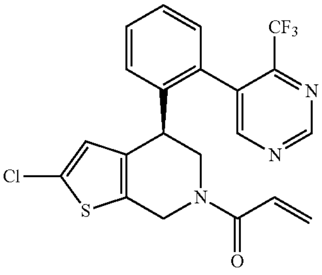
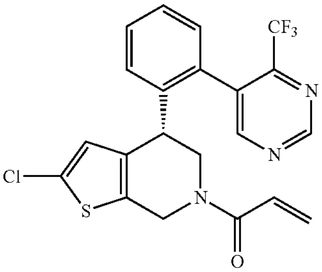

-continued
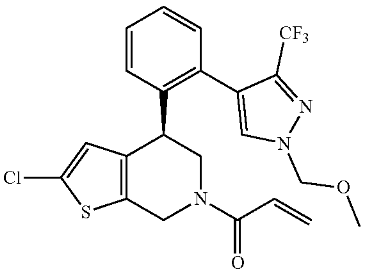
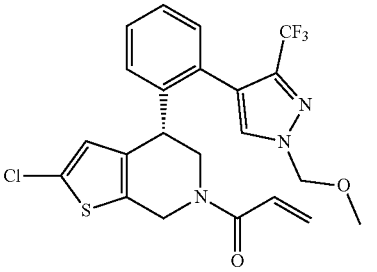
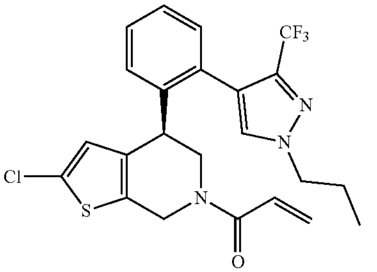
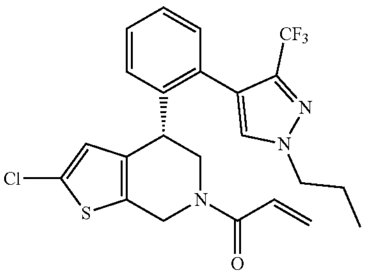
-continued
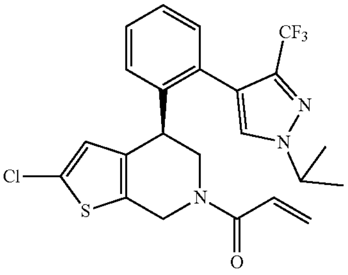
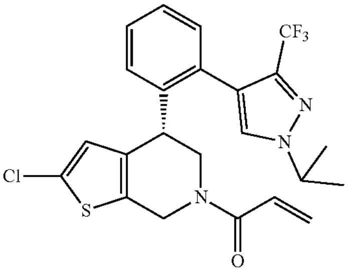
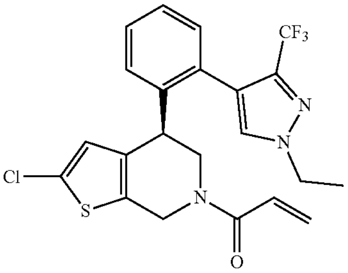
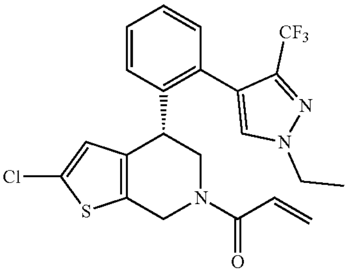

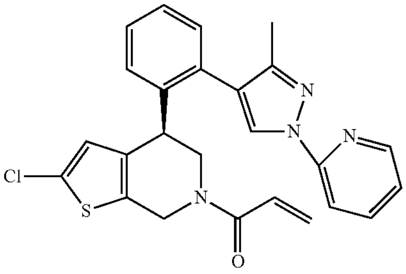
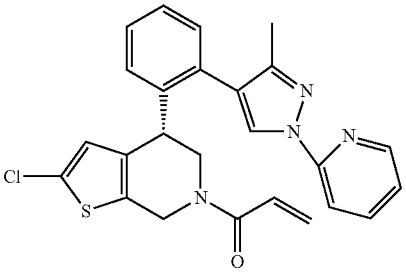
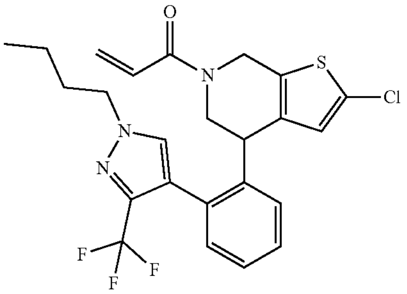 [SMILES: C=CC(=O)N1Cc2sc(Cl)cc2C(c2ccccc2-c2cn(CCCC)nc2C(F)(F)F)C1]
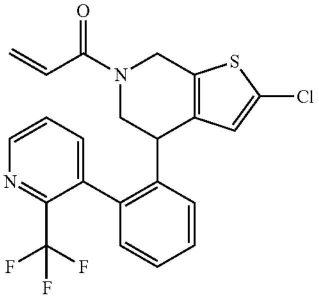
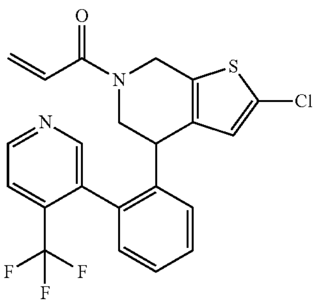 [SMILES: C=CC(=O)N1Cc2sc(Cl)cc2C(c2ccccc2-c2cnccc2C(F)(F)F)C1]
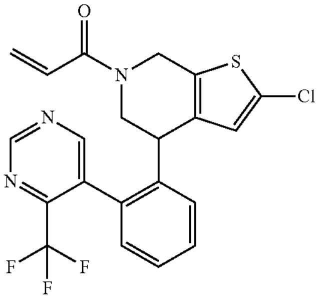 [SMILES: C=CC(=O)N1Cc2sc(Cl)cc2C(c2ccccc2-c2cncnc2C(F)(F)F)C1]
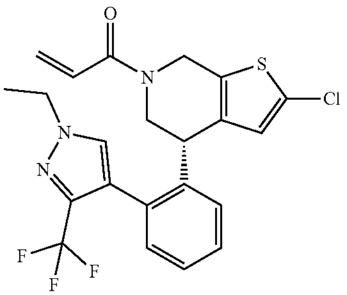
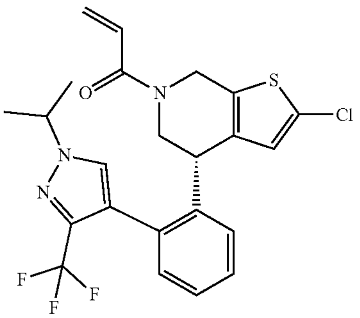 [SMILES: C=CC(=O)N1Cc2sc(Cl)cc2[C@H](c2ccccc2-c2cn(C(C)C)nc2C(F)(F)F)C1]
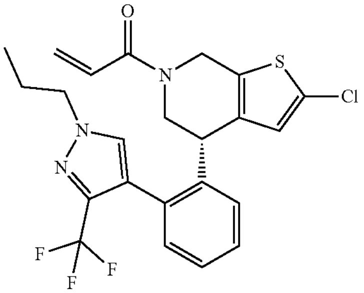 [SMILES: C=CC(=O)N1Cc2sc(Cl)cc2[C@H](c2ccccc2-c2cn(CCC)nc2C(F)(F)F)C1]
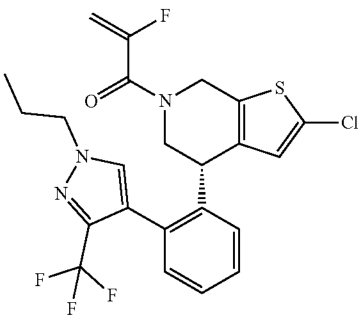 [SMILES: C=C(F)C(=O)N1Cc2sc(Cl)cc2[C@H](c2ccccc2-c2cn(CCC)nc2C(F)(F)F)C1]

-continued
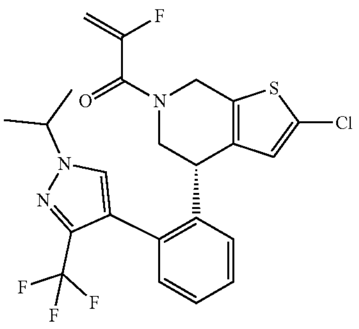 [SMILES: C=C(F)C(=O)N1Cc2sc(Cl)cc2[C@H](c2ccccc2-c2cn(C(C)C)nc2C(F)(F)F)C1]
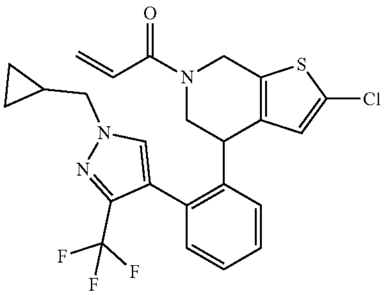 [SMILES: C=CC(=O)N1Cc2sc(Cl)cc2C(c2ccccc2-c2cn(CC3CC3)nc2C(F)(F)F)C1]
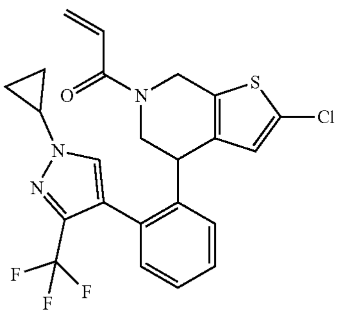 [SMILES: C=CC(=O)N1Cc2sc(Cl)cc2C(c2ccccc2-c2cn(C3CC3)nc2C(F)(F)F)C1]
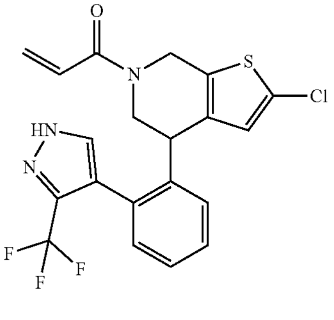 [SMILES: C=CC(=O)N1Cc2sc(Cl)cc2C(c2ccccc2-c2c[nH]nc2C(F)(F)F)C1]
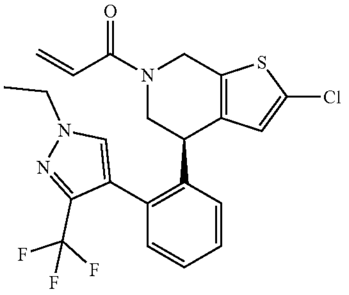
-continued
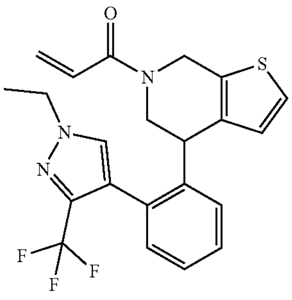
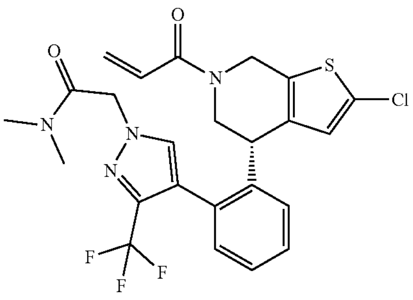 [SMILES: C=CC(=O)N1Cc2sc(Cl)cc2[C@H](c2ccccc2-c2cn(CC(=O)N(C)C)nc2C(F)(F)F)C1]
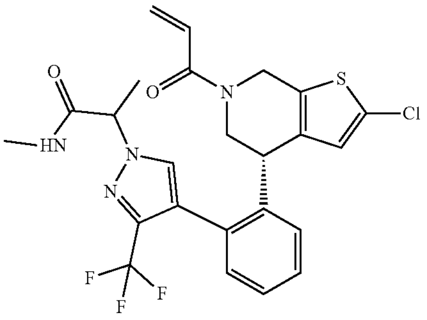 [SMILES: C=CC(=O)N1Cc2sc(Cl)cc2[C@H](c2ccccc2-c2cn(C(C)C(=O)NC)nc2C(F)(F)F)C1]
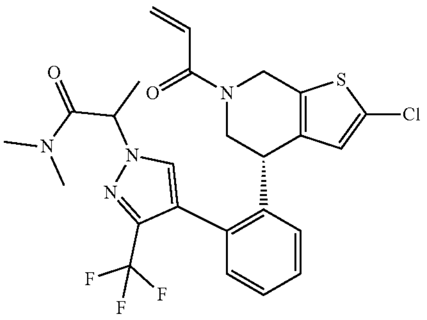 [SMILES: C=CC(=O)N1Cc2sc(Cl)cc2[C@H](c2ccccc2-c2cn(C(C)C(=O)N(C)C)nc2C(F)(F)F)C1]
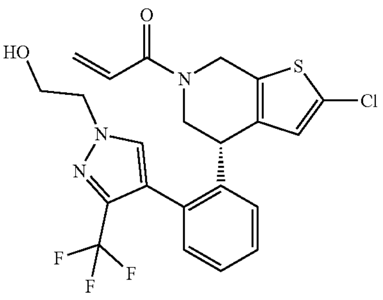 [SMILES: C=CC(=O)N1Cc2sc(Cl)cc2[C@H](c2ccccc2-c2cn(CCO)nc2C(F)(F)F)C1]

-continued
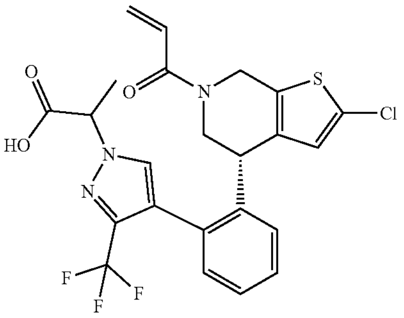 [SMILES: C=CC(=O)N1Cc2sc(Cl)cc2[C@H](c2ccccc2-c2cn(C(C)C(=O)O)nc2C(F)(F)F)C1]
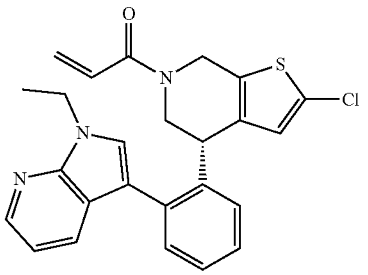 [SMILES: C=CC(=O)N1Cc2sc(Cl)cc2[C@H](c2ccccc2-c2cn(CC)c3ncccc23)C1]
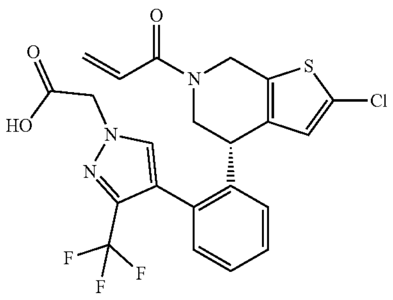 [SMILES: C=CC(=O)N1Cc2sc(Cl)cc2[C@H](c2ccccc2-c2cn(CC(=O)O)nc2C(F)(F)F)C1]
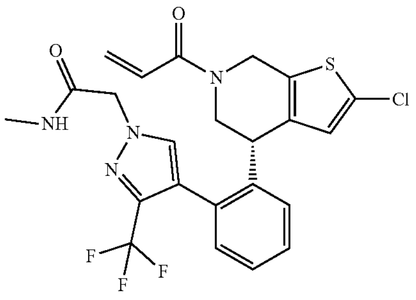 [SMILES: C=CC(=O)N1Cc2sc(Cl)cc2[C@H](c2ccccc2-c2cn(CC(=O)NC)nc2C(F)(F)F)C1]
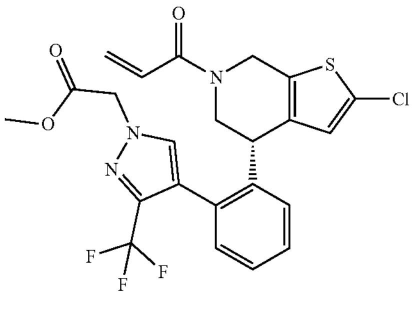 [SMILES: C=CC(=O)N1Cc2sc(Cl)cc2[C@H](c2ccccc2-c2cn(CC(=O)OC)nc2C(F)(F)F)C1]
-continued
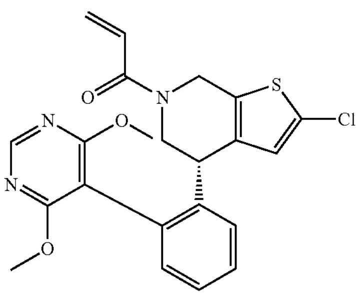 [SMILES: C=CC(=O)N1Cc2sc(Cl)cc2[C@H](c2ccccc2-c2c(OC)ncnc2OC)C1]
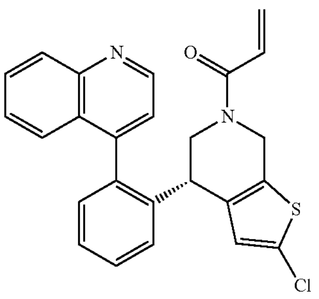 [SMILES: C=CC(=O)N1Cc2sc(Cl)cc2[C@H](c2ccccc2-c2ccnc3ccccc23)C1]
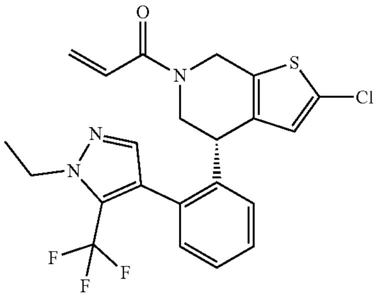 [SMILES: C=CC(=O)N1Cc2sc(Cl)cc2[C@H](c2ccccc2-c2cnn(CC)c2C(F)(F)F)C1]
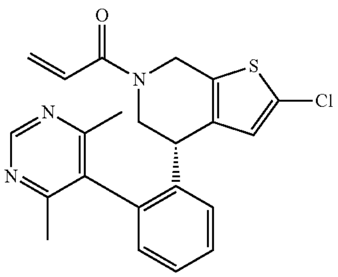 [SMILES: C=CC(=O)N1Cc2sc(Cl)cc2[C@H](c2ccccc2-c2c(C)ncnc2C)C1]
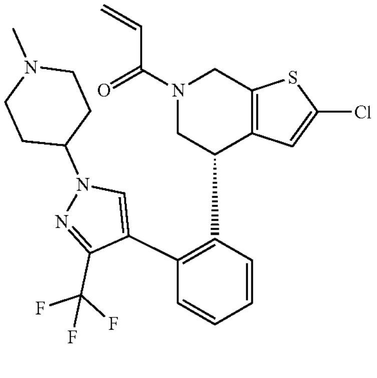 [SMILES: C=CC(=O)N1Cc2sc(Cl)cc2[C@H](c2ccccc2-c2cn(C3CCN(C)CC3)nc2C(F)(F)F)C1]

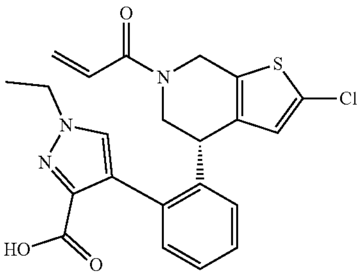 [SMILES: C=CC(=O)N1Cc2sc(Cl)cc2[C@H](c2ccccc2-c2cn(CC)nc2C(=O)O)C1]
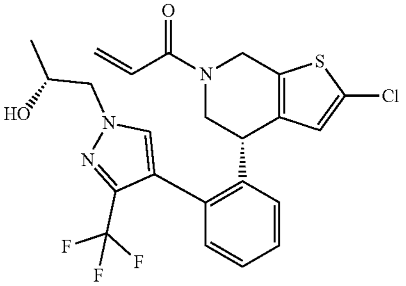 [SMILES: C=CC(=O)N1Cc2sc(Cl)cc2[C@H](c2ccccc2-c2cn(C[C@@H](C)O)nc2C(F)(F)F)C1]
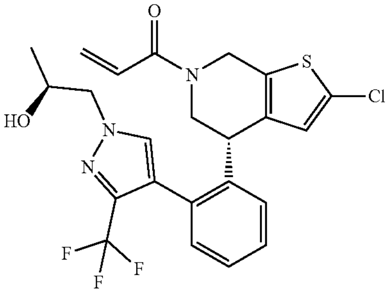 [SMILES: C=CC(=O)N1Cc2sc(Cl)cc2[C@H](c2ccccc2-c2cn(C[C@H](C)O)nc2C(F)(F)F)C1]
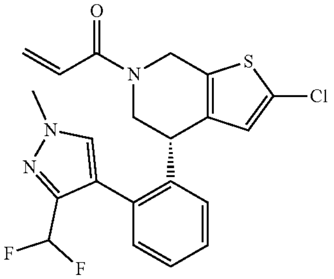 [SMILES: C=CC(=O)N1Cc2sc(Cl)cc2[C@H](c2ccccc2-c2cn(C)nc2C(F)F)C1]
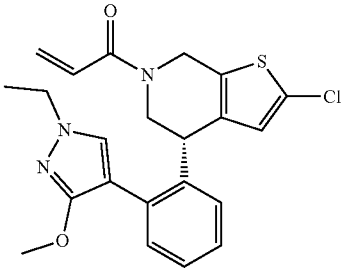 [SMILES: C=CC(=O)N1Cc2sc(Cl)cc2[C@H](c2ccccc2-c2cn(CC)nc2OC)C1]
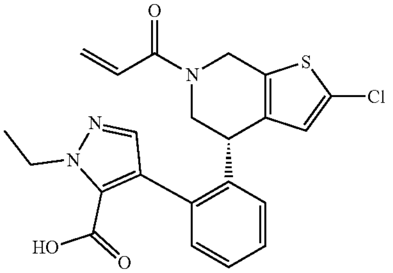 [SMILES: C=CC(=O)N1Cc2sc(Cl)cc2[C@H](c2ccccc2-c2cnn(CC)c2C(=O)O)C1]
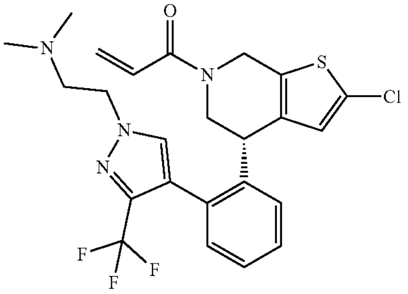 [SMILES: C=CC(=O)N1Cc2sc(Cl)cc2[C@H](c2ccccc2-c2cn(CCN(C)C)nc2C(F)(F)F)C1]
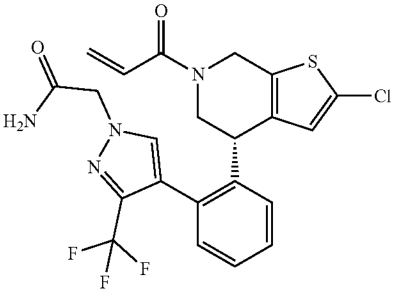 [SMILES: C=CC(=O)N1Cc2sc(Cl)cc2[C@H](c2ccccc2-c2cn(CC(N)=O)nc2C(F)(F)F)C1]
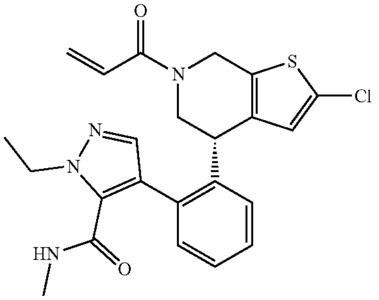 [SMILES: C=CC(=O)N1Cc2sc(Cl)cc2[C@H](c2ccccc2-c2cnn(CC)c2C(=O)NC)C1]
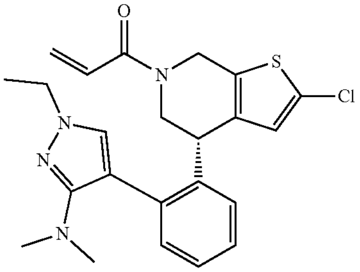 [SMILES: C=CC(=O)N1Cc2sc(Cl)cc2[C@H](c2ccccc2-c2cn(CC)nc2N(C)C)C1]

-continued
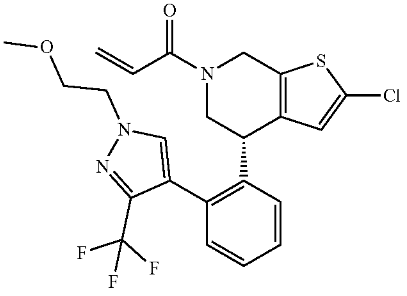
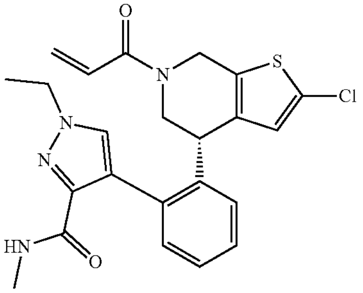 [SMILES: C=CC(=O)N1Cc2sc(Cl)cc2[C@H](c2ccccc2-c2cn(CC)nc2C(=O)NC)C1]
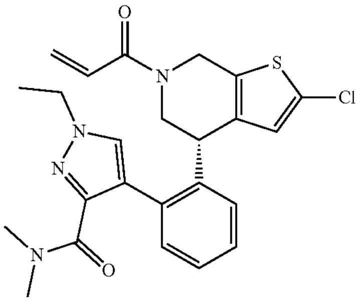 [SMILES: C=CC(=O)N1Cc2sc(Cl)cc2[C@H](c2ccccc2-c2cn(CC)nc2C(=O)N(C)C)C1]
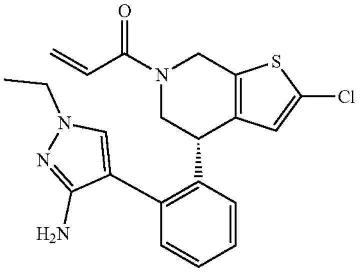 [SMILES: C=CC(=O)N1Cc2sc(Cl)cc2[C@H](c2ccccc2-c2cn(CC)nc2N)C1]
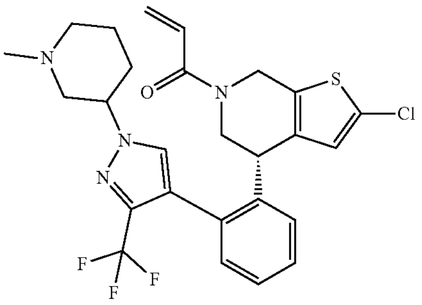 [SMILES: C=CC(=O)N1Cc2sc(Cl)cc2[C@H](c2ccccc2-c2cn(C3CCCN(C)C3)nc2C(F)(F)F)C1]
-continued
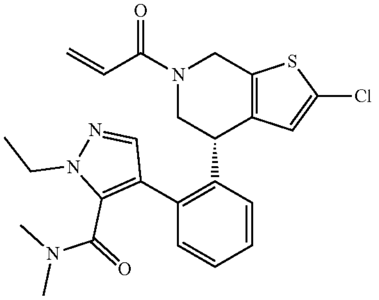 [SMILES: C=CC(=O)N1Cc2sc(Cl)cc2[C@H](c2ccccc2-c2cnn(CC)c2C(=O)N(C)C)C1]
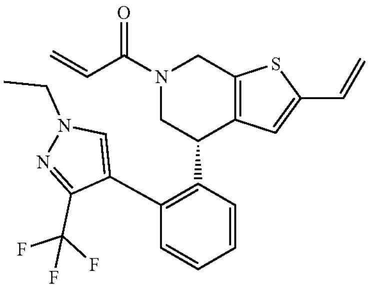 [SMILES: C=CC(=O)N1Cc2sc(C=C)cc2[C@H](c2ccccc2-c2cn(CC)nc2C(F)(F)F)C1]
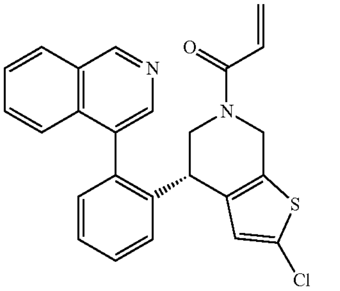 [SMILES: C=CC(=O)N1Cc2sc(Cl)cc2[C@H](c2ccccc2-c2cncc3ccccc23)C1]
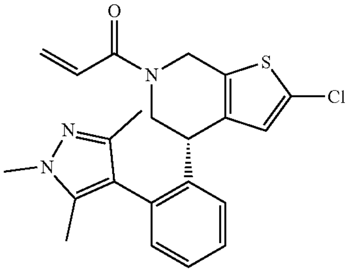 [SMILES: C=CC(=O)N1Cc2sc(Cl)cc2[C@H](c2ccccc2-c2c(C)nn(C)c2C)C1]
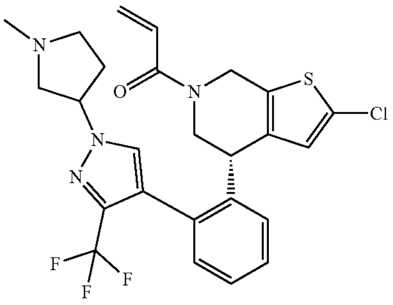 [SMILES: C=CC(=O)N1Cc2sc(Cl)cc2[C@H](c2ccccc2-c2cn(C3CCN(C)C3)nc2C(F)(F)F)C1]

-continued
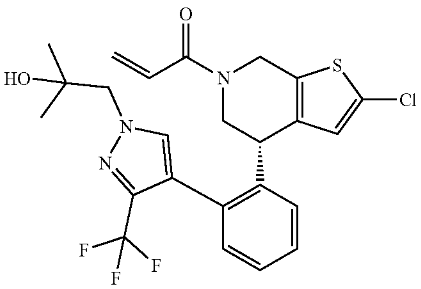 [SMILES: C=CC(=O)N1Cc2sc(Cl)cc2[C@H](c2ccccc2-c2cn(CC(C)(C)O)nc2C(F)(F)F)C1]
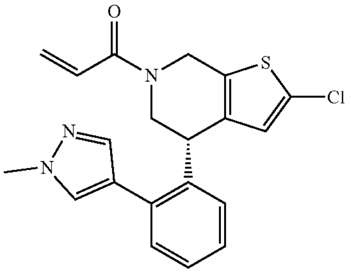 [SMILES: C=CC(=O)N1Cc2sc(Cl)cc2[C@H](c2ccccc2-c2cnn(C)c2)C1]
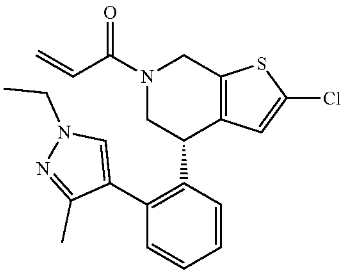 [SMILES: C=CC(=O)N1Cc2sc(Cl)cc2[C@H](c2ccccc2-c2cn(CC)nc2C)C1]
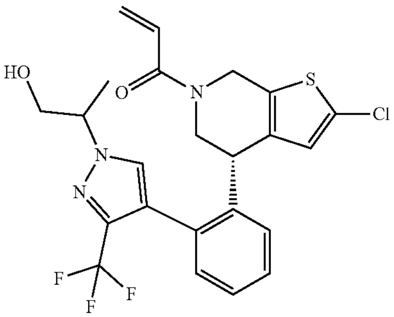 [SMILES: C=CC(=O)N1Cc2sc(Cl)cc2[C@H](c2ccccc2-c2cn(C(C)CO)nc2C(F)(F)F)C1]
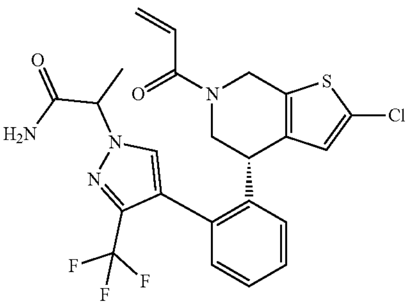 [SMILES: C=CC(=O)N1Cc2sc(Cl)cc2[C@H](c2ccccc2-c2cn(C(C)C(N)=O)nc2C(F)(F)F)C1]
-continued
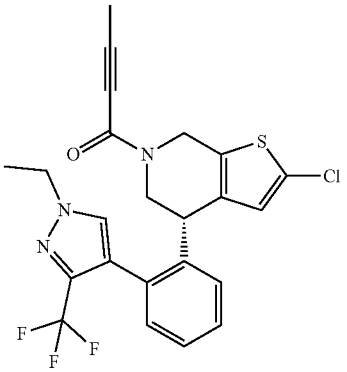 [SMILES: CC#CC(=O)N1Cc2sc(Cl)cc2[C@H](c2ccccc2-c2cn(CC)nc2C(F)(F)F)C1]
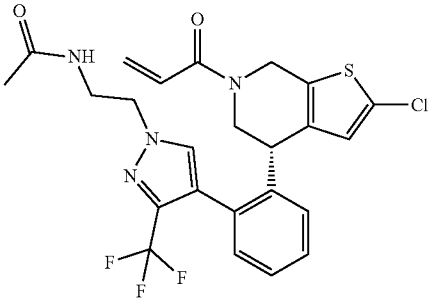 [SMILES: C=CC(=O)N1Cc2sc(Cl)cc2[C@H](c2ccccc2-c2cn(CCNC(C)=O)nc2C(F)(F)F)C1]
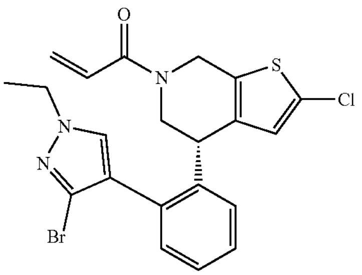 [SMILES: C=CC(=O)N1Cc2sc(Cl)cc2[C@H](c2ccccc2-c2cn(CC)nc2Br)C1]
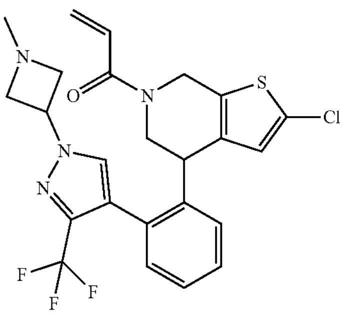 [SMILES: C=CC(=O)N1Cc2sc(Cl)cc2C(c2ccccc2-c2cn(C3CN(C)C3)nc2C(F)(F)F)C1]
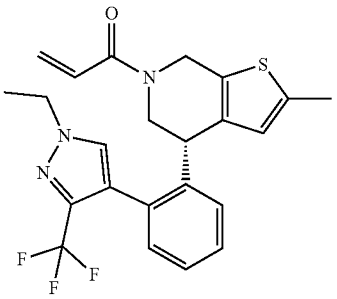 [SMILES: C=CC(=O)N1Cc2sc(C)cc2[C@H](c2ccccc2-c2cn(CC)nc2C(F)(F)F)C1]

-continued
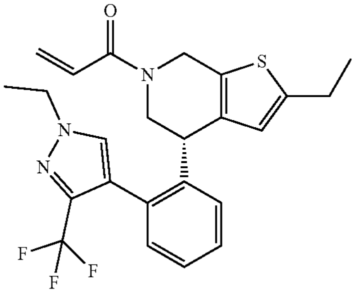 [SMILES: C=CC(=O)N1Cc2sc(CC)cc2[C@H](c2ccccc2-c2cn(CC)nc2C(F)(F)F)C1]
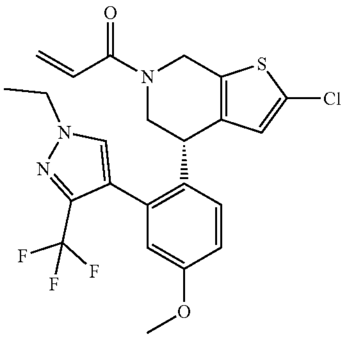 [SMILES: C=CC(=O)N1Cc2sc(Cl)cc2[C@H](c2ccc(OC)cc2-c2cn(CC)nc2C(F)(F)F)C1]
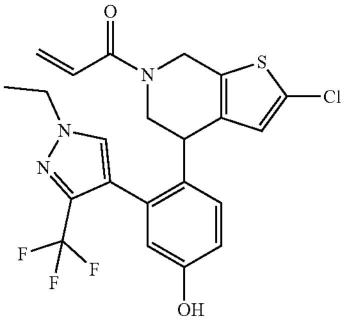 [SMILES: C=CC(=O)N1Cc2sc(Cl)cc2C(c2ccc(O)cc2-c2cn(CC)nc2C(F)(F)F)C1]
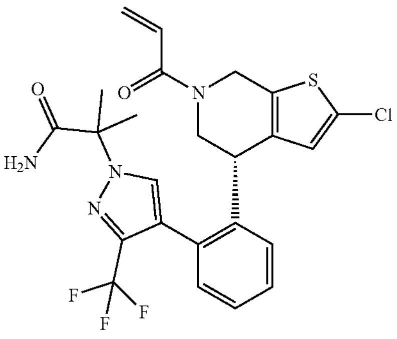 [SMILES: C=CC(=O)N1Cc2sc(Cl)cc2[C@H](c2ccccc2-c2cn(C(C)(C)C(N)=O)nc2C(F)(F)F)C1]
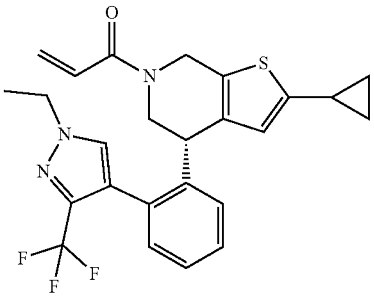 [SMILES: C=CC(=O)N1Cc2sc(C3CC3)cc2[C@H](c2ccccc2-c2cn(CC)nc2C(F)(F)F)C1]
-continued
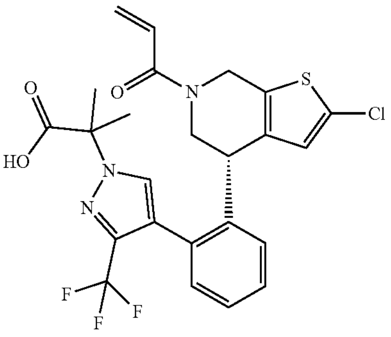 [SMILES: C=CC(=O)N1Cc2sc(Cl)cc2[C@H](c2ccccc2-c2cn(C(C)(C)C(=O)O)nc2C(F)(F)F)C1]
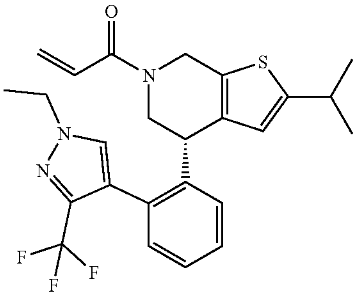 [SMILES: C=CC(=O)N1Cc2sc(C(C)C)cc2[C@H](c2ccccc2-c2cn(CC)nc2C(F)(F)F)C1]
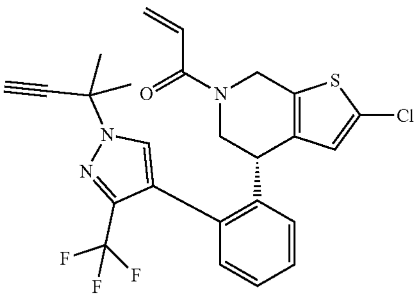 [SMILES: C#CC(C)(C)n1cc(-c2ccccc2[C@@H]2CN(C(=O)C=C)Cc3sc(Cl)cc32)c(C(F)(F)F)n1]
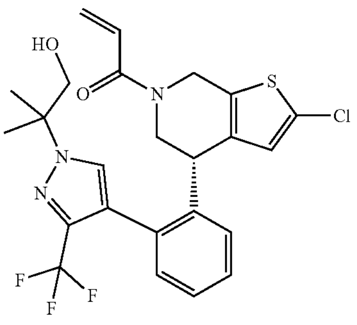 [SMILES: C=CC(=O)N1Cc2sc(Cl)cc2[C@H](c2ccccc2-c2cn(C(C)(C)CO)nc2C(F)(F)F)C1]
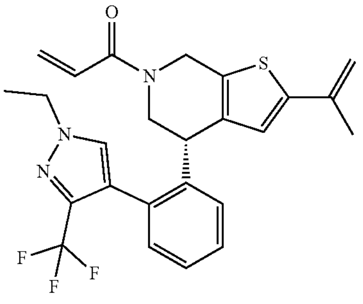 [SMILES: C=CC(=O)N1Cc2sc(C(=C)C)cc2[C@H](c2ccccc2-c2cn(CC)nc2C(F)(F)F)C1]

-continued

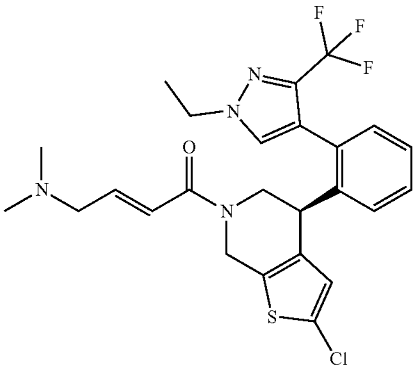 [SMILES: CCn1cc(-c2ccccc2[C@@H]2CN(C(=O)/C=C/CN(C)C)Cc3sc(Cl)cc32)c(C(F)(F)F)n1]

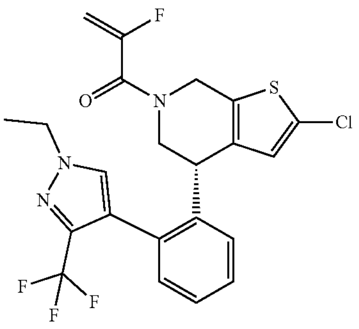 [SMILES: C=C(F)C(=O)N1Cc2sc(Cl)cc2[C@H](c2ccccc2-c2cn(CC)nc2C(F)(F)F)C1]

or a pharmaceutically acceptable salt thereof.

7. A compound of Formula XII

[XII]

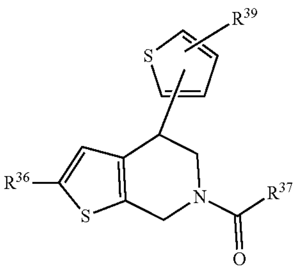

wherein $R^{36}$ is halo or $C_{1-6}$ alkyl;

$R^{37}$ is $C_2$-$C_4$ alkenyl; and $R^{39}$ is H, halo, $C_{1-6}$ alkyl, cyano, substituted or unsubstituted cycloalkyl, substituted or unsubstituted nitrogen containing 5- or 6-membered partially unsaturated heterocyclyl or substituted or unsubstituted 5-10-membered heteroaryl; or a pharmaceutically acceptable salt thereof.

8. The compound of claim 7 selected from

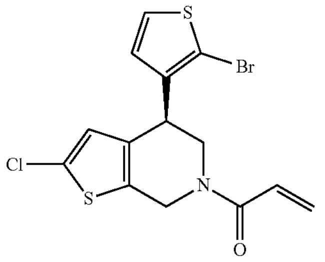

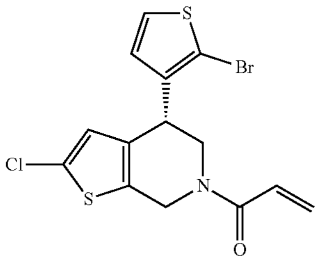

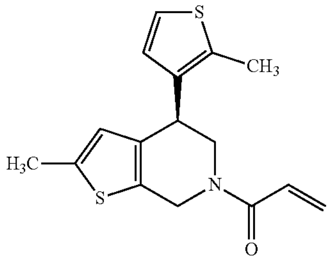

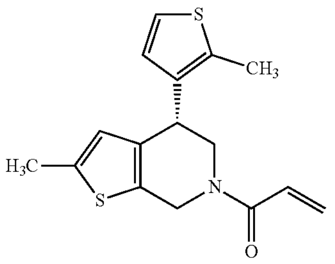

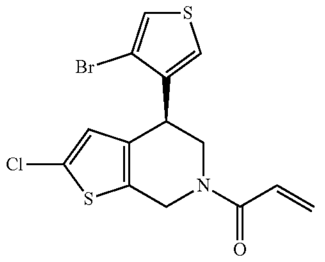

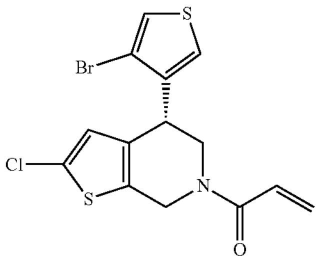

-continued
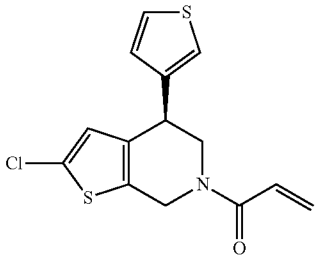
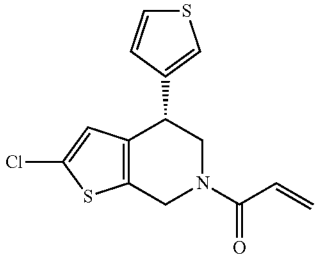
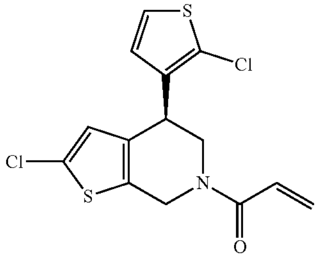
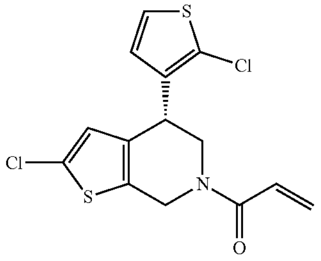
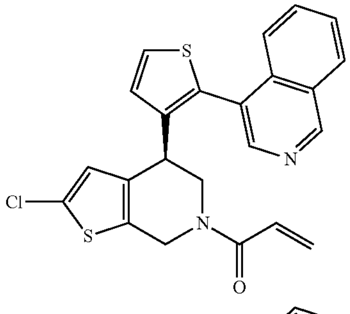
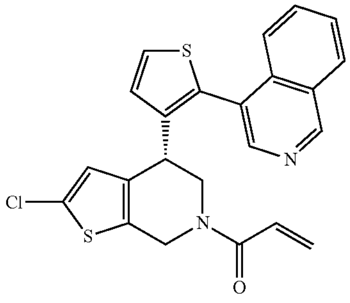
-continued
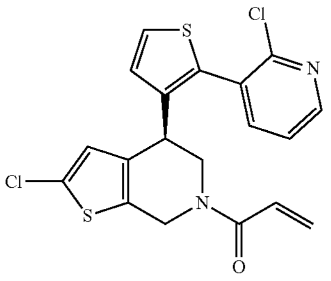
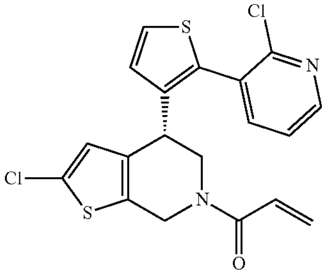
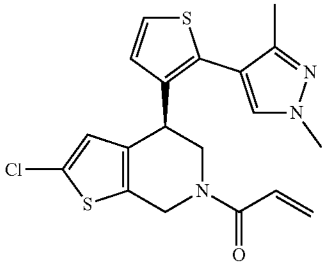
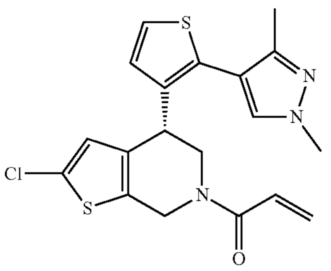

-continued

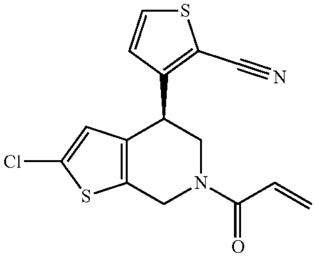

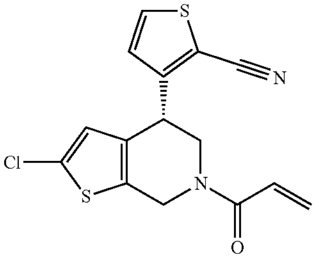

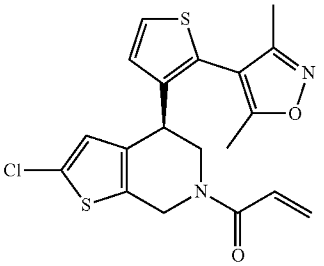

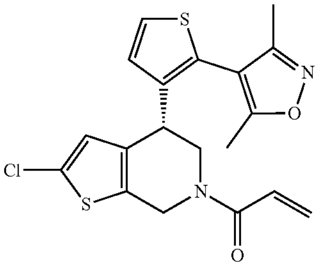

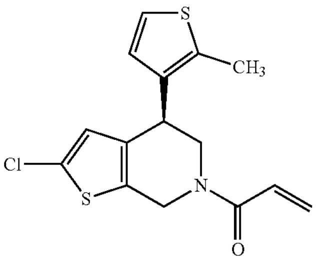

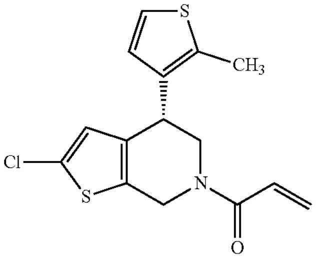

or a pharmaceutically acceptable salt thereof.

9. A compound of Formula XIV

XIV

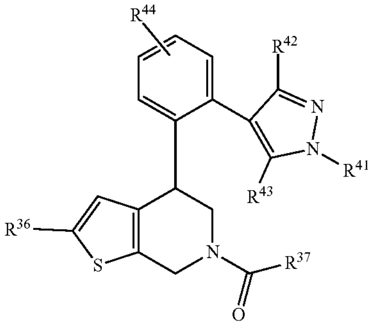

wherein $R^{36}$ is selected from H, halo, $C_1$-$C_4$ alkyl, $C_2$-$C_4$ alkenyl and $C_3$-$C_6$ cycloalkyl;

$R^{37}$ is substituted or unsubstituted $C_2$-$C_4$ alkenyl, or substituted or unsubstituted $C_2$-$C_4$ alkynyl;

$R^{41}$ is selected from H, $C_{1-6}$ alkyl, $C_{1-6}$ hydroxyalkyl, $C_{1-6}$ alkoxy, $C_{1-6}$ alkoxyalkyl, $C_{1-6}$ alkylamino-$C_{1-6}$ alkyl, $C_{1-6}$ alkylaminocarbonyl-$C_{1-6}$ alkyl, aminocarbonyl-$C_{1-6}$ alkyl, $C_{1-6}$ alkoxycarbonyl-$C_{1-6}$ alkyl, carboxy-$C_{1-6}$ alkyl, $C_{1-6}$ alkylcarbonylamino-$C_{1-6}$ alkyl, $C_{1-6}$ cyanoalkyl, $C_{3-6}$ cycloalkyl, $C_{3-6}$ cycloalkyl-$C_{1-6}$ alkyl, aryl-$C_{1-6}$ alkyl, 5 or 6 membered heteroaryl-$C_{1-6}$ alkyl, 5 or 6 membered heterocyclyl and 5 or 6 membered heteroaryl;

$R^{42}$ is selected from H, carboxy, amino, $C_{1-6}$ alkyl, $C_{1-3}$ haloalkyl, $C_{1-6}$ alkoxy, $C_{1-6}$ alkylamino, $C_{1-6}$ alkylaminocarbonyl, and $C_{3-6}$ cycloalkyl;

$R^{43}$ is selected from H, carboxy, $C_{1-4}$ alkyl, $C_{1-3}$ haloalkyl, and $C_{1-6}$ alkylaminocarbonyl; and $R^{44}$ is one or more substituents selected from H, halo, alkoxy and hydroxy; or a pharmaceutically acceptable salt thereof.

10. The compound of claim 9 wherein $R^{41}$ is selected from H, ethyl, isopropyl, butyl, propyl, methyl, 1-hydroxyethyl, 2-hydroxymethylethyl, 1-hydroxy-2,2-dimethylethyl, 2-hydroxypropyl, 2-hydroxy-2-methylpropyl, methoxymethyl, methoxyethyl, dimethylaminoethyl, carboxymethyl, carboxyethyl, methoxycarbonylmethyl, dimethylaminocarbonylmethyl, dimethylaminocarbonylethyl, methylaminocarbonylethyl, methylaminocarbonylmethyl, aminocarbonylmethyl, aminocarbonylethyl, aminocarbonyl-1,1-dimethylmethyl, methylcarbonylaminoethyl, 1-methylcarbonylamino-2.2-dimethylethyl, 2-cyano-2-methylethyl, cyclopropyl, cyclopropylmethyl, benzyl, 3-pyridinylmethyl, 2-pyridinylmethyl, 1-methylazetidin-3-yl, 1-methylpyrrolidin-3-yl, 1-methylpiperidin-4-yl, 1-methylpiperidin-3-yl and 2-pyridyl; or a pharmaceutically acceptable salt thereof.

11. The compound of claim 9 wherein $R^{37}$ is dimethylaminopropenyl, methylaminopropenyl, or aminopropenyl; or a pharmaceutically acceptable salt thereof.

12. A compound of Formula XV

XV

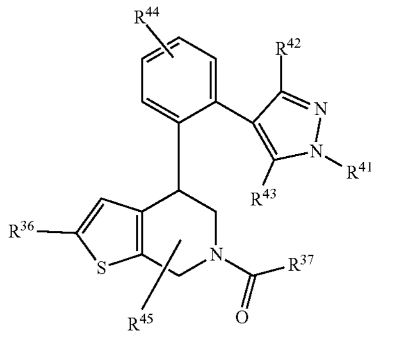

wherein $R^{36}$ is selected from H, halo, $C_1$-$C_4$ alkyl, $C_1$-$C_3$ haloalkyl, $C_2$-$C_4$ alkenyl, substituted or unsubstituted 5-6 membered heteroaryl and $C_3$-$C_6$ cycloalkyl;

$R^{37}$ is substituted or unsubstituted $C_2$-$C_4$ alkenyl, or substituted or unsubstituted $C_2$-$C_4$ alkynyl;

$R^{41}$ is selected from H, $C_{1-6}$ alkyl, $C_{1-6}$ hydroxyalkyl, $C_{1-6}$ alkoxy, $C_{1-6}$ alkoxyalkyl, $C_{1-6}$ alkylamino-$C_{1-6}$ alkyl, $C_{1-6}$ alkylaminocarbonyl-$C_{1-6}$ alkyl, aminocarbonyl-$C_{1-6}$ alkyl, $C_{1-6}$ alkoxycarbonyl-$C_{1-6}$ alkyl, carboxy-$C_{1-6}$ alkyl, $C_{1-6}$ alkylcarbonylamino-$C_{1-6}$ alkyl, $C_{1-6}$ cyanoalkyl, $C_{3-6}$ cycloalkyl, $C_{3-6}$ cycloalkyl-$C_{1-6}$ alkyl, aryl-$C_{1-6}$ alkyl, substituted or unsubstituted 5 or 6 membered heteroaryl-$C_{1-6}$ alkyl, substituted or unsubstituted 5 or 6 membered heterocyclyl and substituted or unsubstituted 5 or 6 membered heteroaryl;

$R^{42}$ is selected from H, carboxy, amino, $C_{1-6}$ alkyl, $C_{1-3}$ haloalkyl, $C_{1-6}$ alkoxy, $C_{1-6}$ alkylamino, $C_{1-6}$ alkylaminocarbonyl, and $C_{3-6}$ cycloalkyl;

$R^{43}$ is selected from H, carboxy, cyano, $C_{1-4}$ alkyl, $C_{1-3}$ haloalkyl, and $C_{1-6}$ alkylaminocarbonyl;

$R^{44}$ is H, halo, hydroxy or $C_{1-6}$ alkoxy; and $R^{45}$ is one or more substituents selected from H, D or $C_{1-4}$ alkyl;

or a pharmaceutically acceptable salt thereof.

13. The compound of claim 12 wherein $R^{41}$ is selected from H, ethyl, isopropyl, butyl, propyl, methyl, $D_3$-methyl, 1-hydroxyethyl, 2-hydroxymethylethyl, 1-hydroxy-2,2-dimethylethyl, 2-hydroxypropyl, 2-hydroxy-2-methylpropyl, methoxymethyl, methoxyethyl, dimethylaminoethyl, carboxymethyl, carboxyethyl, methoxycarbonylmethyl, dimethylaminocarbonylmethyl, dimethylaminocarbonylethyl, methylaminocarbonylethyl, methylaminocarbonylmethyl, aminocarbonylmethyl, aminocarbonylethyl, aminocarbonyl-1,1-dimethylmethyl, methylcarbonylaminoethyl, 1-methylcarbonylamino-2.2-dimethylethyl, 2-cyano-2-methylethyl, cyanomethyl, cyanoethyl, cyclopropyl, cyclopropylmethyl, benzyl, 3-pyridinylmethyl, 2-pyridinylmethyl, 4-oxazolylmethyl, oxadiazol-5-ylmethyl, 1-methylazetidin-3-yl, 1-methylpyrrolidin-3-yl, 1-methylpiperidin-4-yl, 1-methylpiperidin-3-yl, 3,5-difluoro-4-pyridyl, 3-chloro-4-pyridyl, 4-pyridyl and 2-pyridyl; or a pharmaceutically acceptable salt thereof.

14. The compound of claim 12 wherein $R^{36}$ is selected from H, chloro, methyl, ethyl, isopropyl, propenyl, trifluoromethyl, 2-furyl, 2-pyridinyl, and cyclopropyl; or a pharmaceutically acceptable salt thereof.

15. The compound of claim 12 wherein $R^{37}$ is selected from ethenyl, fluoroethenyl, fluoropropenyl, propynyl, dialkylaminopropenyl, alkylaminopropenyl, aminopropenyl, substituted or unsubstituted 3-7 membered nitrogen-containing heterocyclyl-ethenyl and substituted or unsubstituted 3-7 membered nitrogen-containing heterocyclyl-propenyl; or a pharmaceutically acceptable salt thereof.

16. The compound of claim 12 wherein $R^{37}$ is selected from azetidin-1-ylpropenyl, 1-methylpyrrolidin-2-ylethenyl, dimethylaminopropenyl, methylaminopropenyl, piperidin-1-ylpropenyl, 4-hydroxy-piperidin-1-ylpropenyl, pyrrolidin-1-ylpropenyl, 3-hydroxypyrrolidin-1-ylpropenyl, morpholin-1-ylpropenyl, and aminopropenyl; or a pharmaceutically acceptable salt thereof.

17. The compound of claim 12 wherein $R^{42}$ is selected from H, trifluoromethyl, difluoromethyl, methyl, ethyl, methoxy, amino, dimethylamino, carboxy, methylaminocarbonyl, dimethylaminocarbonyl, and cyclopropyl; or a pharmaceutically acceptable salt thereof.

18. The compound of claim 12 wherein $R^{43}$ is selected from H, trifluoromethyl, methyl, ethyl, carboxy, cyano and methylaminocarbonyl; or a pharmaceutically acceptable salt thereof.

19. The compound of claim 12 wherein $R^{44}$ is one or more substituents selected from H, fluoro, hydroxy and methoxy; or a pharmaceutically acceptable salt thereof.

20. The compound of claim 12 wherein $R^{45}$ is one or more substituents selected from H, D, and methyl; or a pharmaceutically acceptable salt thereof.

21. The compound of claim 12 wherein $R^{45}$ is H; or a pharmaceutically acceptable salt thereof.

22. The compound of claim 12 selected from

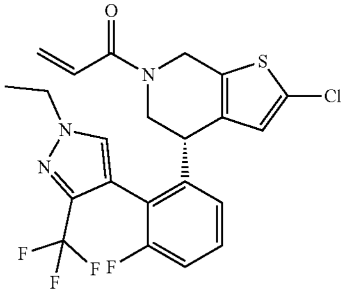 [SMILES: C=CC(=O)N1Cc2sc(Cl)cc2[C@H](c2cccc(F)c2-c2cn(CC)nc2C(F)(F)F)C1]

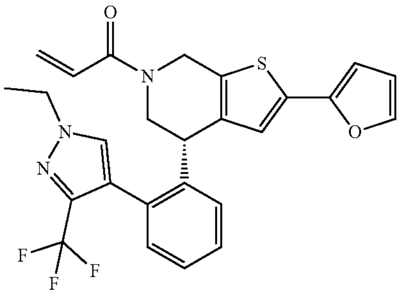 [SMILES: C=CC(=O)N1Cc2sc(-c3ccco3)cc2[C@H](c2ccccc2-c2cn(CC)nc2C(F)(F)F)C1]

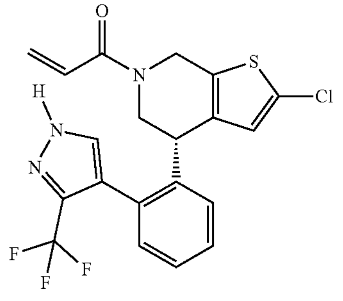 [SMILES: C=CC(=O)N1Cc2sc(Cl)cc2[C@H](c2ccccc2-c2c[nH]nc2C(F)(F)F)C1]

-continued
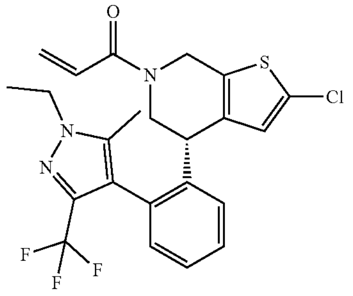 [SMILES: C=CC(=O)N1Cc2sc(Cl)cc2[C@H](c2ccccc2-c2c(C(F)(F)F)nn(CC)c2C)C1]
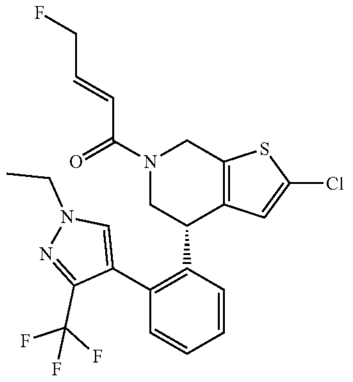 [SMILES: CCn1cc(-c2ccccc2[C@@H]2CN(C(=O)/C=C/CF)Cc3sc(Cl)cc32)c(C(F)(F)F)n1]
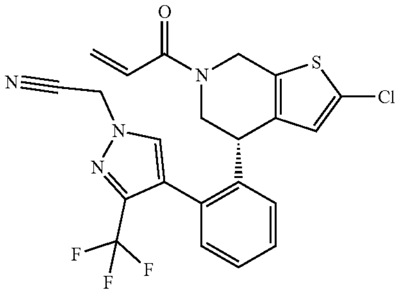 [SMILES: C=CC(=O)N1Cc2sc(Cl)cc2[C@H](c2ccccc2-c2cn(CC#N)nc2C(F)(F)F)C1]
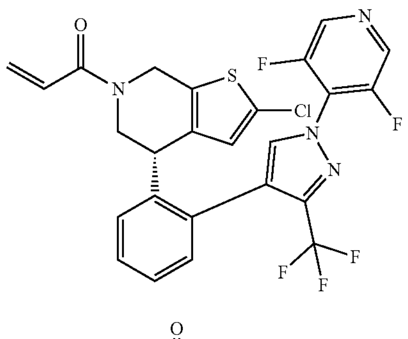
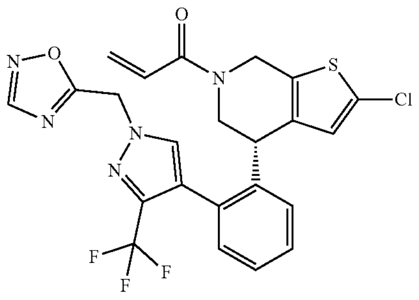 [SMILES: C=CC(=O)N1Cc2sc(Cl)cc2[C@H](c2ccccc2-c2cn(Cc3ncno3)nc2C(F)(F)F)C1]
Blank
-continued
Blank
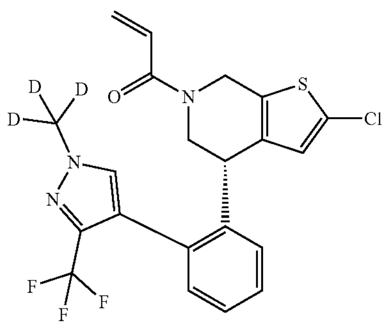 [SMILES: [2H]C([2H])([2H])n1cc(-c2ccccc2[C@@H]2CN(C(=O)C=C)Cc3sc(Cl)cc32)c(C(F)(F)F)n1]
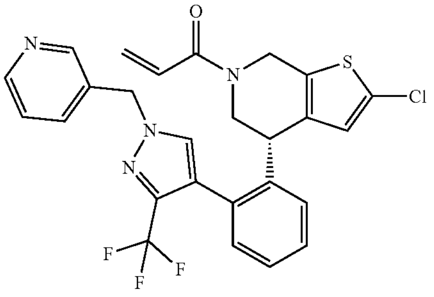 [SMILES: C=CC(=O)N1Cc2sc(Cl)cc2[C@H](c2ccccc2-c2cn(Cc3cccnc3)nc2C(F)(F)F)C1]
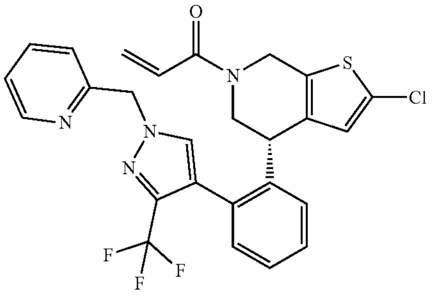 [SMILES: C=CC(=O)N1Cc2sc(Cl)cc2[C@H](c2ccccc2-c2cn(Cc3ccccn3)nc2C(F)(F)F)C1]
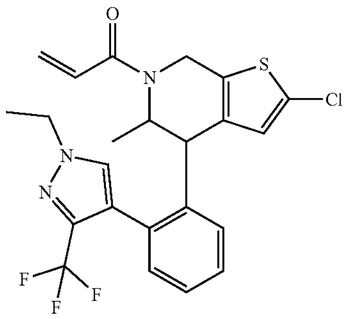 [SMILES: C=CC(=O)N1Cc2sc(Cl)cc2C(c2ccccc2-c2cn(CC)nc2C(F)(F)F)C1C]
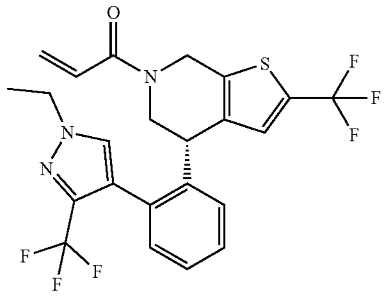 [SMILES: C=CC(=O)N1Cc2sc(C(F)(F)F)cc2[C@H](c2ccccc2-c2cn(CC)nc2C(F)(F)F)C1]

-continued
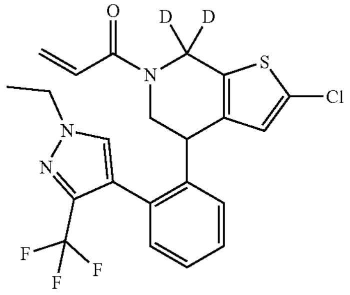
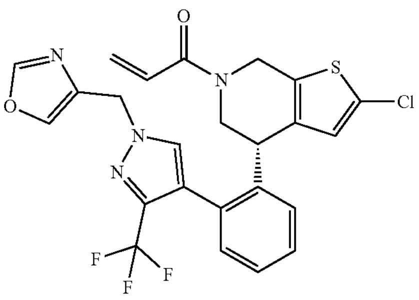 [SMILES: C=CC(=O)N1Cc2sc(Cl)cc2[C@H](c2ccccc2-c2cn(Cc3cocn3)nc2C(F)(F)F)C1]
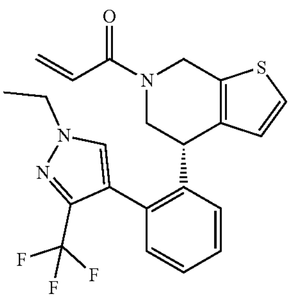
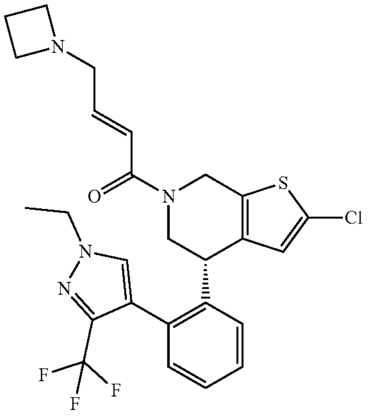 [SMILES: CCn1cc(-c2ccccc2[C@@H]2CN(C(=O)/C=C/CN3CCC3)Cc3sc(Cl)cc32)c(C(F)(F)F)n1]
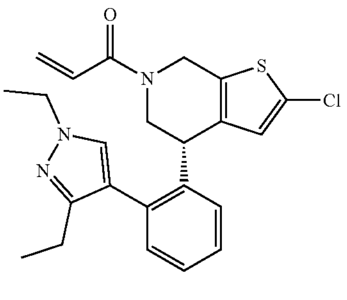
-continued
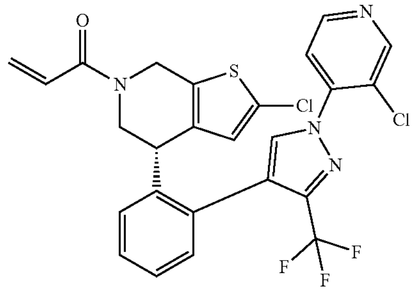 [SMILES: C=CC(=O)N1Cc2sc(Cl)cc2[C@H](c2ccccc2-c2cn(-c3ccncc3Cl)nc2C(F)(F)F)C1]
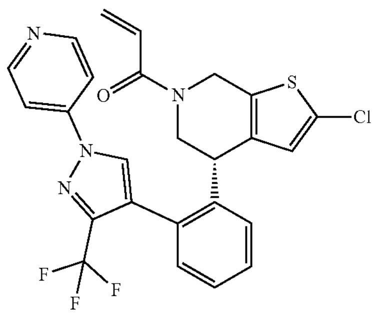 [SMILES: C=CC(=O)N1Cc2sc(Cl)cc2[C@H](c2ccccc2-c2cn(-c3ccncc3)nc2C(F)(F)F)C1]
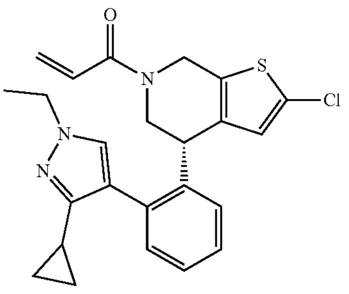 [SMILES: C=CC(=O)N1Cc2sc(Cl)cc2[C@H](c2ccccc2-c2cn(CC)nc2C2CC2)C1]
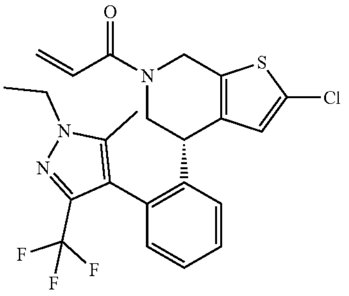 [SMILES: C=CC(=O)N1Cc2sc(Cl)cc2[C@H](c2ccccc2-c2c(C(F)(F)F)nn(CC)c2C)C1]
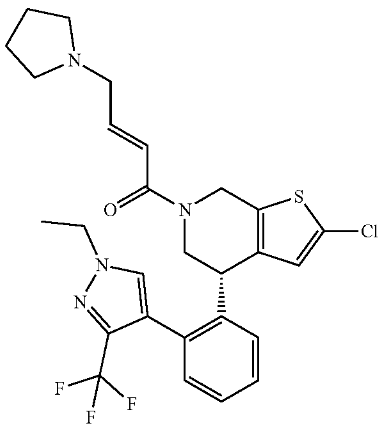 [SMILES: CCn1cc(-c2ccccc2[C@@H]2CN(C(=O)/C=C/CN3CCCC3)Cc3sc(Cl)cc32)c(C(F)(F)F)n1]

-continued
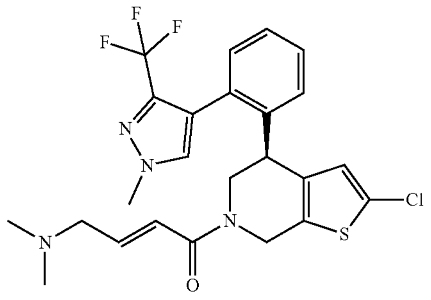 [SMILES: CN(C)C/C=C/C(=O)N1Cc2sc(Cl)cc2[C@H](c2ccccc2-c2cn(C)nc2C(F)(F)F)C1]
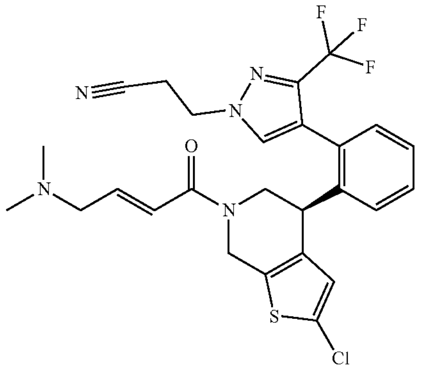 [SMILES: CN(C)C/C=C/C(=O)N1Cc2sc(Cl)cc2[C@H](c2ccccc2-c2cn(CCC#N)nc2C(F)(F)F)C1]
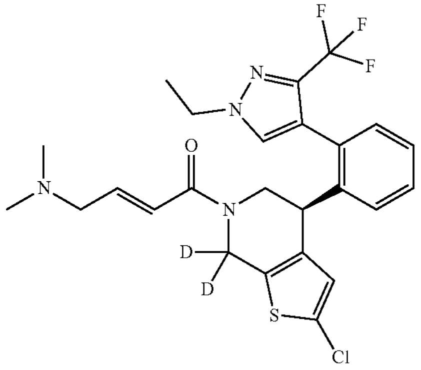 [SMILES: [2H]C1([2H])c2sc(Cl)cc2[C@H](c2ccccc2-c2cn(CC)nc2C(F)(F)F)CN1C(=O)/C=C/CN(C)C]
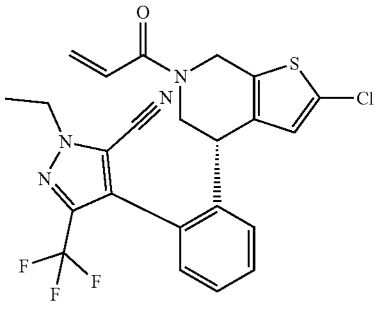 [SMILES: C=CC(=O)N1Cc2sc(Cl)cc2[C@H](c2ccccc2-c2c(C(F)(F)F)nn(CC)c2C#N)C1]
-continued
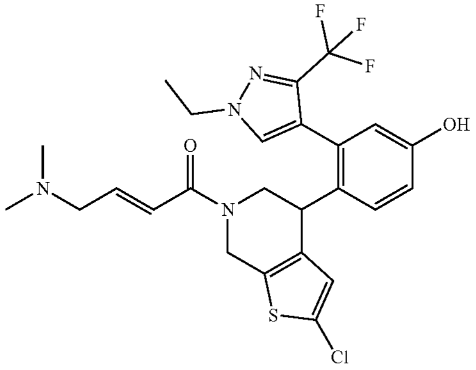 [SMILES: CCn1cc(-c2cc(O)ccc2C2CN(C(=O)/C=C/CN(C)C)Cc3sc(Cl)cc32)c(C(F)(F)F)n1]
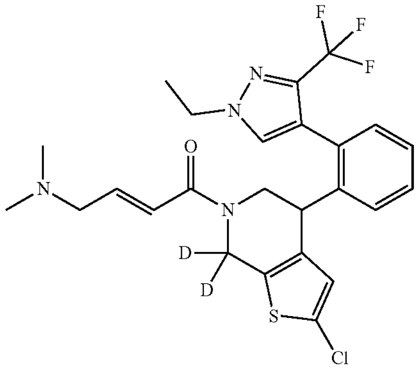 [SMILES: [2H]C1([2H])c2sc(Cl)cc2C(c2ccccc2-c2cn(CC)nc2C(F)(F)F)CN1C(=O)/C=C/CN(C)C]
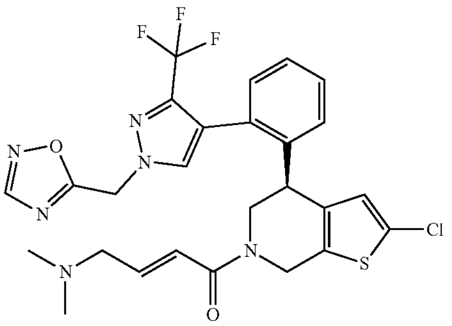 [SMILES: CN(C)C/C=C/C(=O)N1Cc2sc(Cl)cc2[C@H](c2ccccc2-c2cn(Cc3ncno3)nc2C(F)(F)F)C1]
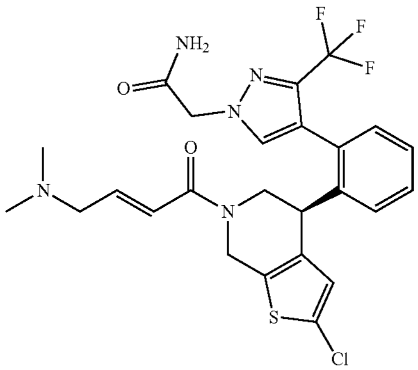 [SMILES: CN(C)C/C=C/C(=O)N1Cc2sc(Cl)cc2[C@H](c2ccccc2-c2cn(CC(N)=O)nc2C(F)(F)F)C1]

-continued
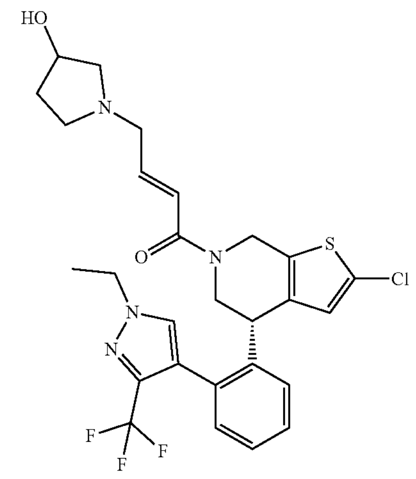 [SMILES: CCn1cc(-c2ccccc2[C@@H]2CN(C(=O)/C=C/CN3CCC(O)C3)Cc3sc(Cl)cc32)c(C(F)(F)F)n1]
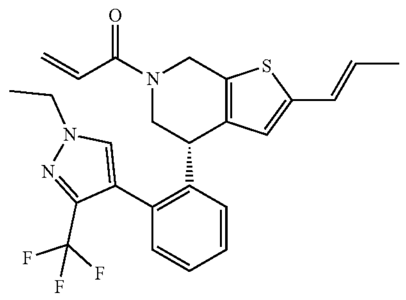 [SMILES: C=CC(=O)N1Cc2sc(/C=C/C)cc2[C@H](c2ccccc2-c2cn(CC)nc2C(F)(F)F)C1]
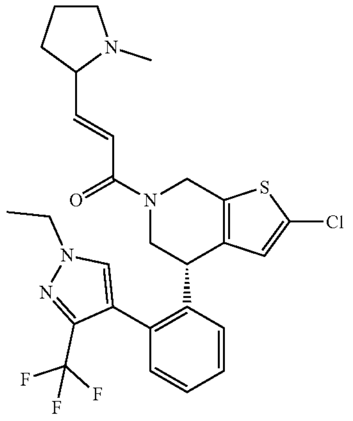 [SMILES: CCn1cc(-c2ccccc2[C@@H]2CN(C(=O)/C=C/C3CCCN3C)Cc3sc(Cl)cc32)c(C(F)(F)F)n1]
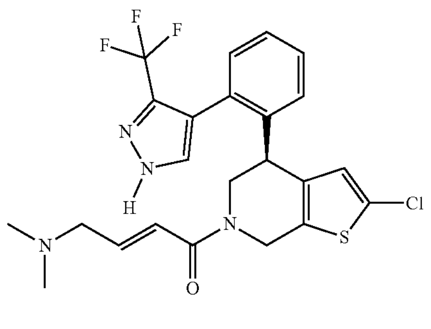
-continued
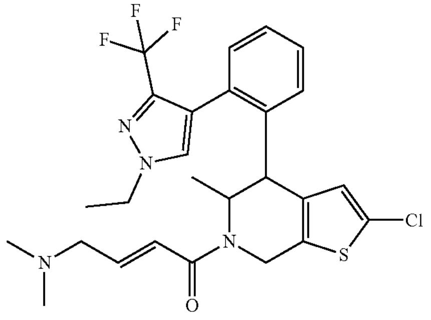 [SMILES: CCn1cc(-c2ccccc2C2c3cc(Cl)sc3CN(C(=O)/C=C/CN(C)C)C2C)c(C(F)(F)F)n1]
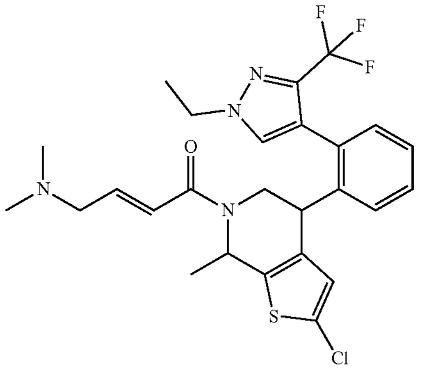 [SMILES: CCn1cc(-c2ccccc2C2CN(C(=O)/C=C/CN(C)C)C(C)c3sc(Cl)cc32)c(C(F)(F)F)n1]
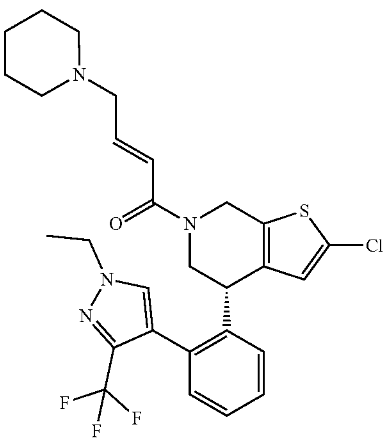 [SMILES: CCn1cc(-c2ccccc2[C@@H]2CN(C(=O)/C=C/CN3CCCCC3)Cc3sc(Cl)cc32)c(C(F)(F)F)n1]
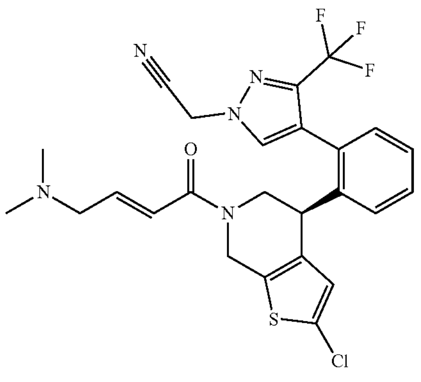 [SMILES: CN(C)C/C=C/C(=O)N1Cc2sc(Cl)cc2[C@H](c2ccccc2-c2cn(CC#N)nc2C(F)(F)F)C1]

-continued
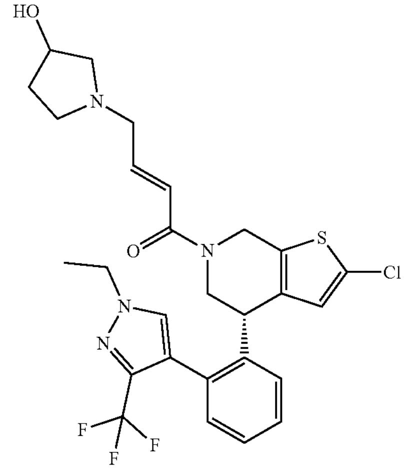 [SMILES: CCn1cc(-c2ccccc2[C@@H]2CN(C(=O)/C=C/CN3CCC(O)C3)Cc3sc(Cl)cc32)c(C(F)(F)F)n1]
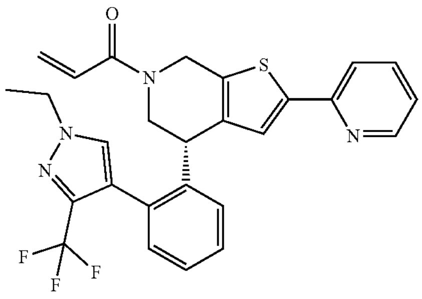 [SMILES: C=CC(=O)N1Cc2sc(-c3ccccn3)cc2[C@H](c2ccccc2-c2cn(CC)nc2C(F)(F)F)C1]
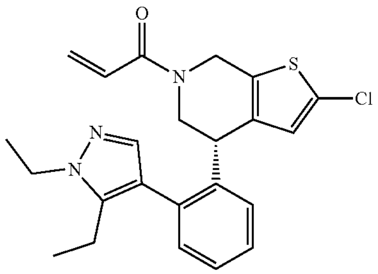 [SMILES: C=CC(=O)N1Cc2sc(Cl)cc2[C@H](c2ccccc2-c2cnn(CC)c2CC)C1]
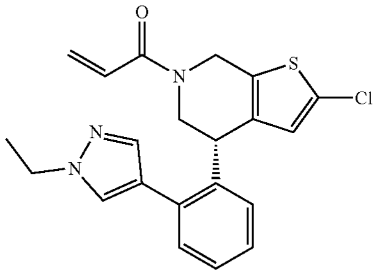 [SMILES: C=CC(=O)N1Cc2sc(Cl)cc2[C@H](c2ccccc2-c2cnn(CC)c2)C1]
-continued
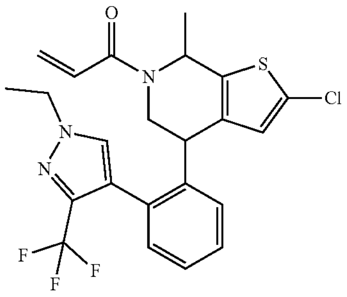 [SMILES: C=CC(=O)N1CC(c2ccccc2-c2cn(CC)nc2C(F)(F)F)c2cc(Cl)sc2C1C]
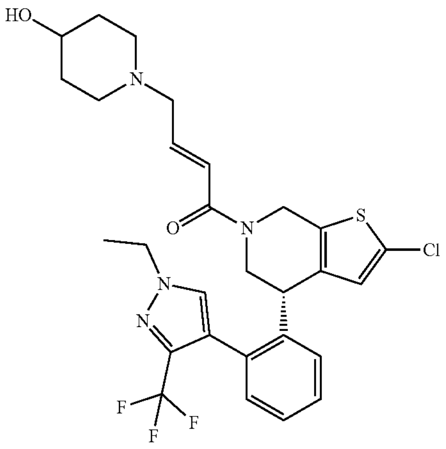 [SMILES: CCn1cc(-c2ccccc2[C@@H]2CN(C(=O)/C=C/CN3CCC(O)CC3)Cc3sc(Cl)cc32)c(C(F)(F)F)n1]
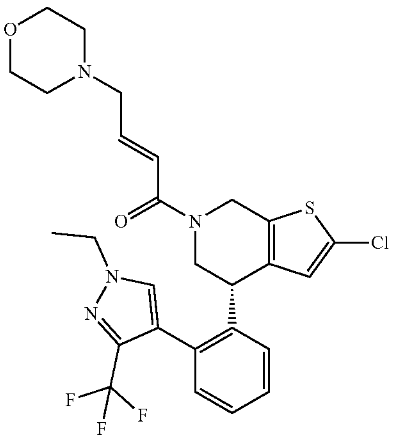 [SMILES: CCn1cc(-c2ccccc2[C@@H]2CN(C(=O)/C=C/CN3CCOCC3)Cc3sc(Cl)cc32)c(C(F)(F)F)n1]
or a pharmaceutically acceptable salt thereof.
23. A method of treating cancer in a subject in need thereof, said method comprising administering to said subject a therapeutically effective amount of the compound of claim 1.
* * * * *

SEQUENCE LISTING

```
<160> NUMBER OF SEQ ID NOS: 6

<210> SEQ ID NO 1
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1

Leu Val Gly Ala Gly Ala Ile Gly Cys Glu Leu Leu Lys
1               5                   10


<210> SEQ ID NO 2
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 2

Val Val Gly Ala Gly Gly Ile Gly Cys Glu Leu Leu Lys
1               5                   10


<210> SEQ ID NO 3
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 3

Val Ile Gly Ala Gly Gly Leu Gly Cys Glu Leu Leu Lys
1               5                   10
```

-continued

<210> SEQ ID NO 4
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 4

Ile Val Gly Cys Gly Gly Leu Gly Cys Pro Ala Gln
1 5 10

<210> SEQ ID NO 5
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 5

Leu Val Gly Ala Gly Ala Ile Gly Cys Glu Leu Leu Lys
1 5 10

<210> SEQ ID NO 6
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 6

Leu Leu Gly Ala Gly Thr Leu Gly Cys Asn Val Ala Arg
1 5 10